(12) United States Patent
DeFrees

(10) Patent No.: US 9,187,532 B2
(45) Date of Patent: Nov. 17, 2015

(54) GLYCOSYLATION OF PEPTIDES VIA O-LINKED GLYCOSYLATION SEQUENCES

(75) Inventor: Shawn DeFrees, North Wales, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 967 days.

(21) Appl. No.: 11/781,888

(22) Filed: Jul. 23, 2007

(65) Prior Publication Data

US 2008/0255040 A1     Oct. 16, 2008

Related U.S. Application Data

(60) Provisional application No. 60/832,461, filed on Jul. 21, 2006, provisional application No. 60/881,130, filed on Jan. 18, 2007, provisional application No. 60/886,616, filed on Jan. 25, 2007, provisional application No. 60/941,920, filed on Jun. 4, 2007.

(51) Int. Cl.
| | |
|---|---|
| *C07K 9/00* | (2006.01) |
| *C07K 1/107* | (2006.01) |
| *C12P 21/00* | (2006.01) |
| *A61K 38/06* | (2006.01) |
| *A61K 38/04* | (2006.01) |
| *C07K 5/00* | (2006.01) |
| *C07K 7/00* | (2006.01) |
| *A61K 38/00* | (2006.01) |
| *A61K 47/48* | (2006.01) |
| *C07K 1/04* | (2006.01) |

(52) U.S. Cl.
CPC ............... *C07K 9/001* (2013.01); *A61K 47/483* (2013.01); *A61K 47/48092* (2013.01); *A61K 47/48215* (2013.01); *A61K 47/48246* (2013.01); *A61K 47/48284* (2013.01); *C07K 1/047* (2013.01); *C07K 1/1077* (2013.01); *C12P 21/005* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,055,635 A | 10/1977 | Green et al. | |
| 4,088,538 A | 5/1978 | Schneider | |
| 4,179,337 A | 12/1979 | Davis et al. | |
| 4,385,260 A | 5/1983 | Watts et al. | |
| 4,412,989 A | 11/1983 | Iwashita et al. | |
| 4,414,147 A | 11/1983 | Klibanov | |
| 4,438,253 A | 3/1984 | Casey et al. | |
| 4,451,566 A | 5/1984 | Spencer | |
| 4,496,689 A | 1/1985 | Mitra | |
| 4,565,653 A | 1/1986 | Ives et al. | |
| 4,675,414 A | 6/1987 | DeFusco et al. | |
| 4,704,361 A | 11/1987 | Miccoli et al. | |
| 4,767,702 A | 8/1988 | Cohenford | |
| 4,806,595 A | 2/1989 | Noishiki et al. | |
| 4,826,945 A | 5/1989 | Cohn et al. | |
| 4,847,325 A | 7/1989 | Shadle et al. | |
| 4,879,236 A | 11/1989 | Smith et al. | |
| 4,918,009 A | 4/1990 | Nilsson | |
| 4,925,796 A | 5/1990 | Bergh et al. | |
| 4,980,502 A | 12/1990 | Felder et al. | |
| 5,032,519 A | 7/1991 | Paulson et al. | |
| 5,047,335 A | 9/1991 | Paulson et al. | |
| 5,104,651 A | 4/1992 | Boone et al. | |
| 5,122,614 A | 6/1992 | Zalipsky | |
| 5,147,788 A | 9/1992 | Page et al. | |
| 5,153,265 A | 10/1992 | Shadle et al. | |
| 5,154,924 A | 10/1992 | Friden | |
| 5,164,374 A | 11/1992 | Rademacher et al. | |
| 5,166,322 A | 11/1992 | Shaw et al. | |
| 5,169,933 A | 12/1992 | Anderson et al. | |
| 5,180,674 A | 1/1993 | Roth | |
| 5,182,107 A | 1/1993 | Friden | |
| 5,194,376 A | 3/1993 | Kang | |
| 5,202,413 A | 4/1993 | Spinu | |
| 5,206,344 A | 4/1993 | Katre et al. | |
| 5,219,564 A | 6/1993 | Zalipsky et al. | |
| 5,272,066 A | 12/1993 | Bergh et al. | |
| 5,278,299 A | 1/1994 | Wong et al. | |
| 5,281,698 A | 1/1994 | Nitecki | |
| 5,288,637 A | 2/1994 | Roth | |
| 5,308,460 A | 5/1994 | Mazid et al. | |
| 5,324,663 A | 6/1994 | Lowe | |
| 5,324,844 A | 6/1994 | Zalipsky | |

(Continued)

FOREIGN PATENT DOCUMENTS

| | | |
|---|---|---|
| AU | 1991/83760 A | 3/1992 |
| AU | 1992/017052 | 12/1992 |

(Continued)

OTHER PUBLICATIONS

Amersham Pharmacia Biotech, "Hydrophobic Interaction Chromatography: Principles and Methods," 104 pp. (2000).
Barrios et al., *J. Mol. Recognit.*, 17(4):332-338 (2004).
Bijsterbosch et al., *Eur. J. Biochem.*, 237(2): 344-349 (1996).
Brockhausen et al., *Acta Anatomica*, 161: 36-78 (1998).
Brockhausen et al., *Glycoconj. J.*, 15: 595-603 (1998).
Cohn et al., *J. Biomed. Mater. Res,*. 22(11): 993-1009 (1988).
Edge et al., *Anal. Biochem.*, 118(1): 131-137 (1981).

(Continued)

*Primary Examiner* — Maury Audet
(74) *Attorney, Agent, or Firm* — Leydig, Voit & Mayer, Ltd.

(57) ABSTRACT

The present invention provides sequon polypeptides with an amino acid sequence including one or more exogenous O-linked glycosylation sequence of the invention. In addition, the present invention provides methods of making polypeptide conjugates as well as methods of using such conjugates and their pharmaceutical compositions. The invention further provides libraries of sequon polypeptides, wherein each member of such library includes at least one exogenous O-linked glycosylation sequence of the invention. Also provided are methods of making and using such libraries.

25 Claims, 13 Drawing Sheets

(56) References Cited

U.S. PATENT DOCUMENTS

| | | | |
|---|---|---|---|
| 5,342,940 A | 8/1994 | Ono et al. |
| 5,346,696 A | 9/1994 | Kim et al. |
| 5,352,670 A | 10/1994 | Venot |
| 5,369,017 A | 11/1994 | Wong et al. |
| 5,374,541 A | 12/1994 | Wong |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer |
| 5,409,817 A | 4/1995 | Ito et al. |
| 5,410,016 A | 4/1995 | Hubbell et al. |
| 5,432,059 A | 7/1995 | Bean |
| 5,446,090 A | 8/1995 | Harris |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | DeFrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 * | 10/2002 | Hassan et al. ............... 435/97 |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 * | 4/2011 | DeFrees et al. ............... 530/397 |
| 7,956,032 B2 | 6/2011 | DeFrees et al. |
| 8,008,252 B2 | 8/2011 | DeFrees et al. |
| 8,063,015 B2 | 11/2011 | DeFrees et al. |
| 8,178,108 B2 | 5/2012 | Buechler et al. |
| 8,207,112 B2 | 6/2012 | Hinderer et al. |
| 8,247,381 B2 | 8/2012 | DeFrees |
| 8,268,967 B2 | 9/2012 | DeFrees et al. |
| 8,361,961 B2 * | 1/2013 | DeFrees et al. ............... 514/7.6 |
| 8,633,157 B2 | 1/2014 | DeFrees et al. |
| 8,716,239 B2 | 5/2014 | DeFrees et al. |
| 8,716,240 B2 | 5/2014 | DeFrees et al. |
| 8,791,066 B2 * | 7/2014 | DeFrees ............... 514/7.2 |
| 8,791,070 B2 | 7/2014 | DeFrees et al. |
| 8,841,439 B2 | 9/2014 | Felo et al. |
| 8,853,161 B2 | 10/2014 | DeFrees et al. |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |

(56) References Cited

U.S. PATENT DOCUMENTS

| | | |
|---|---|---|
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda et al. |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker |
| 2004/0137557 A1 | 7/2004 | DeFrees et al. |
| 2004/0142856 A1 | 7/2004 | DeFrees et al. |
| 2004/0197875 A1* | 10/2004 | Hauser et al. ............... 435/69.6 |
| 2005/0026266 A1 | 2/2005 | Clausen et al. |
| 2005/0031584 A1 | 2/2005 | DeFrees et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | DeFrees |
| 2006/0182714 A1 | 8/2006 | Behrens et al. |
| 2006/0183198 A1 | 8/2006 | Buechler et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | DeFrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees et al. |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |

(56) References Cited

U.S. PATENT DOCUMENTS

| | | |
|---|---|---|
| 2012/0172300 A1 | 7/2012 | DeFrees |
| 2012/0220517 A1 | 8/2012 | DeFrees et al. |
| 2013/0059780 A1 | 3/2013 | DeFrees |
| 2013/0344050 A1 | 12/2013 | DeFrees et al. |
| 2014/0112903 A1 | 4/2014 | DeFrees et al. |
| 2014/0294762 A1 | 10/2014 | DeFrees et al. |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |
| EP | 0474313 A | 3/1992 |
| EP | 0475354 A2 | 3/1992 |
| EP | 0577580 A2 | 1/1994 |
| EP | 0585109 A | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 A1 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H02-076894 A | 3/1990 |
| JP | H03-503759 A | 8/1991 |
| JP | H06-086684 A | 3/1994 |
| JP | H06-160365 A | 6/1994 |
| JP | H06-172375 A | 6/1994 |
| JP | H07-196925 A | 8/1995 |
| JP | H07-223921 A | 8/1995 |
| JP | H08-506023 A | 7/1996 |
| JP | H09-503905 A | 4/1997 |
| JP | H09-208461 A | 8/1997 |
| JP | H10-307356 A | 11/1998 |
| JP | 2000-501607 A | 2/2000 |
| JP | 2001-508783 A | 7/2001 |
| JP | 2001-519784 A | 10/2001 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 A | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 87/00056 | 1/1987 |
| WO | WO 89/06546 A1 | 7/1989 |
| WO | WO 89/10134 A1 | 11/1989 |
| WO | WO 90/07572 | 7/1990 |
| WO | WO 90/08164 A1 | 7/1990 |
| WO | WO 90/08823 A1 | 8/1990 |
| WO | WO 90/12090 A1 | 10/1990 |
| WO | WO 90/13540 A1 | 11/1990 |
| WO | WO 91/06635 A1 | 5/1991 |
| WO | WO 91/09122 | 6/1991 |
| WO | WO 91/14697 A1 | 10/1991 |
| WO | WO 92/001055 A1 | 1/1992 |
| WO | WO 92/15686 A1 | 9/1992 |
| WO | WO 92/16555 A1 | 10/1992 |
| WO | WO 92/16640 A1 | 10/1992 |
| WO | WO 92/18135 | 10/1992 |
| WO | WO 92/22310 A1 | 12/1992 |
| WO | WO 93/08842 A1 | 5/1993 |
| WO | WO 93/13198 A1 | 7/1993 |
| WO | WO 93/15189 A1 | 8/1993 |
| WO | WO 93/18787 A1 | 9/1993 |
| WO | WO 94/04193 A1 | 3/1994 |
| WO | WO 94/05332 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/25614 A1 | 11/1994 |
| WO | WO 94/25615 A1 | 11/1994 |
| WO | WO 94/26760 A1 | 11/1994 |
| WO | WO 94/27631 A1 | 12/1994 |
| WO | WO 94/28024 A1 | 12/1994 |
| WO | WO 95/02421 A1 | 1/1995 |
| WO | WO 95/04278 A1 | 2/1995 |
| WO | WO 95/05465 A1 | 2/1995 |
| WO | WO 96/10089 A1 | 4/1996 |
| WO | WO 96/11953 A1 | 4/1996 |
| WO | WO 96/12800 A1 | 5/1996 |
| WO | WO 96/40731 | 6/1996 |
| WO | WO 96/21468 A1 | 7/1996 |
| WO | WO 96/21469 A1 | 7/1996 |
| WO | WO 96/32491 | 10/1996 |
| WO | WO 96/32492 A1 | 10/1996 |
| WO | WO 96/34015 A1 | 10/1996 |
| WO | WO 96/36357 A1 | 11/1996 |
| WO | WO 96/40881 A1 | 12/1996 |
| WO | WO 97/05330 | 2/1997 |
| WO | WO 97/21822 A2 | 6/1997 |
| WO | WO 87/05330 A1 | 9/1997 |
| WO | WO 97/47651 A1 | 12/1997 |
| WO | WO 98/05363 | 2/1998 |
| WO | WO 98/31826 | 7/1998 |
| WO | WO 98/32466 A1 | 7/1998 |
| WO | WO 98/41562 A1 | 9/1998 |
| WO | WO 98/51784 A1 | 11/1998 |
| WO | WO 98/58964 | 12/1998 |
| WO | WO 99/00150 A2 | 1/1999 |
| WO | WO 99/13063 A1 | 3/1999 |
| WO | WO 99/14259 A1 | 3/1999 |
| WO | WO 99/22764 A1 | 5/1999 |
| WO | WO 99/28491 A1 | 6/1999 |
| WO | WO 99/34833 A1 | 7/1999 |
| WO | WO 99/37779 A1 | 7/1999 |
| WO | WO 99/45964 A1 | 9/1999 |
| WO | WO 99/48515 A1 | 9/1999 |
| WO | WO 99/54342 A1 | 10/1999 |
| WO | WO 99/55376 A1 | 11/1999 |
| WO | WO 00/23114 | 4/2000 |
| WO | WO 00/26354 A1 | 5/2000 |
| WO | WO 00/29558 A1 | 5/2000 |
| WO | WO 00/29603 A2 | 5/2000 |
| WO | WO 00/44785 A1 | 8/2000 |
| WO | WO 00/46379 A1 | 8/2000 |
| WO | WO 00/65087 | 11/2000 |
| WO | WO 01/02017 A2 | 1/2001 |
| WO | WO 01/05434 A2 | 1/2001 |
| WO | WO 01/19955 A2 | 3/2001 |
| WO | WO 01/39788 A2 | 6/2001 |
| WO | WO 01/04983 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | WO 01/83725 A1 | 11/2001 |
| WO | WO 01/87329 A1 | 11/2001 |
| WO | WO 01/87925 A2 | 11/2001 |
| WO | WO 01/88117 A2 | 11/2001 |
| WO | WO 02/02597 A2 | 1/2002 |
| WO | WO 02/13843 A2 | 2/2002 |
| WO | WO 02/13873 A1 | 2/2002 |
| WO | WO 02/29025 A2 | 4/2002 |
| WO | WO 02/44196 A1 | 6/2002 |

(56) References Cited

FOREIGN PATENT DOCUMENTS

| | | |
|---|---|---|
| WO | WO 02/49673 A2 | 6/2002 |
| WO | WO 02/50099 A2 | 6/2002 |
| WO | WO 02/053580 A2 | 7/2002 |
| WO | WO 02/074806 A2 | 9/2002 |
| WO | WO 02/002764 A2 | 10/2002 |
| WO | WO 02/077218 A1 | 10/2002 |
| WO | WO 02/092619 A2 | 11/2002 |
| WO | WO 03/006501 A2 | 1/2003 |
| WO | WO 03/011879 A1 | 2/2003 |
| WO | WO 03/017949 A2 | 3/2003 |
| WO | WO 03/029291 A2 | 4/2003 |
| WO | WO 03/031464 A2 | 4/2003 |
| WO | WO 03/045980 A2 | 6/2003 |
| WO | WO 03/046150 A2 | 6/2003 |
| WO | WO 03/093448 A2 | 11/2003 |
| WO | WO 2004/000366 A1 | 12/2003 |
| WO | WO 2004/009838 A2 | 1/2004 |
| WO | WO 2004/010327 A2 | 1/2004 |
| WO | WO 2004/014417 A2 | 2/2004 |
| WO | WO 2004/022004 A2 | 3/2004 |
| WO | WO 2004/029090 A1 | 4/2004 |
| WO | WO 2004/029091 A2 | 4/2004 |
| WO | WO 2004/033651 A2 | 4/2004 |
| WO | WO 2004/046222 A1 | 6/2004 |
| WO | WO 2004/047858 A1 | 6/2004 |
| WO | WO 2004/067566 A1 | 8/2004 |
| WO | WO 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/093823 A2 | 11/2004 |
| WO | WO 2004/096148 A2 | 11/2004 |
| WO | WO 2004/099231 A2 | 11/2004 |
| WO | WO 2004/101597 A2 | 11/2004 |
| WO | WO 2004/101740 A2 | 11/2004 |
| WO | WO 2004/103275 * | 12/2004 |
| WO | WO 2004/103275 A2 | 12/2004 |
| WO | WO 2004/106373 A1 | 12/2004 |
| WO | WO 2005/001025 A2 | 1/2005 |
| WO | WO 2005/003171 A2 | 1/2005 |
| WO | WO 2005/012484 A2 | 2/2005 |
| WO | WO 2005/014024 A2 | 2/2005 |
| WO | WO 2005/014035 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/079363 A2 | 9/2005 |
| WO | WO 2005/091944 A2 | 10/2005 |
| WO | WO 2005/121331 A2 | 12/2005 |
| WO | WO 2006/005058 A2 | 1/2006 |
| WO | WO 2006/010143 A2 | 1/2006 |
| WO | WO 2006/011839 A1 | 2/2006 |
| WO | WO 2006/013202 A2 | 2/2006 |
| WO | WO 2006/014349 A2 | 2/2006 |
| WO | WO 2006/014466 A2 | 2/2006 |
| WO | WO 2006/018204 A1 | 2/2006 |
| WO | WO 2006/020372 A2 | 2/2006 |
| WO | WO 2006/031811 A2 | 3/2006 |
| WO | WO 2006/035057 A1 | 4/2006 |
| WO | WO 2006/050247 A2 | 5/2006 |
| WO | WO 2006/053299 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | WO 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | WO 2006/134173 A2 | 12/2006 |
| WO | WO 2007/022512 A2 | 2/2007 |
| WO | WO 2007/056191 A2 | 5/2007 |
| WO | WO 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Feldman et al., *Proc. Natl. Acad. Sci. USA*, 102(8): 3016-3021 (2005).
Ge et al., *J. Biol. Chem.*, 272(34): 21357-21363 (1997).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Grabenhorst et al., *J. Biol. Chem.*, 274(51): 36107-36116 (1999).
Harris (ed.), "Poly(Ethylene Glycol) Chemistry: Biotechnical and Biomedical Applications", Plenum Press, New York (1992) (Title Pages).
Harris et al. (eds.), "Poly(ethylene glycol): Chemistry and Biological Applications," ACS Symposium Series, vol. 680, American Chemical Society (1997) (Title Pages).
Hassan et al., *Carbohydrates in Chemistry and Biology*, Part II, 3: 273-292 (2000).
Hermanson et al., *Immobilized Affinity Ligand Techniques*, Academic Press (1992) (Table of Contents).
Hermanson, *Bioconjugate Techniques*, Academic Press, San Diego (1996) (Table of Contents).
Herscovics et al., *FASEB J.*, 7(6): 540-550 (1993).
Höglund, *Med. Oncol.*, 15(4): 229-233 (1998).
Keana et al., *J. Org. Chem.*, 55(11): 3640-3647 (1990).
Keene et al., *J. Biol. Chem.*, 264(9): 4769-4775 (1989).
Kobayashi et al., *Eur. J. Nucl. Med.*, 27(9):1334-1339 (2000).
Kornfeld et al., *Ann. Rev. Biochem.*, 54: 631-664 (1985).
Kukuruzinska et al., *Proc. Natl. Acad. Sci. USA*, 84(8): 2145-2149 (1987).
Langer, *Science*, 249(4976): 1527-1533 (1990).
Legault et al., *J. Biol. Chem.*, 270(36): 20987-20996 (1995).
Lin et al., *Proc. Natl. Acad. Sci. USA*, 82: 7580-7584 (1985).
Meynial-Salles et al., *J. Biotechnol.*, 46(1): 1-14 (1996).
Monaco et al., *Gene*, 180: 145-150 (1996).
Muller et al., *J. Biol. Chem.*, 272(40): 24780-24793 (1997).
Muller et al., *J. Biol. Chem.*, 274(26): 18165-18172 (1999).
Nagata et al., *EMBO J.*, 5(3): 575-581 (1986).
Oh-Eda et al., *J. Biol. Chem.*, 265: 11432-11435 (1990).
Orlean, "vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Prati et al., *Biotech and Bioeng.*, 79(5): 580-585 (2002).
Rotondaro et al., *Mol. Biotech.*, 11: 117-128 (1999).
Rudikoff et al., *Proc. Natl. Acad. Sci. USA*, 79(6):1979-1983 (1982).
Sasaki et al., *J. Biol. Chem.*, 262(25): 12059-12076 (1987).
Sasaki et al., *J.Biol. Chem.*, 269: 14730-14737 (1994).
Schwientek et al., *J. Biol. Chem.*, 277(25): 22623-22638 (2002).
Seitz, *Chembiochem.*, 1(4): 214-246 (2000).
Shen et al., *Biochem. Biophys. Res. Commun.*, 102(3): 1048-1054 (1981).
Shinkai et al., *Prot. Exp. Purif.*, 10: 379-385 (1997).
Sojar et al., *Arch. Biochem. Biophys.*, 259(1): 52-57 (1987).
Stemmer, *Nature*, 370(6488): 389-391 (1994).
Stemmer, *Proc. Natl. Acad. Sci. USA*, 91(22): 10747-10751 (1994).
Stephens et al., *Eur. J. Biochem.*, 135(3): 519-527 (1983).
Strausberg et al., *Proc Natl Acad Sci USA*, 99(26): 16899-16903 (2002).
Ten Hagen et al., *J. Biol. Chem.*, 274(39): 27867-27874 (1999).
Tsunoda et al., *J. Pharmacol. Exp. Ther.*, 209(1): 368-372 (1999).
Van Reis et al., *Biotechnol. Bioeng.*, 38(4): 413-422 (1991).

(56) References Cited

OTHER PUBLICATIONS

Vitetta et al., *Science*, 313: 308-309 (2006).
White et al., *J. Biol. Chem.*, 270(41): 24156-24165 (1995).
Witte et al., *Cancer and Metastasis Rev.*, 17: 155-161 (1998).
Wong et al., *J. Org. Chem.*, 47(27): 5416-5418 (1982).
Yamada et al., *Biochemistry*, 20(17): 4836-4842 (1981).
Younes et al., *J. Biomed. Mater. Res.*, 21(11): 1301-1316 (1987).
Zarling et al., *J. Immunol.*, 124(2): 913-920 (1980).
Abuchowski et al., *J. Biol. Chem.*, 252: 3582-3586 (1977).
Boime et al., *Recent Prog. Horm. Res.*, 54: 271-289 (1999).
Copeland, Robert A., *Enzymes*, Second Edition, 146-150 (2000).
Felix et at., *J. Peptide Res.*, 63: 85-90 (2004).
Gervais et al., *Glycobiology*, 13(3): 179-189 (2003).
Gross et al., *Biochemistry*, 28: 7386-7392 (1989).
Kajihara et al., *Carbohydrate Research*, 315: 137-141 (1999).
Kawasaki et al., *Analytical Biochemistry*, 285: 82-91 (2000).
Katre et al., *Proc. Natl. Acad. Sci. U.S.A.*, 84: 1487-1491 (1987).
Keppler et al., *Glycobiology*, 11: 11R-18R (2001).
Min et al., *Endoor J.*, 43:585-593 (1996).
Seely et al., *Journal of Chromatography*, 908: 235-241 (2001).
Snider et al., *Journal of Chromatography*, 599: 141-155 (1992).
Srinivasachar et al., *Biochemistry*, 28: 2501-2509 (1989).
Taniguchi et al., *Proteomics*, 1(2): 239-247 (2001).
Urdal et al, *J. Chromatog*, 296: 171-179 (1984).
Witte et al., *J. Am. Chem. Soc.* 119: 2114-2118 (1997).
Wu et al., *J. Drug targeting 10*: 239-245 (2002).
Alam et al., 1998. Journal of Biotechnology. 65: 183-190.
Bedard et al., 1994, Cytotechnology 15:129-138.
Bork (2000) Genome Research 10:398-400.
Bork et al. (1996) Trends in Genetics 12(10): 425-427.
Brenner (1999) Trends in Genetics 15(4) 132-133.
Doerks et al. (1998) Trends in Genetics 14(6): 248-250.
Gilbert et al., 1996, Cytotechnology 22:211-216.
Harris et al., Abstracts of Papers of the American Chemical Society, 1991, V 201, APR, P 64-Poly, p. 154-155.
Hink et al., 1991, Biotechnology Progress 7:9-14.
Hollister et al., 2001, Glycobiology 11:1-9.
Ikonomou et al., 1991, in Vitro Cell. Dev. Biol.-Animal 37:549-559.
Inlow, et al., 1989, J. Tissue Culture Meth. 12:13-16.
Lau et al. (1999) Journal of Biotechnology 75:105-115.
Licari P. et al., 1992, Biotechnology and Bioengineering 39(4):432-441.
Licari P. et al., 1992, Biotechnology and Bioengineering 39(9):932-944.
Ngo et al. (1994) "The Protein Folding Problem and Tertiary Structure Prediction, Chapter 14: Computational Complexity Protein Structure Prediction, and the Levinthal Paradox" pp. 433-440 and 492-495.
Oetke, et al., 2002, J. Biol. Chem 277(8):6688-6695.
Reis et al., 1991, Biotechnology and Bioengineering 38:413-422.
Schlaeger, E., 1996, Cytotechnology 20:57-70.
Skolnick et al. (2000) Trends in Biotech. 18(1): 34-39.
Smith et al. (1997) Nature Biotechnology 15:1222-1223.
Wells (1990) Biochemistry 29(37): 8509-8517.
Abeijon et al., 1986, J. Biol. Chem. 261(24):11374-11377.
Abuchowski et al., 1977, J. Biol. Chem. 252:3582-3586.
Abuchowski et al., 1984, Cancer Biochem. Biophys. 7:175-186.
Abuchowski et al., 1977, J. Biol. Chem. 252:3578-3581.
Ailor et al., 2000, Glycobiology 10:837-847.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Bennett et al., 1999, FEBS Letters 460:226-230.
Bennett et al., 1998, J. Biol. Chem. 273:30472-30481.
Berger et al., 1988, Blood 71:1641-1647.
Berg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bouizar et al., 1986, Eur. J. Biochem. 155:141-147.
Boyd et al., 1995, Mol. Immunol. 32:1311-1318.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Fritz et al., 2004, PNAS 101(43):15307-15312.
Fritz et al., 2006, 281(13):8613-8619.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. August 83:1-7.
Ginns, Dr. Edward, PEG Glucocerebrosidase, Internet page from www.gaucher.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hagen et al., 1999, J. Biol. Chem. 274:6797-6803.
Hagen et al., 1999, J. Biol. Chem. 274:27867-27874.
Hagen et al., 2001, J. Biol. Chem. 276:17395-17404.
Hall et al., 2001, Methods in Molecular Biology 166:139-154.
Haneda et al., Carbohydr. Res. 292:61-70.
Hang et al., 2001, J. Am. Chem. Soc. 123:1242-1243.
Harris, 1985, Macronol. Chem. Phys. C25: 325-373.
Harris et al., 2003, Nature Reviews Drug Discovery, 2:214-221.
Hassan et al., 2000, J. Biol. Chem. 275:38197-38205.
Hassen et al., 2000, J. Biol. Chem. 275:38197-38205.
Hayes et al., 1993, J. Biol. Chem. 268(22):16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Inoue et al., 1995, Biotechnology Annual Review 1:297-313.

(56) References Cited

OTHER PUBLICATIONS

Ito et al., 1993, Pure & Appl. Chem. 65(4):753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lee-Huang et al., 1984, Proc. Natl. Acad. Sci. U.S.A. 81:2708-2712.
Lee et al., 1989, Biochemistry 28:1856-1861.
Leung, S., 1995, J. Immunology, 154:5919-5926.
Li et al., 2002, Trends in Pharmacological Sciences 23:206-209.
Li et al., 2002, Medicinal Research Reviews 22:225-250.
Liu et al., 2002, 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Molecular cloning and enzymatic characterization of a *Trichoderma reesei*, 2- α-D-mannosidase, 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
NCBI—Accession No. NCAA26095 (2 pgs.), 2006.
NCBI—Accession No. NP_999299 (2 pgs.), 2007.
NCBI—Accession No. NP_058697 (3 pgs.), 2007.
NCBI Database hits for erythropoietin protein sequences (3 pgs.), 2007.
Nilsson et al., 1984, Methods Enzymol. 104:56-69.
O'Connell et al., 1992, J. Biol. Chem. 267:25010-25018.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Plummer et al., 1995, J. Biol. Chem. 270(22):13192-13196.
PNGase-F Amidase Sequence from F. Meningosepticum (Registry Nos. 128688-70-0), 2007.
PNGase-F Amidase Sequence from F. Meningosepticum (Registry Nos. 128688-71-1), 2007.
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Rosenthal, et al., 1994, Methods Enzymol. 235:253-285.
Sadler et al., 1982, Methods in Enzymology 83:458-514.
Sandberg et al., 2000, Seminars in Hematology 38(2):4-12.
Saneyoshi et al., 2001, Biology of Reproduction 65:1686-1690.
Saxon et al., 2000, Science 287:2007-2010.
Schwientek et al., 1994, Gene 145:299-303.
Schwientek et al., 2002, J. Biol. Chem. 277:22623-22638.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Song et al., 2002, J. Pharmacol. Exp. Ther. 301:605-610.
Srinivasachar et al., 1989, Biochemistry 28:2501-2509.
Stephens et al., 1983, European J. of Biochem., 135(3):519-27.
Stephens et al., 1983, European J. of Biochem., 133(3):481-9.
Stephens et al., 1983, European J. of Biochem., 133(1):155-62.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Tenno et al., 2002, J. Biol. Chem. 277(49):47088-96.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, in Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly (ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.

(56) References Cited

OTHER PUBLICATIONS

Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Drucker et al., "Glucagon Gene Expression in Vertebrate Brain," *J. Biol. Chem.*, 263(27): 13475-13478 (1988).
Monfardini et al., "A Branched Monomethoxypoly (ethylene glycol) for Protein Modification," *Bioconjug. Chem.*, 6(1): 62-69 (1995).
Moscatelli et al., "Enzymatic Properties of a β-Glucanase from *Bacillus subtilis*," *J. Biol. Chem.*, 236(11): 2858-2862 (1961).
Perrin et al., "Common Physical Techniques Used in Purification," in *Purification of Laboratory Chemicals*, pp. 30-31, Pergamon (1980).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Song et al., "Reassembled Biosynthetic Pathway for a Large-Scale Synthesis of CMP-Neu5Ac," *Mar. Drugs*, 1: 34-45 (2003).
Office Action dated Oct. 23, 2012 in U.S. Appl. No. 12/811,963.
Office Action dated Nov. 9, 2012 in U.S. Appl. No. 12/663,056.
Office Action dated Nov. 26, 2012 in U.S. Appl. No. 13/215,439.
Office Action dated Dec. 21, 2012 in U.S. Appl. No. 13/246,512.
Office Action dated Jan. 17, 2013 in U.S. Appl. No. 13/541,185.
Office Action dated Mar. 6, 2013 in U.S. Appl. No. 13/157,575.
Office Action dated Mar. 13, 2013 in U.S. Appl. No. 12/811,963.
Office Action dated Mar. 14, 2013 in U.S. Appl. No. 12/784,323.
Office Action dated Mar. 21, 2013 in U.S. Appl. No. 13/541,185.
Office Action dated May 9, 2013 in U.S. Appl. No. 12/594,326.
Office Action dated May 21, 2013 in U.S. Appl. No. 12/811,963.
Office Action dated Jun. 6, 2013 in U.S. Appl. No. 11/701,949.
Office Action dated Jul. 11, 2013 in U.S. Appl. No. 11/652,467.
Office Action dated Jul. 17, 2013 in U.S. Appl. No. 13/215,439.
Office Action dated Jul. 30, 2013 in U.S. Appl. No. 13/246,512.
Office Action dated Aug. 12, 2013 in U.S. Appl. No. 13/541,185.
Office Action dated Sep. 6, 2013 in U.S. Appl. No. 12/784,323.
Office Action dated Sep. 16, 2013 in U.S. Appl. No. 11/781,885.
Office Action dated Sep. 17, 2013 in U.S. Appl. No. 11/781,888.
Office Action dated Sep. 25, 2013 in U.S. Appl. No. 12/663,748.
Office Action dated Oct. 10, 2013 in U.S. Appl. No. 10/581,538.
Office Action dated Oct. 16, 2013 in U.S. Appl. No. 11/597,258.
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 200 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.

(56) References Cited

OTHER PUBLICATIONS

Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in US U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283
Office Action dated Aug. 17, 2007 in U.S. Appl. No. 10/492,261
Office Action dated Aug. 30, 2007 in U.S. Appl. No. 10/497,284
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.

(56) References Cited

OTHER PUBLICATIONS

Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Adelhorst et al., *J. Biol. Chem.*, 269(9): 6275-6278 (1994).
Broun et al., *Science*, 282(5392): 1315-1317 (1998).
Costa et al., *J. Biol. Chemz.*, 272(17): 11613-11621 (1997).
Culajay et al., *Biochem.*, 39: 7153-7158 (2000).
De Vries et al, *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Fairhall et al., *Endocrinology*, 131(4): 1963-1969 (1992).
Francis et al., *Intl. J. Hematol.*, 68(1): 1-18 (1998).
Hansen et al., *Biochem J.*, 308: 801-813 (1995).
Haro et al., *Biochem. Biophys. Res. Comm.*, 228(2): 549-556 (1996).
Jezek et al., *J. Peptide Sci.*, 5: 46-55 (1999).
Kaneko et al., *Cytogenet. Cell Genet.*, 86(3-4): 329-330 (1999).
Kaneko et al., *FEBS Lett.*, 452(3): 237-242 (1999).
Kimura et al., *Proc. Natl. Acad. Sci. USA*, 96(8): 4530-4535 (1999).
Kisselev, *Structure*, 10(1): 8-9 (2002).
Kukowska-Latallo et al., *Genes Dev.*, 4(8): 1288-1303 (1990).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lönnberg, *Curr. Org. Synth.*, 6(4): 400-425 (2009).
Malissard et al., Biochem. Biophys. Res. Commun., 267(1): 169-173 (2000).
Mollicone et al., *Eur. J. Biochem.*, 191(1): 169-176 (1990).
Nunez et al., *Can. J. Chem.*, 59(14): 2086-2095 (1981).
Orskov et al., *J. Biol. Chem.*, 264(22): 12826-12829 (1989).
Palcic et al., *Carbohydr. Res.*, 190(1): 1-11 (1989).
Prieels et al., *J. Biol. Chem.*, 256(20): 10456-10463 (1981).
Rasko et al., *J. Biol. Chem.*, 275(7): 4988-4994 (2000).
Seffernick et al., *J. Bacteriol.*, 183(8): 2405-2410 (2001).
Sinclair et al., *J. Pharm. Sci.*, 94: 1626-1635 (2005).
Staudacher, *Trends Glycosci. Glycotechnol.*, 8(44): 391-408 (1996).
Trottein et al., *Mol. Biochem. Parasitol.*, 107(2): 279-287 (2000).
Van Tetering et al., *FEBS Lett.*, 461(3): 311-314 (1999).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(34): 24575-24584 (1992).
Wishart et al., *J. Biol. Chem.*, 270(45): 26782-26785 (1995).
Witkowski et al., *Biochemistry*, 38(36): 11643-11650 (1999).
Zhang et al., *Biochim. Biophys. Acta*, 1425: 441-452 (1998).
Arslan et al., *Transf. Apher. Sci.*, 37: 179-185 (2007).
Broxmeyer et al., *J. Exp. Med.*, 201(8): 1307-1318 (2005).
Brumeanu et al., *J. Immunol. Meth.*, 183: 185-197 (1995).
Cantin et al., *Am. J. Respir. Cell Mol. Biol.*, 27(6): 659-665 (2002).
Capoccia et al., *Blood*, 108(7): 2438-2445 (2006).
Cashen et al., *Bone Marrow Trans.*, 39: 577-588 (2007).
Deacon, *Diabetes*, 54: 2181-2189 (2004).
Elhalabi et al., *Curr. Med. Chem.*, 6(2): 93-116 (1999).
Espuelas et al., *Bioorg. Med. Chem. Lett.*, 13(15): 2557-2560 (2003).
Flomenberg et al., *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Gross et al., *Eur. J. Biochem,.* 177(3): 583-589 (1988).
Guo et al., *Appl. Biochem. Biotechnol.*, 68(1-2): 1-20 (1997).
Haneda et al., *Carbohydr. Res.*, 292: 61-70 (1996).
Hällgren et al., *J. Carb. Chem.*, 14(4-5): 453-464 (1995).
Hill et al., *Biol. Blood Marrow Trans.*, 12: 603-607 (2006).
Hu et al., *Mol. Cell. Biol.*, 18(10): 6063-6074 (1998).
Hübel et al., *Ann. Hematol.*, 82: 207-213 (2003).
Kennedy, "Hydrophobic-Interaction Chromatography," in *Current Protocols in Protein Science*, pp. 8.4.1-8.4.21, Wiley (1995).
Kroschinsky et al., *Trans. Apher. Sci.*, 38: 237-244 (2008).
Krystal et al., *Blood*, 67(1): 71-99 (1986).
Liles et al., *Transfusion*, 45: 295-300 (2005).
Liu et al., *Chem. Eur. J.*, 2(11): 1359-1362 (1996).
Natsuka et al., *J. Biol. Chem.*, 269(24): 16789-16794 (1994).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
O'Shannessy et al., *J. Appl. Biochem.*, 7: 347-355 (1985).
PNGase-F Amidase Sequence from F. Meningosepticum (RN 128688-70-0) (2007).
PNGase-F Amidase Sequence from F. Meningosepticum (RN 128688-71-1) (2007).
Quelle et al., *Blood*, 74(2): 652-657 (1989).
R & D Systems, Fibroblast Growth Factors (FGFs), Internet page from www.rndsystems.com/mini_review_detail_objectname_MR01_FGFs.aspx, 2001, printed Mar. 10, 2011.
Rathnam et al., *Biochim. Biophys. Acta*, 624(2): 436-442 (1980).
Saxon et al., *J. Am. Chem. Soc.*, 124(50): 14893-14902 (2002).
Schwarz et al., *Nucl. Med. Biol.*, 26(4):383-388 (1999).
Srivastava et al., *J. Biol. Chem.*, 267(31): 22356-22361 (1992).

(56) References Cited

OTHER PUBLICATIONS

Tom et al., *AAPS Journal*, 9(2): E227-E234 (2007).
Uptima, Detergents: Solubilization of Biomolecules, Internet page from www.interchim.com/interchim/bio/produits_uptima/product_line/p1p_detergents.htm, 2001, printed Nov. 14, 2011.
Veronese, *Biomaterials*, 22(5): 405-417 (2001).
Weston et al., *J. Biol. Chem.*, 267(6): 4152-4160 (1992).
Yin et al., *Pharm. Res.*, 21(12): 2377-2383 (2004).
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).
Brinkman-Van Der Linden et al., *J. Biol. Chem.*, 271(24): 14492-14495 (1996).
Broquet et al., *Eur. J. Biochem.* 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al, *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett 1999*, (9): 1495-1507 (1999).
De Rosa et al., *Phytochemistry*, 42(4): 1031-1034 (1996).
Deangelis et al., *Biochemistry*, 33(31): 9033-9039 (1994).
Deluca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Dudas et al., *Infect. Immun.*, 56(2): 499-504 (1988).
Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia, pp. 568-575 (1988).
EMBL Accession No. M80599 and M86935 (Jan. 23, 1992).
EMBL Accession No. S56361 (May 4, 1993).
EMBL Accession No. U00039 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare, Instructions 28-9064-05 AA (2006).
GE Healthcare, Instructions 28-9064-05 AC (2006).
Genbank Accession No. AAA98726, "Factor IX," pp. 1-3 (Apr. 14, 2009).
Genbank Accession No. CAA01607, "Factor IX of *Homo sapiens*," pp. 1-2 (Apr. 14, 2009).
Genbank Accession No. D49915 (Sep. 1, 1995).
Genbank Accession No. U02304 (Mar. 8, 1994).
Genbank Accession No. U18918 (Oct. 1, 1995).
Gibson et al., *J. Bacteriol.*, 175(9): 2702-2712 (1993).
Gilbert, "Methods in Enzymology" Packer (ed.), 2(251): 8-28, Biothiols Part A, Elsevier (1995).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Gillespie et al., *FASEB Journal*, 4(7): A2068 [Abstract No. 2173] (1990).
Gillespie et al., *J. Biol. Chem.*, 267(29): 21004-21010 (1992).
Goodson et al., *Biotechnology (N. Y.)*, 8(4): 343-346 (1990).
Greenwell et al., *Blood Group A Synthesising Activity of the Blood Group B Gene Specified .alpha.-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Helling et al., *Cancer Res.*, 54(1): 197-203 (1994).
Higa et al., *J. Biol. Chem.*, 260(15): 8838-8849 (1985).
Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990) English Translation.
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).
Koeller et al., "Complex Carbohydrate Synthesis Tools for Glycobiologists: Enzyme-Based Approach and Programmable One-Pot Strategies," *Glycobiology*, 10(11): 1157-1169 (2000).
Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta.*, 1437(2): 101-118 (1999).
Mackenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).

(56) References Cited

OTHER PUBLICATIONS

Manfioletti et al., "The Protein Encoded by a Growth Arrest-Specific Gene (gas6) is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Muramatsu et al., *Comprehensive Research on Clinical Organ Xenotransplantation by Genetic Regulation*, p. 10-12. (1997).
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).
Raju et al., "Glycoengineering of Therapeutic Glycoproteins: In Vitro Galactosylation and Sialylation of Glycoproteins with Terminal N-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbiol.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).
Sandlin et al., *J. Bacteriol.*, 176(10): 2930-2937 (1994).
Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).

Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
SWISS-PROT Accession No. P19817 (Feb. 1, 1991).
SWISS-PROT Accession No. P25740 (May 1, 1992).
SWISS-PROT Accession No. P27129 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl Le$^x$ but Not 6-Sulfo Sialyl Le$^x$ Expressed on the Cell Surface Supports L-selectin-mediated Adhesion," *J. Biol. Chem.*, 271(44): 27213-27216 (1996).
Tsuji, "Molecular Cloning and Functional Analysis of Sialyltransferases," *J. Biochemistry*, 120: 1-13 (1996).
Tsujihara et al., *Chem. Pharm. Bull.*, (Tokyo) 29(11): 3262-3273 (1981).
Van Den Eijnden et al., *J. Biol. Chem.*, 256(7): 3159-3162 (1981).
Van Den Eijnden et al., *J. Biol. Chem.*, 258(6): 3435-3437 (1983).
Van Putten et al., *EMBO J.*, 12(11): 4043-4051 (1993).
Van Roey et al., *Biochemistry*, 33(47): 13989-13996 (1994).
Vann et al., *J Biol Chem.*, 262(36): 17556-17562 (1987).
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).
Webster et al., *J. Biol. Chem.*, 258(17): 10637-10641 (1983).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia, Image:Ceramide.svg, http://en.wikipedia.org/wiki/Ceramide, pp. 1-2 (2007).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).
Yamasaki et al., *J. Bacteriol.*, 175(14): 4565-4568 (1993).
Yoshikawa et al., *Phytochemistry*, 34(5): 1431-1433 (1993).
Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).

\* cited by examiner

FIGURE 4

MQIELSTCFFLCLLRFCFSATRRYYLGAVELSWDYMQSDLGELPVDARFPPRVPKSFPFNTSVVYKKTL
FVEFTVHLFNIAKPRPPWMGLLGPTIQAEVYDTVVITLKNMASHPVSLHAVGVSYWKASEGAEYDDQT
SQREKEDDKVFPGGSHTYVWQVLKENGPMASDPLCLTYSYLSHVDLVKDLNSGLIGALLVCREGSLA
KEKTQTLHKFILLFAVFDEGKSWHSETKNSLMQDRDAASARAWPKMHTVNGYVNRSLPGLIGCHRKS
VYWHVIGMGTTPEVHSIFLEGHTFLVRNHRQASLEISPITFLTAQTLLMDLGQFLLFCHISSHQHDGMEA
YVKVDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILGPLLYGEVG
DTLLIIFKNQASRPYNIYPHGITDVRPLYSRRLPKGVKHLKDFPILPGEIFKYKWTVTVEDGPTKSDPRCL
TRYYSSFVNMERDLASGLIGPLLICYKESVDQRGNQIMSDKRNVILFSVFDENRSWYLTENIQRFLPNPA
GVQLEDPEFQASNIMHSINGYVFDSLQLSVCLHEVAYWYILSIGAQTDFLSVFFSGYTFKHKMVYEDTL
TLFPFSGETVFMSMENPGLWILGCHNSDFRNRGMTALLKVSSCDKNTGDYYEDSYEDISAYLLSKNNA
IEPRSFSQNSRHPSTRQKQFNATTIPENDIEKTDPWFAHRTPMPKIQNVSSSDLLMLLRQSPTPHGLSLSD
LQEAKYETFSDDPSPGAIDSNNSLSEMTHFRPQLHHSGDMVFTPESGLQLRLNEKLGTTAATELKKLDF
KVSSTSNNLISTIPSDNLAAGTDNTSSLGPPSMPVHYDSQLDTTLFGKKSSPLTESGGPLSLSEENNDSKL
LESGLMNSQESSWGKNVSSTESGRLFKGKRAHGPALLTKDNALFKVSISLLKTNKTSNNSATNRKTHID
GPSLLIENSPSVWQNILESDTEFKKVTPLIHDRMLMDKNATALRLNHMSNKTTSSKNMEMVQQKKEGP
IPPDAQNPDMSFFKMLFLPESARWIQRTHGKNSLNSGQGPSPKQLVSLGPEKSVEGQNFLSEKNKVVVG
KGEFTKDVGLKEMVFPSSRNLFLTNLDNLHENNTHNQEKKIQEEIEKKETLIQENVVLPQIHTVTGTKN
FMKNLFLLSTRQNVEGSYEGAYAPVLQDFRSLNDSTNRTKKHTAHFSKKGEEENLEGLGNQTKQIVEK
YACTTRISPNTSQQNFVTQRSKRALKQFRLPLEETELEKRIIVDDTSTQWSKNMKHLTPSTLTQIDYNEK
EKGAITQSPLSDCLTRSHSIPQANRSPLPIAKVSSFPSIRPIYLTRVLFQDNSSHLPAASYRKKDSGVQESS
HFLQGAKKNNLSLAILTLEMTGDQREVGSLGTSATNSVTYKKVENTVLPKPDLPKTSGKVELLPKVHI
YQKDLFPTETSNGSPGHLDLVEGSLLQGTEGAIKWNEANRPGKVPFLRVATESSAKTPSKLLDPLAWD
NHYGTQIPKEEWKSQEKSPEKTAFKKKDTILSLNACESNHAIAAINEGQNKPEIEVTWAKQGRTERLCS
QNPPVLKRHQREITRTTLQSDQEEIDYDDTISVEMKKEDFDIYDEDENQSPRSFQKKTRHYFIAAVERL
WDYGMSSSPHVLRNRAQSGSVPQFKKVVFQEFTDGSFTQPLYRGELNEHLGLLGPYIRAEVEDNIMVT
FRNQASRPYSFYSSLISYEEDQRQGAEPRKNFVKPNETKTYFWKVQHHMAPTKDEFDCKAWAYFSDV
DLEKDVHSGLIGPLLVCHTNTLNPAHGRQVTVQEFALFFTIFDETKSWYFTENMERNCRAPCNIQMEDP
TFKENYRFHAINGYIMDTLPGLVMAQDQRIRWYLLSMGSNENIHSIHFSGHVFTVRKKEEYKMALYNL
YPGVFETVEMLPSKAGIWRVECLIGEHLHAGMSTLFLVYSNKCQTPLGMASGHIRDFQITASGQYGQW
APKLARLHYSGSINAWSTKEPFSWIKVDLLAPMIIHGIKTQGARQKFSSLYISQFIIMYSLDGKKWQTYR
GNSTGTLMVFFGNVDSSGIKHNIFNPPIIARYIRLHPTHYSIRSTLRMELMGCDLNSCSMPLGMESKAISD
AQITASSYFTNMFATWSPSKARLHLQGRSNAWRPQVNNPKEWLQVDFQKTMKVTGVTTQGVKSLLTS
MYVKEFLISSSQDGHQWTLFFQNGKVKVFQGNQDSFTPVVNSLDPPLLTRYLRIHPQSWVHQIALRME
VLGCEAQDLY (SEQ ID NO: 254)

FIGURE 5

ATRRYYLGAVELSWDYMQSDLGELPVDARFPPRVPKSFPFNTSVVYKKTLFVEFTDHLFNIA
KPRPPWMGLLGPTIQAEVYDTVVITLKNMASHPVSLHAVGVSYWKASEGAEYDDQTSQREK
EDDKVFPGGSHTYVWQVLKENGPMASDPLCLTYSYLSHVDLVKDLNSGLIGALLVCREGSL
AKEKTQTLHKFILLFAVFDEGKSWHSETKNSLMQDRDAASARAWPKMHTVNGYVNRSLPG
LIGCHRKSVYWHVIGMGTTPEVHSIFLEGHTFLVRNHRQASLEISPITFLTAQTLLMDLGQFLL
FCHISSHQHDGMEAYVKVDSCPEEPQLRMKNNEEAEDYDDDLTDSEMDVVRFDDDNSPSFI
QIRSVAKKHPKTWVHYIAAEEEDWDYAPLVLAPDDRSYKSQYLNNGPQRIGRKYKKVRFM
AYTDETFKTREAIQHESGILGPLLYGEVGDTLLIIFKNQASRPYNIYPHGITDVRPLYSRRLPKG
VKHLKDFPILPGEIFKYKWTVTVEDGPTKSDPRCLTRYYSSFVNMERDLASGLIGPLLICYKES
VDQRGNQIMSDKRNVILFSVFDENRSWYLTENIQRFLPNPAGVQLEDPEFQASNIMHSINGYV
FDSLQLSVCLHEVAYWYILSIGAQTDFLSVFFSGYTFKHKMVYEDTLTLFPFSGETVFMSMEN
PGLWILGCHNSDFRNRGMTALLKVSSCDKNTGDYYEDSYEDISAYLLSKNNAIEPRSFSQNPP
VLKRHQREITRTTLQSDQEEIDYDDTISVEMKKEDFDIYDEDENQSPRSFQKKTRHYFIAAVE
RLWDYGMSSSPHVLRNRAQSGSVPQFKKVVFQEFTDGSFTQPLYRGELNEHLGLLGPYIRAE
VEDNIMVTFRNQASRPYSFYSSLISYEEDQRQGAEPRKNFVKPNETKTYFWKVQHHMAPTK
DEFDCKAWAYFSDVDLEKDVHSGLIGPLLVCHTNTLNPAHGRQVTVQEFALFFTIFDETKSW
YFTENMERNCRAPCNIQMEDPTFKENYRFHAINGYIMDTLPGLVMAQDQRIRWYLLSMGSN
ENIHSIHFSGHVFTVRKKEEYKMALYNLYPGVFETVEMLPSKAGIWRVECLIGEHLHAGMST
LFLVYSNKCQTPLGMASGHIRDFQITASGQYGQWAPKLARLHYSGSINAWSTKEPFSWIKVD
LLAPMIIHGIKTQGARQKFSSLYISQFIIMYSLDGKKWQTYRGNSTGTLMVFFGNVDSSGIKH
NIFNPPIIARYIRLHPTHYSIRSTLRMELMGCDLNSCSMPLGMESKAISDAQITASSYFTNMFAT
WSPSKARLHLQGRSNAWRPQVNNPKEWLQVDFQKTMKVTGVTTQGVKSLLTSMYVKEFLI
SSSQDGHQWTLFFQNGKVKVFQGNQDSFTPVVNSLDPPLLTRYLRIHPQSWVHQIALRMEVL
GCEAQDLY
(SEQ ID NO: 255)

| Parent Poly-peptide | C-terminal | N-terminal | Internal | Full Insertion | Replacing 1 AA | Replacing 2 AA | Replacing 3 AA | Replacing 4 AA | Replacing 5 AA | Replacing 6 AA | Replacing 7 AA | |
|---|---|---|---|---|---|---|---|---|---|---|---|---|
| BMP-7 | PTP | PTP | PTP | PTP | PTP | PTP | PTP | | | | | (SEQ ID NO: 138) |
| BMP-7 | PTEI | PTEI | PTEI | PTEI | PTEI | PTEI | PTEI | PTEI | | | | (SEQ ID NO: 139) |
| BMP-7 | PTEIP | PTEIP | PTEIP | PTEIP | PTEIP | PTEIP | PTEIP | PTEIP | PTEIP | | | (SEQ ID NO: 140) |
| BMP-7 | PTQA | PTQA | PTQA | PTQA | PTQA | PTQA | PTQA | PTQA | | | | (SEQ ID NO: 141) |
| BMP-7 | PTQAP | PTQAP | PTQAP | PTQAP | PTQAP | PTQAP | PTQAP | PTQAP | PTQAP | | | (SEQ ID NO: 142) |
| BMP-7 | PTINT | PTINT | PTINT | PTINT | PTINT | PTINT | PTINT | PTINT | PTINT | | | (SEQ ID NO: 143) |
| BMP-7 | PTINTP | PTINTP | PTINTP | PTINTP | PTINTP | PTINTP | PTINTP | PTINTP | PTINTP | PTINTP | | (SEQ ID NO: 144) |
| BMP-7 | PTTVS | PTTVS | PTTVS | PTTVS | PTTVS | PTTVS | PTTVS | PTTVS | PTTVS | | | (SEQ ID NO: 145) |
| BMP-7 | PTTVL | PTTVL | PTTVL | PTTVL | PTTVL | PTTVL | PTTVL | PTTVL | PTTVL | | | (SEQ ID NO: 146) |
| BMP-7 | PTQGAM | PTQGAM | PTQGAM | PTQGAM | PTQGAM | PTQGAM | PTQGAM | PTQGAM | PTQGAM | PTQGAM | | (SEQ ID NO: 147) |
| BMP-7 | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| BMP-7 | TETP | TETP | TETP | TETP | TETP | TETP | TETP | TETP | | | | (SEQ ID NO: 149) |
| BMP-15 | PTP | PTP | PTP | PTP | PTP | PTP | PTP | | | | | (SEQ ID NO: 138) |
| BMP-15 | PTEI | PTEI | PTEI | PTEI | PTEI | PTEI | PTEI | PTEI | | | | (SEQ ID NO: 139) |
| BMP-15 | PTEIP | PTEIP | PTEIP | PTEIP | PTEIP | PTEIP | PTEIP | PTEIP | PTEIP | | | (SEQ ID NO: 140) |
| BMP-15 | PTQA | PTQA | PTQA | PTQA | PTQA | PTQA | PTQA | PTQA | | | | (SEQ ID NO: 141) |
| BMP-15 | PTQAP | PTQAP | PTQAP | PTQAP | PTQAP | PTQAP | PTQAP | PTQAP | PTQAP | | | (SEQ ID NO: 142) |
| BMP-15 | PTINT | PTINT | PTINT | PTINT | PTINT | PTINT | PTINT | PTINT | PTINT | | | (SEQ ID NO: 143) |
| BMP-15 | PTINTP | PTINTP | PTINTP | PTINTP | PTINTP | PTINTP | PTINTP | PTINTP | PTINTP | PTINTP | | (SEQ ID NO: 144) |
| BMP-15 | PTTVS | PTTVS | PTTVS | PTTVS | PTTVS | PTTVS | PTTVS | PTTVS | PTTVS | | | (SEQ ID NO: 145) |
| BMP-15 | PTTVL | PTTVL | PTTVL | PTTVL | PTTVL | PTTVL | PTTVL | PTTVL | PTTVL | | | (SEQ ID NO: 146) |

FIGURE 6A

| Parent Poly-peptide | C-terminal | N-terminal | Internal | Full Insertion | Replacing 1 AA | Replacing 2 AA | Replacing 3 AA | Replacing 4 AA | Replacing 5 AA | Replacing 6 AA | Replacing 7 AA | |
|---|---|---|---|---|---|---|---|---|---|---|---|---|
| BMP-15 | PTQGAM | PTQGAM | PTQGAM | PTQGAM | PTQGAM | PTQGAM | PTQGAM | PTQGAM | PTQGAM | PTQGAM | | (SEQ ID NO: 147) |
| BMP-15 | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| BMP-15 | TETP | TETP | TETP | TETP | TETP | TETP | TETP | TETP | | | | (SEQ ID NO: 149) |
| NT3 | PTP | PTP | PTP | PTP | PTP | PTP | PTP | | | | | (SEQ ID NO: 138) |
| NT3 | PTEI | PTEI | PTEI | PTEI | PTEI | PTEI | PTEI | PTEI | | | | (SEQ ID NO: 139) |
| NT3 | PTEIP | PTEIP | PTEIP | PTEIP | PTEIP | PTEIP | PTEIP | PTEIP | PTEIP | | | (SEQ ID NO: 140) |
| NT3 | PTQA | PTQA | PTQA | PTQA | PTQA | PTQA | PTQA | PTQA | | | | (SEQ ID NO: 141) |
| NT3 | PTQAP | PTQAP | PTQAP | PTQAP | PTQAP | PTQAP | PTQAP | PTQAP | PTQAP | | | (SEQ ID NO: 142) |
| NT3 | PTINT | PTINT | PTINT | PTINT | PTINT | PTINT | PTINT | PTINT | PTINT | | | (SEQ ID NO: 143) |
| NT3 | PTINTP | PTINTP | PTINTP | PTINTP | PTINTP | PTINTP | PTINTP | PTINTP | PTINTP | PTINTP | | (SEQ ID NO: 144) |
| NT3 | PTTVS | PTTVS | PTTVS | PTTVS | PTTVS | PTTVS | PTTVS | PTTVS | PTTVS | | | (SEQ ID NO: 145) |
| NT3 | PTTVL | PTTVL | PTTVL | PTTVL | PTTVL | PTTVL | PTTVL | PTTVL | PTTVL | | | (SEQ ID NO: 146) |
| NT3 | PTQGAM | PTQGAM | PTQGAM | PTQGAM | PTQGAM | PTQGAM | PTQGAM | PTQGAM | PTQGAM | PTQGAM | | (SEQ ID NO: 147) |
| NT3 | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| NT3 | TETP | TETP | TETP | TETP | TETP | TETP | TETP | TETP | | | | (SEQ ID NO: 149) |
| FGF-7 | PTP | PTP | PTP | PTP | PTP | PTP | PTP | | | | | (SEQ ID NO: 138) |
| FGF-7 | PTEI | PTEI | PTEI | PTEI | PTEI | PTEI | PTEI | PTEI | | | | (SEQ ID NO: 139) |
| FGF-7 | PTEIP | PTEIP | PTEIP | PTEIP | PTEIP | PTEIP | PTEIP | PTEIP | PTEIP | | | (SEQ ID NO: 140) |
| FGF-7 | PTQA | PTQA | PTQA | PTQA | PTQA | PTQA | PTQA | PTQA | | | | (SEQ ID NO: 141) |
| FGF-7 | PTQAP | PTQAP | PTQAP | PTQAP | PTQAP | PTQAP | PTQAP | PTQAP | PTQAP | | | (SEQ ID NO: 142) |
| FGF-7 | PTINT | PTINT | PTINT | PTINT | PTINT | PTINT | PTINT | PTINT | PTINT | | | (SEQ ID NO: 143) |
| FGF-7 | PTINTP | PTINTP | PTINTP | PTINTP | PTINTP | PTINTP | PTINTP | PTINTP | PTINTP | PTINTP | | (SEQ ID NO: 144) |

FIGURE 6B

| Parent Poly-peptide | C-terminal | N-terminal | Internal | Full Insertion | Replacing 1 AA | Replacing 2 AA | Replacing 3 AA | Replacing 4 AA | Replacing 5 AA | Replacing 6 AA | Replacing 7 AA | |
|---|---|---|---|---|---|---|---|---|---|---|---|---|
| FGF-7 | PTTVS | PTTVS | PTTVS | PTTVS | PTTVS | PTTVS | PTTVS | PTTVS | PTTVS | | | (SEQ ID NO: 145) |
| FGF-7 | PTTVL | PTTVL | PTTVL | PTTVL | PTTVL | PTTVL | PTTVL | PTTVL | PTTVL | | | (SEQ ID NO: 146) |
| FGF-7 | PTQGAM | PTQGAM | PTQGAM | PTQGAM | PTQGAM | PTQGAM | PTQGAM | PTQGAM | PTQGAM | PTQGAM | | (SEQ ID NO: 147) |
| FGF-7 | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| FGF-7 | TETP | TETP | TETP | TETP | TETP | TETP | TETP | TETP | | | | (SEQ ID NO: 149) |
| FGF-21 | PTP | PTP | PTP | PTP | PTP | PTP | PTP | | | | | (SEQ ID NO: 138) |
| FGF-21 | PTEI | PTEI | PTEI | PTEI | PTEI | PTEI | PTEI | PTEI | | | | (SEQ ID NO: 139) |
| FGF-21 | PTEIP | PTEIP | PTEIP | PTEIP | PTEIP | PTEIP | PTEIP | PTEIP | PTEIP | | | (SEQ ID NO: 140) |
| FGF-21 | PTQA | PTQA | PTQA | PTQA | PTQA | PTQA | PTQA | PTQA | | | | (SEQ ID NO: 141) |
| FGF-21 | PTQAP | PTQAP | PTQAP | PTQAP | PTQAP | PTQAP | PTQAP | PTQAP | PTQAP | | | (SEQ ID NO: 142) |
| FGF-21 | PTINT | PTINT | PTINT | PTINT | PTINT | PTINT | PTINT | PTINT | PTINT | | | (SEQ ID NO: 143) |
| FGF-21 | PTINTP | PTINTP | PTINTP | PTINTP | PTINTP | PTINTP | PTINTP | PTINTP | PTINTP | PTINTP | | (SEQ ID NO: 144) |
| FGF-21 | PTTVS | PTTVS | PTTVS | PTTVS | PTTVS | PTTVS | PTTVS | PTTVS | PTTVS | | | (SEQ ID NO: 145) |
| FGF-21 | PTTVL | PTTVL | PTTVL | PTTVL | PTTVL | PTTVL | PTTVL | PTTVL | PTTVL | | | (SEQ ID NO: 146) |
| FGF-21 | PTQGAM | PTQGAM | PTQGAM | PTQGAM | PTQGAM | PTQGAM | PTQGAM | PTQGAM | PTQGAM | PTQGAM | | (SEQ ID NO: 147) |
| FGF-21 | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| FGF-21 | TETP | TETP | TETP | TETP | TETP | TETP | TETP | TETP | | | | (SEQ ID NO: 149) |
| vWF Protease | PTP | PTP | PTP | PTP | PTP | PTP | PTP | | | | | (SEQ ID NO: 138) |
| vWF Protease | PTEI | PTEI | PTEI | PTEI | PTEI | PTEI | PTEI | PTEI | | | | (SEQ ID NO: 139) |
| vWF | PTEIP | PTEIP | PTEIP | PTEIP | PTEIP | PTEIP | PTEIP | PTEIP | PTEIP | | | (SEQ ID NO: 140) |

FIGURE 6C

| Parent Poly-peptide | C-terminal | N-terminal | Internal | Full Insertion | Replacing 1 AA | Replacing 2 AA | Replacing 3 AA | Replacing 4 AA | Replacing 5 AA | Replacing 6 AA | Replacing 7 AA | |
|---|---|---|---|---|---|---|---|---|---|---|---|---|
| vWF Protease | PTQA | PTQA | PTQA | PTQA | PTQA | PTQA | PTQA | PTQA | | | | (SEQ ID NO: 141) |
| vWF Protease | PTQAP | PTQAP | PTQAP | PTQAP | PTQAP | PTQAP | PTQAP | PTQAP | PTQAP | | | (SEQ ID NO: 142) |
| vWF Protease | PTINT | PTINT | PTINT | PTINT | PTINT | PTINT | PTINT | PTINT | PTINT | | | (SEQ ID NO: 143) |
| vWF Protease | PTINTP | PTINTP | PTINTP | PTINTP | PTINTP | PTINTP | PTINTP | PTINTP | PTINTP | PTINTP | | (SEQ ID NO: 144) |
| vWF Protease | PTTVS | PTTVS | PTTVS | PTTVS | PTTVS | PTTVS | PTTVS | PTTVS | PTTVS | | | (SEQ ID NO: 145) |
| vWF Protease | PTTVL | PTTVL | PTTVL | PTTVL | PTTVL | PTTVL | PTTVL | PTTVL | PTTVL | | | (SEQ ID NO: 146) |
| vWF Protease | PTQGAM | PTQGAM | PTQGAM | PTQGAM | PTQGAM | PTQGAM | PTQGAM | PTQGAM | PTQGAM | PTQGAM | | (SEQ ID NO: 147) |
| vWF Protease | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| vWF Protease | TETP | TETP | TETP | TETP | TETP | TETP | TETP | TETP | | | | (SEQ ID NO: 149) |
| Factor VII | PTP | PTP | PTP | PTP | PTP | PTP | PTP | | | | | (SEQ ID NO: 138) |
| Factor VII | PTEI | PTEI | PTEI | PTEI | PTEI | PTEI | PTEI | PTEI | | | | (SEQ ID NO: 139) |
| Factor VII | PTEIP | PTEIP | PTEIP | PTEIP | PTEIP | PTEIP | PTEIP | PTEIP | PTEIP | | | (SEQ ID NO: 140) |
| Factor VII | PTQA | PTQA | PTQA | PTQA | PTQA | PTQA | PTQA | PTQA | | | | (SEQ ID NO: 141) |
| Factor VII | PTQAP | PTQAP | PTQAP | PTQAP | PTQAP | PTQAP | PTQAP | PTQAP | PTQAP | | | (SEQ ID NO: 142) |

FIGURE 6D

| Parent Poly-peptide | C-terminal | N-terminal | Internal | Full Insertion | Replacing 1 AA | Replacing 2 AA | Replacing 3 AA | Replacing 4 AA | Replacing 5 AA | Replacing 6 AA | Replacing 7 AA | |
|---|---|---|---|---|---|---|---|---|---|---|---|---|
| Factor VII | PTINT | PTINT | PTINT | PTINT | PTINT | PTINT | PTINT | PTINT | PTINT | | | (SEQ ID NO: 143) |
| Factor VII | PTINTP | PTINTP | PTINTP | PTINTP | PTINTP | PTINTP | PTINTP | PTINTP | PTINTP | PTINTP | | (SEQ ID NO: 144) |
| Factor VII | PTTVS | PTTVS | PTTVS | PTTVS | PTTVS | PTTVS | PTTVS | PTTVS | PTTVS | | | (SEQ ID NO: 145) |
| Factor VII | PTTVL | PTTVL | PTTVL | PTTVL | PTTVL | PTTVL | PTTVL | PTTVL | PTTVL | | | (SEQ ID NO: 146) |
| Factor VII | PTQGAM | PTQGAM | PTQGAM | PTQGAM | PTQGAM | PTQGAM | PTQGAM | PTQGAM | PTQGAM | PTQGAM | | (SEQ ID NO: 147) |
| Factor VII | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| Factor VII | TETP | TETP | TETP | TETP | TETP | TETP | TETP | TETP | | | | (SEQ ID NO: 149) |
| Factor VIII | PTP | PTP | PTP | PTP | PTP | PTP | PTP | | | | | (SEQ ID NO: 138) |
| Factor VIII | PTEI | PTEI | PTEI | PTEI | PTEI | PTEI | PTEI | PTEI | | | | (SEQ ID NO: 139) |
| Factor VIII | PTEIP | PTEIP | PTEIP | PTEIP | PTEIP | PTEIP | PTEIP | PTEIP | PTEIP | | | (SEQ ID NO: 140) |
| Factor VIII | PTQA | PTQA | PTQA | PTQA | PTQA | PTQA | PTQA | PTQA | | | | (SEQ ID NO: 141) |
| Factor VIII | PTQAP | PTQAP | PTQAP | PTQAP | PTQAP | PTQAP | PTQAP | PTQAP | PTQAP | | | (SEQ ID NO: 142) |
| Factor VIII | PTINT | PTINT | PTINT | PTINT | PTINT | PTINT | PTINT | PTINT | PTINT | | | (SEQ ID NO: 143) |
| Factor VIII | PTINTP | PTINTP | PTINTP | PTINTP | PTINTP | PTINTP | PTINTP | PTINTP | PTINTP | PTINTP | | (SEQ ID NO: 144) |
| Factor VIII | PTTVS | PTTVS | PTTVS | PTTVS | PTTVS | PTTVS | PTTVS | PTTVS | PTTVS | | | (SEQ ID NO: 145) |
| Factor VIII | PTTVL | PTTVL | PTTVL | PTTVL | PTTVL | PTTVL | PTTVL | PTTVL | PTTVL | | | (SEQ ID NO: 146) |
| Factor VIII | PTQGAM | PTQGAM | PTQGAM | PTQGAM | PTQGAM | PTQGAM | PTQGAM | PTQGAM | PTQGAM | PTQGAM | | (SEQ ID NO: 147) |
| Factor VIII | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| Factor VIII | TETP | TETP | TETP | TETP | TETP | TETP | TETP | TETP | | | | (SEQ ID NO: 149) |
| Factor IX | PTP | PTP | PTP | PTP | PTP | PTP | PTP | | | | | (SEQ ID NO: 138) |
| Factor IX | PTEI | PTEI | PTEI | PTEI | PTEI | PTEI | PTEI | PTEI | | | | (SEQ ID NO: 139) |
| Factor IX | PTEIP | PTEIP | PTEIP | PTEIP | PTEIP | PTEIP | PTEIP | PTEIP | PTEIP | | | (SEQ ID NO: 140) |

FIGURE 6E

| Parent Poly-peptide | C-terminal | N-terminal | Internal | Full Insertion | Replacing 1 AA | Replacing 2 AA | Replacing 3 AA | Replacing 4 AA | Replacing 5 AA | Replacing 6 AA | Replacing 7 AA | |
|---|---|---|---|---|---|---|---|---|---|---|---|---|
| Factor IX | PTQA | PTQA | PTQA | PTQA | PTQA | PTQA | PTQA | PTQA | | | | (SEQ ID NO: 141) |
| Factor IX | PTQAP | PTQAP | PTQAP | PTQAP | PTQAP | PTQAP | PTQAP | PTQAP | PTQAP | | | (SEQ ID NO: 142) |
| Factor IX | PTINT | PTINT | PTINT | PTINT | PTINT | PTINT | PTINT | PTINT | PTINT | | | (SEQ ID NO: 143) |
| Factor IX | PTINTP | PTINTP | PTINTP | PTINTP | PTINTP | PTINTP | PTINTP | PTINTP | PTINTP | PTINTP | | (SEQ ID NO: 144) |
| Factor IX | PTTVS | PTTVS | PTTVS | PTTVS | PTTVS | PTTVS | PTTVS | PTTVS | PTTVS | | | (SEQ ID NO: 145) |
| Factor IX | PTTVL | PTTVL | PTTVL | PTTVL | PTTVL | PTTVL | PTTVL | PTTVL | PTTVL | | | (SEQ ID NO: 146) |
| Factor IX | PTQGAM | PTQGAM | PTQGAM | PTQGAM | PTQGAM | PTQGAM | PTQGAM | PTQGAM | PTQGAM | PTQGAM | | (SEQ ID NO: 147) |
| Factor IX | PTQGAMP | PTQGAMP | PTQGAMP | PTQGAMP | PTQGAMP | PTQGAMP | PTQGAMP | PTQGAMP | PTQGAMP | PTQGAMP | PTQGAMP | (SEQ ID NO: 148) |
| Factor IX | TETP | TETP | TETP | TETP | TETP | TETP | TETP | TETP | | | | (SEQ ID NO: 149) |

FIGURE 6F

SEQUENCE LISTING

<160> NUMBER OF SEQ ID NOS: 423

<210> SEQ ID NO 1
<211> LENGTH: 9
<212> TYPE: PRT
<213> ORGANISM: Artificial Sequence
<220> FEATURE:
<221> NAME/KEY: VARIANT
<222> LOCATION: 1, 5
<223> OTHER INFORMATION: Xaa = glu, gln, asp, asn, thr, ser, or any
      uncharged amino acid, and each can be either
      present or absent
<220> FEATURE:
<221> NAME/KEY: VARIANT
<222> LOCATION: (3)...(3)
<223> OTHER INFORMATION: Xaa = ser or thr
<220> FEATURE:
<221> NAME/KEY: VARIANT

```
<222> LOCATION: (4)...(4)
<223> OTHER INFORMATION: Xaa = pro, glu, gln, asp, asn, thr, ser, or any
      uncharged amino acid, and can be either present or
      absent
<220> FEATURE:
<221> NAME/KEY: VARIANT
<222> LOCATION: 6, 7, 8
<223> OTHER INFORMATION: Xaa = glu, gln, asp, asn, thr, ser, tyr, met,
      or any uncharged amino acid, and each can be either
      present or absent
<220> FEATURE:
<221> NAME/KEY: VARIANT
<222> LOCATION: (9)...(9)
<223> OTHER INFORMATION: pro can be either present or absent
<220> FEATURE:
<223> OTHER INFORMATION: O-Linked Glycosylation Sequence

<400> SEQUENCE: 1

Xaa Pro Xaa Xaa Xaa Xaa Xaa Xaa Pro
 1               5

<210> SEQ ID NO 2
<211> LENGTH: 8
<212> TYPE: PRT
<213> ORGANISM: Artificial Sequence
<220> FEATURE:
<221> NAME/KEY: VARIANT
<222> LOCATION: 1,2,5
<223> OTHER INFORMATION: Xaa = glu, gln, asp, asn, thr, ser, or any
      uncharged amino acid, and each can be either
      present or absent
<220> FEATURE:
<221> NAME/KEY: VARIANT
<222> LOCATION: 4
<223> OTHER INFORMATION: Xaa = pro, glu, gln, asp, asn, thr, ser, or any
      uncharged amino acid, and can be either present or
      absent
<220> FEATURE:
<221> NAME/KEY: VARIANT
<222> LOCATION: 6,7
<223> OTHER INFORMATION: Xaa = glu, gln, asp, asn, thr, ser, tyr, met,
      or any uncharged amino acid, and each can be either
      present or absent
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 2

Xaa Xaa Thr Xaa Xaa Xaa Xaa Pro
 1               5

<210> SEQ ID NO 3
<211> LENGTH: 10
<212> TYPE: PRT
<213> ORGANISM: Artificial Sequence
<220> FEATURE:
<221> NAME/KEY: VARIANT
<222> LOCATION: 1
<223> OTHER INFORMATION: Met can be either present or absent
<220> FEATURE:
<223> OTHER INFORMATION: O-Linked Glycosylation Sequence

<400> SEQUENCE: 3

Met Val Thr Pro Thr Pro Thr Pro Thr Cys
 1               5                  10

<210> SEQ ID NO 4
<211> LENGTH: 4
<212> TYPE: PRT
<213> ORGANISM: Artificial Sequence
```

```
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 4
<223> OTHER INFORMATION: pro can be either present or absent
<220> FEATURE:
<223> OTHER INFORMATION: O-Linked Glycosylation Sequence

<400> SEQUENCE: 4

Xaa Pro Xaa Pro
 1

<210> SEQ ID NO 5
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 5

Xaa Pro Xaa Glu Ile Pro
 1               5

<210> SEQ ID NO 6
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be present or absent
<220> FEATURE:
<223> OTHER INFORMATION: O-Linked Glycosylation Sequence

<400> SEQUENCE: 6

Xaa Pro Xaa Gln Ala Pro
 1               5

<210> SEQ ID NO 7
<211> LENGTH: 7
```

```
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 7

Xaa Pro Xaa Gln Ala Ser Pro
 1               5

<210> SEQ ID NO 8
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 8

Xaa Pro Xaa Gln Ala Tyr Pro
 1               5

<210> SEQ ID NO 9
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 9

Xaa Pro Xaa Gln Thr Tyr Pro
 1               5
```

```
<210> SEQ ID NO 10
<211> LENGTH: 7
<212> TYPE: PRT
<213> ORGANISM: Artificial Sequence
<220> FEATURE:
<221> NAME/KEY: CONFLICT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 10

Xaa Pro Xaa Ile Asn Thr Pro
 1               5

<210> SEQ ID NO 11
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 11

Xaa Pro Xaa Ile Asn Ala Pro
 1               5

<210> SEQ ID NO 12
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 12

Xaa Pro Xaa Val Gly Ser Pro
 1               5
```

<210> SEQ ID NO 13
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 13

Xaa Pro Xaa Thr Gly Ser Pro
 1               5

<210> SEQ ID NO 14
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 14

Xaa Pro Xaa Thr Val Ser Pro
 1               5

<210> SEQ ID NO 15
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 15

```
Xaa Pro Xaa Thr Val Ala Pro
1               5
```

<210> SEQ ID NO 16
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 16

```
Xaa Pro Xaa Thr Val Leu Pro
1               5
```

<210> SEQ ID NO 17
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 17

```
Xaa Pro Xaa Val Leu Pro
1               5
```

<210> SEQ ID NO 18
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

```
<400> SEQUENCE: 18

Xaa Pro Xaa Val Gly Ser Pro
 1               5

<210> SEQ ID NO 19
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 19

Xaa Pro Xaa Gln Gly Ala Pro
 1               5

<210> SEQ ID NO 20
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 20

Xaa Pro Xaa Gln Gly Ala Met Pro
 1               5

<210> SEQ ID NO 21
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 21
```

```
Xaa Thr Glu Thr Pro
1               5

<210> SEQ ID NO 22
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 22

Xaa Pro Xaa Glu Thr Gln Ile Pro
1               5

<210> SEQ ID NO 23
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 23

Xaa Pro Xaa Thr Thr Gln Pro
1               5

<210> SEQ ID NO 24
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence
```

```
<400> SEQUENCE: 24

Xaa Pro Xaa Thr Leu Tyr Pro
 1               5

<210> SEQ ID NO 25
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 25

Xaa Pro Xaa Thr Leu Tyr Val Pro
 1               5

<210> SEQ ID NO 26
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 26

Xaa Pro Xaa Leu Ser Pro
 1               5

<210> SEQ ID NO 27
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
```

```
<223> OTHER INFORMATION: O-Linked Glycosylation Sequence

<400> SEQUENCE: 27

Xaa Pro Xaa Asp Ala Pro
 1               5

<210> SEQ ID NO 28
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 28

Xaa Pro Xaa Glu Asn Pro
 1               5

<210> SEQ ID NO 29
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 29

Xaa Pro Xaa Ser Gly Pro
 1               5

<210> SEQ ID NO 30
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
```

```
<223> OTHER INFORMATION: pro can be either present or absent
<220> FEATURE:
<223> OTHER INFORMATION: O-Linked Glycosylation Sequence

<400> SEQUENCE: 30

Xaa Pro Xaa Gln Asp Pro
 1               5

<210> SEQ ID NO 31
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 31

Xaa Pro Xaa Ala Ser Pro
 1               5

<210> SEQ ID NO 32
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 32

Xaa Pro Xaa Leu Ser Pro
 1               5

<210> SEQ ID NO 33
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
```

```
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 33

Xaa Pro Xaa Ser Ser Pro
 1               5

<210> SEQ ID NO 34
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 34

Xaa Pro Xaa Ser Met Val Pro
 1               5

<210> SEQ ID NO 35
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 35

Xaa Pro Xaa Ala Thr Gln Pro
 1               5

<210> SEQ ID NO 36
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
```

```
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 36

Xaa Pro Xaa Ser Ala Val Pro
 1               5

<210> SEQ ID NO 37
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 37

Xaa Pro Xaa Ser Val Gly Pro
 1               5

<210> SEQ ID NO 38
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 4
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 38

Xaa Pro Glu Xaa Tyr Pro
 1               5

<210> SEQ ID NO 39
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
```

```
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 39

Xaa Pro Xaa Ser Gly Pro
 1               5

<210> SEQ ID NO 40
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 40

Xaa Pro Xaa Asp Gly Pro
 1               5

<210> SEQ ID NO 41
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 41

Xaa Pro Xaa Thr Gly Ser Pro
 1               5

<210> SEQ ID NO 42
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
```

```
        absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 42

Xaa Pro Xaa Ser Ala Asp Pro
 1               5

<210> SEQ ID NO 43
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 43

Xaa Pro Xaa Ser Gly Ala Pro
 1               5

<210> SEQ ID NO 44
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 44

Xaa Pro Xaa Ile Asn Ala Pro
 1               5

<210> SEQ ID NO 45
<211> LENGTH: 5
<212> TYPE: PRT
<213> ORGANISM: Artificial Sequence
<220> FEATURE:
<221> NAME/KEY: VARIANT
<222> LOCATION: 1
```

```
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 45

Xaa Thr Gly Ser Pro
 1               5

<210> SEQ ID NO 46
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 46

Xaa Thr Gln Ser Pro
 1               5

<210> SEQ ID NO 47
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 47

Xaa Pro Xaa Asn Gln Glu Pro
 1               5

<210> SEQ ID NO 48
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
```

```
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 48

Xaa Pro Xaa Gly Tyr Ala Pro
 1               5

<210> SEQ ID NO 49
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 49

Xaa Met Ile Ala Thr Pro
 1               5

<210> SEQ ID NO 50
<211> LENGTH: 4
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 50

Xaa Pro Thr Pro
 1

<210> SEQ ID NO 51
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 51

Xaa Pro Thr Glu Ile Pro
 1               5
```

```
<210> SEQ ID NO 52
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 52

Xaa Pro Thr Gln Ala Pro
 1               5

<210> SEQ ID NO 53
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 53

Xaa Pro Thr Gln Ala Ser Pro
 1               5

<210> SEQ ID NO 54
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 54

Xaa Pro Thr Gln Ala Tyr Pro
 1               5

<210> SEQ ID NO 55
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
```

```
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 55

Xaa Pro Thr Gln Thr Tyr Pro
 1               5

<210> SEQ ID NO 56
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 56

Xaa Pro Thr Ile Asn Thr Pro
 1               5

<210> SEQ ID NO 57
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 57

Xaa Pro Thr Ile Asn Ala Pro
 1               5

<210> SEQ ID NO 58
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 58

Xaa Pro Thr Val Gly Ser Pro
```

```
                1               5

<210> SEQ ID NO 59
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 59

Xaa Pro Thr Thr Gly Ser Pro
1               5

<210> SEQ ID NO 60
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 60

Xaa Pro Thr Thr Val Ser Pro
1               5

<210> SEQ ID NO 61
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 61

Xaa Pro Thr Thr Val Ala Pro
1               5

<210> SEQ ID NO 62
<211> LENGTH: 7
<212> TYPE: PRT
<213> ORGANISM: Artificial Sequence
<220> FEATURE:
<221> NAME/KEY: VARIANT
<222> LOCATION: 1
```

```
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 62

Xaa Pro Thr Thr Val Leu Pro
  1               5

<210> SEQ ID NO 63
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 63

Xaa Pro Thr Val Leu Pro
  1               5

<210> SEQ ID NO 64
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 64

Xaa Pro Thr Val Gly Ser Pro
  1               5

<210> SEQ ID NO 65
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence
```

```
<400> SEQUENCE: 65

Xaa Pro Thr Gln Gly Ala Pro
 1               5

<210> SEQ ID NO 66
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 66

Xaa Pro Thr Gln Gly Ala Met Pro
 1               5

<210> SEQ ID NO 67
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 67

Xaa Thr Glu Thr Pro
 1               5

<210> SEQ ID NO 68
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 68

Xaa Pro Thr Glu Thr Gln Ile Pro
 1               5

<210> SEQ ID NO 69
<211> LENGTH: 6
<212> TYPE: PRT
<213> ORGANISM: Artificial Sequence
```

```
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 69

Xaa Pro Thr Val Leu Pro
 1               5

<210> SEQ ID NO 70
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 70

Xaa Pro Thr Thr Thr Gln Pro
 1               5

<210> SEQ ID NO 71
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 71

Xaa Pro Thr Thr Leu Tyr Pro
 1               5

<210> SEQ ID NO 72
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 8
<223> OTHER INFORMATION: pro can be either present or absent
```

```
<220> FEATURE:
<223> OTHER INFORMATION: O-Linked Glycosylation Sequence

<400> SEQUENCE: 72

Xaa Pro Thr Thr Leu Tyr Val Pro
 1               5

<210> SEQ ID NO 73
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 73

Xaa Pro Thr Leu Ser Pro
 1               5

<210> SEQ ID NO 74
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 74

Xaa Pro Thr Asp Ala Pro
 1               5

<210> SEQ ID NO 75
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 75

Xaa Pro Thr Glu Asn Pro
 1               5

<210> SEQ ID NO 76
```

```
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 76

Xaa Pro Ser Ser Gly Pro
 1               5

<210> SEQ ID NO 77
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 77

Xaa Pro Thr Gln Asp Pro
 1               5

<210> SEQ ID NO 78
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 78

Xaa Pro Thr Ala Ser Pro
 1               5

<210> SEQ ID NO 79
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
```

```
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 79

Xaa Pro Thr Leu Ser Pro
 1               5

<210> SEQ ID NO 80
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 80

Xaa Pro Thr Ser Ser Pro
 1               5

<210> SEQ ID NO 81
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 81

Xaa Pro Thr Ser Met Val Pro
 1               5

<210> SEQ ID NO 82
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 82

Xaa Pro Thr Ala Thr Gln Pro
 1               5
```

<210> SEQ ID NO 83
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 83

Xaa Pro Thr Ser Ala Val Pro
 1               5

<210> SEQ ID NO 84
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 84

Xaa Pro Thr Ser Val Gly Pro
 1               5

<210> SEQ ID NO 85
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 85

Xaa Pro Glu Thr Tyr Pro
 1               5

<210> SEQ ID NO 86
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any uncharged amino acid, and can be either present or
          absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 86

Xaa Pro Ser Asp Gly Pro
 1               5

<210> SEQ ID NO 87
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 87

Xaa Pro Ser Thr Gly Ser Pro
 1               5

<210> SEQ ID NO 88
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 88

Xaa Pro Thr Ser Ala Asp Pro
 1               5

<210> SEQ ID NO 89
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 89

```
Xaa Pro Thr Ser Gly Ala Pro
 1               5

<210> SEQ ID NO 90
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 90

Xaa Pro Thr Ile Asn Ala Pro
 1               5

<210> SEQ ID NO 91
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 91

Xaa Thr Gly Ser Pro
 1               5

<210> SEQ ID NO 92
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 92

Xaa Thr Gln Ser Pro
 1               5

<210> SEQ ID NO 93
<211> LENGTH: 7
<212> TYPE: PRT
<213> ORGANISM: Artificial Sequence
<220> FEATURE:
```

```
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 93

Xaa Pro Thr Asn Gln Glu Pro
 1               5

<210> SEQ ID NO 94
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 94

Xaa Pro Thr Gly Tyr Ala Pro
 1               5

<210> SEQ ID NO 95
<211> LENGTH: 4
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 95

Xaa Pro Xaa Pro
 1

<210> SEQ ID NO 96
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
```

```
<223> OTHER INFORMATION: pro can be either present or absent
<220> FEATURE:
<223> OTHER INFORMATION: O-Linked Glycosylation Sequence

<400> SEQUENCE: 96

Xaa Pro Xaa Gln Ala Pro
 1               5

<210> SEQ ID NO 97
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 97

Xaa Pro Xaa Glu Ile Pro
 1               5

<210> SEQ ID NO 98
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 98

Xaa Pro Xaa Ile Asn Thr Pro
 1               5

<210> SEQ ID NO 99
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 99
```

```
Xaa Pro Xaa Thr Val Ser
1               5

<210> SEQ ID NO 100
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 100

Xaa Pro Xaa Thr Val Ser Pro
1               5

<210> SEQ ID NO 101
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 101

Xaa Pro Xaa Gln Gly Ala
1               5

<210> SEQ ID NO 102
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 102

Xaa Pro Xaa Gln Gly Ala Pro
1               5

<210> SEQ ID NO 103
<211> LENGTH: 8
<212> TYPE: PRT
<213> ORGANISM: Artificial Sequence
<220> FEATURE:
<221> NAME/KEY: VARIANT
```

```
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 103

Xaa Pro Xaa Gln Gly Ala Met Pro
 1               5

<210> SEQ ID NO 104
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 104

Xaa Pro Xaa Val Leu
 1               5

<210> SEQ ID NO 105
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 105

Xaa Pro Xaa Val Leu Pro
 1               5

<210> SEQ ID NO 106
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
```

```
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 106

Xaa Pro Xaa Thr Val Leu
 1               5

<210> SEQ ID NO 107
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 107

Xaa Pro Xaa Thr Val Leu Pro
 1               5

<210> SEQ ID NO 108
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 108

Xaa Pro Xaa Thr Leu Tyr Val Pro
 1               5

<210> SEQ ID NO 109
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 109
```

```
Xaa Pro Xaa Thr Leu Tyr Val Pro
 1               5

<210> SEQ ID NO 110
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 110

Xaa Pro Xaa Asp Ala Pro
 1               5

<210> SEQ ID NO 111
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 111

Xaa Pro Xaa Gln Asp Pro
 1               5

<210> SEQ ID NO 112
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence
```

```
<400> SEQUENCE: 112

Xaa Pro Xaa Ala Ser Pro
 1               5

<210> SEQ ID NO 113
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 113

Xaa Pro Xaa Ser Ala Val
 1               5

<210> SEQ ID NO 114
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 114

Xaa Pro Xaa Ser Ala Val Pro
 1               5

<210> SEQ ID NO 115
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 115

Xaa Thr Glu Thr Pro
 1               5

<210> SEQ ID NO 116
<211> LENGTH: 4
<212> TYPE: PRT
<213> ORGANISM: Artificial Sequence
<220> FEATURE:
```

```
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<223> OTHER INFORMATION: O-Linked Glycosylation Sequence

<400> SEQUENCE: 116

Xaa Pro Thr Pro
 1

<210> SEQ ID NO 117
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 117

Xaa Pro Thr Gln Ala Pro
 1               5

<210> SEQ ID NO 118
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 118

Xaa Pro Thr Glu Ile Pro
 1               5

<210> SEQ ID NO 119
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 7
<223> OTHER INFORMATION: pro can be either present or absent
<220> FEATURE:
<223> OTHER INFORMATION: O-Linked Glycosylation Sequence

<400> SEQUENCE: 119

Xaa Pro Thr Ile Asn Thr Pro
 1               5
```

```
<210> SEQ ID NO 120
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<223> OTHER INFORMATION: O-Linked Glycosylation Sequence

<400> SEQUENCE: 120

Xaa Pro Thr Thr Val Ser
 1               5

<210> SEQ ID NO 121
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 121

Xaa Pro Thr Thr Val Ser Pro
 1               5

<210> SEQ ID NO 122
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<223> OTHER INFORMATION: O-Linked Glycosylation Sequence

<400> SEQUENCE: 122

Xaa Pro Thr Gln Gly Ala
 1               5

<210> SEQ ID NO 123
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 123

Xaa Pro Thr Gln Gly Ala Pro
 1               5

<210> SEQ ID NO 124
<211> LENGTH: 8
<212> TYPE: PRT
<213> ORGANISM: Artificial Sequence
<220> FEATURE:
```

```
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 124

Xaa Pro Thr Gln Gly Ala Met Pro
 1               5

<210> SEQ ID NO 125
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<223> OTHER INFORMATION: O-Linked Glycosylation Sequence

<400> SEQUENCE: 125

Xaa Thr Glu Thr Pro
 1               5

<210> SEQ ID NO 126
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 126

Xaa Pro Thr Val Leu
 1               5

<210> SEQ ID NO 127
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 127

Xaa Pro Thr Val Leu Pro
 1               5

<210> SEQ ID NO 128
<211> LENGTH: 6
<212> TYPE: PRT
```

```
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<223> OTHER INFORMATION: O-Linked Glycosylation Sequence

<400> SEQUENCE: 128

Xaa Pro Thr Thr Val Leu
 1               5

<210> SEQ ID NO 129
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 129

Xaa Pro Thr Thr Val Leu Pro
 1               5

<210> SEQ ID NO 130
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 130

Xaa Pro Thr Thr Leu Tyr Val Pro
 1               5

<210> SEQ ID NO 131
<211> LENGTH: 8
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 8
<223> OTHER INFORMATION: pro can be either present or absent
<220> FEATURE:
<223> OTHER INFORMATION: O-Linked Glycosylation Sequence

<400> SEQUENCE: 131

Xaa Pro Thr Thr Leu Tyr Val Pro
 1               5

<210> SEQ ID NO 132
<211> LENGTH: 6
<212> TYPE: PRT
<213> ORGANISM: Artificial Sequence
```

```
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 132

Xaa Pro Thr Asp Ala Pro
 1               5

<210> SEQ ID NO 133
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 133

Xaa Pro Thr Gln Asp Pro
 1               5

<210> SEQ ID NO 134
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 6
<223> OTHER INFORMATION: pro can be either present or absent
<220> FEATURE:
<223> OTHER INFORMATION: O-Linked Glycosylation Sequence

<400> SEQUENCE: 134

Xaa Pro Thr Ala Ser Pro
 1               5

<210> SEQ ID NO 135
<211> LENGTH: 6
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<223> OTHER INFORMATION: O-Linked Glycosylation Sequence

<400> SEQUENCE: 135
```

```
Xaa Pro Thr Ser Ala Val
 1               5

<210> SEQ ID NO 136
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<223> OTHER INFORMATION: O-Linked Glycosylation Sequence

<400> SEQUENCE: 136

Xaa Pro Thr Ser Ala Val Pro
 1               5

<210> SEQ ID NO 137
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 5
<223> OTHER INFORMATION: pro can be either present or absent
<220> FEATURE:
<223> OTHER INFORMATION: O-Linked Glycosylation Sequence

<400> SEQUENCE: 137

Xaa Thr Glu Thr Pro
 1               5

<210> SEQ ID NO 138
<211> LENGTH: 3
<212> TYPE: PRT
<213> ORGANISM: Artificial Sequence
<220> FEATURE:
<223> OTHER INFORMATION: O-Linked Glycosylation Sequence

<400> SEQUENCE: 138

Pro Thr Pro
 1

<210> SEQ ID NO 139
<211> LENGTH: 4
<212> TYPE: PRT
<213> ORGANISM: Artificial Sequence
<220> FEATURE:
<223> OTHER INFORMATION: O-Linked Glycosylation Sequence

<400> SEQUENCE: 139

Pro Thr Glu Ile
 1

<210> SEQ ID NO 140
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 140
```

Pro Thr Glu Ile Pro
1               5

<210> SEQ ID NO 141
<211> LENGTH: 4
<212> TYPE: PRT
<213> ORGANISM: Artificial Sequence
<220> FEATURE:
<223> OTHER INFORMATION: O-Linked Glycosylation Sequence

<400> SEQUENCE: 141

Pro Thr Gln Ala
1

<210> SEQ ID NO 142
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 142

Pro Thr Gln Ala Pro
1               5

<210> SEQ ID NO 143
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 143

Pro Thr Ile Asn Thr
1               5

<210> SEQ ID NO 144
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 144

Pro Thr Ile Asn Thr Pro
1               5

<210> SEQ ID NO 145
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 145

Pro Thr Thr Val Ser
1               5

<210> SEQ ID NO 146
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 146

```
Pro Thr Val Leu
 1               5

<210> SEQ ID NO 147
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 147

Pro Thr Gln Gly Ala Met
 1               5

<210> SEQ ID NO 148
<211> LENGTH: 7
<212> TYPE: PRT
<213> ORGANISM: Artificial Sequence
<220> FEATURE:
<223> OTHER INFORMATION: O-Linked Glycosylation Sequence

<400> SEQUENCE: 148

Pro Thr Gln Gly Ala Met Pro
 1               5

<210> SEQ ID NO 149
<211> LENGTH: 4
<212> TYPE: PRT
<213> ORGANISM: Artificial Sequence
<220> FEATURE:
<223> OTHER INFORMATION: O-Linked Glycosylation Sequence

<400> SEQUENCE: 149

Thr Glu Thr Pro
 1

<210> SEQ ID NO 150
<211> LENGTH: 4
<212> TYPE: PRT
<213> ORGANISM: Artificial Sequence
<220> FEATURE:
<223> OTHER INFORMATION: O-Linked Glycosylation Sequence

<400> SEQUENCE: 150

Pro Thr Val Leu
 1

<210> SEQ ID NO 151
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 151

Pro Thr Val Leu Pro
 1               5

<210> SEQ ID NO 152
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 152

Pro Thr Leu Ser Pro
```

```
<210> SEQ ID NO 153
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 153

Pro Thr Asp Ala Pro
1               5

<210> SEQ ID NO 154
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 154

Pro Thr Glu Asn Pro
1               5

<210> SEQ ID NO 155
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 155

Pro Thr Gln Asp Pro
1               5

<210> SEQ ID NO 156
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 156

Pro Thr Ala Ser Pro
1               5

<210> SEQ ID NO 157
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 157

Pro Thr Thr Val Ser Pro
1               5

<210> SEQ ID NO 158
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 158

Pro Thr Gln Gly Ala
1               5
```

<210> SEQ ID NO 159
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 159

Pro Thr Ser Ala Val
1               5

<210> SEQ ID NO 160
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 160

Pro Thr Thr Leu Tyr Val
1               5

<210> SEQ ID NO 161
<211> LENGTH: 7
<212> TYPE: PRT
<213> ORGANISM: Artificial Sequence
<220> FEATURE:
<223> OTHER INFORMATION: O-Linked Glycosylation Sequence

<400> SEQUENCE: 161

Pro Thr Thr Leu Tyr Val Pro
1               5

<210> SEQ ID NO 162
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 162

Pro Ser Ser Gly Pro
1               5

<210> SEQ ID NO 163
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 163

Pro Ser Asp Gly Pro
1               5

<210> SEQ ID NO 164
<211> LENGTH: 140
<212> TYPE: PRT
<213> ORGANISM: homo sapiens
<220> FEATURE:
<221> NAME/KEY: VARIANT
<222> LOCATION: (1)...(140)
<223> OTHER INFORMATION: BMP-7 wild-type

<400> SEQUENCE: 164

Met Ser Thr Gly Ser Lys Gln Arg Ser Gln Asn Arg Ser Lys Thr Pro

```
                1               5                  10                  15
Lys Asn Gln Glu Ala Leu Arg Met Ala Asn Val Ala Glu Asn Ser Ser
                20                  25                  30

Ser Asp Gln Arg Gln Ala Cys Lys Lys His Glu Leu Tyr Val Ser Phe
            35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
                115                 120                 125

Tyr Arg Asn Met Val Val Arg Ala Cys Gly Cys His
            130                 135                 140
```

<210> SEQ ID NO 165
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 165

```
Met Pro Thr Pro Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
                20                  25                  30

Ser Asp Gln Arg Gln Ala Cys Lys Lys His Glu Leu Tyr Val Ser Phe
            35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
                115                 120                 125

Tyr Arg Asn Met Val Val Arg Ala Cys Gly Cys His
            130                 135                 140
```

<210> SEQ ID NO 166
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 166

```
Met Ser Pro Thr Pro Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
```

```
                        20                  25                  30

Ser Asp Gln Arg Gln Ala Cys Lys Lys His Glu Leu Tyr Val Ser Phe
            35                  40                  45

Arg Asp Leu Gly Trp Gln Asp Trp Ile Ile Ala Pro Glu Gly Tyr Ala
        50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys His
    130                 135                 140

<210> SEQ ID NO 167
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 167

Met Ser Thr Pro Thr Pro Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys His
    130                 135                 140

<210> SEQ ID NO 168
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 168

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
```

```
                    35                  40                  45
Arg Asp Leu Gly Trp Gln Asp Trp Ile Ile Ala Pro Glu Gly Tyr Ala
 50                  55                  60

Ala Tyr Tyr Cys Glu Gly Glu Cys Ala Phe Pro Leu Asn Ser Tyr Met
 65                  70                  75                  80

Asn Ala Thr Asn His Ala Ile Val Gln Thr Leu Val His Phe Ile Asn
                 85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
                115                 120                 125

Tyr Arg Asn Met Val Val Arg Ala Cys Pro Thr Pro
                130                 135                 140
```

<210> SEQ ID NO 169
<211> LENGTH: 141
<212> TYPE: PRT
<213> ORGANISM: Artificial Sequence
<220> FEATURE:
<223> OTHER INFORMATION: BMP-7 variant including O-linked glycosylation sequence PTP

<400> SEQUENCE: 169

```
Met Pro Thr Pro Gly Ser Lys Gln Arg Ser Gln Asn Arg Ser Lys Thr
 1                   5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
                 35                  40                  45

Phe Arg Asp Leu Gly Trp Gln Asp Trp Ile Ile Ala Pro Glu Gly Tyr
 50                  55                  60

Ala Ala Tyr Tyr Cys Glu Gly Glu Cys Ala Phe Pro Leu Asn Ser Tyr
 65                  70                  75                  80

Met Asn Ala Thr Asn His Ala Ile Val Gln Thr Leu Val His Phe Ile
                 85                  90                  95

Asn Pro Glu Thr Val Pro Lys Pro Cys Cys Ala Pro Thr Gln Leu Asn
                100                 105                 110

Ala Ile Ser Val Leu Tyr Phe Asp Asp Ser Ser Asn Val Ile Leu Lys
                115                 120                 125

Lys Tyr Arg Asn Met Val Val Arg Ala Cys Gly Cys His
                130                 135                 140
```

<210> SEQ ID NO 170
<211> LENGTH: 141
<212> TYPE: PRT
<213> ORGANISM: Artificial Sequence
<220> FEATURE:
<223> OTHER INFORMATION: BMP-7 variant including O-linked glycosylation sequence PTP

<400> SEQUENCE: 170

```
Met Ser Pro Thr Pro Ser Lys Gln Arg Ser Gln Asn Arg Ser Lys Thr
 1                   5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
                 35                  40                  45

Phe Arg Asp Leu Gly Trp Gln Asp Trp Ile Ile Ala Pro Glu Gly Tyr
```

```
                    50                  55                  60

Ala Ala Tyr Tyr Cys Glu Gly Glu Cys Ala Phe Pro Leu Asn Ser Tyr
 65                  70                  75                  80

Met Asn Ala Thr Asn His Ala Ile Val Gln Thr Leu Val His Phe Ile
                    85                  90                  95

Asn Pro Glu Thr Val Pro Lys Pro Cys Cys Ala Pro Thr Gln Leu Asn
                   100                 105                 110

Ala Ile Ser Val Leu Tyr Phe Asp Asp Ser Ser Asn Val Ile Leu Lys
                   115                 120                 125

Lys Tyr Arg Asn Met Val Val Arg Ala Cys Gly Cys His
                   130                 135                 140

<210> SEQ ID NO 171
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 171

Met Ser Thr Pro Thr Pro Lys Gln Arg Ser Gln Asn Arg Ser Lys Thr
  1               5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
                 35                  40                  45

Phe Arg Asp Leu Gly Trp Gln Asp Trp Ile Ile Ala Pro Glu Gly Tyr
 50                  55                  60

Ala Ala Tyr Tyr Cys Glu Gly Glu Cys Ala Phe Pro Leu Asn Ser Tyr
 65                  70                  75                  80

Met Asn Ala Thr Asn His Ala Ile Val Gln Thr Leu Val His Phe Ile
                    85                  90                  95

Asn Pro Glu Thr Val Pro Lys Pro Cys Cys Ala Pro Thr Gln Leu Asn
                   100                 105                 110

Ala Ile Ser Val Leu Tyr Phe Asp Asp Ser Ser Asn Val Ile Leu Lys
                   115                 120                 125

Lys Tyr Arg Asn Met Val Val Arg Ala Cys Gly Cys His
                   130                 135                 140

<210> SEQ ID NO 172
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 172

Met Ser Thr Gly Pro Thr Pro Gln Arg Ser Gln Asn Arg Ser Lys Thr
  1               5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
                 35                  40                  45

Phe Arg Asp Leu Gly Trp Gln Asp Trp Ile Ile Ala Pro Glu Gly Tyr
 50                  55                  60

Ala Ala Tyr Tyr Cys Glu Gly Glu Cys Ala Phe Pro Leu Asn Ser Tyr
```

```
                65                  70                  75                  80
Met Asn Ala Thr Asn His Ala Ile Val Gln Thr Leu Val His Phe Ile
                    85                  90                  95

Asn Pro Glu Thr Val Pro Lys Pro Cys Cys Ala Pro Thr Gln Leu Asn
                100                 105                 110

Ala Ile Ser Val Leu Tyr Phe Asp Asp Ser Ser Asn Val Ile Leu Lys
                115                 120                 125

Lys Tyr Arg Asn Met Val Val Arg Ala Cys Gly Cys His
            130                 135                 140

<210> SEQ ID NO 173
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 173

Met Ser Thr Gly Ser Pro Thr Pro Arg Ser Gln Asn Arg Ser Lys Thr
1               5                   10                  15

Pro Lys Asn Gln Glu Ala Leu Arg Met Ala Asn Val Ala Glu Asn Ser
                20                  25                  30

Ser Ser Asp Gln Arg Gln Ala Cys Lys Lys His Glu Leu Tyr Val Ser
            35                  40                  45

Phe Arg Asp Leu Gly Trp Gln Asp Trp Ile Ile Ala Pro Glu Gly Tyr
    50                  55                  60

Ala Ala Tyr Tyr Cys Glu Gly Glu Cys Ala Phe Pro Leu Asn Ser Tyr
65                  70                  75                  80

Met Asn Ala Thr Asn His Ala Ile Val Gln Thr Leu Val His Phe Ile
                    85                  90                  95

Asn Pro Glu Thr Val Pro Lys Pro Cys Cys Ala Pro Thr Gln Leu Asn
                100                 105                 110

Ala Ile Ser Val Leu Tyr Phe Asp Asp Ser Ser Asn Val Ile Leu Lys
                115                 120                 125

Lys Tyr Arg Asn Met Val Val Arg Ala Cys Gly Cys His
            130                 135                 140

<210> SEQ ID NO 174
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 174

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
                20                  25                  30

Ser Asp Gln Arg Gln Ala Cys Lys Lys His Glu Leu Tyr Val Ser Phe
            35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
```

```
              85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Pro Thr Pro
    130                 135                 140

<210> SEQ ID NO 175
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 175

Met Pro Thr Pro Thr Gly Ser Lys Gln Arg Ser Gln Asn Arg Ser Lys
  1               5                  10                  15

Thr Pro Lys Asn Gln Glu Ala Leu Arg Met Ala Asn Val Ala Glu Asn
             20                  25                  30

Ser Ser Ser Asp Gln Arg Gln Ala Cys Lys Lys His Glu Leu Tyr Val
         35                  40                  45

Ser Phe Arg Asp Leu Gly Trp Gln Asp Trp Ile Ile Ala Pro Glu Gly
 50                  55                  60

Tyr Ala Ala Tyr Tyr Cys Glu Gly Glu Cys Ala Phe Pro Leu Asn Ser
 65                  70                  75                  80

Tyr Met Asn Ala Thr Asn His Ala Ile Val Gln Thr Leu Val His Phe
             85                  90                  95

Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
        115                 120                 125

Lys Lys Tyr Arg Asn Met Val Val Arg Ala Cys Gly Cys His
    130                 135                 140

<210> SEQ ID NO 176
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 176

Met Ser Pro Thr Pro Gly Ser Lys Gln Arg Ser Gln Asn Arg Ser Lys
  1               5                  10                  15

Thr Pro Lys Asn Gln Glu Ala Leu Arg Met Ala Asn Val Ala Glu Asn
             20                  25                  30

Ser Ser Ser Asp Gln Arg Gln Ala Cys Lys Lys His Glu Leu Tyr Val
         35                  40                  45

Ser Phe Arg Asp Leu Gly Trp Gln Asp Trp Ile Ile Ala Pro Glu Gly
 50                  55                  60

Tyr Ala Ala Tyr Tyr Cys Glu Gly Glu Cys Ala Phe Pro Leu Asn Ser
 65                  70                  75                  80

Tyr Met Asn Ala Thr Asn His Ala Ile Val Gln Thr Leu Val His Phe
             85                  90                  95

Ile Asn Pro Glu Thr Val Pro Lys Pro Cys Cys Ala Pro Thr Gln Leu
```

```
                    100                 105                 110

Asn Ala Ile Ser Val Leu Tyr Phe Asp Asp Ser Ser Asn Val Ile Leu
            115                 120                 125

Lys Lys Tyr Arg Asn Met Val Val Arg Ala Cys Gly Cys His
130                 135                 140

<210> SEQ ID NO 177
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 177

Met Ser Thr Pro Thr Pro Ser Lys Gln Arg Ser Gln Asn Arg Ser Lys
1               5                   10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
    50                  55                  60

Tyr Ala Ala Tyr Tyr Cys Glu Gly Glu Cys Ala Phe Pro Leu Asn Ser
65                  70                  75                  80

Tyr Met Asn Ala Thr Asn His Ala Ile Val Gln Thr Leu Val His Phe
                85                  90                  95

Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
            115                 120                 125

Lys Lys Tyr Arg Asn Met Val Val Arg Ala Cys Gly Cys His
130                 135                 140

<210> SEQ ID NO 178
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 178

Met Ser Thr Gly Pro Thr Pro Lys Gln Arg Ser Gln Asn Arg Ser Lys
1               5                   10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
    50                  55                  60

Tyr Ala Ala Tyr Tyr Cys Glu Gly Glu Cys Ala Phe Pro Leu Asn Ser
65                  70                  75                  80

Tyr Met Asn Ala Thr Asn His Ala Ile Val Gln Thr Leu Val His Phe
                85                  90                  95

Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
```

```
            115                 120                 125

Lys Lys Tyr Arg Asn Met Val Val Arg Ala Cys Gly Cys His
    130                 135                 140

<210> SEQ ID NO 179
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 179

Met Ser Thr Gly Ser Pro Thr Pro Gln Arg Ser Gln Asn Arg Ser Lys
 1               5                   10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
    50                  55                  60

Tyr Ala Ala Tyr Tyr Cys Glu Gly Glu Cys Ala Phe Pro Leu Asn Ser
65                  70                  75                  80

Tyr Met Asn Ala Thr Asn His Ala Ile Val Gln Thr Leu Val His Phe
                85                  90                  95

Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
        115                 120                 125

Lys Lys Tyr Arg Asn Met Val Val Arg Ala Cys Gly Cys His
    130                 135                 140

<210> SEQ ID NO 180
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 180

Met Ser Thr Gly Ser Lys Gln Arg Ser Gln Asn Arg Ser Lys Thr Pro
 1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys Pro Thr Pro
```

130                 135                 140

<210> SEQ ID NO 181
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 181

Met Pro Thr Pro Ser Thr Gly Ser Lys Gln Arg Ser Gln Asn Arg Ser
1               5                   10                  15

Lys Thr Pro Lys Asn Gln Glu Ala Leu Arg Met Ala Asn Val Ala Glu
            20                  25                  30

Asn Ser Ser Ser Asp Gln Arg Gln Ala Cys Lys Lys His Glu Leu Tyr
        35                  40                  45

Val Ser Phe Arg Asp Leu Gly Trp Gln Asp Trp Ile Ile Ala Pro Glu
    50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125

Leu Lys Lys Tyr Arg Asn Met Val Val Arg Ala Cys Gly Cys His
    130                 135                 140

<210> SEQ ID NO 182
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 182

Met Ser Pro Thr Pro Thr Gly Ser Lys Gln Arg Ser Gln Asn Arg Ser
1               5                   10                  15

Lys Thr Pro Lys Asn Gln Glu Ala Leu Arg Met Ala Asn Val Ala Glu
            20                  25                  30

Asn Ser Ser Ser Asp Gln Arg Gln Ala Cys Lys Lys His Glu Leu Tyr
        35                  40                  45

Val Ser Phe Arg Asp Leu Gly Trp Gln Asp Trp Ile Ile Ala Pro Glu
    50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125

Leu Lys Lys Tyr Arg Asn Met Val Val Arg Ala Cys Gly Cys His
    130                 135                 140

```
<210> SEQ ID NO 183
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 183

Met Ser Thr Pro Thr Pro Gly Ser Lys Gln Arg Ser Gln Asn Arg Ser
 1               5                  10                  15

Lys Thr Pro Lys Asn Gln Glu Ala Leu Arg Met Ala Asn Val Ala Glu
                20                  25                  30

Asn Ser Ser Ser Asp Gln Arg Gln Ala Cys Lys Lys His Glu Leu Tyr
            35                  40                  45

Val Ser Phe Arg Asp Leu Gly Trp Gln Asp Trp Ile Ile Ala Pro Glu
        50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125

Leu Lys Lys Tyr Arg Asn Met Val Val Arg Ala Cys Gly Cys His
    130                 135                 140

<210> SEQ ID NO 184
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 184

Met Ser Thr Gly Pro Thr Pro Ser Lys Gln Arg Ser Gln Asn Arg Ser
 1               5                  10                  15

Lys Thr Pro Lys Asn Gln Glu Ala Leu Arg Met Ala Asn Val Ala Glu
                20                  25                  30

Asn Ser Ser Ser Asp Gln Arg Gln Ala Cys Lys Lys His Glu Leu Tyr
            35                  40                  45

Val Ser Phe Arg Asp Leu Gly Trp Gln Asp Trp Ile Ile Ala Pro Glu
        50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125

Leu Lys Lys Tyr Arg Asn Met Val Val Arg Ala Cys Gly Cys His
    130                 135                 140

<210> SEQ ID NO 185
<211> LENGTH: 143
<212> TYPE: PRT
```

<213> ORGANISM: Artificial Sequence
<220> FEATURE:
<223> OTHER INFORMATION: BMP-7 variant including O-linked glycosylation sequence PTP

<400> SEQUENCE: 185

```
Met Ser Thr Gly Ser Lys Gln Arg Ser Gln Asn Arg Ser Lys Thr Pro
 1               5                  10                  15
Lys Asn Gln Glu Ala Leu Arg Met Ala Asn Val Ala Glu Asn Ser Ser
            20                  25                  30
Ser Asp Gln Arg Gln Ala Cys Lys Lys His Glu Leu Tyr Val Ser Phe
        35                  40                  45
Arg Asp Leu Gly Trp Gln Asp Trp Ile Ile Ala Pro Glu Gly Tyr Ala
    50                  55                  60
Ala Tyr Tyr Cys Glu Gly Glu Cys Ala Phe Pro Leu Asn Ser Tyr Met
65                  70                  75                  80
Asn Ala Thr Asn His Ala Ile Val Gln Thr Leu Val His Phe Ile Asn
                85                  90                  95
Pro Glu Thr Val Pro Lys Pro Cys Cys Ala Pro Thr Gln Leu Asn Ala
            100                 105                 110
Ile Ser Val Leu Tyr Phe Asp Asp Ser Ser Asn Val Ile Leu Lys Lys
        115                 120                 125
Tyr Arg Asn Met Val Val Arg Ala Cys Gly Cys His Pro Thr Pro
    130                 135                 140
```

<210> SEQ ID NO 186
<211> LENGTH: 140
<212> TYPE: PRT
<213> ORGANISM: Artificial Sequence
<220> FEATURE:
<223> OTHER INFORMATION: BMP-7 variant including O-linked glycosylation sequence PTINT

<400> SEQUENCE: 186

```
Met Pro Thr Ile Asn Thr Gln Arg Ser Gln Asn Arg Ser Lys Thr Pro
 1               5                  10                  15
Lys Asn Gln Glu Ala Leu Arg Met Ala Asn Val Ala Glu Asn Ser Ser
            20                  25                  30
Ser Asp Gln Arg Gln Ala Cys Lys Lys His Glu Leu Tyr Val Ser Phe
        35                  40                  45
Arg Asp Leu Gly Trp Gln Asp Trp Ile Ile Ala Pro Glu Gly Tyr Ala
    50                  55                  60
Ala Tyr Tyr Cys Glu Gly Glu Cys Ala Phe Pro Leu Asn Ser Tyr Met
65                  70                  75                  80
Asn Ala Thr Asn His Ala Ile Val Gln Thr Leu Val His Phe Ile Asn
                85                  90                  95
Pro Glu Thr Val Pro Lys Pro Cys Cys Ala Pro Thr Gln Leu Asn Ala
            100                 105                 110
Ile Ser Val Leu Tyr Phe Asp Asp Ser Ser Asn Val Ile Leu Lys Lys
        115                 120                 125
Tyr Arg Asn Met Val Val Arg Ala Cys Gly Cys His
    130                 135                 140
```

<210> SEQ ID NO 187
<211> LENGTH: 140
<212> TYPE: PRT
<213> ORGANISM: Artificial Sequence
<220> FEATURE:
<223> OTHER INFORMATION: BMP-7 variant including O-linked glycosylation sequence PTINT

<400> SEQUENCE: 187

Met Ser Pro Thr Ile Asn Thr Arg Ser Gln Asn Arg Ser Lys Thr Pro
1               5                   10                  15

Lys Asn Gln Glu Ala Leu Arg Met Ala Asn Val Ala Gly Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys His
    130                 135                 140

<210> SEQ ID NO 188
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 188

Met Ser Thr Pro Thr Ile Asn Thr Ser Gln Asn Arg Ser Lys Thr Pro
1               5                   10                  15

Lys Asn Gln Glu Ala Leu Arg Met Ala Asn Val Ala Gly Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys His
    130                 135                 140

<210> SEQ ID NO 189
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 189

```
Met Ser Thr Gly Pro Thr Ile Asn Thr Gln Asn Arg Ser Lys Thr Pro
 1               5                  10                  15

Lys Asn Gln Glu Ala Leu Arg Met Ala Asn Val Ala Glu Asn Ser Ser
                20                  25                  30

Ser Asp Gln Arg Gln Ala Cys Lys Lys His Glu Leu Tyr Val Ser Phe
                35                  40                  45

Arg Asp Leu Gly Trp Gln Asp Trp Ile Ile Ala Pro Glu Gly Tyr Ala
         50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
            115                 120                 125

Tyr Arg Asn Met Val Val Arg Ala Cys Gly Cys His
            130                 135                 140

<210> SEQ ID NO 190
<211> LENGTH: 140
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 190

Met Ser Thr Gly Ser Lys Gln Arg Ser Gln Asn Arg Ser Lys Thr Pro
 1               5                  10                  15

Lys Asn Gln Glu Ala Leu Arg Met Ala Asn Val Ala Glu Asn Ser Ser
                20                  25                  30

Ser Asp Gln Arg Gln Ala Cys Lys Lys His Glu Leu Tyr Val Ser Phe
                35                  40                  45

Arg Asp Leu Gly Trp Gln Asp Trp Ile Ile Ala Pro Glu Gly Tyr Ala
         50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
            115                 120                 125

Tyr Arg Asn Met Val Val Arg Pro Thr Ile Asn Thr
            130                 135                 140

<210> SEQ ID NO 191
<211> LENGTH: 145
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 191

Met Pro Thr Ile Asn Thr Ser Thr Gly Ser Lys Gln Arg Ser Gln Asn
 1               5                  10                  15
```

```
Arg Ser Lys Thr Pro Lys Asn Gln Glu Ala Leu Arg Met Ala Asn Val
         20                  25                  30

Ala Glu Asn Ser Ser Asp Gln Arg Gln Ala Cys Lys Lys His Glu
     35                  40                  45

Leu Tyr Val Ser Phe Arg Asp Leu Gly Trp Gln Asp Trp Ile Ile Ala
 50                  55                  60

Pro Glu Gly Tyr Ala Ala Tyr Tyr Cys Glu Gly Glu Cys Ala Phe Pro
 65                  70                  75                  80

Leu Asn Ser Tyr Met Asn Ala Thr Asn His Ala Ile Val Gln Thr Leu
                 85                  90                  95

Val His Phe Ile Asn Pro Glu Thr Val Pro Lys Pro Cys Cys Ala Pro
                100                 105                 110

Thr Gln Leu Asn Ala Ile Ser Val Leu Tyr Phe Asp Asp Ser Ser Asn
            115                 120                 125

Val Ile Leu Lys Lys Tyr Arg Asn Met Val Val Arg Ala Cys Gly Cys
        130                 135                 140

His
145

<210> SEQ ID NO 192
<211> LENGTH: 144
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 192

Met Pro Thr Ile Asn Thr Thr Gly Ser Lys Gln Arg Ser Gln Asn Arg
 1               5                  10                  15

Ser Lys Thr Pro Lys Asn Gln Glu Ala Leu Arg Met Ala Asn Val Ala
             20                  25                  30

Glu Asn Ser Ser Asp Gln Arg Gln Ala Cys Lys Lys His Glu Leu
         35                  40                  45

Tyr Val Ser Phe Arg Asp Leu Gly Trp Gln Asp Trp Ile Ile Ala Pro
 50                  55                  60

Glu Gly Tyr Ala Ala Tyr Tyr Cys Glu Gly Glu Cys Ala Phe Pro Leu
65                  70                  75                  80

Asn Ser Tyr Met Asn Ala Thr Asn His Ala Ile Val Gln Thr Leu Val
                 85                  90                  95

His Phe Ile Asn Pro Glu Thr Val Pro Lys Pro Cys Cys Ala Pro Thr
                100                 105                 110

Gln Leu Asn Ala Ile Ser Val Leu Tyr Phe Asp Asp Ser Ser Asn Val
            115                 120                 125

Ile Leu Lys Lys Tyr Arg Asn Met Val Val Arg Ala Cys Gly Cys His
        130                 135                 140

<210> SEQ ID NO 193
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 193

Met Pro Thr Ile Asn Thr Gly Ser Lys Gln Arg Ser Gln Asn Arg Ser
 1               5                  10                  15
```

Lys Thr Pro Lys Asn Gln Glu Ala Leu Arg Met Ala Asn Val Ala Glu
            20                  25                  30

Asn Ser Ser Ser Asp Gln Arg Gln Ala Cys Lys Lys His Glu Leu Tyr
        35                  40                  45

Val Ser Phe Arg Asp Leu Gly Trp Gln Asp Trp Ile Ile Ala Pro Glu
 50                  55                  60

Gly Tyr Ala Ala Tyr Tyr Cys Glu Gly Glu Cys Ala Phe Pro Leu Asn
 65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
            115                 120                 125

Leu Lys Lys Tyr Arg Asn Met Val Val Arg Ala Cys Gly Cys His
        130                 135                 140

<210> SEQ ID NO 194
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 194

Met Pro Thr Ile Asn Thr Ser Lys Gln Arg Ser Gln Asn Arg Ser Lys
 1               5                  10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
 50                  55                  60

Tyr Ala Ala Tyr Tyr Cys Glu Gly Glu Cys Ala Phe Pro Leu Asn Ser
 65                  70                  75                  80

Tyr Met Asn Ala Thr Asn His Ala Ile Val Gln Thr Leu Val His Phe
                85                  90                  95

Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
            115                 120                 125

Lys Lys Tyr Arg Asn Met Val Val Arg Ala Cys Gly Cys His
        130                 135                 140

<210> SEQ ID NO 195
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 195

Met Pro Thr Ile Asn Thr Lys Gln Arg Ser Gln Asn Arg Ser Lys Thr
 1               5                  10                  15

Pro Lys Asn Gln Glu Ala Leu Arg Met Ala Asn Val Ala Glu Asn Ser
            20                  25                  30

Ser Ser Asp Gln Arg Gln Ala Cys Lys Lys His Glu Leu Tyr Val Ser
          35                  40                  45

Phe Arg Asp Leu Gly Trp Gln Asp Trp Ile Ile Ala Pro Glu Gly Tyr
    50                  55                  60

Ala Ala Tyr Tyr Cys Glu Gly Glu Cys Ala Phe Pro Leu Asn Ser Tyr
65                  70                  75                  80

Met Asn Ala Thr Asn His Ala Ile Val Gln Thr Leu Val His Phe Ile
              85                  90                  95

Asn Pro Glu Thr Val Pro Lys Pro Cys Cys Ala Pro Thr Gln Leu Asn
              100                 105                 110

Ala Ile Ser Val Leu Tyr Phe Asp Asp Ser Ser Asn Val Ile Leu Lys
              115                 120                 125

Lys Tyr Arg Asn Met Val Val Arg Ala Cys Gly Cys His
        130                 135                 140

<210> SEQ ID NO 196
<211> LENGTH: 145
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 196

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
              20                  25                  30

Ser Asp Gln Arg Gln Ala Cys Lys Lys His Glu Leu Tyr Val Ser Phe
          35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
              85                  90                  95

Pro Glu Thr Val Pro Lys Pro Cys Cys Ala Pro Thr Gln Leu Asn Ala
              100                 105                 110

Ile Ser Val Leu Tyr Phe Asp Asp Ser Ser Asn Val Ile Leu Lys Lys
              115                 120                 125

Tyr Arg Asn Met Val Val Arg Ala Cys Gly Cys His Pro Thr Ile Asn
        130                 135                 140

Thr
145

<210> SEQ ID NO 197
<211> LENGTH: 144
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 197

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
              20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
                115                 120                 125

Tyr Arg Asn Met Val Val Arg Ala Cys Gly Cys Pro Thr Ile Asn Thr
    130                 135                 140

<210> SEQ ID NO 198
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 198

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
                115                 120                 125

Tyr Arg Asn Met Val Val Arg Ala Cys Gly Pro Thr Ile Asn Thr
    130                 135                 140

<210> SEQ ID NO 199
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 199

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

```
Arg Asp Leu Gly Trp Gln Asp Trp Ile Ile Ala Pro Glu Gly Tyr Ala
 50                  55                  60

Ala Tyr Tyr Cys Glu Gly Glu Cys Ala Phe Pro Leu Asn Ser Tyr Met
 65                  70                  75                  80

Asn Ala Thr Asn His Ala Ile Val Gln Thr Leu Val His Phe Ile Asn
                 85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
            115                 120                 125

Tyr Arg Asn Met Val Val Arg Ala Cys Pro Thr Ile Asn Thr
130                 135                 140
```

<210> SEQ ID NO 200
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTINT

<400> SEQUENCE: 200

```
Met Ser Thr Gly Ser Lys Gln Arg Ser Gln Asn Arg Ser Lys Thr Pro
 1                   5                  10                  15

Lys Asn Gln Glu Ala Leu Arg Met Ala Asn Val Ala Glu Asn Ser Ser
                 20                  25                  30

Ser Asp Gln Arg Gln Ala Cys Lys Lys His Glu Leu Tyr Val Ser Phe
             35                  40                  45

Arg Asp Leu Gly Trp Gln Asp Trp Ile Ile Ala Pro Glu Gly Tyr Ala
 50                  55                  60

Ala Tyr Tyr Cys Glu Gly Glu Cys Ala Phe Pro Leu Asn Ser Tyr Met
 65                  70                  75                  80

Asn Ala Thr Asn His Ala Ile Val Gln Thr Leu Val His Phe Ile Asn
                 85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Ser Ser Asn Val Ile Leu Lys Lys
            115                 120                 125

Tyr Arg Asn Met Val Val Arg Ala Pro Thr Ile Asn Thr
130                 135                 140
```

<210> SEQ ID NO 201
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 201

```
Met Pro Thr Thr Val Ser Lys Gln Arg Ser Gln Asn Arg Ser Lys Thr
 1                   5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
             35                  40                  45

Phe Arg Asp Leu Gly Trp Gln Asp Trp Ile Ile Ala Pro Glu Gly Tyr
 50                  55                  60
```

```
Ala Ala Tyr Tyr Cys Glu Gly Glu Cys Ala Phe Pro Leu Asn Ser Tyr
 65                  70                  75                  80

Met Asn Ala Thr Asn His Ala Ile Val Gln Thr Leu Val His Phe Ile
                 85                  90                  95

Asn Pro Glu Thr Val Pro Lys Pro Cys Cys Ala Pro Thr Gln Leu Asn
                100                 105                 110

Ala Ile Ser Val Leu Tyr Phe Asp Asp Ser Ser Asn Val Ile Leu Lys
            115                 120                 125

Lys Tyr Arg Asn Met Val Val Arg Ala Cys Gly Cys His
130                 135                 140

<210> SEQ ID NO 202
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 202

Met Ser Pro Thr Thr Val Ser Gln Arg Ser Gln Asn Arg Ser Lys Thr
  1               5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
             35                  40                  45

Phe Arg Asp Leu Gly Trp Gln Asp Trp Ile Ile Ala Pro Glu Gly Tyr
 50                  55                  60

Ala Ala Tyr Tyr Cys Glu Gly Glu Cys Ala Phe Pro Leu Asn Ser Tyr
 65                  70                  75                  80

Met Asn Ala Thr Asn His Ala Ile Val Gln Thr Leu Val His Phe Ile
                 85                  90                  95

Asn Pro Glu Thr Val Pro Lys Pro Cys Cys Ala Pro Thr Gln Leu Asn
                100                 105                 110

Ala Ile Ser Val Leu Tyr Phe Asp Asp Ser Ser Asn Val Ile Leu Lys
            115                 120                 125

Lys Tyr Arg Asn Met Val Val Arg Ala Cys Gly Cys His
130                 135                 140

<210> SEQ ID NO 203
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 203

Met Ser Thr Pro Thr Thr Val Ser Arg Ser Gln Asn Arg Ser Lys Thr
  1               5                  10                  15

Pro Lys Asn Gln Glu Ala Leu Arg Met Ala Asn Val Ala Glu Asn Ser
                 20                  25                  30

Ser Ser Asp Gln Arg Gln Ala Cys Lys Lys His Glu Leu Tyr Val Ser
             35                  40                  45

Phe Arg Asp Leu Gly Trp Gln Asp Trp Ile Ile Ala Pro Glu Gly Tyr
 50                  55                  60

Ala Ala Tyr Tyr Cys Glu Gly Glu Cys Ala Phe Pro Leu Asn Ser Tyr
 65                  70                  75                  80
```

Met Asn Ala Thr Asn His Ala Ile Val Gln Thr Leu Val His Phe Ile
                85                  90                  95

Asn Pro Glu Thr Val Pro Lys Pro Cys Cys Ala Pro Thr Gln Leu Asn
            100                 105                 110

Ala Ile Ser Val Leu Tyr Phe Asp Asp Ser Ser Asn Val Ile Leu Lys
        115                 120                 125

Lys Tyr Arg Asn Met Val Val Arg Ala Cys Gly Cys His
    130                 135                 140

<210> SEQ ID NO 204
<211> LENGTH: 141
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 204

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Pro Thr Thr Val Ser
    130                 135                 140

<210> SEQ ID NO 205
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 205

Met Pro Thr Thr Val Ser Ser Lys Gln Arg Ser Gln Asn Arg Ser Lys
1               5                   10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
    50                  55                  60

Tyr Ala Ala Tyr Tyr Cys Glu Gly Glu Cys Ala Phe Pro Leu Asn Ser
65                  70                  75                  80

Tyr Met Asn Ala Thr Asn His Ala Ile Val Gln Thr Leu Val His Phe
                85                  90                  95

```
Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
        115                 120                 125

Lys Lys Tyr Arg Asn Met Val Val Arg Ala Cys Gly Cys His
    130                 135                 140

<210> SEQ ID NO 206
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 206

Met Ser Pro Thr Thr Val Ser Lys Gln Arg Ser Gln Asn Arg Ser Lys
1               5                   10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
    50                  55                  60

Tyr Ala Ala Tyr Tyr Cys Glu Gly Glu Cys Ala Phe Pro Leu Asn Ser
65                  70                  75                  80

Tyr Met Asn Ala Thr Asn His Ala Ile Val Gln Thr Leu Val His Phe
                85                  90                  95

Ile Asn Pro Glu Thr Val Pro Lys Pro Cys Cys Ala Pro Thr Gln Leu
            100                 105                 110

Asn Ala Ile Ser Val Leu Tyr Phe Asp Asp Ser Ser Asn Val Ile Leu
        115                 120                 125

Lys Lys Tyr Arg Asn Met Val Val Arg Ala Cys Gly Cys His
    130                 135                 140

<210> SEQ ID NO 207
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 207

Met Ser Thr Pro Thr Val Ser Gln Arg Ser Gln Asn Arg Ser Lys
1               5                   10                  15

Thr Pro Lys Asn Gln Glu Ala Leu Arg Met Ala Asn Val Ala Glu Asn
            20                  25                  30

Ser Ser Ser Asp Gln Arg Gln Ala Cys Lys Lys His Glu Leu Tyr Val
        35                  40                  45

Ser Phe Arg Asp Leu Gly Trp Gln Asp Trp Ile Ile Ala Pro Glu Gly
    50                  55                  60

Tyr Ala Ala Tyr Tyr Cys Glu Gly Glu Cys Ala Phe Pro Leu Asn Ser
65                  70                  75                  80

Tyr Met Asn Ala Thr Asn His Ala Ile Val Gln Thr Leu Val His Phe
                85                  90                  95

Ile Asn Pro Glu Thr Val Pro Lys Pro Cys Cys Ala Pro Thr Gln Leu
            100                 105                 110
```

```
Asn Ala Ile Ser Val Leu Tyr Phe Asp Asp Ser Ser Asn Val Ile Leu
        115                 120                 125

Lys Lys Tyr Arg Asn Met Val Val Arg Ala Cys Gly Cys His
    130                 135                 140

<210> SEQ ID NO 208
<211> LENGTH: 142
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 208

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Pro Thr Thr Val Ser
    130                 135                 140

<210> SEQ ID NO 209
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 209

Met Pro Thr Thr Val Ser Gly Ser Lys Gln Arg Ser Gln Asn Arg Ser
1               5                   10                  15

Lys Thr Pro Lys Asn Gln Glu Ala Leu Arg Met Ala Asn Val Ala Glu
            20                  25                  30

Asn Ser Ser Ser Asp Gln Arg Gln Ala Cys Lys Lys His Glu Leu Tyr
        35                  40                  45

Val Ser Phe Arg Asp Leu Gly Trp Gln Asp Trp Ile Ile Ala Pro Glu
    50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125
```

Leu Lys Lys Tyr Arg Asn Met Val Val Arg Ala Cys Gly Cys His
130                 135                 140

<210> SEQ ID NO 210
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 210

Met Ser Pro Thr Thr Val Ser Ser Lys Gln Arg Ser Gln Asn Arg Ser
1               5                   10                  15

Lys Thr Pro Lys Asn Gln Glu Ala Leu Arg Met Ala Asn Val Ala Glu
            20                  25                  30

Asn Ser Ser Asp Gln Arg Gln Ala Cys Lys Lys His Glu Leu Tyr
        35                  40                  45

Val Ser Phe Arg Asp Leu Gly Trp Gln Asp Trp Ile Ile Ala Pro Glu
50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125

Leu Lys Lys Tyr Arg Asn Met Val Val Arg Ala Cys Gly Cys His
130                 135                 140

<210> SEQ ID NO 211
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 211

Met Ser Thr Pro Thr Thr Val Ser Lys Gln Arg Ser Gln Asn Arg Ser
1               5                   10                  15

Lys Thr Pro Lys Asn Gln Glu Ala Leu Arg Met Ala Asn Val Ala Glu
            20                  25                  30

Asn Ser Ser Asp Gln Arg Gln Ala Cys Lys Lys His Glu Leu Tyr
        35                  40                  45

Val Ser Phe Arg Asp Leu Gly Trp Gln Asp Trp Ile Ile Ala Pro Glu
50                  55                  60

Gly Tyr Ala Ala Tyr Tyr Cys Glu Gly Glu Cys Ala Phe Pro Leu Asn
65                  70                  75                  80

Ser Tyr Met Asn Ala Thr Asn His Ala Ile Val Gln Thr Leu Val His
                85                  90                  95

Phe Ile Asn Pro Glu Thr Val Pro Lys Pro Cys Cys Ala Pro Thr Gln
            100                 105                 110

Leu Asn Ala Ile Ser Val Leu Tyr Phe Asp Asp Ser Ser Asn Val Ile
        115                 120                 125

Leu Lys Lys Tyr Arg Asn Met Val Val Arg Ala Cys Gly Cys His
130                 135                 140

<210> SEQ ID NO 212
<211> LENGTH: 143
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 212

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Pro Thr Thr Val Ser
    130                 135                 140

<210> SEQ ID NO 213
<211> LENGTH: 144
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 213

Met Pro Thr Thr Val Ser Thr Gly Ser Lys Gln Arg Ser Gln Asn Arg
1               5                   10                  15

Ser Lys Thr Pro Lys Asn Gln Glu Ala Leu Arg Met Ala Asn Val Ala
            20                  25                  30

Glu Asn Ser Ser Ser Asp Gln Arg Gln Ala Cys Lys Lys His Glu Leu
        35                  40                  45

Tyr Val Ser Phe Arg Asp Leu Gly Trp Gln Asp Trp Ile Ile Ala Pro
    50                  55                  60

Glu Gly Tyr Ala Ala Tyr Tyr Cys Glu Gly Glu Cys Ala Phe Pro Leu
65                  70                  75                  80

Asn Ser Tyr Met Asn Ala Thr Asn His Ala Ile Val Gln Thr Leu Val
                85                  90                  95

His Phe Ile Asn Pro Glu Thr Val Pro Lys Pro Cys Cys Ala Pro Thr
            100                 105                 110

Gln Leu Asn Ala Ile Ser Val Leu Tyr Phe Asp Asp Ser Ser Asn Val
        115                 120                 125

Ile Leu Lys Lys Tyr Arg Asn Met Val Val Arg Ala Cys Gly Cys His
    130                 135                 140

<210> SEQ ID NO 214

<211> LENGTH: 144
<212> TYPE: PRT
<213> ORGANISM: Artificial Sequence
<220> FEATURE:
<223> OTHER INFORMATION: BMP-7 variant including O-linked glycosylation
       sequence PTTVS

<400> SEQUENCE: 214

Met Ser Pro Thr Thr Val Ser Gly Ser Lys Gln Arg Ser Gln Asn Arg
 1               5                  10                  15

Ser Lys Thr Pro Lys Asn Gln Glu Ala Leu Arg Met Ala Asn Val Ala
            20                  25                  30

Glu Asn Ser Ser Ser Asp Gln Arg Gln Ala Cys Lys Lys His Glu Leu
        35                  40                  45

Tyr Val Ser Phe Arg Asp Leu Gly Trp Gln Asp Trp Ile Ile Ala Pro
 50                  55                  60

Glu Gly Tyr Ala Ala Tyr Tyr Cys Glu Gly Glu Cys Ala Phe Pro Leu
 65                  70                  75                  80

Asn Ser Tyr Met Asn Ala Thr Asn His Ala Ile Val Gln Thr Leu Val
                85                  90                  95

His Phe Ile Asn Pro Glu Thr Val Pro Lys Pro Cys Cys Ala Pro Thr
            100                 105                 110

Gln Leu Asn Ala Ile Ser Val Leu Tyr Phe Asp Asp Ser Ser Asn Val
        115                 120                 125

Ile Leu Lys Lys Tyr Arg Asn Met Val Val Arg Ala Cys Gly Cys His
130                 135                 140

<210> SEQ ID NO 215
<211> LENGTH: 144
<212> TYPE: PRT
<213> ORGANISM: Artificial Sequence
<220> FEATURE:
<223> OTHER INFORMATION: BMP-7 variant including O-linked glycosylation
       sequence PTTVS

<400> SEQUENCE: 215

Met Ser Thr Pro Thr Thr Val Ser Ser Lys Gln Arg Ser Gln Asn Arg
 1               5                  10                  15

Ser Lys Thr Pro Lys Asn Gln Glu Ala Leu Arg Met Ala Asn Val Ala
            20                  25                  30

Glu Asn Ser Ser Ser Asp Gln Arg Gln Ala Cys Lys Lys His Glu Leu
        35                  40                  45

Tyr Val Ser Phe Arg Asp Leu Gly Trp Gln Asp Trp Ile Ile Ala Pro
 50                  55                  60

Glu Gly Tyr Ala Ala Tyr Tyr Cys Glu Gly Glu Cys Ala Phe Pro Leu
 65                  70                  75                  80

Asn Ser Tyr Met Asn Ala Thr Asn His Ala Ile Val Gln Thr Leu Val
                85                  90                  95

His Phe Ile Asn Pro Glu Thr Val Pro Lys Pro Cys Cys Ala Pro Thr
            100                 105                 110

Gln Leu Asn Ala Ile Ser Val Leu Tyr Phe Asp Asp Ser Ser Asn Val
        115                 120                 125

Ile Leu Lys Lys Tyr Arg Asn Met Val Val Arg Ala Cys Gly Cys His
130                 135                 140

<210> SEQ ID NO 216
<211> LENGTH: 144
<212> TYPE: PRT
<213> ORGANISM: Artificial Sequence

```
<220> FEATURE:
<223> OTHER INFORMATION: BMP-7 variant including O-linked glycosylation
      sequence PTTVS

<400> SEQUENCE: 216

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys Pro Thr Thr Val Ser
130                 135                 140

<210> SEQ ID NO 217
<211> LENGTH: 145
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 217

Met Pro Thr Thr Val Ser Ser Thr Gly Ser Lys Gln Arg Ser Gln Asn
1               5                   10                  15

Arg Ser Lys Thr Pro Lys Asn Gln Glu Ala Leu Arg Met Ala Asn Val
            20                  25                  30

Ala Glu Asn Ser Ser Ser Asp Gln Arg Gln Ala Cys Lys Lys His Glu
        35                  40                  45

Leu Tyr Val Ser Phe Arg Asp Leu Gly Trp Gln Asp Trp Ile Ile Ala
    50                  55                  60

Pro Glu Gly Tyr Ala Ala Tyr Tyr Cys Glu Gly Glu Cys Ala Phe Pro
65                  70                  75                  80

Leu Asn Ser Tyr Met Asn Ala Thr Asn His Ala Ile Val Gln Thr Leu
                85                  90                  95

Val His Phe Ile Asn Pro Glu Thr Val Pro Lys Pro Cys Cys Ala Pro
            100                 105                 110

Thr Gln Leu Asn Ala Ile Ser Val Leu Tyr Phe Asp Asp Ser Ser Asn
        115                 120                 125

Val Ile Leu Lys Lys Tyr Arg Asn Met Val Val Arg Ala Cys Gly Cys
    130                 135                 140

His
145

<210> SEQ ID NO 218
<211> LENGTH: 145
<212> TYPE: PRT
<213> ORGANISM: Artificial Sequence
```

<220> FEATURE:
<223> OTHER INFORMATION: BMP-7 variant including O-linked glycosylation
      sequence PTTVS

<400> SEQUENCE: 218

Met Ser Pro Thr Thr Val Ser Thr Gly Ser Lys Gln Arg Ser Gln Asn
 1               5                  10                  15

Arg Ser Lys Thr Pro Lys Asn Gln Glu Ala Leu Arg Met Ala Asn Val
             20                  25                  30

Ala Glu Asn Ser Ser Asp Gln Arg Gln Ala Cys Lys Lys His Glu
         35                  40                  45

Leu Tyr Val Ser Phe Arg Asp Leu Gly Trp Gln Asp Trp Ile Ile Ala
 50                  55                  60

Pro Glu Gly Tyr Ala Ala Tyr Tyr Cys Glu Gly Glu Cys Ala Phe Pro
65                   70                  75                  80

Leu Asn Ser Tyr Met Asn Ala Thr Asn His Ala Ile Val Gln Thr Leu
                 85                  90                  95

Val His Phe Ile Asn Pro Glu Thr Val Pro Lys Pro Cys Cys Ala Pro
             100                 105                 110

Thr Gln Leu Asn Ala Ile Ser Val Leu Tyr Phe Asp Asp Ser Ser Asn
         115                 120                 125

Val Ile Leu Lys Lys Tyr Arg Asn Met Val Val Arg Ala Cys Gly Cys
    130                 135                 140

His
145

<210> SEQ ID NO 219
<211> LENGTH: 145
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 219

Met Ser Thr Pro Thr Thr Val Ser Gly Ser Lys Gln Arg Ser Gln Asn
 1               5                  10                  15

Arg Ser Lys Thr Pro Lys Asn Gln Glu Ala Leu Arg Met Ala Asn Val
             20                  25                  30

Ala Glu Asn Ser Ser Asp Gln Arg Gln Ala Cys Lys Lys His Glu
         35                  40                  45

Leu Tyr Val Ser Phe Arg Asp Leu Gly Trp Gln Asp Trp Ile Ile Ala
 50                  55                  60

Pro Glu Gly Tyr Ala Ala Tyr Tyr Cys Glu Gly Glu Cys Ala Phe Pro
65                   70                  75                  80

Leu Asn Ser Tyr Met Asn Ala Thr Asn His Ala Ile Val Gln Thr Leu
                 85                  90                  95

Val His Phe Ile Asn Pro Glu Thr Val Pro Lys Pro Cys Cys Ala Pro
             100                 105                 110

Thr Gln Leu Asn Ala Ile Ser Val Leu Tyr Phe Asp Asp Ser Ser Asn
         115                 120                 125

Val Ile Leu Lys Lys Tyr Arg Asn Met Val Val Arg Ala Cys Gly Cys
    130                 135                 140

His
145

<210> SEQ ID NO 220

```
<211> LENGTH: 145
<212> TYPE: PRT
<213> ORGANISM: Artificial Sequence
<220> FEATURE:
<223> OTHER INFORMATION: BMP-7 variant including O-linked glycosylation
      sequence PTTVS

<400> SEQUENCE: 220

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Glu Gly Tyr Ala
    50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys His Pro Thr Thr Val
    130                 135                 140

Ser
145

<210> SEQ ID NO 221
<211> LENGTH: 31
<212> TYPE: PRT
<213> ORGANISM: homo sapiens
<220> FEATURE:
<221> NAME/KEY: VARIANT
<222> LOCATION: (73)...(103)
<223> OTHER INFORMATION: BMP-7 wild-type partial sequence

<400> SEQUENCE: 221

Ala Phe Pro Leu Asn Ser Tyr Met Asn Ala Thr Asn His Ala Ile Val
1               5                   10                  15

Gln Thr Leu Val His Phe Ile Asn Pro Glu Thr Val Pro Lys Pro
            20                  25                  30

<210> SEQ ID NO 222
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 222

Pro Thr Pro Leu Asn Ser Tyr Met Asn Ala Thr Asn His Ala Ile Val
1               5                   10                  15

Gln Thr Leu Val His Phe Ile Asn Pro Glu Thr Val Pro Lys Pro
            20                  25                  30

<210> SEQ ID NO 223
<211> LENGTH: 31
<212> TYPE: PRT
<213> ORGANISM: Artificial Sequence
```

```
<220> FEATURE:
<223> OTHER INFORMATION: BMP-7 variant including O-linked glycosylation
      sequence PTP

<400> SEQUENCE: 223

Ala Pro Thr Pro Asn Ser Tyr Met Asn Ala Thr Asn His Ala Ile Val
1               5                   10                  15

Gln Thr Leu Val His Phe Ile Asn Pro Glu Thr Val Pro Lys Pro
            20                  25                  30

<210> SEQ ID NO 224
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 224

Ala Phe Pro Thr Pro Ser Tyr Met Asn Ala Thr Asn His Ala Ile Val
1               5                   10                  15

Gln Thr Leu Val His Phe Ile Asn Pro Glu Thr Val Pro Lys Pro
            20                  25                  30

<210> SEQ ID NO 225
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 225

Ala Phe Pro Pro Thr Pro Tyr Met Asn Ala Thr Asn His Ala Ile Val
1               5                   10                  15

Gln Thr Leu Val His Phe Ile Asn Pro Glu Thr Val Pro Lys Pro
            20                  25                  30

<210> SEQ ID NO 226
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 226

Ala Phe Pro Leu Pro Thr Pro Met Asn Ala Thr Asn His Ala Ile Val
1               5                   10                  15

Gln Thr Leu Val His Phe Ile Asn Pro Glu Thr Val Pro Lys Pro
            20                  25                  30

<210> SEQ ID NO 227
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 227

Ala Phe Pro Leu Asn Pro Thr Pro Asn Ala Thr Asn His Ala Ile Val
1               5                   10                  15

Gln Thr Leu Val His Phe Ile Asn Pro Glu Thr Val Pro Lys Pro
            20                  25                  30
```

<210> SEQ ID NO 228
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 228

Ala Phe Pro Leu Asn Ser Pro Thr Pro Ala Thr Asn His Ala Ile Val
 1               5                  10                  15

Gln Thr Leu Val His Phe Ile Asn Pro Glu Thr Val Pro Lys Pro
            20                  25                  30

<210> SEQ ID NO 229
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 229

Ala Phe Pro Leu Asn Ser Tyr Pro Thr Pro Thr Asn His Ala Ile Val
 1               5                  10                  15

Gln Thr Leu Val His Phe Ile Asn Pro Glu Thr Val Pro Lys Pro
            20                  25                  30

<210> SEQ ID NO 230
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 230

Ala Phe Pro Leu Asn Ser Tyr Met Asn Ala Thr Asn His Ala Ile Val
 1               5                  10                  15

Gln Thr Leu Val His Phe Pro Thr Pro Glu Thr Val Pro Lys Pro
            20                  25                  30

<210> SEQ ID NO 231
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 231

Ala Phe Pro Leu Asn Ser Tyr Met Asn Ala Thr Asn His Ala Ile Val
 1               5                  10                  15

Gln Thr Leu Val His Phe Ile Pro Thr Pro Thr Val Pro Lys Pro
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 232

```
Ala Phe Pro Leu Asn Ser Tyr Met Asn Ala Thr Asn His Ala Ile Val
1               5                   10                  15

Gln Thr Leu Val His Phe Ile Asn Pro Thr Pro Val Pro Lys Pro
            20                  25                  30
```

<210> SEQ ID NO 233
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 233

```
Ala Phe Pro Leu Asn Ser Tyr Met Asn Ala Thr Asn His Ala Ile Val
1               5                   10                  15

Gln Thr Leu Val His Phe Ile Asn Pro Pro Thr Pro Pro Lys Pro
            20                  25                  30
```

<210> SEQ ID NO 234
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 234

```
Ala Phe Pro Leu Asn Ser Tyr Met Asn Ala Thr Asn His Ala Ile Val
1               5                   10                  15

Gln Thr Leu Val His Phe Ile Asn Pro Glu Pro Thr Pro Lys Pro
            20                  25                  30
```

<210> SEQ ID NO 235
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 235

```
Ala Phe Pro Leu Asn Ser Tyr Met Asn Ala Thr Asn His Ala Ile Val
1               5                   10                  15

Gln Thr Leu Val His Phe Ile Asn Pro Glu Thr Pro Thr Pro Pro
            20                  25                  30
```

<210> SEQ ID NO 236
<211> LENGTH: 31
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 236

```
Ala Phe Pro Leu Asn Ser Tyr Met Asn Ala Thr Asn His Ala Ile Val
1               5                   10                  15

Gln Thr Leu Val His Phe Ile Asn Pro Glu Thr Val Pro Thr Pro
            20                  25                  30
```

<210> SEQ ID NO 237
<211> LENGTH: 32
<212> TYPE: PRT

<213> ORGANISM: Artificial Sequence
<220> FEATURE:
<223> OTHER INFORMATION: BMP-7 variant including O-linked glycosylation
      sequence PTP

<400> SEQUENCE: 237

Pro Thr Pro Pro Leu Asn Ser Tyr Met Asn Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 238

Ala Pro Thr Pro Leu Asn Ser Tyr Met Asn Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 239

Ala Phe Pro Thr Pro Asn Ser Tyr Met Asn Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 240

Ala Phe Pro Pro Thr Pro Ser Tyr Met Asn Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 241

Ala Phe Pro Leu Pro Thr Pro Tyr Met Asn Ala Thr Asn His Ala Ile
1               5                   10                  15

Val Gln Thr Leu Val His Phe Ile Asn Pro Glu Thr Val Pro Lys Pro

<210> SEQ ID NO 242
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 242

Ala Phe Pro Leu Asn Pro Thr Pro Met Asn Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 243
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 243

Ala Phe Pro Leu Asn Ser Pro Thr Pro Asn Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 244

Ala Phe Pro Leu Asn Ser Tyr Pro Thr Pro Ala Thr Asn His Ala Ile
1               5                   10                  15

Val Gln Thr Leu Val His Phe Ile Asn Pro Glu Thr Val Pro Lys Pro
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 245

Ala Phe Pro Leu Asn Ser Tyr Met Pro Thr Pro Thr Asn His Ala Ile
1               5                   10                  15

Val Gln Thr Leu Val His Phe Ile Asn Pro Glu Thr Val Pro Lys Pro
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

```
<400> SEQUENCE: 246

Ala Phe Pro Leu Asn Ser Tyr Met Asn Ala Thr Asn His Ala Ile Val
1               5                   10                  15

Gln Thr Leu Val His Phe Pro Thr Pro Pro Glu Thr Val Pro Lys Pro
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 247

Ala Phe Pro Leu Asn Ser Tyr Met Asn Ala Thr Asn His Ala Ile Val
1               5                   10                  15

Gln Thr Leu Val His Phe Ile Pro Thr Pro Glu Thr Val Pro Lys Pro
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 248

Ala Phe Pro Leu Asn Ser Tyr Met Asn Ala Thr Asn His Ala Ile Val
1               5                   10                  15

Gln Thr Leu Val His Phe Ile Asn Pro Thr Pro Thr Val Pro Lys Pro
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 249

Ala Phe Pro Leu Asn Ser Tyr Met Asn Ala Thr Asn His Ala Ile Val
1               5                   10                  15

Gln Thr Leu Val His Phe Ile Asn Pro Pro Thr Pro Val Pro Lys Pro
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 250

Ala Phe Pro Leu Asn Ser Tyr Met Asn Ala Thr Asn His Ala Ile Val
1               5                   10                  15

Gln Thr Leu Val His Phe Ile Asn Pro Glu Pro Thr Pro Pro Lys Pro
            20                  25                  30

<210> SEQ ID NO 251
<211> LENGTH: 32
```

-continued

```
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 251

Ala Phe Pro Leu Asn Ser Tyr Met Asn Ala Thr Asn His Ala Ile Val
1               5                   10                  15

Gln Thr Leu Val His Phe Ile Asn Pro Glu Thr Pro Thr Pro Lys Pro
            20                  25                  30

<210> SEQ ID NO 252
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 252

Ala Phe Pro Leu Asn Ser Tyr Met Asn Ala Thr Asn His Ala Ile Val
1               5                   10                  15

Gln Thr Leu Val His Phe Ile Asn Pro Glu Thr Val Pro Thr Pro Pro
            20                  25                  30

<210> SEQ ID NO 253
<211> LENGTH: 32
<212> TYPE: PRT
<213> ORGANISM: Artificial Sequence
<220> FEATURE:
<223> OTHER INFORMATION: BMP-7 variant including O-linked glycosylation
      sequence PTP

<400> SEQUENCE: 253

Ala Phe Pro Leu Asn Ser Tyr Met Asn Ala Thr Asn His Ala Ile Val
1               5                   10                  15

Gln Thr Leu Val His Phe Ile Asn Pro Glu Thr Val Pro Pro Thr Pro
            20                  25                  30

<210> SEQ ID NO 254
<211> LENGTH: 2351
<212> TYPE: PRT
<213> ORGANISM: homo sapiens
<220> FEATURE:
<221> NAME/KEY: VARIANT
<222> LOCATION: (1)...(2351)
<223> OTHER INFORMATION: Factor XIII, wild-type

<400> SEQUENCE: 254

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
```

-continued

```
               100                 105                 110
His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525
```

```
Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
930                 935                 940
```

-continued

```
Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                1000                1005

Leu Phe Lys Val Ser Ile Ser Leu Leu Lys Thr Asn Lys Thr Ser Asn
    1010                1015                1020

Asn Ser Ala Thr Asn Arg Lys Thr His Ile Asp Gly Pro Ser Leu Leu
1025                1030                1035                1040

Ile Glu Asn Ser Pro Ser Val Trp Gln Asn Ile Leu Glu Ser Asp Thr
                1045                1050                1055

Glu Phe Lys Lys Val Thr Pro Leu Ile His Asp Arg Met Leu Met Asp
                1060                1065                1070

Lys Asn Ala Thr Ala Leu Arg Leu Asn His Met Ser Asn Lys Thr Thr
            1075                1080                1085

Ser Ser Lys Asn Met Glu Met Val Gln Gln Lys Lys Glu Gly Pro Ile
    1090                1095                1100

Pro Pro Asp Ala Gln Asn Pro Asp Met Ser Phe Phe Lys Met Leu Phe
1105                1110                1115                1120

Leu Pro Glu Ser Ala Arg Trp Ile Gln Arg Thr His Gly Lys Asn Ser
                1125                1130                1135

Leu Asn Ser Gly Gln Gly Pro Ser Pro Lys Gln Leu Val Ser Leu Gly
            1140                1145                1150

Pro Glu Lys Ser Val Glu Gly Gln Asn Phe Leu Ser Glu Lys Asn Lys
        1155                1160                1165

Val Val Val Gly Lys Gly Glu Phe Thr Lys Asp Val Gly Leu Lys Glu
    1170                1175                1180

Met Val Phe Pro Ser Ser Arg Asn Leu Phe Leu Thr Asn Leu Asp Asn
1185                1190                1195                1200

Leu His Glu Asn Asn Thr His Asn Gln Glu Lys Lys Ile Gln Glu Glu
                1205                1210                1215

Ile Glu Lys Lys Glu Thr Leu Ile Gln Glu Asn Val Val Leu Pro Gln
        1220                1225                1230

Ile His Thr Val Thr Gly Thr Lys Asn Phe Met Lys Asn Leu Phe Leu
    1235                1240                1245

Leu Ser Thr Arg Gln Asn Val Glu Gly Ser Tyr Glu Gly Ala Tyr Ala
    1250                1255                1260

Pro Val Leu Gln Asp Phe Arg Ser Leu Asn Asp Ser Thr Asn Arg Thr
1265                1270                1275                1280

Lys Lys His Thr Ala His Phe Ser Lys Lys Gly Glu Glu Asn Leu
        1285                1290                1295

Glu Gly Leu Gly Asn Gln Thr Lys Gln Ile Val Glu Lys Tyr Ala Cys
        1300                1305                1310

Thr Thr Arg Ile Ser Pro Asn Thr Ser Gln Gln Asn Phe Val Thr Gln
        1315                1320                1325

Arg Ser Lys Arg Ala Leu Lys Gln Phe Arg Leu Pro Leu Glu Glu Thr
    1330                1335                1340

Glu Leu Glu Lys Arg Ile Ile Val Asp Asp Thr Ser Thr Gln Trp Ser
1345                1350                1355                1360

Lys Asn Met Lys His Leu Thr Pro Ser Thr Leu Thr Gln Ile Asp Tyr
```

-continued

```
                1365                1370                1375

Asn Glu Lys Glu Lys Gly Ala Ile Thr Gln Ser Pro Leu Ser Asp Cys
            1380                1385                1390

Leu Thr Arg Ser His Ser Ile Pro Gln Ala Asn Arg Ser Pro Leu Pro
        1395                1400                1405

Ile Ala Lys Val Ser Ser Phe Pro Ser Ile Arg Pro Ile Tyr Leu Thr
    1410                1415                1420

Arg Val Leu Phe Gln Asp Asn Ser Ser His Leu Pro Ala Ala Ser Tyr
1425                1430                1435                1440

Arg Lys Lys Asp Ser Gly Val Gln Glu Ser Ser His Phe Leu Gln Gly
            1445                1450                1455

Ala Lys Lys Asn Asn Leu Ser Leu Ala Ile Leu Thr Leu Glu Met Thr
        1460                1465                1470

Gly Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp Leu
1490                1495                1500

Pro Lys Thr Ser Gly Lys Val Glu Leu Leu Pro Lys Val His Ile Tyr
1505                1510                1515                1520

Gln Lys Asp Leu Phe Pro Thr Glu Thr Ser Asn Gly Ser Pro Gly His
            1525                1530                1535

Leu Asp Leu Val Glu Gly Ser Leu Leu Gln Gly Thr Glu Gly Ala Ile
        1540                1545                1550

Lys Trp Asn Glu Ala Asn Arg Pro Gly Lys Val Pro Phe Leu Arg Val
    1555                1560                1565

Ala Thr Glu Ser Ser Ala Lys Thr Pro Ser Lys Leu Leu Asp Pro Leu
1570                1575                1580

Ala Trp Asp Asn His Tyr Gly Thr Gln Ile Pro Lys Glu Glu Trp Lys
1585                1590                1595                1600

Ser Gln Glu Lys Ser Pro Glu Lys Thr Ala Phe Lys Lys Lys Asp Thr
            1605                1610                1615

Ile Leu Ser Leu Asn Ala Cys Glu Ser Asn His Ala Ile Ala Ala Ile
        1620                1625                1630

Asn Glu Gly Gln Asn Lys Pro Glu Ile Glu Val Thr Trp Ala Lys Gln
    1635                1640                1645

Gly Arg Thr Glu Arg Leu Cys Ser Gln Asn Pro Pro Val Leu Lys Arg
1650                1655                1660

His Gln Arg Glu Ile Thr Arg Thr Thr Leu Gln Ser Asp Gln Glu Glu
1665                1670                1675                1680

Ile Asp Tyr Asp Asp Thr Ile Ser Val Glu Met Lys Lys Glu Asp Phe
            1685                1690                1695

Asp Ile Tyr Asp Glu Asp Glu Asn Gln Ser Pro Arg Ser Phe Gln Lys
        1700                1705                1710

Lys Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser Gly
1730                1735                1740

Ser Val Pro Gln Phe Lys Lys Val Val Phe Gln Glu Phe Thr Asp Gly
1745                1750                1755                1760

Ser Phe Thr Gln Pro Leu Tyr Arg Gly Glu Leu Asn Glu His Leu Gly
            1765                1770                1775

Leu Leu Gly Pro Tyr Ile Arg Ala Glu Val Glu Asp Asn Ile Met Val
        1780                1785                1790
```

```
Thr Phe Arg Asn Gln Ala Ser Arg Pro Tyr Ser Phe Tyr Ser Ser Leu
        1795                1800                1805

Ile Ser Tyr Glu Glu Asp Gln Arg Gln Gly Ala Glu Pro Arg Lys Asn
    1810                1815                1820

Phe Val Lys Pro Asn Glu Thr Lys Thr Tyr Phe Trp Lys Val Gln His
1825                1830                1835                1840

His Met Ala Pro Thr Lys Asp Glu Phe Asp Cys Lys Ala Trp Ala Tyr
            1845                1850                1855

Phe Ser Asp Val Asp Leu Glu Lys Asp Val His Ser Gly Leu Ile Gly
        1860                1865                1870

Pro Leu Leu Val Cys His Thr Asn Thr Leu Asn Pro Ala His Gly Arg
        1875                1880                1885

Gln Val Thr Val Gln Glu Phe Ala Leu Phe Phe Thr Ile Phe Asp Glu
        1890                1895                1900

Thr Lys Ser Trp Tyr Phe Thr Glu Asn Met Glu Arg Asn Cys Arg Ala
1905                1910                1915                1920

Pro Cys Asn Ile Gln Met Glu Asp Pro Thr Phe Lys Glu Asn Tyr Arg
            1925                1930                1935

Phe His Ala Ile Asn Gly Tyr Ile Met Asp Thr Leu Pro Gly Leu Val
        1940                1945                1950

Met Ala Gln Asp Gln Arg Ile Arg Trp Tyr Leu Leu Ser Met Gly Ser
        1955                1960                1965

Asn Glu Asn Ile His Ser Ile His Phe Ser Gly His Val Phe Thr Val
        1970                1975                1980

Arg Lys Lys Glu Glu Tyr Lys Met Ala Leu Tyr Asn Leu Tyr Pro Gly
1985                1990                1995                2000

Val Phe Glu Thr Val Glu Met Leu Pro Ser Lys Ala Gly Ile Trp Arg
            2005                2010                2015

Val Glu Cys Leu Ile Gly Glu His Leu His Ala Gly Met Ser Thr Leu
        2020                2025                2030

Phe Leu Val Tyr Ser Asn Lys Cys Gln Thr Pro Leu Gly Met Ala Ser
        2035                2040                2045

Gly His Ile Arg Asp Phe Gln Ile Thr Ala Ser Gly Gln Tyr Gly Gln
        2050                2055                2060

Trp Ala Pro Lys Leu Ala Arg Leu His Tyr Ser Gly Ser Ile Asn Ala
2065                2070                2075                2080

Trp Ser Thr Lys Glu Pro Phe Ser Trp Ile Lys Val Asp Leu Leu Ala
            2085                2090                2095

Pro Met Ile Ile His Gly Ile Lys Thr Gln Gly Ala Arg Gln Lys Phe
        2100                2105                2110

Ser Ser Leu Tyr Ile Ser Gln Phe Ile Ile Met Tyr Ser Leu Asp Gly
        2115                2120                2125

Lys Lys Trp Gln Thr Tyr Arg Gly Asn Ser Thr Gly Thr Leu Met Val
    2130                2135                2140

Phe Phe Gly Asn Val Asp Ser Ser Gly Ile Lys His Asn Ile Phe Asn
2145                2150                2155                2160

Pro Pro Ile Ile Ala Arg Tyr Ile Arg Leu His Pro Thr His Tyr Ser
            2165                2170                2175

Ile Arg Ser Thr Leu Arg Met Glu Leu Met Gly Cys Asp Leu Asn Ser
        2180                2185                2190

Cys Ser Met Pro Leu Gly Met Glu Ser Lys Ala Ile Ser Asp Ala Gln
        2195                2200                2205
```

```
Ile Thr Ala Ser Ser Tyr Phe Thr Asn Met Phe Ala Thr Trp Ser Pro
    2210                2215                2220

Ser Lys Ala Arg Leu His Leu Gln Gly Arg Ser Asn Ala Trp Arg Pro
2225                2230                2235                2240

Gln Val Asn Asn Pro Lys Glu Trp Leu Gln Val Asp Phe Gln Lys Thr
                2245                2250                2255

Met Lys Val Thr Gly Val Thr Gln Gly Val Lys Ser Leu Leu Thr
            2260                2265                2270

Ser Met Tyr Val Lys Glu Phe Leu Ile Ser Ser Gln Asp Gly His
        2275                2280                2285

Gln Trp Thr Leu Phe Phe Gln Asn Gly Lys Val Lys Val Phe Gln Gly
    2290                2295                2300

Asn Gln Asp Ser Phe Thr Pro Val Val Asn Ser Leu Asp Pro Pro Leu
2305                2310                2315                2320

Leu Thr Arg Tyr Leu Arg Ile His Pro Gln Ser Trp Val His Gln Ile
                2325                2330                2335

Ala Leu Arg Met Glu Val Leu Gly Cys Glu Ala Gln Asp Leu Tyr
            2340                2345                2350

<210> SEQ ID NO 255
<211> LENGTH: 1438
<212> TYPE: PRT
<213> ORGANISM: Artificial Sequence
<220> FEATURE:
<223> OTHER INFORMATION: Factor VIII, B-domain deleted

<400> SEQUENCE: 255

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220
```

-continued

```
Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
```

-continued

```
                645                 650                 655
Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
            770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
            930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
            995                 1000                1005

Cys Asn Ile Gln Met Glu Asp Pro Thr Phe Lys Glu Asn Tyr Arg Phe
            1010                1015                1020

His Ala Ile Asn Gly Tyr Ile Met Asp Thr Leu Pro Gly Leu Val Met
1025                1030                1035                1040

Ala Gln Asp Gln Arg Ile Arg Trp Tyr Leu Leu Ser Met Gly Ser Asn
                1045                1050                1055

Glu Asn Ile His Ser Ile His Phe Ser Gly His Val Phe Thr Val Arg
            1060                1065                1070
```

Lys Lys Glu Glu Tyr Lys Met Ala Leu Tyr Asn Leu Tyr Pro Gly Val
        1075                1080                1085

Phe Glu Thr Val Glu Met Leu Pro Ser Lys Ala Gly Ile Trp Arg Val
        1090                1095                1100

Glu Cys Leu Ile Gly Glu His Leu His Ala Gly Met Ser Thr Leu Phe
1105                1110                1115                1120

Leu Val Tyr Ser Asn Lys Cys Gln Thr Pro Leu Gly Met Ala Ser Gly
            1125                1130                1135

His Ile Arg Asp Phe Gln Ile Thr Ala Ser Gly Gln Tyr Gly Gln Trp
        1140                1145                1150

Ala Pro Lys Leu Ala Arg Leu His Tyr Ser Gly Ser Ile Asn Ala Trp
        1155                1160                1165

Ser Thr Lys Glu Pro Phe Ser Trp Ile Lys Val Asp Leu Leu Ala Pro
        1170                1175                1180

Met Ile Ile His Gly Ile Lys Thr Gln Gly Ala Arg Gln Lys Phe Ser
1185                1190                1195                1200

Ser Leu Tyr Ile Ser Gln Phe Ile Ile Met Tyr Ser Leu Asp Gly Lys
            1205                1210                1215

Lys Trp Gln Thr Tyr Arg Gly Asn Ser Thr Gly Thr Leu Met Val Phe
        1220                1225                1230

Phe Gly Asn Val Asp Ser Ser Gly Ile Lys His Asn Ile Phe Asn Pro
        1235                1240                1245

Pro Ile Ile Ala Arg Tyr Ile Arg Leu His Pro Thr His Tyr Ser Ile
        1250                1255                1260

Arg Ser Thr Leu Arg Met Glu Leu Met Gly Cys Asp Leu Asn Ser Cys
1265                1270                1275                1280

Ser Met Pro Leu Gly Met Glu Ser Lys Ala Ile Ser Asp Ala Gln Ile
            1285                1290                1295

Thr Ala Ser Ser Tyr Phe Thr Asn Met Phe Ala Thr Trp Ser Pro Ser
        1300                1305                1310

Lys Ala Arg Leu His Leu Gln Gly Arg Ser Asn Ala Trp Arg Pro Gln
        1315                1320                1325

Val Asn Asn Pro Lys Glu Trp Leu Gln Val Asp Phe Gln Lys Thr Met
        1330                1335                1340

Lys Val Thr Gly Val Thr Thr Gln Gly Val Lys Ser Leu Leu Thr Ser
1345                1350                1355                1360

Met Tyr Val Lys Glu Phe Leu Ile Ser Ser Ser Gln Asp Gly His Gln
            1365                1370                1375

Trp Thr Leu Phe Phe Gln Asn Gly Lys Val Lys Val Phe Gln Gly Asn
        1380                1385                1390

Gln Asp Ser Phe Thr Pro Val Val Asn Ser Leu Asp Pro Pro Leu Leu
        1395                1400                1405

Thr Arg Tyr Leu Arg Ile His Pro Gln Ser Trp Val His Gln Ile Ala
        1410                1415                1420

Leu Arg Met Glu Val Leu Gly Cys Glu Ala Gln Asp Leu Tyr
1425                1430                1435

<210> SEQ ID NO 256
<211> LENGTH: 571
<212> TYPE: PRT
<213> ORGANISM: homo sapiens
<220> FEATURE:
<221> NAME/KEY: VARIANT
<222> LOCATION: (1)...(571)
<223> OTHER INFORMATION: human GalNAc-T2

<400> SEQUENCE: 256

```
Met Arg Arg Arg Ser Arg Met Leu Leu Cys Phe Ala Phe Leu Trp Val
 1               5                  10                  15
Leu Gly Ile Ala Tyr Tyr Met Tyr Ser Gly Gly Ser Ala Leu Ala
             20                  25                  30
Gly Gly Ala Gly Gly Ala Gly Arg Lys Glu Asp Trp Asn Glu Ile
             35                  40                  45
Asp Pro Ile Lys Lys Asp Leu His His Ser Asn Gly Glu Glu Lys
 50                  55                  60
Ala Gln Ser Met Glu Thr Leu Pro Pro Gly Lys Val Arg Trp Pro Asp
 65                  70                  75                  80
Phe Asn Gln Glu Ala Tyr Val Gly Gly Thr Met Val Arg Ser Gly Gln
                     85                  90                  95
Asp Pro Tyr Ala Arg Asn Lys Phe Asn Gln Val Glu Ser Asp Lys Leu
                    100                 105                 110
Arg Met Asp Arg Ala Ile Pro Asp Thr Arg His Asp Gln Cys Gln Arg
                    115                 120                 125
Lys Gln Trp Arg Val Asp Leu Pro Ala Thr Ser Val Ile Thr Phe
130                 135                 140
His Asn Glu Ala Arg Ser Ala Leu Leu Arg Thr Val Val Ser Val Leu
145                 150                 155                 160
Lys Lys Ser Pro Pro His Leu Ile Lys Glu Ile Ile Leu Val Asp Asp
                    165                 170                 175
Tyr Ser Asn Asp Pro Glu Asp Gly Ala Leu Leu Gly Lys Ile Glu Lys
                    180                 185                 190
Val Arg Val Leu Arg Asn Asp Arg Arg Glu Gly Leu Met Arg Ser Arg
                    195                 200                 205
Val Arg Gly Ala Asp Ala Ala Gln Ala Lys Val Leu Thr Phe Leu Asp
210                 215                 220
Ser His Cys Glu Cys Asn Glu His Trp Leu Glu Pro Leu Leu Glu Arg
225                 230                 235                 240
Val Ala Glu Asp Arg Thr Arg Val Val Ser Pro Ile Ile Asp Val Ile
                    245                 250                 255
Asn Met Asp Asn Phe Gln Tyr Val Gly Ala Ser Ala Asp Leu Lys Gly
                    260                 265                 270
Gly Phe Asp Trp Asn Leu Val Phe Lys Trp Asp Tyr Met Thr Pro Glu
                    275                 280                 285
Gln Arg Arg Ser Arg Gln Gly Asn Pro Val Ala Pro Ile Lys Thr Pro
                    290                 295                 300
Met Ile Ala Gly Gly Leu Phe Val Met Asp Lys Phe Tyr Phe Glu Glu
305                 310                 315                 320
Leu Gly Lys Tyr Asp Met Met Met Asp Val Trp Gly Gly Glu Asn Leu
                    325                 330                 335
Glu Ile Ser Phe Arg Val Trp Gln Cys Gly Gly Ser Leu Glu Ile Ile
                    340                 345                 350
Pro Cys Ser Arg Val Gly His Val Phe Arg Lys Gln His Pro Tyr Thr
                    355                 360                 365
Phe Pro Gly Gly Ser Gly Thr Val Phe Ala Arg Asn Thr Arg Arg Ala
                    370                 375                 380
Ala Glu Val Trp Met Asp Glu Tyr Lys Asn Phe Tyr Tyr Ala Ala Val
385                 390                 395                 400
Pro Ser Ala Arg Asn Val Pro Tyr Gly Asn Ile Gln Ser Arg Leu Glu
```

```
                    405                 410                 415
Leu Arg Lys Lys Leu Ser Cys Lys Pro Phe Lys Trp Tyr Leu Glu Asn
                420                 425                 430

Val Tyr Pro Glu Leu Arg Val Pro Asp His Gln Asp Ile Ala Phe Gly
                435                 440                 445

Ala Leu Gln Gln Gly Thr Asn Cys Leu Asp Thr Leu Gly His Phe Ala
                450                 455                 460

Asp Gly Val Val Gly Val Tyr Glu Cys His Asn Ala Gly Gly Asn Gln
465                 470                 475                 480

Glu Trp Ala Leu Thr Lys Glu Lys Ser Val Lys His Met Asp Leu Cys
                485                 490                 495

Leu Thr Val Val Asp Arg Ala Pro Gly Ser Leu Ile Lys Leu Gln Gly
                500                 505                 510

Cys Arg Glu Asn Asp Ser Arg Gln Lys Trp Glu Gln Ile Glu Gly Asn
                515                 520                 525

Ser Lys Leu Arg His Val Gly Ser Asn Leu Cys Leu Asp Ser Arg Thr
                530                 535                 540

Ala Lys Ser Gly Gly Leu Ser Val Glu Val Cys Gly Pro Ala Leu Ser
545                 550                 555                 560

Gln Gln Trp Lys Phe Thr Leu Asn Leu Gln Gln
                565                 570

<210> SEQ ID NO 257
<211> LENGTH: 520
<212> TYPE: PRT
<213> ORGANISM: Artificial Sequence
<220> FEATURE:
<223> OTHER INFORMATION: human GalNAc-T2
      amino acid residues 1-51 deleted

<400> SEQUENCE: 257

Lys Lys Lys Asp Leu His His Ser Asn Gly Glu Glu Lys Ala Gln Ser
1               5                   10                  15

Met Glu Thr Leu Pro Pro Gly Lys Val Arg Trp Pro Asp Phe Asn Gln
                20                  25                  30

Glu Ala Tyr Val Gly Gly Thr Met Val Arg Ser Gly Gln Asp Pro Tyr
                35                  40                  45

Ala Arg Asn Lys Phe Asn Gln Val Glu Ser Asp Lys Leu Arg Met Asp
50                  55                  60

Arg Ala Ile Pro Asp Thr Arg His Asp Gln Cys Gln Arg Lys Gln Trp
65                  70                  75                  80

Arg Val Asp Leu Pro Ala Thr Ser Val Val Ile Thr Phe His Asn Glu
                85                  90                  95

Ala Arg Ser Ala Leu Leu Arg Thr Val Val Ser Val Leu Lys Lys Ser
                100                 105                 110

Pro Pro His Leu Ile Lys Glu Ile Ile Leu Val Asp Asp Tyr Ser Asn
                115                 120                 125

Asp Pro Glu Asp Gly Ala Leu Leu Gly Lys Ile Glu Lys Val Arg Val
                130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
                180                 185                 190
```

```
Asp Arg Thr Arg Val Val Ser Pro Ile Ile Asp Val Ile Asn Met Asp
            195                 200                 205

Asn Phe Gln Tyr Val Gly Ala Ser Ala Asp Leu Lys Gly Gly Phe Asp
210                 215                 220

Trp Asn Leu Val Phe Lys Trp Asp Tyr Met Thr Pro Glu Gln Arg Arg
225                 230                 235                 240

Ser Arg Gln Gly Asn Pro Val Ala Pro Ile Lys Thr Pro Met Ile Ala
            245                 250                 255

Gly Gly Leu Phe Val Met Asp Lys Phe Tyr Phe Glu Glu Leu Gly Lys
            260                 265                 270

Tyr Asp Met Met Met Asp Val Trp Gly Gly Glu Asn Leu Glu Ile Ser
            275                 280                 285

Phe Arg Val Trp Gln Cys Gly Gly Ser Leu Glu Ile Ile Pro Cys Ser
290                 295                 300

Arg Val Gly His Val Phe Arg Lys Gln His Pro Tyr Thr Phe Pro Gly
305                 310                 315                 320

Gly Ser Gly Thr Val Phe Ala Arg Asn Thr Arg Arg Ala Ala Glu Val
            325                 330                 335

Trp Met Asp Glu Tyr Lys Asn Phe Tyr Tyr Ala Ala Val Pro Ser Ala
            340                 345                 350

Arg Asn Val Pro Tyr Gly Asn Ile Gln Ser Arg Leu Glu Leu Arg Lys
            355                 360                 365

Lys Leu Ser Cys Lys Pro Phe Lys Trp Tyr Leu Glu Asn Val Tyr Pro
            370                 375                 380

Glu Leu Arg Val Pro Asp His Gln Asp Ile Ala Phe Gly Ala Leu Gln
385                 390                 395                 400

Gln Gly Thr Asn Cys Leu Asp Thr Leu Gly His Phe Ala Asp Gly Val
            405                 410                 415

Val Gly Val Tyr Glu Cys His Asn Ala Gly Asn Gln Glu Trp Ala
            420                 425                 430

Leu Thr Lys Glu Lys Ser Val Lys His Met Asp Leu Cys Leu Thr Val
            435                 440                 445

Val Asp Arg Ala Pro Gly Ser Leu Ile Lys Leu Gln Gly Cys Arg Glu
450                 455                 460

Asn Asp Ser Arg Gln Lys Trp Glu Gln Ile Glu Gly Asn Ser Lys Leu
465                 470                 475                 480

Arg His Val Gly Ser Asn Leu Cys Leu Asp Ser Arg Thr Ala Lys Ser
            485                 490                 495

Gly Gly Leu Ser Val Glu Val Cys Gly Pro Ala Leu Ser Gln Gln Trp
            500                 505                 510

Lys Phe Thr Leu Asn Leu Gln Gln
            515                 520

<210> SEQ ID NO 258
<211> LENGTH: 393
<212> TYPE: PRT
<213> ORGANISM: Artificial Sequence
<220> FEATURE:
<223> OTHER INFORMATION: human GalNAc-T2
      amino acid residues 1-51 and 445-571 deleted

<400> SEQUENCE: 258

Lys Lys Lys Asp Leu His His Ser Asn Gly Glu Glu Lys Ala Gln Ser
1               5                   10                  15

Met Glu Thr Leu Pro Pro Gly Lys Val Arg Trp Pro Asp Phe Asn Gln
            20                  25                  30
```

Glu Ala Tyr Val Gly Gly Thr Met Val Arg Ser Gly Gln Asp Pro Tyr
                35                  40                  45

Ala Arg Asn Lys Phe Asn Gln Val Glu Ser Asp Lys Leu Arg Met Asp
    50                  55                  60

Arg Ala Ile Pro Asp Thr Arg His Asp Gln Cys Gln Arg Lys Gln Trp
65                  70                  75                  80

Arg Val Asp Leu Pro Ala Thr Ser Val Ile Thr Phe His Asn Glu
                85                  90                  95

Ala Arg Ser Ala Leu Leu Arg Thr Val Val Ser Val Leu Lys Lys Ser
                100                 105                 110

Pro Pro His Leu Ile Lys Glu Ile Ile Leu Val Asp Asp Tyr Ser Asn
        115                 120                 125

Asp Pro Glu Asp Gly Ala Leu Leu Gly Lys Ile Glu Lys Val Arg Val
        130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
                180                 185                 190

Asp Arg Thr Arg Val Val Ser Pro Ile Ile Asp Val Ile Asn Met Asp
                195                 200                 205

Asn Phe Gln Tyr Val Gly Ala Ser Ala Asp Leu Lys Gly Gly Phe Asp
    210                 215                 220

Trp Asn Leu Val Phe Lys Trp Asp Tyr Met Thr Pro Glu Gln Arg Arg
225                 230                 235                 240

Ser Arg Gln Gly Asn Pro Val Ala Pro Ile Lys Thr Pro Met Ile Ala
                245                 250                 255

Gly Gly Leu Phe Val Met Asp Lys Phe Tyr Phe Glu Glu Leu Gly Lys
                260                 265                 270

Tyr Asp Met Met Met Asp Val Trp Gly Gly Glu Asn Leu Glu Ile Ser
                275                 280                 285

Phe Arg Val Trp Gln Cys Gly Gly Ser Leu Glu Ile Ile Pro Cys Ser
                290                 295                 300

Arg Val Gly His Val Phe Arg Lys Gln His Pro Tyr Thr Phe Pro Gly
305                 310                 315                 320

Gly Ser Gly Thr Val Phe Ala Arg Asn Thr Arg Arg Ala Ala Glu Val
                325                 330                 335

Trp Met Asp Glu Tyr Lys Asn Phe Tyr Tyr Ala Ala Val Pro Ser Ala
                340                 345                 350

Arg Asn Val Pro Tyr Gly Asn Ile Gln Ser Arg Leu Glu Leu Arg Lys
                355                 360                 365

Lys Leu Ser Cys Lys Pro Phe Lys Trp Tyr Leu Glu Asn Val Tyr Pro
370                 375                 380

Glu Leu Arg Val Pro Asp His Gln Asp
385                 390

<210> SEQ ID NO 259
<211> LENGTH: 522
<212> TYPE: PRT
<213> ORGANISM: Artificial Sequence
<220> FEATURE:
<223> OTHER INFORMATION: human GalNAc-T2
    amino acid residues 1-51 deleted (alternate form)

-continued

```
<400> SEQUENCE: 259

Met Ser Lys Lys Lys Asp Leu His His Ser Asn Gly Glu Glu Lys Ala
1               5                   10                  15

Gln Ser Met Glu Thr Leu Pro Pro Gly Lys Val Arg Trp Pro Asp Phe
            20                  25                  30

Asn Gln Glu Ala Tyr Val Gly Gly Thr Met Val Arg Ser Gly Gln Asp
        35                  40                  45

Pro Tyr Ala Arg Asn Lys Phe Asn Gln Val Glu Ser Asp Lys Leu Arg
    50                  55                  60

Met Asp Arg Ala Ile Pro Asp Thr Arg His Asp Gln Cys Gln Arg Lys
65                  70                  75                  80

Gln Trp Arg Val Asp Leu Pro Ala Thr Ser Val Val Ile Thr Phe His
                85                  90                  95

Asn Glu Ala Arg Ser Ala Leu Leu Arg Thr Val Val Ser Val Leu Lys
            100                 105                 110

Lys Ser Pro Pro His Leu Ile Lys Glu Ile Ile Leu Val Asp Asp Tyr
        115                 120                 125

Ser Asn Asp Pro Glu Asp Gly Ala Leu Leu Gly Lys Ile Glu Lys Val
    130                 135                 140

Arg Val Leu Arg Asn Asp Arg Arg Glu Gly Leu Met Arg Ser Arg Val
145                 150                 155                 160

Arg Gly Ala Asp Ala Ala Gln Ala Lys Val Leu Thr Phe Leu Asp Ser
                165                 170                 175

His Cys Glu Cys Asn Glu His Trp Leu Glu Pro Leu Leu Glu Arg Val
            180                 185                 190

Ala Glu Asp Arg Thr Arg Val Val Ser Pro Ile Ile Asp Val Ile Asn
        195                 200                 205

Met Asp Asn Phe Gln Tyr Val Gly Ala Ser Ala Asp Leu Lys Gly Gly
    210                 215                 220

Phe Asp Trp Asn Leu Val Phe Lys Trp Asp Tyr Met Thr Pro Glu Gln
225                 230                 235                 240

Arg Arg Ser Arg Gln Gly Asn Pro Val Ala Pro Ile Lys Thr Pro Met
                245                 250                 255

Ile Ala Gly Gly Leu Phe Val Met Asp Lys Phe Tyr Phe Glu Glu Leu
            260                 265                 270

Gly Lys Tyr Asp Met Met Met Asp Val Trp Gly Gly Glu Asn Leu Glu
        275                 280                 285

Ile Ser Phe Arg Val Trp Gln Cys Gly Gly Ser Leu Glu Ile Ile Pro
    290                 295                 300

Cys Ser Arg Val Gly His Val Phe Arg Lys Gln His Pro Tyr Thr Phe
305                 310                 315                 320

Pro Gly Gly Ser Gly Thr Val Phe Ala Arg Asn Thr Arg Arg Ala Ala
                325                 330                 335

Glu Val Trp Met Asp Glu Tyr Lys Asn Phe Tyr Tyr Ala Ala Val Pro
            340                 345                 350

Ser Ala Arg Asn Val Pro Tyr Gly Asn Ile Gln Ser Arg Leu Glu Leu
        355                 360                 365

Arg Lys Lys Leu Ser Cys Lys Pro Phe Lys Trp Tyr Leu Glu Asn Val
    370                 375                 380

Tyr Pro Glu Leu Arg Val Pro Asp His Gln Asp Ile Ala Phe Gly Ala
385                 390                 395                 400

Leu Gln Gln Gly Thr Asn Cys Leu Asp Thr Leu Gly His Phe Ala Asp
                405                 410                 415
```

```
Gly Val Val Gly Val Tyr Glu Cys His Asn Ala Gly Gly Asn Gln Glu
            420                 425                 430

Trp Ala Leu Thr Lys Glu Lys Ser Val Lys His Met Asp Leu Cys Leu
            435                 440                 445

Thr Val Val Asp Arg Ala Pro Gly Ser Leu Ile Lys Leu Gln Gly Cys
450                 455                 460

Arg Glu Asn Asp Ser Arg Gln Lys Trp Glu Gln Ile Glu Gly Asn Ser
465                 470                 475                 480

Lys Leu Arg His Val Gly Ser Asn Leu Cys Leu Asp Ser Arg Thr Ala
                485                 490                 495

Lys Ser Gly Gly Leu Ser Val Glu Val Cys Gly Pro Ala Leu Ser Gln
            500                 505                 510

Gln Trp Lys Phe Thr Leu Asn Leu Gln Gln
            515                 520

<210> SEQ ID NO 260
<211> LENGTH: 395
<212> TYPE: PRT
<213> ORGANISM: Artificial Sequence
<220> FEATURE:
<223> OTHER INFORMATION: human GalNAc-T2
      amino acid residues 1-51 and 445-571 deleted
      (alternate form)

<400> SEQUENCE: 260

Met Ser Lys Lys Lys Asp Leu His His Ser Asn Gly Glu Glu Lys Ala
1               5                   10                  15

Gln Ser Met Glu Thr Leu Pro Pro Gly Lys Val Arg Trp Pro Asp Phe
            20                  25                  30

Asn Gln Glu Ala Tyr Val Gly Gly Thr Met Val Arg Ser Gly Gln Asp
        35                  40                  45

Pro Tyr Ala Arg Asn Lys Phe Asn Gln Val Glu Ser Asp Lys Leu Arg
    50                  55                  60

Met Asp Arg Ala Ile Pro Asp Thr Arg His Asp Gln Cys Gln Arg Lys
65                  70                  75                  80

Gln Trp Arg Val Asp Leu Pro Ala Thr Ser Val Ile Thr Phe His
                85                  90                  95

Asn Glu Ala Arg Ser Ala Leu Leu Arg Thr Val Val Ser Val Leu Lys
            100                 105                 110

Lys Ser Pro Pro His Leu Ile Lys Glu Ile Ile Leu Val Asp Asp Tyr
        115                 120                 125

Ser Asn Asp Pro Glu Asp Gly Ala Leu Leu Gly Lys Ile Glu Lys Val
130                 135                 140

Arg Val Leu Arg Asn Asp Arg Arg Glu Gly Leu Met Arg Ser Arg Val
145                 150                 155                 160

Arg Gly Ala Asp Ala Ala Gln Ala Lys Val Leu Thr Phe Leu Asp Ser
                165                 170                 175

His Cys Glu Cys Asn Glu His Trp Leu Glu Pro Leu Leu Glu Arg Val
            180                 185                 190

Ala Glu Asp Arg Thr Arg Val Val Ser Pro Ile Ile Asp Val Ile Asn
        195                 200                 205

Met Asp Asn Phe Gln Tyr Val Gly Ala Ser Ala Asp Leu Lys Gly Gly
    210                 215                 220

Phe Asp Trp Asn Leu Val Phe Lys Trp Asp Tyr Met Thr Pro Glu Gln
225                 230                 235                 240
```

```
Arg Arg Ser Arg Gln Gly Asn Pro Val Ala Pro Ile Lys Thr Pro Met
                245                 250                 255

Ile Ala Gly Gly Leu Phe Val Met Asp Lys Phe Tyr Phe Glu Glu Leu
            260                 265                 270

Gly Lys Tyr Asp Met Met Met Asp Val Trp Gly Gly Glu Asn Leu Glu
        275                 280                 285

Ile Ser Phe Arg Val Trp Gln Cys Gly Gly Ser Leu Glu Ile Ile Pro
290                 295                 300

Cys Ser Arg Val Gly His Val Phe Arg Lys Gln His Pro Tyr Thr Phe
305                 310                 315                 320

Pro Gly Gly Ser Gly Thr Val Phe Ala Arg Asn Thr Arg Arg Ala Ala
                325                 330                 335

Glu Val Trp Met Asp Glu Tyr Lys Asn Phe Tyr Tyr Ala Ala Val Pro
            340                 345                 350

Ser Ala Arg Asn Val Pro Tyr Gly Asn Ile Gln Ser Arg Leu Glu Leu
        355                 360                 365

Arg Lys Lys Leu Ser Cys Lys Pro Phe Lys Trp Tyr Leu Glu Asn Val
370                 375                 380

Tyr Pro Glu Leu Arg Val Pro Asp His Gln Asp
385                 390                 395

<210> SEQ ID NO 261
<211> LENGTH: 518
<212> TYPE: PRT
<213> ORGANISM: Artificial Sequence
<220> FEATURE:
<223> OTHER INFORMATION: human GalNAc-T2
      amino acid residues 1-53 deleted

<400> SEQUENCE: 261

Lys Asp Leu His His Ser Asn Gly Glu Glu Lys Ala Gln Ser Met Glu
1               5                   10                  15

Thr Leu Pro Pro Gly Lys Val Arg Trp Pro Asp Phe Asn Gln Glu Ala
            20                  25                  30

Tyr Val Gly Gly Thr Met Val Arg Ser Gly Gln Asp Pro Tyr Ala Arg
        35                  40                  45

Asn Lys Phe Asn Gln Val Glu Ser Asp Lys Leu Arg Met Asp Arg Ala
    50                  55                  60

Ile Pro Asp Thr Arg His Asp Gln Cys Gln Arg Lys Gln Trp Arg Val
65                  70                  75                  80

Asp Leu Pro Ala Thr Ser Val Val Ile Thr Phe His Asn Glu Ala Arg
                85                  90                  95

Ser Ala Leu Leu Arg Thr Val Val Ser Val Leu Lys Lys Ser Pro Pro
            100                 105                 110

His Leu Ile Lys Glu Ile Ile Leu Val Asp Asp Tyr Ser Asn Asp Pro
        115                 120                 125

Glu Asp Gly Ala Leu Leu Gly Lys Ile Glu Lys Val Arg Val Leu Arg
130                 135                 140

Asn Asp Arg Arg Glu Gly Leu Met Arg Ser Arg Val Arg Gly Ala Asp
145                 150                 155                 160

Ala Ala Gln Ala Lys Val Leu Thr Phe Leu Asp Ser His Cys Glu Cys
                165                 170                 175

Asn Glu His Trp Leu Glu Pro Leu Leu Glu Arg Val Ala Glu Asp Arg
            180                 185                 190

Thr Arg Val Val Ser Pro Ile Ile Asp Val Ile Asn Met Asp Asn Phe
        195                 200                 205
```

```
Gln Tyr Val Gly Ala Ser Ala Asp Leu Lys Gly Gly Phe Asp Trp Asn
    210                 215                 220
Leu Val Phe Lys Trp Asp Tyr Met Thr Pro Glu Gln Arg Arg Ser Arg
225                 230                 235                 240
Gln Gly Asn Pro Val Ala Pro Ile Lys Thr Pro Met Ile Ala Gly Gly
                245                 250                 255
Leu Phe Val Met Asp Lys Phe Tyr Phe Glu Leu Gly Lys Tyr Asp
                260                 265                 270
Met Met Met Asp Val Trp Gly Gly Glu Asn Leu Glu Ile Ser Phe Arg
            275                 280                 285
Val Trp Gln Cys Gly Gly Ser Leu Glu Ile Ile Pro Cys Ser Arg Val
        290                 295                 300
Gly His Val Phe Arg Lys Gln His Pro Tyr Thr Phe Pro Gly Gly Ser
305                 310                 315                 320
Gly Thr Val Phe Ala Arg Asn Thr Arg Arg Ala Ala Glu Val Trp Met
                325                 330                 335
Asp Glu Tyr Lys Asn Phe Tyr Tyr Ala Ala Val Pro Ser Ala Arg Asn
                340                 345                 350
Val Pro Tyr Gly Asn Ile Gln Ser Arg Leu Glu Leu Arg Lys Lys Leu
                355                 360                 365
Ser Cys Lys Pro Phe Lys Trp Tyr Leu Glu Asn Val Tyr Pro Glu Leu
370                 375                 380
Arg Val Pro Asp His Gln Asp Ile Ala Phe Gly Ala Leu Gln Gln Gly
385                 390                 395                 400
Thr Asn Cys Leu Asp Thr Leu Gly His Phe Ala Asp Gly Val Val Gly
                405                 410                 415
Val Tyr Glu Cys His Asn Ala Gly Gly Asn Gln Glu Trp Ala Leu Thr
                420                 425                 430
Lys Glu Lys Ser Val Lys His Met Asp Leu Cys Leu Thr Val Val Asp
            435                 440                 445
Arg Ala Pro Gly Ser Leu Ile Lys Leu Gln Gly Cys Arg Glu Asn Asp
            450                 455                 460
Ser Arg Gln Lys Trp Glu Gln Ile Glu Gly Asn Ser Lys Leu Arg His
465                 470                 475                 480
Val Gly Ser Asn Leu Cys Leu Asp Ser Arg Thr Ala Lys Ser Gly Gly
                485                 490                 495
Leu Ser Val Glu Val Cys Gly Pro Ala Leu Ser Gln Gln Trp Lys Phe
            500                 505                 510
Thr Leu Asn Leu Gln Gln
            515

<210> SEQ ID NO 262
<211> LENGTH: 391
<212> TYPE: PRT
<213> ORGANISM: Artificial Sequence
<220> FEATURE:
<223> OTHER INFORMATION: human GalNAc-T2
      amino acid residues 1-53 and 445-571 deleted

<400> SEQUENCE: 262

Lys Asp Leu His His Ser Asn Gly Glu Glu Lys Ala Gln Ser Met Glu
1               5                   10                  15
Thr Leu Pro Pro Gly Lys Val Arg Trp Pro Asp Phe Asn Gln Glu Ala
            20                  25                  30
Tyr Val Gly Gly Thr Met Val Arg Ser Gly Gln Asp Pro Tyr Ala Arg
```

```
           35                  40                  45
Asn Lys Phe Asn Gln Val Glu Ser Asp Lys Leu Arg Met Asp Arg Ala
 50                  55                  60
Ile Pro Asp Thr Arg His Asp Gln Cys Gln Arg Lys Gln Trp Arg Val
65                  70                  75                  80
Asp Leu Pro Ala Thr Ser Val Val Ile Thr Phe His Asn Glu Ala Arg
                 85                  90                  95
Ser Ala Leu Leu Arg Thr Val Val Ser Val Leu Lys Lys Ser Pro Pro
            100                 105                 110
His Leu Ile Lys Glu Ile Ile Leu Val Asp Asp Tyr Ser Asn Asp Pro
        115                 120                 125
Glu Asp Gly Ala Leu Leu Gly Lys Ile Glu Lys Val Arg Val Leu Arg
    130                 135                 140
Asn Asp Arg Arg Glu Gly Leu Met Arg Ser Arg Val Arg Gly Ala Asp
145                 150                 155                 160
Ala Ala Gln Ala Lys Val Leu Thr Phe Leu Asp Ser His Cys Glu Cys
                165                 170                 175
Asn Glu His Trp Leu Glu Pro Leu Leu Glu Arg Val Ala Glu Asp Arg
            180                 185                 190
Thr Arg Val Val Ser Pro Ile Ile Asp Val Ile Asn Met Asp Asn Phe
        195                 200                 205
Gln Tyr Val Gly Ala Ser Ala Asp Leu Lys Gly Phe Asp Trp Asn
    210                 215                 220
Leu Val Phe Lys Trp Asp Tyr Met Thr Pro Glu Gln Arg Arg Ser Arg
225                 230                 235                 240
Gln Gly Asn Pro Val Ala Pro Ile Lys Thr Pro Met Ile Ala Gly Gly
                245                 250                 255
Leu Phe Val Met Asp Lys Phe Tyr Phe Glu Glu Leu Gly Lys Tyr Asp
            260                 265                 270
Met Met Met Asp Val Trp Gly Gly Glu Asn Leu Glu Ile Ser Phe Arg
        275                 280                 285
Val Trp Gln Cys Gly Gly Ser Leu Glu Ile Ile Pro Cys Ser Arg Val
    290                 295                 300
Gly His Val Phe Arg Lys Gln His Pro Tyr Thr Phe Pro Gly Gly Ser
305                 310                 315                 320
Gly Thr Val Phe Ala Arg Asn Thr Arg Arg Ala Ala Glu Val Trp Met
                325                 330                 335
Asp Glu Tyr Lys Asn Phe Tyr Tyr Ala Ala Val Pro Ser Ala Arg Asn
            340                 345                 350
Val Pro Tyr Gly Asn Ile Gln Ser Arg Leu Glu Leu Arg Lys Lys Leu
        355                 360                 365
Ser Cys Lys Pro Phe Lys Trp Tyr Leu Glu Asn Val Tyr Pro Glu Leu
    370                 375                 380
Arg Val Pro Asp His Gln Asp
385                 390

<210> SEQ ID NO 263
<211> LENGTH: 520
<212> TYPE: PRT
<213> ORGANISM: Artificial Sequence
<220> FEATURE:
<223> OTHER INFORMATION: human GalNAc-T2
      amino acid residues 1-53 deleted (alternate form)

<400> SEQUENCE: 263
```

```
Met Ser Lys Asp Leu His His Ser Asn Gly Glu Glu Lys Ala Gln Ser
1               5                   10                  15

Met Glu Thr Leu Pro Pro Gly Lys Val Arg Trp Pro Asp Phe Asn Gln
            20                  25                  30

Glu Ala Tyr Val Gly Gly Thr Met Val Arg Ser Gly Gln Asp Pro Tyr
                35                  40                  45

Ala Arg Asn Lys Phe Asn Gln Val Glu Ser Asp Lys Leu Arg Met Asp
50                  55                  60

Arg Ala Ile Pro Asp Thr Arg His Asp Gln Cys Gln Arg Lys Gln Trp
65                  70                  75                  80

Arg Val Asp Leu Pro Ala Thr Ser Val Val Ile Thr Phe His Asn Glu
            85                  90                  95

Ala Arg Ser Ala Leu Leu Arg Thr Val Val Ser Val Leu Lys Lys Ser
                100                 105                 110

Pro Pro His Leu Ile Lys Glu Ile Ile Leu Val Asp Asp Tyr Ser Asn
            115                 120                 125

Asp Pro Glu Asp Gly Ala Leu Leu Gly Lys Ile Glu Lys Val Arg Val
    130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
            180                 185                 190

Asp Arg Thr Arg Val Val Ser Pro Ile Ile Asp Val Ile Asn Met Asp
    195                 200                 205

Asn Phe Gln Tyr Val Gly Ala Ser Ala Asp Leu Lys Gly Gly Phe Asp
    210                 215                 220

Trp Asn Leu Val Phe Lys Trp Asp Tyr Met Thr Pro Glu Gln Arg Arg
225                 230                 235                 240

Ser Arg Gln Gly Asn Pro Val Ala Pro Ile Lys Thr Pro Met Ile Ala
                245                 250                 255

Gly Gly Leu Phe Val Met Asp Lys Phe Tyr Phe Glu Glu Leu Gly Lys
            260                 265                 270

Tyr Asp Met Met Met Asp Val Trp Gly Gly Glu Asn Leu Glu Ile Ser
            275                 280                 285

Phe Arg Val Trp Gln Cys Gly Gly Ser Leu Glu Ile Ile Pro Cys Ser
    290                 295                 300

Arg Val Gly His Val Phe Arg Lys Gln His Pro Tyr Thr Phe Pro Gly
305                 310                 315                 320

Gly Ser Gly Thr Val Phe Ala Arg Asn Thr Arg Arg Ala Ala Glu Val
                325                 330                 335

Trp Met Asp Glu Tyr Lys Asn Phe Tyr Tyr Ala Ala Val Pro Ser Ala
            340                 345                 350

Arg Asn Val Pro Tyr Gly Asn Ile Gln Ser Arg Leu Glu Leu Arg Lys
            355                 360                 365

Lys Leu Ser Cys Lys Pro Phe Lys Trp Tyr Leu Glu Asn Val Tyr Pro
370                 375                 380

Glu Leu Arg Val Pro Asp His Gln Asp Ile Ala Phe Gly Ala Leu Gln
385                 390                 395                 400

Gln Gly Thr Asn Cys Leu Asp Thr Leu Gly His Phe Ala Asp Gly Val
                405                 410                 415

Val Gly Val Tyr Glu Cys His Asn Ala Gly Gly Asn Gln Glu Trp Ala
```

-continued

```
                420                 425                 430
Leu Thr Lys Glu Lys Ser Val Lys His Met Asp Leu Cys Leu Thr Val
                435                 440                 445

Val Asp Arg Ala Pro Gly Ser Leu Ile Lys Leu Gln Gly Cys Arg Glu
            450                 455                 460

Asn Asp Ser Arg Gln Lys Trp Glu Gln Ile Glu Gly Asn Ser Lys Leu
465                 470                 475                 480

Arg His Val Gly Ser Asn Leu Cys Leu Asp Ser Arg Thr Ala Lys Ser
                485                 490                 495

Gly Gly Leu Ser Val Glu Val Cys Gly Pro Ala Leu Ser Gln Gln Trp
            500                 505                 510

Lys Phe Thr Leu Asn Leu Gln Gln
            515                 520

<210> SEQ ID NO 264
<211> LENGTH: 393
<212> TYPE: PRT
<213> ORGANISM: Artificial Sequence
<220> FEATURE:
<223> OTHER INFORMATION: human GalNAc-T2
      amino acid residues 1-53 and 445-571 deleted
      (alternate form)

<400> SEQUENCE: 264

Met Ser Lys Asp Leu His His Ser Asn Gly Glu Glu Lys Ala Gln Ser
  1               5                  10                  15

Met Glu Thr Leu Pro Pro Gly Lys Val Arg Trp Pro Asp Phe Asn Gln
                20                  25                  30

Glu Ala Tyr Val Gly Gly Thr Met Val Arg Ser Gly Gln Asp Pro Tyr
            35                  40                  45

Ala Arg Asn Lys Phe Asn Gln Val Glu Ser Asp Lys Leu Arg Met Asp
        50                  55                  60

Arg Ala Ile Pro Asp Thr Arg His Asp Gln Cys Gln Arg Lys Gln Trp
 65                  70                  75                  80

Arg Val Asp Leu Pro Ala Thr Ser Val Val Ile Thr Phe His Asn Glu
                85                  90                  95

Ala Arg Ser Ala Leu Leu Arg Thr Val Val Ser Val Leu Lys Lys Ser
                100                 105                 110

Pro Pro His Leu Ile Lys Glu Ile Ile Leu Val Asp Asp Tyr Ser Asn
            115                 120                 125

Asp Pro Glu Asp Gly Ala Leu Leu Gly Lys Ile Glu Lys Val Arg Val
        130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
            180                 185                 190

Asp Arg Thr Arg Val Val Ser Pro Ile Ile Asp Val Ile Asn Met Asp
        195                 200                 205

Asn Phe Gln Tyr Val Gly Ala Ser Ala Asp Leu Lys Gly Gly Phe Asp
    210                 215                 220

Trp Asn Leu Val Phe Lys Trp Asp Tyr Met Thr Pro Glu Gln Arg Arg
225                 230                 235                 240

Ser Arg Gln Gly Asn Pro Val Ala Pro Ile Lys Thr Pro Met Ile Ala
                245                 250                 255
```

```
Gly Gly Leu Phe Val Met Asp Lys Phe Tyr Phe Glu Leu Gly Lys
            260                 265                 270
Tyr Asp Met Met Met Asp Val Trp Gly Gly Glu Asn Leu Glu Ile Ser
        275                 280                 285
Phe Arg Val Trp Gln Cys Gly Gly Ser Leu Glu Ile Ile Pro Cys Ser
290                 295                 300
Arg Val Gly His Val Phe Arg Lys Gln His Pro Tyr Thr Phe Pro Gly
305                 310                 315                 320
Gly Ser Gly Thr Val Phe Ala Arg Asn Thr Arg Ala Ala Glu Val
                325                 330                 335
Trp Met Asp Glu Tyr Lys Asn Phe Tyr Tyr Ala Ala Val Pro Ser Ala
        340                 345                 350
Arg Asn Val Pro Tyr Gly Asn Ile Gln Ser Arg Leu Glu Leu Arg Lys
            355                 360                 365
Lys Leu Ser Cys Lys Pro Phe Lys Trp Tyr Leu Glu Asn Val Tyr Pro
    370                 375                 380
Glu Leu Arg Val Pro Asp His Gln Asp
385                 390
```

```
<210> SEQ ID NO 265
<211> LENGTH: 519
<212> TYPE: PRT
<213> ORGANISM: Artificial Sequence
<220> FEATURE:
<223> OTHER INFORMATION: human GalNAc-T1, amino acid residues 1-40
      deleted

<400> SEQUENCE: 265

Gly Leu Pro Ala Gly Asp Val Leu Glu Pro Val Gln Lys Pro His Glu
1               5                   10                  15
Gly Pro Gly Glu Met Gly Lys Pro Val Val Ile Pro Lys Glu Asp Gln
            20                  25                  30
Glu Lys Met Lys Glu Met Phe Lys Ile Asn Gln Phe Asn Leu Met Ala
        35                  40                  45
Ser Glu Met Ile Ala Leu Asn Arg Ser Leu Pro Asp Val Arg Leu Glu
    50                  55                  60
Gly Cys Lys Thr Lys Val Tyr Pro Asp Asn Leu Pro Thr Thr Ser Val
65                  70                  75                  80
Val Ile Val Phe His Asn Glu Ala Trp Ser Thr Leu Leu Arg Thr Val
                85                  90                  95
His Ser Val Ile Asn Arg Ser Pro Arg His Met Ile Glu Glu Ile Val
            100                 105                 110
Leu Val Asp Asp Ala Ser Glu Arg Asp Phe Leu Lys Arg Pro Leu Glu
        115                 120                 125
Ser Tyr Val Lys Lys Leu Lys Val Pro Val His Val Ile Arg Met Glu
    130                 135                 140
Gln Arg Ser Gly Leu Ile Arg Ala Arg Leu Lys Gly Ala Ala Val Ser
145                 150                 155                 160
Lys Gly Gln Val Ile Thr Phe Leu Asp Ala His Cys Glu Cys Thr Val
                165                 170                 175
Gly Trp Leu Glu Pro Leu Leu Ala Arg Ile Lys His Asp Arg Arg Thr
            180                 185                 190
Val Val Cys Pro Ile Ile Asp Val Ile Ser Asp Asp Thr Phe Glu Tyr
        195                 200                 205
Met Ala Gly Ser Asp Met Thr Tyr Gly Gly Phe Asn Trp Lys Leu Asn
```

```
            210                 215                 220
Phe Arg Trp Tyr Pro Val Pro Gln Arg Glu Met Asp Arg Arg Lys Gly
225                 230                 235                 240

Asp Arg Thr Leu Pro Val Arg Thr Pro Thr Met Ala Gly Gly Leu Phe
                245                 250                 255

Ser Ile Asp Arg Asp Tyr Phe Gln Glu Ile Gly Thr Tyr Asp Ala Gly
                260                 265                 270

Met Asp Ile Trp Gly Gly Glu Asn Leu Glu Ile Ser Phe Arg Ile Trp
            275                 280                 285

Gln Cys Gly Gly Thr Leu Glu Ile Val Thr Cys Ser His Val Gly His
        290                 295                 300

Val Phe Arg Lys Ala Thr Pro Tyr Thr Phe Pro Gly Gly Thr Gly Gln
305                 310                 315                 320

Ile Ile Asn Lys Asn Asn Arg Arg Leu Ala Glu Val Trp Met Asp Glu
                325                 330                 335

Phe Lys Asn Phe Phe Tyr Ile Ile Ser Pro Gly Val Thr Lys Val Asp
                340                 345                 350

Tyr Gly Asp Ile Ser Ser Arg Val Gly Leu Arg His Lys Leu Gln Cys
            355                 360                 365

Lys Pro Phe Ser Trp Tyr Leu Glu Asn Ile Tyr Pro Asp Ser Gln Ile
        370                 375                 380

Pro Arg His Tyr Phe Ser Leu Gly Glu Ile Arg Asn Val Glu Thr Asn
385                 390                 395                 400

Gln Cys Leu Asp Asn Met Ala Arg Lys Glu Asn Glu Lys Val Gly Ile
                405                 410                 415

Phe Asn Cys His Gly Met Gly Gly Asn Gln Val Phe Ser Tyr Thr Ala
                420                 425                 430

Asn Lys Glu Ile Arg Thr Asp Asp Leu Cys Leu Asp Val Ser Lys Leu
            435                 440                 445

Asn Gly Pro Val Thr Met Leu Lys Cys His His Leu Lys Gly Asn Gln
        450                 455                 460

Leu Trp Glu Tyr Asp Pro Val Lys Leu Thr Leu Gln His Val Asn Ser
465                 470                 475                 480

Asn Gln Cys Leu Asp Lys Ala Thr Glu Glu Asp Ser Gln Val Pro Ser
                485                 490                 495

Ile Arg Asp Cys Asn Gly Ser Arg Ser Gln Gln Trp Leu Leu Arg Asn
                500                 505                 510

Val Thr Leu Pro Glu Ile Phe
            515

<210> SEQ ID NO 266
<211> LENGTH: 520
<212> TYPE: PRT
<213> ORGANISM: Artificial Sequence
<220> FEATURE:
<223> OTHER INFORMATION: human GalNAc-T1, amino acid residues 1-40
      deleted (alternate form)

<400> SEQUENCE: 266

Met Gly Leu Pro Ala Gly Asp Val Leu Glu Pro Val Gln Lys Pro His
1               5                   10                  15

Glu Gly Pro Gly Glu Met Gly Lys Pro Val Val Ile Pro Lys Glu Asp
                20                  25                  30

Gln Glu Lys Met Lys Glu Met Phe Lys Ile Asn Gln Phe Asn Leu Met
            35                  40                  45
```

```
Ala Ser Glu Met Ile Ala Leu Asn Arg Ser Leu Pro Asp Val Arg Leu
     50                  55                  60

Glu Gly Cys Lys Thr Lys Val Tyr Pro Asp Asn Leu Pro Thr Thr Ser
 65                  70                  75                  80

Val Val Ile Val Phe His Asn Glu Ala Trp Ser Thr Leu Leu Arg Thr
                 85                  90                  95

Val His Ser Val Ile Asn Arg Ser Pro Arg His Met Ile Glu Glu Ile
            100                 105                 110

Val Leu Val Asp Asp Ala Ser Glu Arg Asp Phe Leu Lys Arg Pro Leu
            115                 120                 125

Glu Ser Tyr Val Lys Lys Leu Lys Val Pro Val His Val Ile Arg Met
130                 135                 140

Glu Gln Arg Ser Gly Leu Ile Arg Ala Arg Leu Lys Gly Ala Ala Val
145                 150                 155                 160

Ser Lys Gly Gln Val Ile Thr Phe Leu Asp Ala His Cys Glu Cys Thr
                165                 170                 175

Val Gly Trp Leu Glu Pro Leu Leu Ala Arg Ile Lys His Asp Arg Arg
            180                 185                 190

Thr Val Val Cys Pro Ile Ile Asp Val Ile Ser Asp Asp Thr Phe Glu
            195                 200                 205

Tyr Met Ala Gly Ser Asp Met Thr Tyr Gly Gly Phe Asn Trp Lys Leu
210                 215                 220

Asn Phe Arg Trp Tyr Pro Val Pro Gln Arg Glu Met Asp Arg Arg Lys
225                 230                 235                 240

Gly Asp Arg Thr Leu Pro Val Arg Thr Pro Thr Met Ala Gly Gly Leu
                245                 250                 255

Phe Ser Ile Asp Arg Asp Tyr Phe Gln Glu Ile Gly Thr Tyr Asp Ala
            260                 265                 270

Gly Met Asp Ile Trp Gly Gly Glu Asn Leu Glu Ile Ser Phe Arg Ile
            275                 280                 285

Trp Gln Cys Gly Gly Thr Leu Glu Ile Val Thr Cys Ser His Val Gly
290                 295                 300

His Val Phe Arg Lys Ala Thr Pro Tyr Thr Phe Pro Gly Gly Thr Gly
305                 310                 315                 320

Gln Ile Ile Asn Lys Asn Asn Arg Arg Leu Ala Glu Val Trp Met Asp
                325                 330                 335

Glu Phe Lys Asn Phe Phe Tyr Ile Ile Ser Pro Gly Val Thr Lys Val
            340                 345                 350

Asp Tyr Gly Asp Ile Ser Ser Arg Val Gly Leu Arg His Lys Leu Gln
            355                 360                 365

Cys Lys Pro Phe Ser Trp Tyr Leu Glu Asn Ile Tyr Pro Asp Ser Gln
370                 375                 380

Ile Pro Arg His Tyr Phe Ser Leu Gly Glu Ile Arg Asn Val Glu Thr
385                 390                 395                 400

Asn Gln Cys Leu Asp Asn Met Ala Arg Lys Glu Asn Glu Lys Val Gly
                405                 410                 415

Ile Phe Asn Cys His Gly Met Gly Gly Asn Gln Val Phe Ser Tyr Thr
            420                 425                 430

Ala Asn Lys Glu Ile Arg Thr Asp Asp Leu Cys Leu Asp Val Ser Lys
            435                 440                 445

Leu Asn Gly Pro Val Thr Met Leu Lys Cys His His Leu Lys Gly Asn
450                 455                 460

Gln Leu Trp Glu Tyr Asp Pro Val Lys Leu Thr Leu Gln His Val Asn
```

```
               465                 470                 475                 480
Ser Asn Gln Cys Leu Asp Lys Ala Thr Glu Glu Asp Ser Gln Val Pro
            485                 490                 495

Ser Ile Arg Asp Cys Asn Gly Ser Arg Ser Gln Gln Trp Leu Leu Arg
            500                 505                 510

Asn Val Thr Leu Pro Glu Ile Phe
            515                 520

<210> SEQ ID NO 267
<211> LENGTH: 633
<212> TYPE: PRT
<213> ORGANISM: homo sapiens
<220> FEATURE:
<221> NAME/KEY: VARIANT
<222> LOCATION: (1)...(633)
<223> OTHER INFORMATION: human GalNAc-T3

<400> SEQUENCE: 267

Met Ala His Leu Lys Arg Leu Val Lys Leu His Ile Lys Arg His Tyr
  1               5                  10                  15

His Lys Lys Phe Trp Lys Leu Gly Ala Val Ile Phe Phe Ile Ile
             20                  25                  30

Val Leu Val Leu Met Gln Arg Glu Val Ser Val Gln Tyr Ser Lys Glu
         35                  40                  45

Glu Ser Arg Met Glu Arg Asn Met Lys Asn Lys Asn Lys Met Leu Asp
     50                  55                  60

Leu Met Leu Glu Ala Val Asn Asn Ile Lys Asp Ala Met Pro Lys Met
 65                  70                  75                  80

Gln Ile Gly Ala Pro Val Arg Gln Asn Ile Asp Ala Gly Glu Arg Pro
                 85                  90                  95

Cys Leu Gln Gly Tyr Tyr Thr Ala Ala Glu Leu Lys Pro Val Leu Asp
            100                 105                 110

Arg Pro Pro Gln Asp Ser Asn Ala Pro Gly Ala Ser Gly Lys Ala Phe
        115                 120                 125

Lys Thr Thr Asn Leu Ser Val Glu Glu Gln Lys Glu Lys Glu Arg Gly
130                 135                 140

Glu Ala Lys His Cys Phe Asn Ala Phe Ala Ser Asp Arg Ile Ser Leu
145                 150                 155                 160

His Arg Asp Leu Gly Pro Asp Thr Arg Pro Pro Glu Cys Ile Glu Gln
                165                 170                 175

Lys Phe Lys Arg Cys Pro Pro Leu Pro Thr Thr Ser Val Ile Ile Val
            180                 185                 190

Phe His Asn Glu Ala Trp Ser Thr Leu Leu Arg Thr Val His Ser Val
        195                 200                 205

Leu Tyr Ser Ser Pro Ala Ile Leu Leu Lys Glu Ile Ile Leu Val Asp
    210                 215                 220

Asp Ala Ser Val Asp Glu Tyr Leu His Asp Lys Leu Asp Glu Tyr Val
225                 230                 235                 240

Lys Gln Phe Ser Ile Val Lys Ile Val Arg Gln Arg Glu Arg Lys Gly
                245                 250                 255

Leu Ile Thr Ala Arg Leu Leu Gly Ala Thr Val Ala Thr Ala Glu Thr
            260                 265                 270

Leu Thr Phe Leu Asp Ala His Cys Glu Cys Phe Tyr Gly Trp Leu Glu
        275                 280                 285

Pro Leu Leu Ala Arg Ile Ala Glu Asn Tyr Thr Ala Val Val Ser Pro
    290                 295                 300
```

```
Asp Ile Ala Ser Ile Asp Leu Asn Thr Phe Glu Phe Asn Lys Pro Ser
305                 310                 315                 320

Pro Tyr Gly Ser Asn His Asn Arg Gly Asn Phe Asp Trp Ser Leu Ser
            325                 330                 335

Phe Gly Trp Glu Ser Leu Pro Asp His Glu Lys Gln Arg Arg Lys Asp
        340                 345                 350

Glu Thr Tyr Pro Ile Lys Thr Pro Thr Phe Ala Gly Gly Leu Phe Ser
    355                 360                 365

Ile Ser Lys Glu Tyr Phe Glu Tyr Ile Gly Ser Tyr Asp Glu Glu Met
370                 375                 380

Glu Ile Trp Gly Gly Asn Ile Glu Met Ser Phe Arg Val Trp Gln
385                 390                 395                 400

Cys Gly Gly Gln Leu Glu Ile Met Pro Cys Ser Val Val Gly His Val
                405                 410                 415

Phe Arg Ser Lys Ser Pro His Ser Phe Pro Lys Gly Thr Gln Val Ile
            420                 425                 430

Ala Arg Asn Gln Val Arg Leu Ala Glu Val Trp Met Asp Glu Tyr Lys
        435                 440                 445

Glu Ile Phe Tyr Arg Arg Asn Thr Asp Ala Ala Lys Ile Val Lys Gln
    450                 455                 460

Lys Ala Phe Gly Asp Leu Ser Lys Arg Phe Glu Ile Lys His Arg Leu
465                 470                 475                 480

Arg Cys Lys Asn Phe Thr Trp Tyr Leu Asn Asn Ile Tyr Pro Glu Val
                485                 490                 495

Tyr Val Pro Asp Leu Asn Pro Val Ile Ser Gly Tyr Ile Lys Ser Val
            500                 505                 510

Gly Gln Pro Leu Cys Leu Asp Val Gly Glu Asn Asn Gln Gly Gly Lys
        515                 520                 525

Pro Leu Ile Met Tyr Thr Cys His Gly Leu Gly Gly Asn Gln Tyr Phe
    530                 535                 540

Glu Tyr Ser Ala Gln His Glu Ile Arg His Asn Ile Gln Lys Glu Leu
545                 550                 555                 560

Cys Leu His Ala Ala Gln Gly Leu Val Gln Leu Lys Ala Cys Thr Tyr
                565                 570                 575

Lys Gly His Lys Thr Val Val Thr Gly Glu Gln Ile Trp Glu Ile Gln
            580                 585                 590

Lys Asp Gln Leu Leu Tyr Asn Pro Phe Leu Lys Met Cys Leu Ser Ala
        595                 600                 605

Asn Gly Glu His Pro Ser Leu Val Ser Cys Asn Pro Ser Asp Pro Leu
    610                 615                 620

Gln Lys Trp Ile Leu Ser Gln Asn Asp
625                 630

<210> SEQ ID NO 268
<211> LENGTH: 667
<212> TYPE: PRT
<213> ORGANISM: drosophila melanogaster
<220> FEATURE:
<221> NAME/KEY: VARIANT
<222> LOCATION: (1)...(667)
<223> OTHER INFORMATION: GalNAc-T3

<400> SEQUENCE: 268

Met Gly Leu Arg Phe Gln Gln Leu Lys Lys Leu Trp Leu Leu Tyr Leu
1               5                   10                  15
```

```
Phe Leu Leu Phe Phe Ala Phe Phe Met Phe Ala Ile Ser Ile Asn Leu
            20                  25                  30

Tyr Val Ala Ser Ile Gln Gly Gly Asp Ala Glu Met Arg His Pro Lys
        35                  40                  45

Pro Pro Pro Lys Arg Arg Ser Leu Trp Pro His Lys Asn Ile Val Ala
50                  55                  60

His Tyr Ile Gly Lys Gly Asp Ile Phe Gly Asn Met Thr Ala Asp Asp
65                  70                  75                  80

Tyr Asn Ile Asn Leu Phe Gln Pro Ile Asn Gly Glu Gly Ala Asp Gly
                85                  90                  95

Arg Pro Val Val Val Pro Pro Arg Asp Arg Phe Arg Met Gln Arg Phe
                100                 105                 110

Phe Arg Leu Asn Ser Phe Asn Leu Leu Ala Ser Asp Arg Ile Pro Leu
            115                 120                 125

Asn Arg Thr Leu Lys Asp Tyr Arg Thr Pro Glu Cys Arg Asp Lys Lys
        130                 135                 140

Tyr Ala Ser Gly Leu Pro Ser Thr Ser Val Ile Val Phe His Asn
145                 150                 155                 160

Glu Ala Trp Ser Val Leu Leu Arg Thr Ile Thr Ser Val Ile Asn Arg
                165                 170                 175

Ser Pro Arg His Leu Leu Lys Glu Ile Ile Leu Val Asp Asp Ala Ser
            180                 185                 190

Asp Arg Ser Tyr Leu Lys Arg Gln Leu Glu Ser Tyr Val Lys Val Leu
        195                 200                 205

Ala Val Pro Thr Arg Ile Phe Arg Met Lys Lys Arg Ser Gly Leu Val
210                 215                 220

Pro Ala Arg Leu Leu Gly Ala Glu Asn Ala Arg Gly Asp Val Leu Thr
225                 230                 235                 240

Phe Leu Asp Ala His Cys Glu Cys Ser Arg Gly Trp Leu Glu Pro Leu
                245                 250                 255

Leu Ser Arg Ile Lys Glu Ser Arg Lys Val Val Ile Cys Pro Val Ile
            260                 265                 270

Asp Ile Ile Ser Asp Asp Asn Phe Ser Tyr Thr Lys Thr Phe Glu Asn
        275                 280                 285

His Trp Gly Ala Phe Asn Trp Gln Leu Ser Phe Arg Trp Phe Ser Ser
290                 295                 300

Asp Arg Lys Arg Gln Thr Ala Gly Asn Ser Ser Lys Asp Ser Thr Asp
305                 310                 315                 320

Pro Ile Ala Thr Pro Gly Met Ala Gly Gly Leu Phe Ala Ile Asp Arg
                325                 330                 335

Lys Tyr Phe Tyr Glu Met Gly Ser Tyr Asp Ser Asn Met Arg Val Trp
            340                 345                 350

Gly Gly Glu Asn Val Glu Met Ser Phe Arg Ile Trp Gln Cys Gly Gly
        355                 360                 365

Arg Val Glu Ile Ser Pro Cys Ser His Val Gly His Val Phe Arg Ser
370                 375                 380

Ser Thr Pro Tyr Thr Phe Pro Gly Gly Met Ser Glu Val Leu Thr Asp
385                 390                 395                 400

Asn Leu Ala Arg Ala Ala Thr Val Trp Met Asp Trp Gln Tyr Phe
                405                 410                 415

Ile Met Leu Tyr Thr Ser Gly Leu Thr Leu Gly Ala Lys Asp Lys Val
            420                 425                 430

Asn Val Thr Glu Arg Val Ala Leu Arg Glu Arg Leu Gln Cys Lys Pro
```

Phe Ser Trp Tyr Leu Glu Asn Ile Trp Pro Glu His Phe Pro Ala
450                 455                 460

Pro Asp Arg Phe Phe Gly Lys Ile Ile Trp Leu Asp Gly Glu Thr Glu
465                 470                 475                 480

Cys Ala Gln Ala Tyr Ser Lys His Met Lys Asn Leu Pro Gly Arg Ala
                485                 490                 495

Leu Ser Arg Glu Trp Lys Arg Ala Phe Glu Glu Ile Asp Ser Lys Ala
                500                 505                 510

Glu Glu Leu Met Ala Leu Ile Asp Leu Glu Arg Asp Lys Cys Leu Arg
                515                 520                 525

Pro Leu Lys Glu Asp Val Pro Arg Ser Ser Leu Ser Ala Val Thr Val
530                 535                 540

Gly Asp Cys Thr Ser His Ala Gln Ser Met Asp Met Phe Val Ile Thr
545                 550                 555                 560

Pro Lys Gly Gln Ile Met Thr Asn Asp Asn Val Cys Leu Thr Tyr Arg
                565                 570                 575

Gln Gln Lys Leu Gly Val Ile Lys Met Leu Lys Asn Arg Asn Ala Thr
                580                 585                 590

Thr Ser Asn Val Met Leu Ala Gln Cys Ala Ser Asp Ser Ser Gln Leu
                595                 600                 605

Trp Thr Tyr Asp Met Asp Thr Gln Gln Ile Ser His Arg Asp Thr Lys
610                 615                 620

Leu Cys Leu Thr Leu Lys Ala Ala Thr Asn Ser Arg Leu Gln Lys Val
625                 630                 635                 640

Glu Lys Val Val Leu Ser Met Glu Cys Asp Phe Lys Asp Ile Thr Gln
                645                 650                 655

Lys Trp Gly Phe Ile Pro Leu Pro Trp Arg Met
                660                 665

<210> SEQ ID NO 269
<211> LENGTH: 633
<212> TYPE: PRT
<213> ORGANISM: mus musculus
<220> FEATURE:
<221> NAME/KEY: VARIANT
<222> LOCATION: (1)...(633)
<223> OTHER INFORMATION: murine GalNAc-T3

<400> SEQUENCE: 269

Met Ala His Leu Lys Arg Leu Val Lys Leu His Ile Lys Arg His Tyr
1               5                   10                  15

His Arg Lys Phe Trp Lys Leu Gly Ala Val Ile Phe Phe Leu Val
                20                  25                  30

Val Leu Ile Leu Met Gln Arg Glu Val Ser Val Gln Tyr Ser Lys Glu
                35                  40                  45

Glu Ser Lys Met Glu Arg Asn Leu Lys Asn Lys Asn Lys Met Leu Asp
                50                  55                  60

Phe Met Leu Glu Ala Val Asn Asn Ile Lys Asp Ala Met Pro Lys Met
65                  70                  75                  80

Gln Ile Gly Ala Pro Ile Lys Glu Asn Ile Asp Val Arg Glu Arg Pro
                85                  90                  95

Cys Leu Gln Gly Tyr Tyr Thr Ala Ala Glu Leu Lys Pro Val Phe Asp
                100                 105                 110

Arg Pro Pro Gln Asp Ser Asn Ala Pro Gly Ala Ser Gly Lys Pro Phe
                115                 120                 125

```
Lys Ile Thr His Leu Ser Pro Glu Glu Gln Lys Glu Arg Gly
130                 135                 140

Glu Thr Lys His Cys Phe Asn Ala Phe Ala Ser Asp Arg Ile Ser Leu
145                 150                 155                 160

His Arg Asp Leu Gly Pro Asp Thr Arg Pro Pro Glu Cys Ile Glu Gln
                165                 170                 175

Lys Phe Lys Arg Cys Pro Pro Leu Pro Thr Thr Ser Val Ile Ile Val
                180                 185                 190

Phe His Asn Glu Ala Trp Ser Thr Leu Leu Arg Thr Val His Ser Val
                195                 200                 205

Leu Tyr Ser Ser Pro Ala Ile Leu Leu Lys Glu Ile Ile Leu Val Asp
210                 215                 220

Asp Ala Ser Val Asp Asp Tyr Leu His Glu Lys Leu Glu Glu Tyr Ile
225                 230                 235                 240

Lys Gln Phe Ser Ile Val Lys Ile Val Arg Gln Gln Glu Arg Lys Gly
                245                 250                 255

Leu Ile Thr Ala Arg Leu Leu Gly Ala Ala Val Ala Thr Ala Glu Thr
                260                 265                 270

Leu Thr Phe Leu Asp Ala His Cys Glu Cys Phe Tyr Gly Trp Leu Glu
                275                 280                 285

Pro Leu Leu Ala Arg Ile Ala Glu Asn Tyr Thr Ala Val Val Ser Pro
290                 295                 300

Asp Ile Ala Ser Ile Asp Leu Asn Thr Phe Glu Phe Asn Lys Pro Ser
305                 310                 315                 320

Pro Tyr Gly Asn Asn His Asn Arg Gly Asn Phe Asp Trp Ser Leu Ser
                325                 330                 335

Phe Gly Trp Glu Ser Leu Pro Asp His Glu Lys Gln Arg Arg Lys Asp
                340                 345                 350

Glu Thr Tyr Pro Ile Lys Thr Pro Thr Phe Ala Gly Gly Leu Phe Ser
                355                 360                 365

Ile Ser Lys Lys Tyr Phe Glu His Ile Gly Ser Tyr Asp Glu Glu Met
370                 375                 380

Glu Ile Trp Gly Gly Glu Asn Ile Glu Met Ser Phe Arg Val Trp Gln
385                 390                 395                 400

Cys Gly Gly Gln Leu Glu Ile Met Pro Cys Ser Val Val Gly His Val
                405                 410                 415

Phe Arg Ser Lys Ser Pro His Thr Phe Pro Lys Gly Thr Gln Val Ile
                420                 425                 430

Ala Arg Asn Gln Val Arg Leu Ala Glu Val Trp Met Asp Glu Tyr Lys
                435                 440                 445

Glu Ile Phe Tyr Arg Arg Asn Thr Asp Ala Ala Lys Ile Val Lys Gln
450                 455                 460

Lys Ser Phe Gly Asp Leu Ser Lys Arg Phe Glu Ile Lys Lys Arg Leu
465                 470                 475                 480

Gln Cys Lys Asn Phe Thr Trp Tyr Leu Asn Thr Ile Tyr Pro Glu Ala
                485                 490                 495

Tyr Val Pro Asp Leu Asn Pro Val Ile Ser Gly Tyr Ile Lys Ser Val
                500                 505                 510

Gly Gln Pro Leu Cys Leu Asp Val Gly Glu Asn Asn Gln Gly Gly Lys
                515                 520                 525

Pro Leu Ile Leu Tyr Thr Cys His Gly Leu Gly Gly Asn Gln Tyr Phe
530                 535                 540
```

```
Glu Tyr Ser Ala Gln Arg Glu Ile Arg His Asn Ile Gln Lys Glu Leu
545                 550                 555                 560

Cys Leu His Ala Thr Gln Gly Val Val Gln Leu Lys Ala Cys Val Tyr
                565                 570                 575

Lys Gly His Arg Thr Ile Ala Pro Gly Glu Gln Ile Trp Glu Ile Arg
            580                 585                 590

Lys Asp Gln Leu Leu Tyr Asn Pro Leu Phe Lys Met Cys Leu Ser Ser
        595                 600                 605

Asn Gly Glu His Pro Asn Leu Val Pro Cys Asp Ala Thr Asp Leu Leu
    610                 615                 620

Gln Lys Trp Ile Phe Ser Gln Asn Asp
625                 630

<210> SEQ ID NO 270
<211> LENGTH: 608
<212> TYPE: PRT
<213> ORGANISM: homo sapiens
<220> FEATURE:
<221> NAME/KEY: VARIANT
<222> LOCATION: (1)...(608)
<223> OTHER INFORMATION: human GalNAc-T11

<400> SEQUENCE: 270

Met Gly Ser Val Thr Val Arg Tyr Phe Cys Tyr Gly Cys Leu Phe Thr
1               5                   10                  15

Ser Ala Thr Trp Thr Val Leu Leu Phe Val Tyr Phe Asn Phe Ser Glu
            20                  25                  30

Val Thr Gln Pro Leu Lys Asn Val Pro Val Lys Gly Ser Gly Pro His
        35                  40                  45

Gly Pro Ser Pro Lys Lys Phe Tyr Pro Arg Phe Thr Arg Gly Pro Ser
    50                  55                  60

Arg Val Leu Glu Pro Gln Phe Lys Ala Asn Lys Ile Asp Asp Val Ile
65                  70                  75                  80

Asp Ser Arg Val Glu Asp Pro Glu Glu Gly His Leu Lys Phe Ser Ser
                85                  90                  95

Glu Leu Gly Met Ile Phe Asn Glu Arg Asp Gln Glu Leu Arg Asp Leu
            100                 105                 110

Gly Tyr Gln Lys His Ala Phe Asn Met Leu Ile Ser Asp Arg Leu Gly
        115                 120                 125

Tyr His Arg Asp Val Pro Asp Thr Arg Asn Ala Ala Cys Lys Glu Lys
    130                 135                 140

Phe Tyr Pro Pro Asp Leu Pro Ala Ala Ser Val Val Ile Cys Phe Tyr
145                 150                 155                 160

Asn Glu Ala Phe Ser Ala Leu Leu Arg Thr Val His Ser Val Ile Asp
                165                 170                 175

Arg Thr Pro Ala His Leu Leu His Glu Ile Ile Leu Val Asp Asp Asp
            180                 185                 190

Ser Asp Phe Asp Asp Leu Lys Gly Glu Leu Asp Glu Tyr Val Gln Lys
        195                 200                 205

Tyr Leu Pro Gly Lys Ile Lys Val Ile Arg Asn Thr Lys Arg Glu Gly
    210                 215                 220

Leu Ile Arg Gly Arg Met Ile Gly Ala Ala His Ala Thr Gly Glu Val
225                 230                 235                 240

Leu Val Phe Leu Asp Ser His Cys Glu Val Asn Val Met Trp Leu Gln
                245                 250                 255

Pro Leu Leu Ala Ala Ile Arg Glu Asp Arg His Thr Val Val Cys Pro
```

```
                260                 265                 270
Val Ile Asp Ile Ile Ser Ala Asp Thr Leu Ala Tyr Ser Ser Ser Pro
            275                 280                 285

Val Val Arg Gly Gly Phe Asn Trp Gly Leu His Phe Lys Trp Asp Leu
        290                 295                 300

Val Pro Leu Ser Glu Leu Gly Arg Ala Glu Ala Thr Ala Pro Ile
305                 310                 315                 320

Lys Ser Pro Thr Met Ala Gly Gly Leu Phe Ala Met Asn Arg Gln Tyr
                325                 330                 335

Phe His Glu Leu Gly Gln Tyr Asp Ser Gly Met Asp Ile Trp Gly Gly
            340                 345                 350

Glu Asn Leu Glu Ile Ser Phe Arg Ile Trp Met Cys Gly Gly Lys Leu
        355                 360                 365

Phe Ile Ile Pro Cys Ser Arg Val Gly His Ile Phe Arg Lys Arg Arg
    370                 375                 380

Pro Tyr Gly Ser Pro Glu Gly Gln Asp Thr Met Thr His Asn Ser Leu
385                 390                 395                 400

Arg Leu Ala His Val Trp Leu Asp Glu Tyr Lys Glu Gln Tyr Phe Ser
                405                 410                 415

Leu Arg Pro Asp Leu Lys Thr Lys Ser Tyr Gly Asn Ile Ser Glu Arg
            420                 425                 430

Val Glu Leu Arg Lys Lys Leu Gly Cys Lys Ser Phe Lys Trp Tyr Leu
        435                 440                 445

Asp Asn Val Tyr Pro Glu Met Gln Ile Ser Gly Ser His Ala Lys Pro
    450                 455                 460

Gln Gln Pro Ile Phe Val Asn Arg Gly Pro Lys Arg Pro Lys Val Leu
465                 470                 475                 480

Gln Arg Gly Arg Leu Tyr His Leu Gln Thr Asn Lys Cys Leu Val Ala
                485                 490                 495

Gln Gly Arg Pro Ser Gln Lys Gly Gly Leu Val Val Leu Lys Ala Cys
            500                 505                 510

Asp Tyr Ser Asp Pro Asn Gln Ile Trp Ile Tyr Asn Glu Glu His Glu
        515                 520                 525

Leu Val Leu Asn Ser Leu Leu Cys Leu Asp Met Ser Glu Thr Arg Ser
    530                 535                 540

Ser Asp Pro Pro Arg Leu Met Lys Cys His Gly Ser Gly Gly Ser Gln
545                 550                 555                 560

Gln Trp Thr Phe Gly Lys Asn Asn Arg Leu Tyr Gln Val Ser Val Gly
                565                 570                 575

Gln Cys Leu Arg Ala Val Asp Pro Leu Gly Gln Lys Gly Ser Val Ala
            580                 585                 590

Met Ala Ile Cys Asp Gly Ser Ser Ser Gln Gln Trp His Leu Glu Gly
        595                 600                 605

<210> SEQ ID NO 271
<211> LENGTH: 357
<212> TYPE: PRT
<213> ORGANISM: Artificial Sequence
<220> FEATURE:
<223> OTHER INFORMATION: soluble human Core-1-GalT1

<400> SEQUENCE: 271

Gly Phe Cys Leu Ala Glu Leu Phe Val Tyr Ser Thr Pro Glu Arg Ser
1               5                   10                  15

Glu Phe Met Pro Tyr Asp Gly His Arg His Gly Asp Val Asn Asp Ala
```

```
                20                  25                  30
His His Ser His Asp Met Met Glu Met Ser Gly Pro Glu Gln Asp Val
            35                  40                  45
Gly Gly His Glu His Val His Glu Asn Ser Thr Ile Ala Glu Arg Leu
            50                  55                  60
Tyr Ser Glu Val Arg Val Leu Cys Trp Ile Met Thr Asn Pro Ser Asn
 65                  70                  75                  80
His Gln Lys Lys Ala Arg His Val Lys Arg Thr Trp Gly Lys Arg Cys
            85                  90                  95
Asn Lys Leu Ile Phe Met Ser Ser Ala Lys Asp Asp Glu Leu Asp Ala
           100                 105                 110
Val Ala Leu Pro Val Gly Glu Gly Arg Asn Asn Leu Trp Gly Lys Thr
           115                 120                 125
Lys Glu Ala Tyr Lys Tyr Ile Tyr Glu His His Ile Asn Asp Ala Asp
           130                 135                 140
Trp Phe Leu Lys Ala Asp Asp Asp Thr Tyr Thr Ile Val Glu Asn Met
145                 150                 155                 160
Arg Tyr Met Leu Tyr Pro Tyr Ser Pro Glu Thr Pro Val Tyr Phe Gly
           165                 170                 175
Cys Lys Phe Lys Pro Tyr Val Lys Gln Gly Tyr Met Ser Gly Gly Ala
           180                 185                 190
Gly Tyr Val Leu Ser Arg Glu Ala Val Arg Arg Phe Val Glu Ala
           195                 200                 205
Leu Pro Asn Pro Lys Leu Cys Lys Ser Asp Asn Ser Gly Ala Glu Asp
           210                 215                 220
Val Glu Ile Gly Lys Cys Leu Gln Asn Val Asn Val Leu Ala Gly Asp
225                 230                 235                 240
Ser Arg Asp Ser Asn Gly Arg Gly Arg Phe Phe Pro Phe Val Pro Glu
           245                 250                 255
His His Leu Ile Pro Ser His Thr Asp Lys Lys Phe Trp Tyr Trp Gln
           260                 265                 270
Tyr Ile Phe Tyr Lys Thr Asp Glu Gly Leu Asp Cys Cys Ser Asp Asn
           275                 280                 285
Ala Ile Ser Phe His Tyr Val Ser Pro Asn Gln Met Tyr Val Leu Asp
           290                 295                 300
Tyr Leu Ile Tyr His Leu Arg Pro Tyr Gly Ile Ile Asn Thr Pro Asp
305                 310                 315                 320
Ala Leu Pro Asn Lys Leu Ala Val Gly Glu Leu Met Pro Glu Ile Lys
           325                 330                 335
Glu Gln Ala Thr Glu Ser Thr Ser Asp Gly Val Ser Lys Arg Ser Ala
           340                 345                 350
Glu Thr Lys Thr Gln
           355

<210> SEQ ID NO 272
<211> LENGTH: 6
<212> TYPE: PRT
<213> ORGANISM: homo sapiens
<220> FEATURE:
<221> NAME/KEY: VARIANT
<222> LOCATION: (1)...(6)
<223> OTHER INFORMATION: BMP-7, wild-type

<400> SEQUENCE: 272

Met Ser Thr Gly Ser Lys
 1               5
```

```
<210> SEQ ID NO 273
<211> LENGTH: 8
<212> TYPE: PRT
<213> ORGANISM: Artificial Sequence
<220> FEATURE:
<223> OTHER INFORMATION: BMP-7 variant

<400> SEQUENCE: 273

Met Phe Pro Ser Thr Gly Ser Lys
 1               5

<210> SEQ ID NO 274
<211> LENGTH: 8
<212> TYPE: PRT
<213> ORGANISM: Artificial Sequence
<220> FEATURE:
<223> OTHER INFORMATION: BMP-7 variant

<400> SEQUENCE: 274

Met Phe Pro Thr Thr Gly Ser Lys
 1               5

<210> SEQ ID NO 275
<211> LENGTH: 8
<212> TYPE: PRT
<213> ORGANISM: Artificial Sequence
<220> FEATURE:
<223> OTHER INFORMATION: BMP-7 variant

<400> SEQUENCE: 275

Met Phe Pro Ser Thr Gly Ser Ala
 1               5

<210> SEQ ID NO 276
<211> LENGTH: 8
<212> TYPE: PRT
<213> ORGANISM: Artificial Sequence
<220> FEATURE:
<223> OTHER INFORMATION: BMP-7 variant

<400> SEQUENCE: 276

Met Phe Pro Thr Ile Asn Thr Lys
 1               5

<210> SEQ ID NO 277
<211> LENGTH: 8
<212> TYPE: PRT
<213> ORGANISM: Artificial Sequence
<220> FEATURE:
<223> OTHER INFORMATION: BMP-7 variant

<400> SEQUENCE: 277

Met Phe Pro Thr Ile Asn Thr Ala
 1               5

<210> SEQ ID NO 278
<211> LENGTH: 12
<212> TYPE: PRT
<213> ORGANISM: homo sapiens
<220> FEATURE:
<221> NAME/KEY: VARIANT
<222> LOCATION: (9)...(20)
<223> OTHER INFORMATION: BMP-7, wild-type

<400> SEQUENCE: 278

Gln Asn Arg Ser Lys Thr Pro Lys Asn Gln Glu Ala
```

```
1               5                   10
```

<210> SEQ ID NO 279
<211> LENGTH: 12
<212> TYPE: PRT
<213> ORGANISM: Artificial Sequence
<220> FEATURE:
<223> OTHER INFORMATION: BMP-7 variant

<400> SEQUENCE: 279

```
Gln Asn Gly Thr Glu Thr Pro Lys Asn Gln Glu Ala
1               5                   10
```

<210> SEQ ID NO 280
<211> LENGTH: 12
<212> TYPE: PRT
<213> ORGANISM: Artificial Sequence
<220> FEATURE:
<223> OTHER INFORMATION: BMP-7 variant

<400> SEQUENCE: 280

```
Gln Asn Arg Ser Lys Thr Pro Thr Asn Gln Glu Ala
1               5                   10
```

<210> SEQ ID NO 281
<211> LENGTH: 12
<212> TYPE: PRT
<213> ORGANISM: Artificial Sequence
<220> FEATURE:
<223> OTHER INFORMATION: BMP-7 variant

<400> SEQUENCE: 281

```
Gln Asn Arg Ser Lys Thr Pro Thr Ile Asn Thr Ala
1               5                   10
```

<210> SEQ ID NO 282
<211> LENGTH: 12
<212> TYPE: PRT
<213> ORGANISM: Artificial Sequence
<220> FEATURE:
<223> OTHER INFORMATION: BMP-7 variant

<400> SEQUENCE: 282

```
Gln Asn Arg Ser Ala Thr Pro Thr Ile Asn Thr Ala
1               5                   10
```

<210> SEQ ID NO 283
<211> LENGTH: 12
<212> TYPE: PRT
<213> ORGANISM: Artificial Sequence
<220> FEATURE:
<223> OTHER INFORMATION: BMP-7 variant

<400> SEQUENCE: 283

```
Gln Asn Arg Ser Ala Thr Pro Thr Thr Val Ser Ala
1               5                   10
```

<210> SEQ ID NO 284
<211> LENGTH: 9
<212> TYPE: PRT
<213> ORGANISM: homo sapiens
<220> FEATURE:
<221> NAME/KEY: VARIANT
<222> LOCATION: (27)...(35)
<223> OTHER INFORMATION: BMP-7, wild-type

<400> SEQUENCE: 284

Val Ala Glu Asn Ser Ser Asp Gln Arg
1               5

<210> SEQ ID NO 285
<211> LENGTH: 10
<212> TYPE: PRT
<213> ORGANISM: Artificial Sequence
<220> FEATURE:
<223> OTHER INFORMATION: BMP-7 variant

<400> SEQUENCE: 285

Val Ala Glu Pro Ser Ser Asp Gln Arg
1               5                   10

<210> SEQ ID NO 286
<211> LENGTH: 10
<212> TYPE: PRT
<213> ORGANISM: Artificial Sequence
<220> FEATURE:
<223> OTHER INFORMATION: BMP-7 variant

<400> SEQUENCE: 286

Val Ala Glu Pro Thr Ser Ala Asp Gln Arg
1               5                   10

<210> SEQ ID NO 287
<211> LENGTH: 10
<212> TYPE: PRT
<213> ORGANISM: Artificial Sequence
<220> FEATURE:
<223> OTHER INFORMATION: BMP-7 variant

<400> SEQUENCE: 287

Val Ala Thr Pro Thr Ser Ala Asp Gln Arg
1               5                   10

<210> SEQ ID NO 288
<211> LENGTH: 11
<212> TYPE: PRT
<213> ORGANISM: homo sapiens
<220> FEATURE:
<221> NAME/KEY: VARIANT
<222> LOCATION: (55)...(65)
<223> OTHER INFORMATION: BMP-7, wild-type

<400> SEQUENCE: 288

Asp Trp Ile Ile Ala Pro Glu Gly Tyr Ala Ala
1               5                   10

<210> SEQ ID NO 289
<211> LENGTH: 11
<212> TYPE: PRT
<213> ORGANISM: Artificial Sequence
<220> FEATURE:
<223> OTHER INFORMATION: BMP-7 variant

<400> SEQUENCE: 289

Asp Trp Ile Ile Ala Pro Thr Gly Tyr Ala Ala
1               5                   10

<210> SEQ ID NO 290
<211> LENGTH: 11
<212> TYPE: PRT
<213> ORGANISM: Artificial Sequence
<220> FEATURE:
<223> OTHER INFORMATION: BMP-7 variant

<400> SEQUENCE: 290

```
Asp Trp Ile Ile Ala Pro Thr Ile Asn Thr Ala
 1               5                   10

<210> SEQ ID NO 291
<211> LENGTH: 11
<212> TYPE: PRT
<213> ORGANISM: Artificial Sequence
<220> FEATURE:
<223> OTHER INFORMATION: BMP-7 variant

<400> SEQUENCE: 291

Asp Trp Ile Ile Ala Pro Thr Thr Val Ser Ala
 1               5                   10

<210> SEQ ID NO 292
<211> LENGTH: 8
<212> TYPE: PRT
<213> ORGANISM: homo sapiens
<220> FEATURE:
<221> NAME/KEY: VARIANT
<222> LOCATION: (73)...(80)
<223> OTHER INFORMATION: BMP-7, wild-type

<400> SEQUENCE: 292

Ala Phe Pro Leu Asn Ser Tyr Met
 1               5

<210> SEQ ID NO 293
<211> LENGTH: 8
<212> TYPE: PRT
<213> ORGANISM: Artificial Sequence
<220> FEATURE:
<223> OTHER INFORMATION: BMP-7 variant

<400> SEQUENCE: 293

Ala Phe Pro Thr Asn Ser Tyr Met
 1               5

<210> SEQ ID NO 294
<211> LENGTH: 8
<212> TYPE: PRT
<213> ORGANISM: Artificial Sequence
<220> FEATURE:
<223> OTHER INFORMATION: BMP-7 variant

<400> SEQUENCE: 294

Ala Phe Pro Thr Ile Asn Thr Met
 1               5

<210> SEQ ID NO 295
<211> LENGTH: 8
<212> TYPE: PRT
<213> ORGANISM: Artificial Sequence
<220> FEATURE:
<223> OTHER INFORMATION: BMP-7 variant

<400> SEQUENCE: 295

Ala Phe Pro Thr Thr Val Ser Met
 1               5

<210> SEQ ID NO 296
<211> LENGTH: 8
<212> TYPE: PRT
<213> ORGANISM: Artificial Sequence
<220> FEATURE:
<223> OTHER INFORMATION: BMP-7 variant
```

```
<400> SEQUENCE: 296

Ala Ser Pro Thr Ile Asn Thr Met
1               5

<210> SEQ ID NO 297
<211> LENGTH: 11
<212> TYPE: PRT
<213> ORGANISM: homo sapiens
<220> FEATURE:
<221> NAME/KEY: VARIANT
<222> LOCATION: (75)...(85)
<223> OTHER INFORMATION: BMP-7, wild-type

<400> SEQUENCE: 297

Pro Leu Asn Ser Tyr Met Asn Ala Thr Asn His
1               5                   10

<210> SEQ ID NO 298
<211> LENGTH: 11
<212> TYPE: PRT
<213> ORGANISM: Artificial Sequence
<220> FEATURE:
<223> OTHER INFORMATION: BMP-7 variant

<400> SEQUENCE: 298

Pro Thr Gln Ala Pro Met Asn Ala Thr Asn His
1               5                   10

<210> SEQ ID NO 299
<211> LENGTH: 11
<212> TYPE: PRT
<213> ORGANISM: Artificial Sequence
<220> FEATURE:
<223> OTHER INFORMATION: BMP-7 variant

<400> SEQUENCE: 299

Pro Thr Ile Asn Thr Pro Asn Ala Thr Asn His
1               5                   10

<210> SEQ ID NO 300
<211> LENGTH: 11
<212> TYPE: PRT
<213> ORGANISM: Artificial Sequence
<220> FEATURE:
<223> OTHER INFORMATION: BMP-7 variant

<400> SEQUENCE: 300

Pro Thr Thr Val Ser Pro Asn Ala Thr Asn His
1               5                   10

<210> SEQ ID NO 301
<211> LENGTH: 11
<212> TYPE: PRT
<213> ORGANISM: Artificial Sequence
<220> FEATURE:
<223> OTHER INFORMATION: BMP-7 variant

<400> SEQUENCE: 301

Pro Thr Glu Ile Pro Met Asn Ala Thr Asn His
1               5                   10

<210> SEQ ID NO 302
<211> LENGTH: 11
<212> TYPE: PRT
<213> ORGANISM: Artificial Sequence
<220> FEATURE:
<223> OTHER INFORMATION: BMP-7 variant
```

```
<400> SEQUENCE: 302

Pro Leu Asn Ser Tyr Pro Thr Ala Thr Asn His
1               5                   10

<210> SEQ ID NO 303
<211> LENGTH: 11
<212> TYPE: PRT
<213> ORGANISM: Artificial Sequence
<220> FEATURE:
<223> OTHER INFORMATION: BMP-7 variant

<400> SEQUENCE: 303

Pro Leu Asn Ser Ser Pro Thr Ile Asn Thr His
1               5                   10

<210> SEQ ID NO 304
<211> LENGTH: 11
<212> TYPE: PRT
<213> ORGANISM: Artificial Sequence
<220> FEATURE:
<223> OTHER INFORMATION: BMP-7 variant

<400> SEQUENCE: 304

Pro Leu Asn Ser Pro Thr Ile Asn Thr Asn His
1               5                   10

<210> SEQ ID NO 305
<211> LENGTH: 11
<212> TYPE: PRT
<213> ORGANISM: Artificial Sequence
<220> FEATURE:
<223> OTHER INFORMATION: BMP-7 variant

<400> SEQUENCE: 305

Pro Leu Asn Ser Pro Thr Thr Val Ser Asn His
1               5                   10

<210> SEQ ID NO 306
<211> LENGTH: 9
<212> TYPE: PRT
<213> ORGANISM: homo sapiens
<220> FEATURE:
<221> NAME/KEY: VARIANT
<222> LOCATION: (117)...(125)
<223> OTHER INFORMATION: BMP-7, wild-type

<400> SEQUENCE: 306

Tyr Phe Asp Asp Ser Ser Asn Val Ile
1               5

<210> SEQ ID NO 307
<211> LENGTH: 9
<212> TYPE: PRT
<213> ORGANISM: Artificial Sequence
<220> FEATURE:
<223> OTHER INFORMATION: BMP-7 variant

<400> SEQUENCE: 307

Tyr Phe Asp Pro Ser Ser Asn Val Ile
1               5

<210> SEQ ID NO 308
<211> LENGTH: 9
<212> TYPE: PRT
<213> ORGANISM: Artificial Sequence
<220> FEATURE:
```

<223> OTHER INFORMATION: BMP-7 variant

<400> SEQUENCE: 308

Tyr Phe Asp Pro Thr Thr Val Ser Ile
1               5

<210> SEQ ID NO 309
<211> LENGTH: 9
<212> TYPE: PRT
<213> ORGANISM: Artificial Sequence
<220> FEATURE:
<223> OTHER INFORMATION: BMP-7 variant

<400> SEQUENCE: 309

Tyr Phe Ser Pro Thr Thr Val Ser Ile
1               5

<210> SEQ ID NO 310
<211> LENGTH: 14
<212> TYPE: PRT
<213> ORGANISM: homo sapiens
<220> FEATURE:
<221> NAME/KEY: VARIANT
<222> LOCATION: (72)...(85)
<223> OTHER INFORMATION: BMP-7, wild-type partial sequence

<400> SEQUENCE: 310

Cys Ala Phe Pro Leu Asn Ser Tyr Met Asn Ala Thr His Ala
1               5                   10

<210> SEQ ID NO 311
<211> LENGTH: 14
<212> TYPE: PRT
<213> ORGANISM: Artificial Sequence
<220> FEATURE:
<223> OTHER INFORMATION: BMP-7 variant

<400> SEQUENCE: 311

Cys Ala Pro Thr Pro Asn Ser Tyr Met Asn Ala Thr His Ala
1               5                   10

<210> SEQ ID NO 312
<211> LENGTH: 14
<212> TYPE: PRT
<213> ORGANISM: Artificial Sequence
<220> FEATURE:
<223> OTHER INFORMATION: BMP-7 variant

<400> SEQUENCE: 312

Cys Ala Phe Pro Thr Pro Ser Tyr Met Asn Ala Thr His Ala
1               5                   10

<210> SEQ ID NO 313
<211> LENGTH: 14
<212> TYPE: PRT
<213> ORGANISM: Artificial Sequence
<220> FEATURE:
<223> OTHER INFORMATION: BMP-7 variant

<400> SEQUENCE: 313

Cys Ala Phe Pro Pro Thr Pro Tyr Met Asn Ala Thr His Ala
1               5                   10

<210> SEQ ID NO 314
<211> LENGTH: 14
<212> TYPE: PRT
<213> ORGANISM: Artificial Sequence

```
<220> FEATURE:
<223> OTHER INFORMATION: BMP-7 variant

<400> SEQUENCE: 314

Cys Ala Phe Pro Leu Pro Thr Pro Met Asn Ala Thr His Ala
1               5                  10

<210> SEQ ID NO 315
<211> LENGTH: 14
<212> TYPE: PRT
<213> ORGANISM: Artificial Sequence
<220> FEATURE:
<223> OTHER INFORMATION: BMP-7 variant

<400> SEQUENCE: 315

Cys Ala Phe Pro Leu Asn Pro Thr Pro Asn Ala Thr His Ala
1               5                  10

<210> SEQ ID NO 316
<211> LENGTH: 14
<212> TYPE: PRT
<213> ORGANISM: Artificial Sequence
<220> FEATURE:
<223> OTHER INFORMATION: BMP-7 variant

<400> SEQUENCE: 316

Cys Ala Phe Pro Leu Asn Ser Pro Thr Pro Ala Thr His Ala
1               5                  10

<210> SEQ ID NO 317
<211> LENGTH: 14
<212> TYPE: PRT
<213> ORGANISM: Artificial Sequence
<220> FEATURE:
<223> OTHER INFORMATION: BMP-7 variant

<400> SEQUENCE: 317

Cys Ala Phe Pro Leu Asn Ser Tyr Pro Thr Pro Thr His Ala
1               5                  10

<210> SEQ ID NO 318
<211> LENGTH: 14
<212> TYPE: PRT
<213> ORGANISM: Artificial Sequence
<220> FEATURE:
<223> OTHER INFORMATION: BMP-7 variant

<400> SEQUENCE: 318

Cys Ala Phe Pro Leu Asn Ser Tyr Met Pro Thr Pro His Ala
1               5                  10

<210> SEQ ID NO 319
<211> LENGTH: 14
<212> TYPE: PRT
<213> ORGANISM: Artificial Sequence
<220> FEATURE:
<223> OTHER INFORMATION: BMP-7 variant

<400> SEQUENCE: 319

Cys Ala Phe Pro Leu Asn Ser Tyr Met Asn Pro Thr Pro Ala
1               5                  10

<210> SEQ ID NO 320
<211> LENGTH: 14
<212> TYPE: PRT
<213> ORGANISM: Artificial Sequence
<220> FEATURE:
```

<223> OTHER INFORMATION: BMP-7 variant

<400> SEQUENCE: 320

Cys Ala Phe Pro Leu Asn Ser Tyr Met Asn Ala Pro Thr Pro
1               5                   10

<210> SEQ ID NO 321
<211> LENGTH: 14
<212> TYPE: PRT
<213> ORGANISM: Artificial Sequence
<220> FEATURE:
<223> OTHER INFORMATION: BMP-7 variant

<400> SEQUENCE: 321

Cys Ala Pro Thr Ile Asn Thr Tyr Met Asn Ala Thr His Ala
1               5                   10

<210> SEQ ID NO 322
<211> LENGTH: 14
<212> TYPE: PRT
<213> ORGANISM: Artificial Sequence
<220> FEATURE:
<223> OTHER INFORMATION: BMP-7 variant

<400> SEQUENCE: 322

Cys Ala Phe Pro Thr Ile Asn Thr Met Asn Ala Thr His Ala
1               5                   10

<210> SEQ ID NO 323
<211> LENGTH: 14
<212> TYPE: PRT
<213> ORGANISM: Artificial Sequence
<220> FEATURE:
<223> OTHER INFORMATION: BMP-7 variant

<400> SEQUENCE: 323

Cys Ala Phe Pro Pro Thr Ile Asn Thr Asn Ala Thr His Ala
1               5                   10

<210> SEQ ID NO 324
<211> LENGTH: 14
<212> TYPE: PRT
<213> ORGANISM: Artificial Sequence
<220> FEATURE:
<223> OTHER INFORMATION: BMP-7 variant

<400> SEQUENCE: 324

Cys Ala Phe Pro Leu Pro Thr Ile Asn Thr Ala Thr His Ala
1               5                   10

<210> SEQ ID NO 325
<211> LENGTH: 14
<212> TYPE: PRT
<213> ORGANISM: Artificial Sequence
<220> FEATURE:
<223> OTHER INFORMATION: BMP-7 variant

<400> SEQUENCE: 325

Cys Ala Phe Pro Leu Asn Pro Thr Ile Asn Thr Thr His Ala
1               5                   10

<210> SEQ ID NO 326
<211> LENGTH: 14
<212> TYPE: PRT
<213> ORGANISM: Artificial Sequence
<220> FEATURE:
<223> OTHER INFORMATION: BMP-7 variant

```
<400> SEQUENCE: 326

Cys Ala Phe Pro Leu Asn Ser Pro Thr Ile Asn Thr His Ala
1               5                   10

<210> SEQ ID NO 327
<211> LENGTH: 14
<212> TYPE: PRT
<213> ORGANISM: Artificial Sequence
<220> FEATURE:
<223> OTHER INFORMATION: BMP-7 variant

<400> SEQUENCE: 327

Cys Ala Phe Pro Leu Asn Ser Tyr Pro Thr Ile Asn Thr Ala
1               5                   10

<210> SEQ ID NO 328
<211> LENGTH: 14
<212> TYPE: PRT
<213> ORGANISM: Artificial Sequence
<220> FEATURE:
<223> OTHER INFORMATION: BMP-7 variant

<400> SEQUENCE: 328

Cys Ala Phe Pro Leu Asn Ser Tyr Met Pro Thr Ile Asn Thr
1               5                   10

<210> SEQ ID NO 329
<211> LENGTH: 10
<212> TYPE: PRT
<213> ORGANISM: homo sapiens
<220> FEATURE:
<221> NAME/KEY: VARIANT
<222> LOCATION: (96)...(105)
<223> OTHER INFORMATION: BMP-7, wild-typ partial sequence

<400> SEQUENCE: 329

Asn Pro Glu Thr Val Pro Lys Pro Cys Cys
1               5                   10

<210> SEQ ID NO 330
<211> LENGTH: 10
<212> TYPE: PRT
<213> ORGANISM: Artificial Sequence
<220> FEATURE:
<223> OTHER INFORMATION: BMP-7 variant

<400> SEQUENCE: 330

Pro Thr Pro Thr Val Pro Lys Pro Cys Cys
1               5                   10

<210> SEQ ID NO 331
<211> LENGTH: 10
<212> TYPE: PRT
<213> ORGANISM: Artificial Sequence
<220> FEATURE:
<223> OTHER INFORMATION: BMP-7 variant

<400> SEQUENCE: 331

Asn Pro Thr Pro Val Pro Lys Pro Cys Cys
1               5                   10

<210> SEQ ID NO 332
<211> LENGTH: 10
<212> TYPE: PRT
<213> ORGANISM: Artificial Sequence
<220> FEATURE:
```

<223> OTHER INFORMATION: BMP-7 variant

<400> SEQUENCE: 332

Asn Pro Pro Thr Pro Pro Lys Pro Cys Cys
1               5                   10

<210> SEQ ID NO 333
<211> LENGTH: 10
<212> TYPE: PRT
<213> ORGANISM: Artificial Sequence
<220> FEATURE:
<223> OTHER INFORMATION: BMP-7 variant

<400> SEQUENCE: 333

Asn Pro Glu Pro Thr Pro Lys Pro Cys Cys
1               5                   10

<210> SEQ ID NO 334
<211> LENGTH: 10
<212> TYPE: PRT
<213> ORGANISM: Artificial Sequence
<220> FEATURE:
<223> OTHER INFORMATION: BMP-7 variant

<400> SEQUENCE: 334

Asn Pro Glu Thr Pro Thr Pro Pro Cys Cys
1               5                   10

<210> SEQ ID NO 335
<211> LENGTH: 10
<212> TYPE: PRT
<213> ORGANISM: Artificial Sequence
<220> FEATURE:
<223> OTHER INFORMATION: BMP-7 variant

<400> SEQUENCE: 335

Asn Pro Glu Thr Val Pro Thr Pro Cys Cys
1               5                   10

<210> SEQ ID NO 336
<211> LENGTH: 10
<212> TYPE: PRT
<213> ORGANISM: Artificial Sequence
<220> FEATURE:
<223> OTHER INFORMATION: BMP-7 variant

<400> SEQUENCE: 336

Pro Thr Ile Asn Thr Pro Lys Pro Cys Cys
1               5                   10

<210> SEQ ID NO 337
<211> LENGTH: 10
<212> TYPE: PRT
<213> ORGANISM: Artificial Sequence
<220> FEATURE:
<223> OTHER INFORMATION: BMP-7 variant

<400> SEQUENCE: 337

Asn Pro Thr Ile Asn Thr Lys Pro Cys Cys
1               5                   10

<210> SEQ ID NO 338
<211> LENGTH: 10
<212> TYPE: PRT
<213> ORGANISM: Artificial Sequence
<220> FEATURE:
<223> OTHER INFORMATION: BMP-7 variant

<400> SEQUENCE: 338

Asn Pro Pro Thr Ile Asn Thr Pro Cys Cys
1               5                   10

<210> SEQ ID NO 339
<211> LENGTH: 10
<212> TYPE: PRT
<213> ORGANISM: Artificial Sequence
<220> FEATURE:
<223> OTHER INFORMATION: BMP-7 variant

<400> SEQUENCE: 339

Asn Pro Glu Pro Thr Ile Asn Thr Cys Cys
1               5                   10

<210> SEQ ID NO 340
<211> LENGTH: 120
<212> TYPE: PRT
<213> ORGANISM: homo sapiens
<220> FEATURE:
<221> NAME/KEY: VARIANT
<222> LOCATION: (1)...(120)
<223> OTHER INFORMATION: human NT-3, wild-type

<400> SEQUENCE: 340

Met Tyr Ala Glu His Lys Ser His Arg Gly Glu Tyr Ser Val Cys Asp
1               5                   10                  15

Ser Glu Ser Leu Trp Val Thr Asp Lys Ser Ser Ala Ile Asp Ile Arg
            20                  25                  30

Gly His Gln Val Thr Val Leu Gly Glu Ile Lys Thr Gly Asn Ser Pro
        35                  40                  45

Val Lys Gln Tyr Phe Tyr Glu Thr Arg Cys Lys Glu Ala Arg Pro Val
    50                  55                  60

Lys Asn Gly Cys Arg Gly Ile Asp Asp Lys His Trp Asn Ser Gln Cys
65                  70                  75                  80

Lys Thr Ser Gln Thr Tyr Val Arg Ala Leu Thr Ser Glu Asn Asn Lys
                85                  90                  95

Leu Val Gly Trp Arg Trp Ile Arg Ile Asp Thr Ser Cys Val Cys Ala
            100                 105                 110

Leu Ser Arg Lys Ile Gly Arg Thr
        115                 120

<210> SEQ ID NO 341
<211> LENGTH: 9
<212> TYPE: PRT
<213> ORGANISM: homo sapiens
<220> FEATURE:
<221> NAME/KEY: VARIANT
<222> LOCATION: (1)...(9)
<223> OTHER INFORMATION: human NT-3, wild-type partial sequence

<400> SEQUENCE: 341

Met Tyr Ala Glu His Lys Ser His Arg
1               5

<210> SEQ ID NO 342
<211> LENGTH: 10
<212> TYPE: PRT
<213> ORGANISM: Artificial Sequence
<220> FEATURE:
<223> OTHER INFORMATION: NT-3 variant

<400> SEQUENCE: 342

```
Met Phe Pro Thr Glu Ile Pro Leu Ser Arg
 1               5                  10

<210> SEQ ID NO 343
<211> LENGTH: 10
<212> TYPE: PRT
<213> ORGANISM: Artificial Sequence
<220> FEATURE:
<223> OTHER INFORMATION: NT-3 variant

<400> SEQUENCE: 343

Met Phe Pro Thr Glu Ile Pro Ser His Arg
 1               5                  10

<210> SEQ ID NO 344
<211> LENGTH: 9
<212> TYPE: PRT
<213> ORGANISM: homo sapiens
<220> FEATURE:
<221> NAME/KEY: VARIANT
<222> LOCATION: (22)...(30)
<223> OTHER INFORMATION: NT-3, wild-type partial sequence

<400> SEQUENCE: 344

Val Thr Asp Lys Ser Ser Ala Ile Asp
 1               5

<210> SEQ ID NO 345
<211> LENGTH: 9
<212> TYPE: PRT
<213> ORGANISM: Artificial Sequence
<220> FEATURE:
<223> OTHER INFORMATION: NT-3 variant

<400> SEQUENCE: 345

Val Thr Asp Pro Thr Ile Asn Thr Asp
 1               5

<210> SEQ ID NO 346
<211> LENGTH: 9
<212> TYPE: PRT
<213> ORGANISM: Artificial Sequence
<220> FEATURE:
<223> OTHER INFORMATION: NT-3 variant

<400> SEQUENCE: 346

Val Thr Asp Pro Thr Thr Val Ser Asp
 1               5

<210> SEQ ID NO 347
<211> LENGTH: 9
<212> TYPE: PRT
<213> ORGANISM: Artificial Sequence
<220> FEATURE:
<223> OTHER INFORMATION: NT-3 variant

<400> SEQUENCE: 347

Val Thr Pro Thr Thr Val Ser Ile Asp
 1               5

<210> SEQ ID NO 348
<211> LENGTH: 10
<212> TYPE: PRT
<213> ORGANISM: homo sapiens
<220> FEATURE:
<221> NAME/KEY: VARIANT
<222> LOCATION: (45)...(54)
```

```
<223> OTHER INFORMATION: NT-3, wild-type partial sequence

<400> SEQUENCE: 348

Gly Asn Ser Pro Val Lys Gln Tyr Phe Tyr
1               5                   10

<210> SEQ ID NO 349
<211> LENGTH: 10
<212> TYPE: PRT
<213> ORGANISM: Artificial Sequence
<220> FEATURE:
<223> OTHER INFORMATION: NT-3 variant

<400> SEQUENCE: 349

Gly Asn Ser Pro Thr Thr Val Ser Phe Tyr
1               5                   10

<210> SEQ ID NO 350
<211> LENGTH: 10
<212> TYPE: PRT
<213> ORGANISM: Artificial Sequence
<220> FEATURE:
<223> OTHER INFORMATION: NT-3 variant

<400> SEQUENCE: 350

Gly Asn Ser Pro Thr Ile Asn Thr Phe Tyr
1               5                   10

<210> SEQ ID NO 351
<211> LENGTH: 10
<212> TYPE: PRT
<213> ORGANISM: Artificial Sequence
<220> FEATURE:
<223> OTHER INFORMATION: NT-3 variant

<400> SEQUENCE: 351

Gly Asn Ala Pro Thr Ile Asn Thr Phe Tyr
1               5                   10

<210> SEQ ID NO 352
<211> LENGTH: 9
<212> TYPE: PRT
<213> ORGANISM: homo sapiens
<220> FEATURE:
<221> NAME/KEY: VARIANT
<222> LOCATION: (91)...(99)
<223> OTHER INFORMATION: NT-3, wild-type partial sequence

<400> SEQUENCE: 352

Thr Ser Glu Asn Asn Lys Leu Val Gly
1               5

<210> SEQ ID NO 353
<211> LENGTH: 9
<212> TYPE: PRT
<213> ORGANISM: Artificial Sequence
<220> FEATURE:
<223> OTHER INFORMATION: NT-3 variant

<400> SEQUENCE: 353

Thr Ser Pro Thr Ile Asn Thr Val Gly
1               5

<210> SEQ ID NO 354
<211> LENGTH: 9
<212> TYPE: PRT
<213> ORGANISM: Artificial Sequence
```

```
<220> FEATURE:
<223> OTHER INFORMATION: NT-3 variant

<400> SEQUENCE: 354

Thr Ala Pro Thr Ile Asn Thr Val Gly
 1               5

<210> SEQ ID NO 355
<211> LENGTH: 9
<212> TYPE: PRT
<213> ORGANISM: Artificial Sequence
<220> FEATURE:
<223> OTHER INFORMATION: NT-3 variant

<400> SEQUENCE: 355

Thr Ser Pro Thr Thr Val Ser Val Gly
 1               5

<210> SEQ ID NO 356
<211> LENGTH: 9
<212> TYPE: PRT
<213> ORGANISM: Artificial Sequence
<220> FEATURE:
<223> OTHER INFORMATION: NT-3 variant

<400> SEQUENCE: 356

Thr Ala Pro Thr Thr Val Ser Val Gly
 1               5

<210> SEQ ID NO 357
<211> LENGTH: 9
<212> TYPE: PRT
<213> ORGANISM: Artificial Sequence
<220> FEATURE:
<223> OTHER INFORMATION: NT-3 variant

<400> SEQUENCE: 357

Thr Ser Pro Thr Gln Gly Ala Val Gly
 1               5

<210> SEQ ID NO 358
<211> LENGTH: 9
<212> TYPE: PRT
<213> ORGANISM: Artificial Sequence
<220> FEATURE:
<223> OTHER INFORMATION: NT-3 variant

<400> SEQUENCE: 358

Thr Ala Pro Thr Gln Gly Ala Val Gly
 1               5

<210> SEQ ID NO 359
<211> LENGTH: 9
<212> TYPE: PRT
<213> ORGANISM: Artificial Sequence
<220> FEATURE:
<223> OTHER INFORMATION: NT-3 variant

<400> SEQUENCE: 359

Thr Ser Glu Pro Thr Ile Asn Thr Gly
 1               5

<210> SEQ ID NO 360
<211> LENGTH: 9
<212> TYPE: PRT
<213> ORGANISM: Artificial Sequence
<220> FEATURE:
```

```
<223> OTHER INFORMATION: NT-3 variant

<400> SEQUENCE: 360

Thr Ser Glu Pro Thr Thr Val Ser Gly
  1               5

<210> SEQ ID NO 361
<211> LENGTH: 182
<212> TYPE: PRT
<213> ORGANISM: homo sapiens
<220> FEATURE:
<221> NAME/KEY: VARIANT
<222> LOCATION: (1)...(182)
<223> OTHER INFORMATION: human FGF-21, wild-type

<400> SEQUENCE: 361

Met His Pro Ile Pro Asp Ser Ser Pro Leu Leu Gln Phe Gly Gly Gln
  1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
         50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 362
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 362

Pro Thr Ser Ser Pro
  1               5

<210> SEQ ID NO 363
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 363

Pro Thr Gln Ala Pro
```

```
1               5

<210> SEQ ID NO 364
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 364

Pro Thr Pro Asp Ser Ser
1               5

<210> SEQ ID NO 365
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 365

Met Phe Pro Thr Pro
1               5

<210> SEQ ID NO 366
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 366

Pro Thr Ser Leu Leu
1               5

<210> SEQ ID NO 367
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 367

Pro Thr Ile Asn Thr
1               5

<210> SEQ ID NO 368
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 368

Pro Thr Val Gly Ser
1               5

<210> SEQ ID NO 369
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 369

Pro Thr Gln Ala Gly
1               5
```

```
<210> SEQ ID NO 370
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 370

Ala Pro Thr Val
 1

<210> SEQ ID NO 371
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 371

Ala Pro Thr Ser Val Gly
 1               5

<210> SEQ ID NO 372
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 372

Ala Pro Thr Ile Asn Thr
 1               5

<210> SEQ ID NO 373
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 373

Ser Pro Thr Ile Asn Thr
 1               5

<210> SEQ ID NO 374
<211> LENGTH: 3
<212> TYPE: PRT
<213> ORGANISM: Artificial Sequence
<220> FEATURE:
<223> OTHER INFORMATION: human FGF-21 variant

<400> SEQUENCE: 374

Ser Pro Thr
 1

<210> SEQ ID NO 375
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 375

Ala Pro Thr Gln
 1
```

```
<210> SEQ ID NO 376
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 376

Ala Pro Thr Ile Asn Thr
 1               5

<210> SEQ ID NO 377
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 377

Pro Thr Gln Ala Pro
 1               5

<210> SEQ ID NO 378
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 378

Thr Pro Thr Glu Ile
 1               5

<210> SEQ ID NO 379
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 379

Pro Thr Ile Asn Thr
 1               5

<210> SEQ ID NO 380
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 380

Pro Thr Ser Val Gly
 1               5

<210> SEQ ID NO 381
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 381

Pro Thr Glu Thr
 1
```

```
<210> SEQ ID NO 382
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 382

Pro Thr Gln Ala
  1

<210> SEQ ID NO 383
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 383

Pro Thr Glu Ile
  1

<210> SEQ ID NO 384
<211> LENGTH: 2
<212> TYPE: PRT
<213> ORGANISM: Artificial Sequence
<220> FEATURE:
<223> OTHER INFORMATION: human FGF-21 variant

<400> SEQUENCE: 384

Pro Thr
  1

<210> SEQ ID NO 385
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 385

Ala Asp Pro Thr Pro Ala
  1               5

<210> SEQ ID NO 386
<211> LENGTH: 8
<212> TYPE: PRT
<213> ORGANISM: Artificial Sequence
<220> FEATURE:
<223> OTHER INFORMATION: human FGF-21 variant

<400> SEQUENCE: 386

Pro Arg Gly Pro Thr Ile Asn Thr
  1               5

<210> SEQ ID NO 387
<211> LENGTH: 8
<212> TYPE: PRT
<213> ORGANISM: Artificial Sequence
<220> FEATURE:
<223> OTHER INFORMATION: human FGF-21 variant

<400> SEQUENCE: 387

Pro Arg Gly Pro Thr Ser Val Gly
  1               5

<210> SEQ ID NO 388
```

```
<211> LENGTH: 8
<212> TYPE: PRT
<213> ORGANISM: Artificial Sequence
<220> FEATURE:
<223> OTHER INFORMATION: human FGF-21 variant

<400> SEQUENCE: 388

Pro Ala Gly Pro Thr Ile Asn Thr
 1               5

<210> SEQ ID NO 389
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 389

Pro Thr Pro Gly
 1

<210> SEQ ID NO 390
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 390

Pro Thr Pro Pro Gly
 1               5

<210> SEQ ID NO 391
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 391

Pro Thr Ile Asn Ala Pro
 1               5

<210> SEQ ID NO 392
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 392

Pro Thr Ile Asn Thr Pro
 1               5

<210> SEQ ID NO 393
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 393

Pro Thr Thr Val
 1

<210> SEQ ID NO 394
<211> LENGTH: 5
```

```
<212> TYPE: PRT
<213> ORGANISM: Artificial Sequence
<220> FEATURE:
<223> OTHER INFORMATION: human FGF-21 variant

<400> SEQUENCE: 394

Pro Thr Thr Val Ser
 1               5

<210> SEQ ID NO 395
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 395

Pro Thr Pro Pro Asp
 1               5

<210> SEQ ID NO 396
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 396

Pro Thr Val Gly Ser Ser
 1               5

<210> SEQ ID NO 397
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 397

Pro Thr Ile Asn Thr
 1               5

<210> SEQ ID NO 398
<211> LENGTH: 4
<212> TYPE: PRT
<213> ORGANISM: Artificial Sequence
<220> FEATURE:
<223> OTHER INFORMATION: human FGF-21 variant

<400> SEQUENCE: 398

Thr Glu Thr Pro
 1

<210> SEQ ID NO 399
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 399

Pro Thr Ser Met Val
 1               5

<210> SEQ ID NO 400
<211> LENGTH: 5
<212> TYPE: PRT
```

<213> ORGANISM: Artificial Sequence
<220> FEATURE:
<223> OTHER INFORMATION: human FGF-21 variant

<400> SEQUENCE: 400

Pro Thr Ser Val Gly
 1               5

<210> SEQ ID NO 401
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 401

Pro Thr Gln Gly Ala Met
 1               5

<210> SEQ ID NO 402
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 402

Pro Thr Gln Gly Ala Ser
 1               5

<210> SEQ ID NO 403
<211> LENGTH: 6
<212> TYPE: PRT
<213> ORGANISM: Artificial Sequence
<220> FEATURE:
<223> OTHER INFORMATION: human FGF-21 variant

<400> SEQUENCE: 403

Pro Thr Gln Gly Ala Met
 1               5

<210> SEQ ID NO 404
<211> LENGTH: 3
<212> TYPE: PRT
<213> ORGANISM: Artificial Sequence
<220> FEATURE:
<223> OTHER INFORMATION: human FGF-21 variant

<400> SEQUENCE: 404

Pro Thr Gln
 1

<210> SEQ ID NO 405
<211> LENGTH: 5
<212> TYPE: PRT
<213> ORGANISM: Artificial Sequence
<220> FEATURE:
<223> OTHER INFORMATION: human FGF-21 variant

<400> SEQUENCE: 405

Pro Thr Ile Asn Thr
 1               5

<210> SEQ ID NO 406
<211> LENGTH: 9
<212> TYPE: PRT
<213> ORGANISM: Artificial Sequence

```
<220> FEATURE:
<223> OTHER INFORMATION: O-linked Glycosylation Sequence

<400> SEQUENCE: 406

Met Val Thr Pro Thr Pro Thr Pro Thr
1               5

<210> SEQ ID NO 407
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 3
<223> OTHER INFORMATION: Xaa = ser or thr
<220> FEATURE:
<223> OTHER INFORMATION: O-Linked Glycosylation Sequence

<400> SEQUENCE: 407

Xaa Pro Xaa Glu Ile
1               5

<210> SEQ ID NO 408
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid
<220> FEATURE:
<221> NAME/KEY: VARIANT
<222> LOCATION: 4
<223> OTHER INFORMATION: Xaa = ser or thr
<220> FEATURE:
<223> OTHER INFORMATION: O-Linked Glycosylation Sequence

<400> SEQUENCE: 408

Xaa Thr Glu Xaa Pro
1               5

<210> SEQ ID NO 409
<211> LENGTH: 4
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = glu, gln, asp, asn, thr, ser, or any
      uncharged amino acid, and can be either present or
      absent
<220> FEATURE:
<221> NAME/KEY: VARIANT
<222> LOCATION: 4
<223> OTHER INFORMATION: pro can be either present or absent
<220> FEATURE:
<223> OTHER INFORMATION: O-Linked Glycosylation Sequence

<400> SEQUENCE: 409

Xaa Pro Thr Pro
1

<210> SEQ ID NO 410
<211> LENGTH: 4
```

```
<212> TYPE: PRT
<213> ORGANISM: Artificial Sequence
<220> FEATURE:
<223> OTHER INFORMATION: O-Linked Glycosylation Sequence

<400> SEQUENCE: 410

Pro Thr Gln Gly
 1

<210> SEQ ID NO 411
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 411

Pro Thr Gln Ala Tyr
 1               5

<210> SEQ ID NO 412
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 412

Pro Thr Thr Leu Tyr
 1               5

<210> SEQ ID NO 413
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 413

Pro Thr Gly Ser Leu Pro
 1               5

<210> SEQ ID NO 414
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 414

Pro Thr Thr Ser Glu Pro
 1               5

<210> SEQ ID NO 415
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 415

Pro Thr Ala Val Ile Pro
 1               5

<210> SEQ ID NO 416
<211> LENGTH: 6
<212> TYPE: PRT
```

```
<213> ORGANISM: Artificial Sequence
<220> FEATURE:
<223> OTHER INFORMATION: O-Linked Glycosylation Sequence

<400> SEQUENCE: 416

Pro Thr Ser Gly Glu Pro
 1               5

<210> SEQ ID NO 417
<211> LENGTH: 6
<212> TYPE: PRT
<213> ORGANISM: Artificial Sequence
<220> FEATURE:
<223> OTHER INFORMATION: O-Linked Glycosylation Sequence

<400> SEQUENCE: 417

Pro Thr Thr Leu Tyr Pro
 1               5

<210> SEQ ID NO 418
<211> LENGTH: 5
<212> TYPE: PRT
<213> ORGANISM: Artificial Sequence
<220> FEATURE:
<223> OTHER INFORMATION: O-Linked Glycosylation Sequence

<400> SEQUENCE: 418

Pro Thr Glu Val Pro
 1               5

<210> SEQ ID NO 419
<211> LENGTH: 4
<212> TYPE: PRT
<213> ORGANISM: Artificial Sequence
<220> FEATURE:
<223> OTHER INFORMATION: O-Linked Glycosylation Sequence

<400> SEQUENCE: 419

Ala Pro Thr Pro
 1

<210> SEQ ID NO 420
<211> LENGTH: 7
<212> TYPE: PRT
<213> ORGANISM: Artificial Sequence
<220> FEATURE:
<223> OTHER INFORMATION: O-Linked Glycosylation Sequence

<400> SEQUENCE: 420

Pro Thr Ser Ala Val Ala Ala
 1               5

<210> SEQ ID NO 421
<211> LENGTH: 20
<212> TYPE: PRT
<213> ORGANISM: Artificial Sequence
<220> FEATURE:
<223> OTHER INFORMATION: MUC1 O-Linked Glycosylation Sequence

<400> SEQUENCE: 421

His Gly Val Thr Ser Ala Pro Asp Thr Arg Pro Ala Pro Gly Ser Thr
 1               5                  10                  15

Ala Pro Pro Ala
            20

<210> SEQ ID NO 422
```

```
<211> LENGTH: 24
<212> TYPE: PRT
<213> ORGANISM: Artificial Sequence
<220> FEATURE:
<223> OTHER INFORMATION: MUC1 O-Linked Glycosylation Sequence

<400> SEQUENCE: 422

Thr Ala Pro Pro Ala His Gly Val Thr Ser Ala Pro Asp Thr Arg Pro
1               5                   10                  15

Ala Pro Gly Ser Thr Ala Pro Pro
            20

<210> SEQ ID NO 423
<211> LENGTH: 10
<212> TYPE: PRT
<213> ORGANISM: Artificial Sequence
<220> FEATURE:
<221> NAME/KEY: VARIANT
<222> LOCATION: 1
<223> OTHER INFORMATION: Met can be either present or absent
<220> FEATURE:
<223> OTHER INFORMATION: O-Linked Glycosylation Sequence

<400> SEQUENCE: 423

Met Val Thr Pro Thr Pro Thr Pro Thr Cys
1               5                   10
```

GLYCOSYLATION OF PEPTIDES VIA O-LINKED GLYCOSYLATION SEQUENCES

CROSS-REFERENCE TO RELATED APPLICATIONS

The present application claims priority to U.S. Provisional Patent Application No. 60/832,461 filed Jul. 21, 2006, U.S. Provisional Patent Application No. 60/886,616 filed Jan. 25, 2007, U.S. Provisional Patent Application No. 60/941,920 filed Jun. 4, 2007 and U.S. Provisional Patent Application No. 60/881,130 filed Jan. 18, 2007, each of which is incorporated herein by reference in their entirety for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 286,499 bytes ASCII (Text) file named "705749SequenceListing-3rd.txt" created Aug. 11, 2010.

FIELD OF THE INVENTION

The invention pertains to the field of polypeptide modification by glycosylation. In particular, the invention relates to a method of preparing glycosylated polypeptides using short enzyme-recognized O-linked or S-linked glycosylation sequences.

BACKGROUND OF THE INVENTION

The present invention relates to glycosylation and modification of polypeptides, preferably polypeptides of therapeutic value. The administration of glycosylated and non-glycosylated polypeptides for engendering a particular physiological response is well known in the medicinal arts. For example, both purified and recombinant hGH are used for treating conditions and diseases associated with hGH deficiency, e.g., dwarfism in children. Other examples involve interferon, which has known antiviral activity as well as granulocyte colony stimulating factor (G-CSF), which stimulates the production of white blood cells.

The lack of expression systems that can be used to manufacture polypeptides with wild-type glycosylation patterns has limited the use of such polypeptides as therapeutic agents. It is known in the art that improperly or incompletely glycosylated polypeptides can be immunogenic, leading to rapid neutralization of the peptide and/or the development of an allergic response. Other deficiencies of recombinantly produced glycopeptides include suboptimal potency and rapid clearance from the bloodstream.

One approach to solving the problems inherent in the production of glycosylated polypeptide therapeutics has been to modify the polypeptides in vitro after their expression. Post-expression in vitro modification of polypeptides has been used for both the modification of existing glycan structures and the attachment of glycosyl moieties to non-glycosylated amino acid residues. A comprehensive selection of recombinant eukaryotic glycosyltransferases has become available, making in vitro enzymatic synthesis of mammalian glycoconjugates with custom designed glycosylation patterns and glycosyl structures possible. See, for example, U.S. Pat. Nos. 5,876,980; 6,030,815; 5,728,554; 5,922,577; as well as WO/9831826; US2003180835; and WO 03/031464.

In addition, glycopeptides have been derivatized with one or more non-saccharide modifying groups, such as water soluble polymers. An exemplary polymer that has been conjugated to peptides is poly(ethylene glycol) ("PEG"). PEG-conjugation, which increases the molecular size of the polypeptide, has been used to reduce immunogenicity and to prolong the clearance time of PEG-conjugated polypeptides in circulation. For example, U.S. Pat. No. 4,179,337 to Davis et al. discloses non-immunogenic polypeptides such as enzymes and polypeptide-hormones coupled to polyethylene glycol (PEG) or polypropylene glycol (PPG).

The principal method for the attachment of PEG and its derivatives to polypeptides involves non-specific bonding through an amino acid residue (see e.g., U.S. Pat. No. 4,088,538 U.S. Pat. No. 4,496,689, U.S. Pat. No. 4,414,147, U.S. Pat. No. 4,055,635, and PCT WO 87/00056). Another method of PEG-conjugation involves the non-specific oxidation of glycosyl residues of a glycopeptide (see e.g., WO 94/05332).

In these non-specific methods, PEG is added in a random, non-specific manner to reactive residues on a polypeptide backbone. This approach has significant drawbacks, including a lack of homogeneity of the final product, and the possibility of reduced biological or enzymatic activity of the modified polypeptide. Therefore, a derivatization method for therapeutic polypeptides that results in the formation of a specifically labeled, readily characterizable and essentially homogeneous product is highly desirable.

Specifically modified, homogeneous polypeptide therapeutics can be produced in vitro through the use of enzymes. Unlike non-specific methods for attaching a modifying group, such as a synthetic polymer, to a polypeptide, enzyme-based syntheses have the advantages of regioselectivity and stereoselectivity. Two principal classes of enzymes for use in the synthesis of labeled polypeptides are glycosyltransferases (e.g., sialyltransferases, oligosaccharyltransferases, N-acetylglucosaminyltransferases), and glycosidases. These enzymes can be used for the specific attachment of sugars which can subsequently be altered to comprise a modifying group. Alternatively, glycosyltransferases and modified glycosidases can be used to directly transfer modified sugars to a polypeptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic approaches are also known (see e.g., Yamamoto et al., Carbohydr. Res. 305: 415-422 (1998) and U.S. Patent Application Publication 20040137557, which is incorporated herein by reference).

Carbohydrates are attached to glycopeptides in several ways of which N-linked to asparagine and O-linked to serine and threonine are the most relevant for recombinant glycoprotein therapeuctics. O-linked glycosylation is found on secreted and cell surface associated glycoproteins of all eukaryotic cells. There is great diversity in the structures created by O-linked glycosylation. Such glycans are produced by the catalytic activity of hundreds of enzymes (glycosyltransferases) that are resident in the Golgi complex. Diversity exists at the level of the glycan structure and in positions of attachment of O-glycans to the protein backbones. Despite the high degree of potential diversity, it is clear that O-linked glycosylation is a highly regulated process that shows a high degree of conservation among multicellular organisms.

Antibodies are glycosylated at conserved positions in their constant regions (Jefferis and Lund (1997) Chem. Immunol. 65:111-128; Wright and Morrison (1997) TibTECH 15:26-

32). The oligosaccharide side chains of antibodies influence their function (Wittwer & Howard. (1990) Biochem. 29:4175; Boyd et al., (1996) Mol. Immunol. 32:1311) as well as inter- and intra-molecular interactions (Goochee, et al., (1991) Bio/Technology, 9:1347; Parekh, (1991) Curr. Opin. Struct. Biol., 1:750; Hart, (1992) Curr. Opin. Cell Biol., 4:1017; Jefferis & Lund supra; Wyss & Wagner (1996) Curr. Opin. Biotech. 7:409).

For human IgG, the core oligosaccharide usually consists of $GlcNAc_2Man_3$ GlcNAc, with slight differences in the numbers of outer residues. For example, variation among individual IgG occurs via attachment of galactose and/or galactose-sialic acid at the two terminal GlcNAc or via attachment of a third GlcNAc arm (bisecting GlcNAc). Removal of the carbohydrate moiety, either by glycosidase cleavage or mutagenesis, has been found to affect binding to C1q and FcγR and the downstream responses such as complement activation and ADCC. (Leatherbarrow et al. *Molec. Immunol* 22:407-415 (1985); Duncan et al. *Nature* 332:738-740 (1988); Walker et al. *Biochem. J.* 259:347-353 (1989)). When the carbohydrate is present, the nature of the sugar residues can influence the IgG effector functions (Wright et al. *J. Immunol.* 160:3393-3402 (1998)).

Not all polypeptides comprise a glycosylation sequence as part of their amino acid sequence. In addition, existing glycosylation sequences may not be suitable for the attachment of a modifying group. Such modification may, for example, cause an undesirable decrease in biological activity of the modified polypeptide. Thus, there is a need in the art for methods that permit both the precise creation of glycosylation sequences within the amino acid sequence of a polypeptide and the ability to precisely direct the modification to those sites. The current invention addresses these and other needs.

SUMMARY OF THE INVENTION

The present invention describes the discovery that enzymatic glycoconjugation reactions can be specifically targeted to certain O-linked or S-linked glycosylation sequences within a polypeptide. Additional glycosyl residues that optionally contain a modifying group can then be added to the resulting glycoconjugate, either enzymatically or chemically. In one example, the targeted glycosylation sequence is introduced into a parent polypeptide (e.g., wild-type polypeptide) by mutation creating a mutant polypeptide that includes a glycosylation sequence, wherein this glycosylation sequence is not present, or not present at the same position, in the corresponding parent polypeptide (exogenous glycosylation sequence). Such mutant polypeptides are termed herein "sequon polypeptides". Accordingly, the present invention provides sequon polypeptides that include one or more O-linked or S-linked glycosylation sequence. In one embodiment, each glycosylation sequence is a substrate for an enzyme, such as a glycosyltransferase, such as a GalNAc-transferase (e.g., GalNAc-T2). In addition, the present invention provides conjugates between a sequon polypeptide and a modifying group (e.g., a water-soluble polymeric modifying group). The invention further provides methods of making a sequon polypeptide as well as methods of making and using the polypeptide conjugates. The invention further provides pharmaceutical compositions including the polypeptide conjugates of the invention. The invention also provides libraries of sequon polypeptides, wherein each member of such library includes at least one O-linked glycosylation sequence of the invention. Also provided are methods of making and using such libraries.

In a first aspect, the invention provides a covalent conjugate between a glycosylated or non-glycosylated sequon polypeptide and a polymeric modifying group. The sequon polypeptide comprises an exogenous O-linked glycosylation sequence of the invention. The polymeric modifying group is conjugated to the sequon polypeptide at the O-linked glycosylation sequence via a glycosyl linking group, wherein said glycosyl linking group is interposed between and covalently linked to both the sequon polypeptide and the polymeric modifying group. In one embodiment, the parent polypeptide is not human growth hormone (hGH). In another embodiment, the parent polypeptide is not granulocyte colony stimulating factor (G-CSF). In yet another embodiment, the parent polypeptide is not interferon-alpha (INF-alpha). In a further embodiment, the parent polypeptide is not glucagon-like peptide-1 (GLP-1). In another embodiment, the parent polypeptide is not a fibroblast growth factor (FGF).

In a second aspect, the invention provides a polypeptide conjugate including a sequon polypeptide, wherein the sequon polypeptide includes an exogenous O-linked glycosylation sequence. The polypeptide conjugate includes a moiety according to Formula (V), wherein q can be 0 or 1:

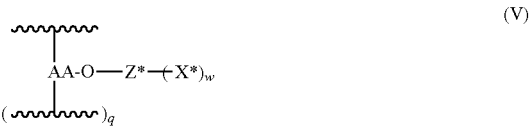

(V)

In Formula (V), w is an integer selected from 0 and 1. AA-O— is a moiety derived from an amino acid having a side chain, which is substituted with a hydroxyl group (e.g., serine or threonine). This amino acid is found within the O-linked glycosylation sequence. When q is 1, then the amino acid is an internal amino acid, and when q is 0, then the amino acid is an N-terminal or C-terminal amino acid. In one embodiment, Z* is a glycosyl moiety. In another embodiment, Z* is a glycosyl linking group. In one embodiment, X* is a polymeric modifying group. In another embodiment, X* is a glycosyl linking group that is covalently linked to a polymeric modifying group. In one embodiment, the parent polypeptide is not human growth hormone (hGH). In another embodiment, the parent polypeptide is not granulocyte colony stimulating factor (G-CSF). In yet another embodiment, the parent polypeptide is not interferon-alpha (INF-alpha). In a further embodiment, the parent polypeptide is not glucagon-like peptide-1 (GLP-1). In another embodiment, the parent polypeptide is not a fibroblast growth factor (FGF).

The invention also provides pharmaceutical compositions including a polypeptide conjugate of the invention and a pharmaceutically acceptable carrier.

In a third aspect, the invention provides a sequon polypeptide that includes an exogenous O-linked glycosylation sequence. In one embodiment, the O-linked glycosylation sequence has an amino acid sequence according to Formula (I). In another embodiment, the O-linked glycosylation sequence has an amino acid sequence according to Formula (II):

$(X)_m$ **P O\* U** $(B)_p (Z)_r (J)_s (O)_t (P)_n;$     (SEQ ID NO: 1) (I)

and $(X)_m (B^1)_p$ T U B $(Z)_r (J)_s (P)_n.$     (SEQ ID NO: 2) (II)

In one embodiment, In Formula (I) and Formula (II), the integer m is 0. In another embodiment, m is 1. In one embodiment, the integer n is 0. In another embodiment, n is 1. In one embodiment, the integer p is 0. In another embodiment, p is 1. In one embodiment, the integer r is 0. In another embodiment, r is 1. In one embodiment, the integer s is 0. In another embodiment, s is 1. In one embodiment, the integer t is 0. In another embodiment, t is 1.

In Formula (I) and Formula (II), P is proline. In one embodiment, O* is serine (S). In another embodiment, O* is threonine (T). In one embodiment, U is proline (P). In another embodiment, U is glutamic acid (E). In yet another embodiment, U is glutamine (Q). In a further embodiment, U is aspartic acid (D). In a related embodiment, U is asparagine (N). In another embodiment, U is threonine (T). In yet another embodiment, U is serine (S). In a further embodiment, U is an uncharged amino acid, such as glycine (G) or alanine (A). X, B and $B^1$ are members independently selected from glutamic acid (E), glutamine (Q), aspartic acid (D), asparagine (N), threonine (T), serine (S) and uncharged amino acids. Z, J and O are members independently selected from glutamic acid (E), glutamine (Q), aspartic acid (D), asparagine (N), threonine (T), serine (S), tyrosine (Y), methionine (M) and uncharged amino acids. In one embodiment, the parent polypeptide is not human growth hormone (hGH). In another embodiment, the parent polypeptide is not granulocyte colony stimulating factor (G-CSF). In yet another embodiment, the parent polypeptide is not interferon-alpha (INF-alpha). In a further embodiment, the parent polypeptide is not glucagon-like peptide-1 (GLP-1). In another embodiment, the parent polypeptide is not a fibroblast growth factor (FGF).

In one embodiment, the O-linked glycosylation sequence is XPO*P (SEQ ID NO: 95). In another embodiment, the O-linked glycosylation sequence is XPO*EI(P)$_n$ (SEQ ID NO: 97). In yet another embodiment, the O-linked glycosylation sequence is (X)$_m$PO*EI (SEQ ID NO: 407). In a further embodiment, the O-linked glycosylation sequence is XPO*QA(P)$_n$ (SEQ ID NO: 96). In one embodiment, the O-linked glycosylation sequence is XPO*TVS (SEQ ID NO: 99). In another embodiment, the O-linked glycosylation sequence is (X)$_m$PO*TVSP (SEQ ID NO: 100). In yet another embodiment, the O-linked glycosylation sequence is XPO*QGA (SEQ ID NO: 101). In a further embodiment, the O-linked glycosylation sequence is (X)$_m$PO*QGAP (SEQ ID NO: 102). In one embodiment, the O-linked glycosylation sequence is XPO*QGAM(P)$_n$ (SEQ ID NO: 103). In another embodiment, the O-linked glycosylation sequence is XTEO*P (SEQ ID NO: 408). In yet another embodiment, the O-linked glycosylation sequence is (X)$_m$PO*VL (SEQ ID NO: 104). In a further embodiment, the O-linked glycosylation sequence is XPO*VL(P)$_n$ (SEQ ID NO: 105). In one embodiment, the O-linked glycosylation sequence is XPO*TVL (SEQ ID NO: 106). In another embodiment, the O-linked glycosylation sequence is (X)$_m$PO*TVLP (SEQ ID NO: 107). In yet another embodiment, the O-linked glycosylation sequence is (X)$_m$PO*TLYVP (SEQ ID NO: 108). In a further embodiment, the O-linked glycosylation sequence is XPO*TLYV(P)$_n$ (SEQ ID NO: 109). In one embodiment, the O-linked glycosylation sequence is (X)$_m$PO*LS(P)$_n$ (SEQ ID NO: 26). In another embodiment, the O-linked glycosylation sequence is (X)$_m$PO*DA(P)$_n$ (SEQ ID NO: 110). In yet another embodiment, the O-linked glycosylation sequence is (X)$_m$PO*EN(P)$_n$ (SEQ ID NO: 28). In a further embodiment, the O-linked glycosylation sequence is (X)$_m$PO*QD(P)$_n$ (SEQ ID NO: 30). In one embodiment, the O-linked glycosylation sequence is (X)$_m$PO*AS(P)$_n$ (SEQ ID NO: 31). In another embodiment, the O-linked glycosylation sequence is XPO*SAV (SEQ ID NO: 113). In yet another embodiment, the O-linked glycosylation sequence is (X)$_m$PO*SAVP (SEQ ID NO: 114). In a further embodiment, the O-linked glycosylation sequence is (X)$_m$PO*SG(P)$_n$ (SEQ ID NO: 29). In one embodiment, the O-linked glycosylation sequence is XTEO*P (SEQ ID NO: 408). In another embodiment, the O-linked glycosylation sequence is (X)$_m$PO*DG(P)$_n$ (SEQ ID NO: 40).

In the above sequences, m, n, O* and X are defined as above.

In another aspect, the invention provides a library of sequon polypeptides including a plurality of members, wherein each member of the library corresponds to a common parent polypeptide and wherein each member of the library includes an exogenous O-linked glycosylation sequence. In one embodiment, the O-linked glycosylation sequence has an amino acid sequence according to Formula (I) (SEQ ID NO: 1). In another embodiment, the O-linked glycosylation sequence has an amino acid sequence according to Formula (II) (SEQ ID NO: 2). Formula (I) and Formula (II) are described herein above. In one embodiment, the parent polypeptide is not human growth hormone (hGH). In another embodiment, the parent polypeptide is not granulocyte colony stimulating factor (G-CSF). In yet another embodiment, the parent polypeptide is not interferon-alpha (INF-alpha). In a further embodiment, the parent polypeptide is not glucagon-like peptide-1 (GLP-1). In another embodiment, the parent polypeptide is not a fibroblast growth factor (FGF).

In a further aspect, the invention provides a method that includes: expressing a sequon polypeptide in a host cell, wherein the sequon polypeptide includes an exogenous O-linked glycosylation sequence of the invention. In one embodiment, the O-linked glycosylation sequence has an amino acid sequence according to Formula (I) (SEQ ID NO: 1). In another embodiment, the O-linked glycosylation sequence has an amino acid sequence according to Formula (II) (SEQ ID NO: 2). Formula (I) and Formula (II) are described herein above. In one embodiment, the parent polypeptide is not human growth hormone (hGH). In another embodiment, the parent polypeptide is not granulocyte colony stimulating factor (G-CSF). In yet another embodiment, the parent polypeptide is not interferon-alpha (INF-alpha). In a further embodiment, the parent polypeptide is not glucagon-like peptide-1 (GLP-1). In another embodiment, the parent polypeptide is not a fibroblast growth factor (FGF).

In yet another aspect, the invention provides a method for making a polypeptide conjugate of the invention. The method includes: (i) recombinantly producing the sequon polypeptide; and (ii) enzymatically glycosylating the sequon polypeptide at the exogenous O-linked glycosylation sequence. The method may further include: glycoPEGylating the glycosylated polyeptide of step (ii).

The invention also provides a method for making a library of sequon polypeptides, wherein each sequon polypeptide corresponds to a common parent polypeptide. The method includes: (i) recombinantly producing a first sequon polypeptide by introducing an O-linked glycosylation sequence at a first amino acid position within the parent polypeptide; and (ii) recombinantly producing at least one additional sequon polypeptide by introducing the same O-linked glycosylation sequence at an additional amino acid position within the parent polypeptide.

In addition, the invention provides a method for identifying a lead polypeptide. The method includes: (i) generating a library of sequon polypeptides of the invention; and (ii) subjecting at least one member of the library to an enzymatic glycosylation reaction, transferring a glycosyl moiety from a glycosyl donor molecule onto at least one of the O-linked glycosylation sequence, wherein said glycosyl moiety is optionally derivatized with a modifying group.

Additional aspects, advantages and objects of the present invention will be apparent from the detailed description that follows.

BRIEF DESCRIPTION OF THE DRAWINGS

FIG. 1 shows MALFI-TOF mass spectra of an exemplary non-glycosylated and an exemplary glycosylated mutant NT-3 polypeptide (A.2 in Table 16) (SEQ ID NO: 343).

FIG. 2 shows MALFI-TOF mass spectra of an exemplary non-glycosylated and an exemplary glycosylated mutant FGF-21 polypeptide (B.20 in Table 18) (SEQ ID NO: 381).

FIG. 4 shows an exemplary amino acid sequence for Factor VIII (SEQ ID NO: 254).

FIG. 5 shows an exemplary amino acid sequence for B-domain deleted (BDD) Factor VIII (SEQ ID NO: 255).

FIG. 6 is a summary of exemplary parent polypeptide/O-linked glycosylation sequence combinations. Each row represents one embodiment of the invention, in which the indicated O-linked glycosylation sequence (e.g., PTP) (SEQ ID NO: 138) is introduced into the indicated parent polypeptide (e.g., BMP-7) resulting in a sequon polypeptide of the invention. The O-linked glycosylation sequence may be introduced into the parent polypeptide at different amino acid positions (e.g., at the N-terminus, at the C-terminus or at an internal amino acid position). The O-linked glycosylation sequence may be introduced into the parent polypeptide with or without replacing existing amino acids.

DETAILED DESCRIPTION OF THE INVENTION

I. Abbreviations

Figure 1A:
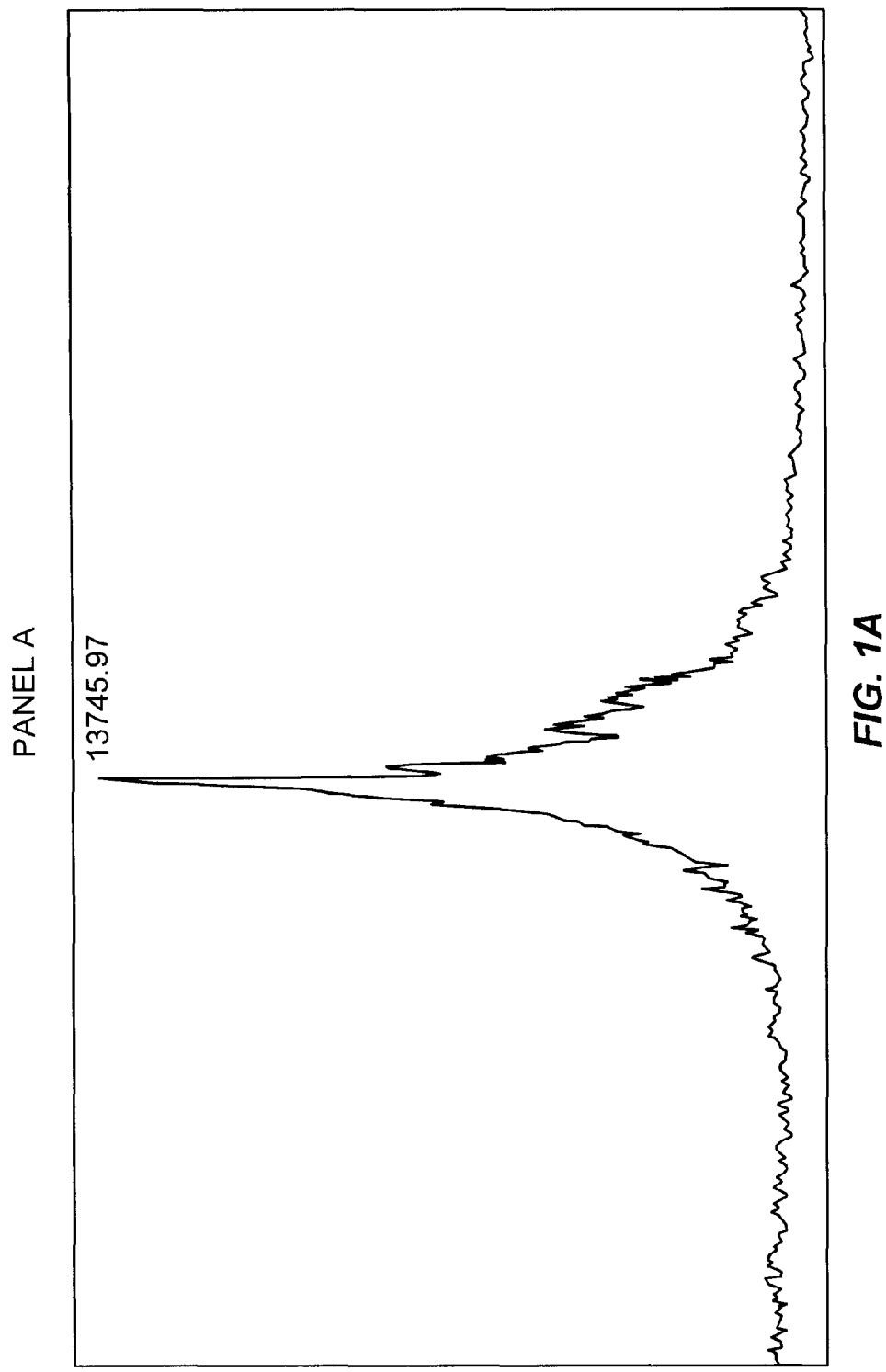
FIG. 1A shows a MALFI-TOF mass spectrum of non-glycosylated NT-3. The polypeptide was expressed as inclusion bodies in W3110 E. coli, refolded and purified.

PEG, poly(ethyleneglycol); m-PEG, methoxy-poly(ethylene glycol); PPG, poly(propyleneglycol); m-PPG, methoxy-poly(propylene glycol); Fuc, fucose or fucosyl; Gal, galactose or galactosyl; GalNAc, N-acetylgalactosamine or N-acetylgalactosaminyl; Glc, glucose or glucosyl; GlcNAc, N-acetylglucosamine or N-acetylglucosaminyl; Man, mannose or mannosyl; ManAc, mannosamine acetate or mannosaminyl acetate; Sia, sialic acid or sialyl; and NeuAc, N-acetylneuramine or N-acetylneuraminyl.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures of analytical and synthetic organic chemistry described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, for example, *Essentials of Glycobiology* Varki et al. eds. CSHL Press (1999). Oligosaccharides may include a glycosyl mimetic moiety as one of the sugar components. Oligosaccharides are considered to have a reducing end and a non-reducing end, whether or not the saccharide at the reducing end is in fact a reducing sugar.

The term "glycosyl moiety" means any radical derived from a sugar residue. "Glycosyl moiety" includes mono- and oligosaccharides and encompasses "glycosyl-mimetic moiety."

The term "glycosyl-mimetic moiety," as used herein refers to a moiety, which structurally resembles a glycosyl moiety (e.g., a hexose or a pentose). Examples of "glycosyl-mimetic moiety" include those moieties, wherein the glycosidic oxygen or the ring oxygen of a glycosyl moiety, or both, has been replaced with a bond or another atom (e.g., sufur), or another moiety, such as a carbon- (e.g., $CH_2$), or nitrogen-containing group (e.g., NH). Examples include substituted or unsubstituted cyclohexyl derivatives, cyclic thioethers, cyclic secondary amines, moieties including a thioglycosidic bond, and the like. In one example, the "glycosyl-mimetic moiety" is transferred in an enzymatically catalyzed reaction onto an amino acid residue of a polypeptide or a glycosyl moiety of a glycopeptide. This can, for instance, be accomplished by activating the "glycosyl-mimetic moiety" with a leaving group, such as a halogen.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

The term "uncharged amino acid" refers to amino acids, that do not include an acidic (e.g., —COOH) or basic (e.g., —$NH_2$) functional group. Basic amino acids include lysine (K) and arginine (R). Acidic amino acids include aspartic acid (D) and glutamic acid (E). "Uncharged amino acids include, e.g., glycine (G), valine (V), leucine (L), phenylalanine (F), but also those amino acids that include —OH or —SH groups (e.g., threonine (T), serine (S), tyrosine (Y) and cysteine (C)).

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Peptide" refers to a polymer in which the monomers are amino acids and are joined together through amide bonds. Peptides of the present invention can vary in size, e.g., from two amino acids to hundreds or thousands of amino acids. A larger peptide (e.g., at least 10, at least 20, at least 30 or at least 50 amino acid residues) is alternatively referred to as a "polypeptide" or "protein". Additionally, unnatural amino acids, for example, β-alanine, phenylglycine, homoarginine and homophenylalanine are also included. Amino acids that are not gene-encoded may also be used in the present invention. Furthermore, amino acids that have been modified to include reactive groups, glycosylation sequences, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" or "polypeptide" refers to both glycosylated and non-glycosylated peptides or "polypeptides". Also included are polypetides that are incompletely glycosylated by a system that expresses the polypeptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

In the present application, amino acid residues are numbered (typically in the superscript) according to their relative positions from the N-terminal amino acid (e.g., N-terminal methionine) of the polypeptide, which is numbered "1". The N-terminal amino acid may be a methionine (M), numbered "1". The numbers associated with each amino acid residue can be readily adjusted to reflect the absence of N-terminal methionine if the N-terminus of the polypeptide starts without a methionine. It is understood that the N-terminus of an exemplary polypeptide can start with or without a methionine.

The term "parent polypeptide" refers to any polypeptide, which has an amino acid sequence, which does not include an "exogenous" O-linked or S-linked glycosylation sequence of the invention. However, a "parent polypeptide" may include one or more naturally ocurring (endogenous) O-linked or S-linked glycosylation sequence. For example, a wild-type polypeptide may include the O-linked glycosylation sequence PTP. The term "parent polypeptide" refers to any polypeptide including wild-type polypeptides, fusion polypeptides, synthetic polypeptides, recombinant polypeptides (e.g., therapeutic polypeptides) as well as any variants thereof (e.g., previously modified through one or more replacement of amino acids, insertions of amino acids, deletions of amino acids and the like) as long as such modification does not amount to forming an O-linked or S-linked glycosylation sequence of the invention. In one embodiment, the amino acid sequence of the parent polypeptide, or the nucleic acid sequence encoding the parent polypeptide, is defined and accessible to the public in any way. For example, the parent polypeptide is a wild-type polypeptide and the amino acid sequence or nucleotide sequence of the wild-type polypeptide is part of a publicly accessible protein database (e.g., EMBL Nucleotide Sequence Database, NCBI Entrez, ExPasy, Protein Data Bank and the like). In another example, the parent polypeptide is not a wild-type polypeptide but is used as a therapeutic polypeptide (i.e., authorized drug) and the sequence of such polypeptide is publicly available in a scientific publication or patent. In yet another example, the amino acid sequence of the parent polypeptide or the nucleic acid sequence encoding the parent polypeptide was accessible to the public in any way at the time of the invention. In one embodiment, the parent polypeptide is part of a larger structure. For example, the parent polypeptide corresponds to the constant region ($F_c$) region or $C_H2$ domain of an antibody, wherein these domains may be part of an entire antibody. In one embodiment, the parent polypeptide is not an antibody of unknown sequence.

The term "mutant polypeptide" or "polypeptide variant" refers to a form of a polypeptide, wherein its amino acid sequence differs from the amino acid sequence of its corresponding wild-type form, naturally existing form or any other parent form. A mutant polypeptide can contain one or more mutations, e.g., replacement, insertion, deletion, etc. which result in the mutant polypeptide.

The term "sequon polypeptide" refers to a polypeptide variant that includes in its amino acid sequence an "exogenous O-linked glycosylation sequence" of the invention. A "sequon polypeptide" contains at least one exogenous O-linked glycosylation sequence, but may also include one or more endogenous (e.g., naturally occurring) O-linked glycosylation sequence.

The term "exogenous O-linked glycosylation sequence" refers to an O-linked glycosylation sequence of the invention that is introduced into the amino acid sequence of a parent polypeptide (e.g., wild-type polypeptide), wherein the parent polypeptide does either not include an O-linked glycosylation sequence or includes an O-linked glycosylation sequence at a different position. In one example, an O-linked glycosylation sequence is introduced into a wild-type polypeptide that does not have an O-linked glycosylation sequence. In another example, a wild-type polypeptide naturally includes a first O-linked glycosylation sequence at a first position. A second O-linked glycosylation is introduced into this wild-type polypeptide at a second position. This modification results in a polypeptide having an "exogenous O-linked glycosylation sequence" at the second position. The exogenous O-linked glycosylation sequence may be introduced into the parent polypeptide by mutation. Alternatively, a polypeptide with an exogenous O-linked glycosylation sequence can be made by chemical synthesis.

The term "corresponding to a parent polypeptide" (or grammatical variations of this term) is used to describe a sequon polypeptide of the invention, wherein the amino acid sequence of the sequon polypeptide differs from the amino acid sequence of the corresponding parent polypeptide only by the presence of at least one exogenous O-linked glycosylation sequence of the invention. Typically, the amino acid sequences of the sequon polypeptide and the parent polypeptide exhibit a high percentage of identity. In one example, "corresponding to a parent polypetide" means that the amino acid sequence of the sequon polypeptide has at least about 50% identity, at least about 60%, at least about 70%, at least about 80%, at least about 90%, at least about 95% or at least about 98% identity to the amino acid sequence of the parent polypeptide. In another example, the nucleic acid sequence that encodes the sequon polypeptide has at least about 50% identity, at least about 60%, at least about 70%, at least about 80%, at least about 90%, at least about 95% or at least about 98% identity to the nucleic acid sequence encoding the parent polypeptide.

The term "introducing (or adding etc.) a glycosylation sequence (e.g., an O-linked glycosylation sequence) into a parent polypeptide" (or grammatical variations thereof), or "modifying a parent polypeptide" to include a glycosylation sequence (or grammatical variations thereof) do not necessarily mean that the parent polypeptide is a physical starting material for such conversion, but rather that the parent polypeptide provides the guiding amino acid sequence for the making of another polypeptide. In one example, "introducing a glycosylation sequence into a parent polypeptide" means that the gene for the parent polypeptide is modified through appropriate mutations to create a nucleotide sequence that encodes a sequon polypeptide. In another example, "introducing a glycosylation sequence into a parent polypeptide" means that the resulting polypeptide is theoretically designed using the parent polypeptide sequence as a guide. The designed polypeptide may then be generated by chemical or other means.

The term "lead polypeptide" refers to a sequon polypeptide of the invention that can be effectively glycosylated and/or glycoPEGylated. For a sequon polypeptide of the invention to qualify as a lead polypeptide, such polypeptide, when subjected to suitable reaction conditions, is glycosylated or glycoPEGylated with a reaction yield of at least about 50%, preferably at least about 60%, more preferably at least about 70% and even more preferably about 80%, about 85%, about 90% or about 95%. Most preferred are those lead polypeptides of the invention, which can be glycosylated or glycoPEGylated with a reaction yield of greater than 95%. In one preferred embodiment, the lead polypeptide is glycosylated or glycoPEGylated in such a fashion that only one amino acid residue of each O-linked glycosylation sequence is glycosylated or glycoPEGylated (mono-glycosylation).

The term "library" refers to a collection of different polypeptides each corresponding to a common parent polypeptide. Each polypeptide species in the library is referred to as a member of the library. Preferably, the library of the present invention represents a collection of polypeptides of sufficient number and diversity to afford a population from which to identify a lead polypeptide. A library includes at least two different polypeptides. In one embodiment, the library includes from about 2 to about 10 members. In another embodiment, the library includes from about 10 to about 20 members. In yet another embodiment, the library includes from about 20 to about 30 members. In a further embodiment, the library includes from about 30 to about 50 members. In another embodiment, the library includes from about 50 to about 100 members. In yet another embodiment, the library includes more than 100 members. The members of the library may be part of a mixture or may be isolated from each other. In one example, the members of the library are part of a mixture that optionally includes other components. For example, at least two sequon polypeptides are present in a volume of cell-culture broth. In another example, the members of the library are each expressed separately and are optionally isolated. The isolated sequon polypeptides may optionally be contained in a multi-well container, in which each well contains a different type of sequon polypeptide.

The term "$C_H2$" domain of the present invention is meant to describe an immunoglobulin heavy chain constant $C_H2$ domain. In defining an immunoglobulin $C_H2$ domain reference is made to immunoglobulins in general and in particular to the domain structure of immunoglobulins as applied to human IgG1 by Kabat E. A. (1978) *Adv. Protein Chem.* 32:1-75.

The term "polypeptide comprising a $C_H2$ domain" or "polypeptide comprising at least one $C_H2$ domain" is intended to include whole antibody molecules, antibody fragments (e.g., Fc domain), or fusion proteins that include a region equivalent to the $C_H2$ region of an immunoglobulin.

The term "polypeptide conjugate," refers to species of the invention in which a polypeptide is glycoconjugated with a sugar moiety (e.g., modified sugar) as set forth herein. In a representative example, the polypeptide is a sequon polypeptide having an exogenous O-linked glycosylation sequence.

"Proximate a proline residue" or "in proximity to a proline residue" as used herein refers to an amino acid that is less than about 10 amino acids removed from a proline residue, preferably, less than about 9, 8, 7, 6 or 5 amino acids removed from a proline residue, more preferably, less than about 4, 3 or 2 residues removed from a proline residue. The amino acid "proximate a proline residue" may be on the C- or N-terminal side of the proline residue.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

As used herein, the term "modified sugar," refers to a naturally- or non-naturally-occurring carbohydrate. In one embodiment, the "modified sugar" is enzymatically added onto an amino acid or a glycosyl residue of a polypeptide using a method of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, polymeric modifying groups (e.g., water-soluble polymers), therapeutic moieties, diagnostic moieties, biomolecules and the like. In one embodiment, the modifying group is not a naturally occurring glycosyl moiety (e.g., naturally occurring polysaccharide). The modifying group is preferably non-naturally occurring. In one example, the "non-naturally occurring modifying group" is a polymeric modifying group, in which at least one polymeric moiety is non-naturally occurring. In another example, the non-naturally occurring modifying group is a modified carbohydrate. The locus of functionalization with the modifying group is selected such that it does not prevent the "modified sugar" from being added enzymatically to a polypeptide. "Modified sugar" also refers to any glycosyl mimetic moiety that is functionalized with a modifying group and which is a substrate for a natural or modified enzyme, such as a glycosyltransferase.

As used herein, the term "polymeric modifying group" is a modifying group that includes at least one polymeric moiety (polymer). The polymeric modifying group added to a polypeptide can alter a property of such polypeptide, for example, its bioavailability, biological activity or its half-life in the body. Exemplary polymers include water soluble and water insoluble polymers. A polymeric modifying group can be linear or branched and can include one or more independently selected polymeric moieties, such as poly(alkylene glycol) and derivatives thereof. In one example, the polymer is non-naturally occurring. In an exemplary embodiment, the polymeric modifying group includes a water-soluble polymer, e.g., poly(ethylene glycol) and derivatived thereof (PEG, m-PEG), poly(propylene glycol) and derivatives thereof (PPG, m-PPG) and the like. In a preferred embodiment, the poly(ethylene glycol) or poly(propylene glycol) has a molecular weight that is essentially homodisperse. In one embodiment the polymeric modifying group is not a naturally occurring polysaccharide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine or cysteine. In one example, the branched poly(ethylene glycol) can be represented in general form as $R(-PEG-OH)_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly($\alpha$-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, as well as copolymers, terpolymers, and mixtures thereof. Although the molecular weight of each chain of the polymer backbone can vary, it is typically in the range of from about 100 Da to about 100,000 Da, often from about 5,000 Da to about 80,000 Da.

The term "glycoconjugation," as used herein, refers to the enzymatically mediated conjugation of a modified sugar species to an amino acid or glycosyl residue of a polypeptide, e.g., a mutant human growth hormone of the present invention. In one example, the modified sugar is covalently attached to one or more modifying groups. A subgenus of "glycoconjugation" is "glycol-PEGylation" or "glyco-PEGylation", in which the modifying group of the modified sugar is poly(ethylene glycol) or a derivative thereof, such as an alkyl derivative (e.g., m-PEG) or a derivative with a reactive functional group (e.g., $H_2N$-PEG, HOOC-PEG).

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term "O-linked glycosylation sequence" or "sequon" refers to any amino acid sequence (e.g., containing from about 3 to about 9 amino acids, preferably about 3 to about 6 amino acids) that includes an amino acid residue having a hydroxyl group (e.g., serine or threonine). In one embodiment, the O-linked glycosylation sequence is a substrate for an enzyme, such as a glycosyltransferase, preferably when part of an amino acid sequence of a polypeptide. In a typical embodiment, the enzyme transfers a glycosyl moiety onto the O-linked glycosylation sequence by modifying the above described hydroxyl group, which is referred to as the "site of glycosylation". The invention distinguishes between an O-linked glycosylation sequence that is naturally occurring in a wild-type polypeptide or any other parent form thereof (endogenous O-linked glycosylation sequence) and an "exogenous O-linked glycosylation sequence". A polypeptide that includes an exogenous O-linked glycosylation sequence is termed "sequon polypeptide". The amino acid sequence of a parent polypeptide may be modified to include an exogenous O-linked glycosylation sequence through recombinat technology, chemical syntheses or other means. The related term "S-linked glycosylation sequence" is analoguous and refers to any amino acid sequence that includes an amino acid residue having a sulfhydryl group (e.g., cysteine, Me-cysteine) and that is is a substrate for an enzyme, such as a glycosyltransferase, preferably when part of an amino acid sequence of a polypeptide.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated polypeptide, thereby linking the modifying group to an amino acid and/or glycosyl residue of the polypeptide. A "glycosyl linking group" is generally derived from a "modified sugar" by the enzymatic attachment of the "modified sugar" to an amino acid and/or glycosyl residue of the polypeptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure. A "glycosyl linking group" may include a glycosyl-mimetic moiety. For example, the glycosyl transferase (e.g., sialyl transferase), which is used to add the modified sugar to a glycosylated polypeptide, exhibits tolerance for a glycosyl-mimetic substrate (e.g., a modified sugar in which the sugar moiety is a glycosyl-mimetic moiety—e.g., sialyl-mimetic moiety). The transfer of the modified glycosyl-mimetic sugar results in a conjugate having a glycosyl linking group that is a glycosyl-mimetic moiety.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins. Exemplary proteins include, but are not limited to, Erythropoietin (EPO), Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of polypeptides with anti-tumor activity, e.g. TNF-α. Conjugates include, but are not limited to those formed between a therapeutic protein and a glycoprotein of the invention. A representative conjugate is that formed between PSGL-1 and TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

As used herein, "pharmaceutically acceptable carrier" includes any material, which when combined with the conjugate retains the conjugates' activity and is non-reactive with the subject's immune systems. "Pharmaceutically acceptable carrier" includes solids and liquids, such as vehicles, diluents and solvents. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in a subject (e.g., human) that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any gramatically equivalent term means the amount that, when administered to an animal or human for treating a disease, is sufficient to effect treatment for that disease.

The term "isolated" refers to a material that is substantially or essentially free from components, which are used to produce the material. For polypeptide conjugates of the invention, the term "isolated" refers to material that is substantially or essentially free from components, which normally accompany the material in the mixture used to prepare the polypeptide conjugate. "Isolated" and "pure" are used interchangeably. Typically, isolated polypeptide conjugates of the invention have a level of purity preferably expressed as a range. The lower end of the range of purity for the polypeptide conjugates is about 60%, about 70% or about 80% and the upper end of the range of purity is about 70%, about 80%, about 90% or more than about 90%.

When the polypeptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, mass-spectroscopy, or a similar means).

"Essentially each member of the population," as used herein, describes a characteristic of a population of polypeptide conjugates of the invention in which a selected percentage of the modified sugars added to a polypeptide are added to multiple, identical acceptor sites on the polypeptide. "Essentially each member of the population" speaks to the "homogeneity" of the sites on the polypeptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a polypeptide conjugate of the invention in which each modified sugar moiety is conjugated to an acceptor site having the same structure as the acceptor site to which every other modified sugar is conjugated, the polypeptide conjugate is said to be about 100% homogeneous. Homogeneity is typically expressed as a range. The lower end of the range of homogeneity for the polypeptide conjugates is about 50%, about 60%, about 70% or about 80% and the upper end of the range of purity is about 70%, about 80%, about 90% or more than about 90%.

When the polypeptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the polypeptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., GalNAc transferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl" by itself or as part of another substituent, means, unless otherwise stated, a straight or branched chain, or cyclic (i.e., cycloalkyl) hydrocarbon radical, or combination thereof, which may be fully saturated, mono- or polyunsaturated and can include di- (e.g., alkylene) and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene."

Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, alkoxy, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

The symbol "R" is a general abbreviation that represents a substituent group. Exemplary substituent groups include substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, sulfonate, thiosulfate, and thiosulfonate.

A "glycosyltransferase truncation" or a "truncated glycosyltransferase" or grammatical variants, as well as "domain-deleted glycosyltransferase" or grammatical variants, refer to a glycosyltransferase that has fewer amino acid residues than a naturally occurring glycosyltransferase, but that retains certain enzymatic activity. Truncated glycosyltransferases include, e.g., truncated GnT1 enzymes, truncated GalT1 enzymes, truncated ST3GalIII enzymes, truncated GalNAc-T2 enzymes, truncated Core-1-GalT1 enzymes, amino acid residues from about 32 to about 90 (see e.g., the human enzyme); truncated ST3Gal1 enzymes, truncated ST6GalNAc-1 enzymes, and truncated GalNAc-T2 enzymes. Any number of amino acid residues can be deleted so long as the enzyme retains activity. In some embodiments, domains or portions of domains can be deleted, e.g., a signal-anchor domain can be deleted leaving a truncation comprising a stem region and a catalytic domain; a signal-anchor domain and a portion of a stem region can be deleted leaving a truncation comprising the remaining stem region and a catalytic domain; or a signal-anchor domain and a stem region can be deleted leaving a truncation comprising a catalytic domain. Glycosyltransferase truncations can also occur at the C-terminus of the protein. For example, some GalNAcT enzymes, such as GalNAc-T2, have a C-terminal lectin domain that can be deleted without diminishing enzymatic activity.

"Refolding expression system" refers to a bacteria or other microorganism with an oxidative intracellular environment, which has the ability to refold disulfide-containing protein in their proper/active form when expressed in this microorganism. Exemplars include systems based on *E. coli* (e.g., Origami™ (modified *E. coli* trxB−/gor−), Origami 2™ and the like), *Pseudomonas* (e.g., fluorescens). For exemplary references on Origami™ technology see, e.g., Lobel et al. (2001) *Endocrine* 14(2), 205-212; and Lobel et al. (2002) *Protein Express. Purif.* 25(1), 124-133.

III. Introduction

The present invention provides sequon polypeptides that include at least one exogenous O-linked or S-linked glycosylation sequence. Each sequon polypeptide corresponds to a parent polypeptide. In one embodiment, the parent polypeptide does not include an O-linked or S-linked glycosylation sequence. In another embodiment, the parent polypeptide (e.g., wild-type polypeptide) naturally includes an O-linked or S-linked glycosylation sequence. The sequon polypeptide that corresponds to such parent polypeptide includes an additional O-linked or S-linked glycosylation sequence at a different position. In one embodiment, each glycosylation sequence is a substrate for an enzyme (e.g., a glycosyltransferase, such as GalNAc-T2). The enzyme catalyses the transfer of a glycosyl moiety from a glycosyl donor molecule to an oxygen- or sulfur atom of an amino acid side chain that is substituted with either a hydroxyl group (e.g., serine or threonein) or a sulfhydryl group (e.g., cysteine). The amino acid is part of the O-linked or S-linked glycosylation sequence. Exemplary glycosyl moieties that can be conjugated to the glycosylation sequence include GalNAc, galactose, mannose, GlcNAc, glucose, fucose or xylose moieties.

The invention also provides polypeptide conjugates, in which a modified sugar moiety is attached either directly (e.g., through a glycoPEGylation reaction) or indirectly (e.g., through an intervening glycosyl residue) to an O-linked or S-linked glycosylation sequence located within a polypeptide. The polypeptide can be any polypeptide including wild-type polypeptides and authorized biologic drugs for which amino acid sequences or nucleotide sequences are known. In one embodiment, the parent polypeptide is a therapeutic polypeptide, such as human growth hormone (hGH), erythropoietin (EPO), a therapeutic antibody, bone morphogenetic proteins (e.g., BMP-7) or blood factors (e.g., Factor VI, Factor VIII or FIX). Accordingly, the present invention provides therapeutic polypeptide variants that include within their amino acid sequence one or more exogenous O-linked or S-linked glycosylation sequence. The invention further provides glycoconjugates of such polypeptides.

Also provided are methods for producing such polypeptide conjugates. The glycosylation and glycoPEGylation methods of the invention can be practiced on any polypeptide incorporating an O-linked or S-linked glycosylation sequence. The methods are especially useful to generate polypeptide conjugates of sequon polypeptides, which differ from the corresponding parent polypeptide by including an exogenous glycosylation sequence.

The methods of the invention provide polypeptide conjugates with increased therapeutic half-life due to, for example, reduced clearance rate, or reduced rate of uptake by the immune or reticuloendothelial system (RES). Moreover, the methods of the invention provide a means for masking antigenic determinants on polypeptides, thus reducing or eliminating a host immune response against the polypeptide. Selective attachment of targeting agents to a polypeptide using an appropriate modified sugar can be used to target a polypeptide to a particular tissue or cell surface receptor that is specific for the particular targeting agent. Also provided are proteins that display enhanced resistance to degradation by proteolysis, a result that is achieved by altering certain sites on the protein that are cleaved by or recognized by proteolytic enzymes. In one embodiment, such sites are replaced or partially replaced with an O-linked or S-linked glycosylation sequence of the invention.

In addition, the methods of the invention can be used to modulate the "biological activity profile" of a parent polypeptide. The inventors have recognized that the covalent attachment of a modifying group, such as a water soluble polymer (e.g., mPEG) to a parent polypeptide using the methods of the invention can alter not only bioavailability, pharmacodynamic properties, immunogenicity, metabolic stability, biodistribution and water solubility of the resulting polypeptide species, but can also lead to the reduction of undesired therapeutic activities or to the augmentation of desired therapeutic activities. For example, the former has been observed for the hematopoietic agent erythropoietin (EPO). For example, certain chemically PEgylated EPO variants showed reduced erythropoietic activity while the tissue-protective activity of the wild-type polypeptide was maintained. Such results are described e.g., in U.S. Pat. No. 6,531,121; WO2004/096148, WO2006/014466, WO2006/014349, WO2005/025606 and WO2002/053580. Exemplary cell-lines, which are useful for the evaluation of differential biological activities of selected polypeptides are summarized in Table 1, below:

TABLE 1

Cell-lines used for biological evaluation of various polypeptides

| Polypeptide | Cell-line | Biological Activity |
|---|---|---|
| EPO | UT7 | erythropoiesis |
|  | SY5Y | neuroprotection |
| BMP-7 | MG-63 | osteoinduction |
|  | HK-2 | nephrotoxicity |
| NT-3 | Neuro2 | neuroprotection (TrkC binding) |
|  | NIH3T3 | neuroprotection (p75 binding) |

In one embodiment, a polypeptide conjugate of the invention shows reduced or enhanced binding affinity to a biological target protein (e.g., a receptor), a natural ligand or a non-natural ligand, such as an inhibitor. For instance, abrogating binding affinity to a class of specific receptors may reduce or eliminate associated cellular signaling and downstream biological events (e.g., immune response). Hence, the methods of the invention can be used to create polypeptide conjugates, which have identical, similar or different therapeutic profiles than the parent polypeptide to which the conjugates correspond. The methods of the invention can be used to identify glycoPEGylated therapeutics with specific (e.g., improved) biological functions and to "fine-tune" the therapeutic profile of any therapeutic polypeptide or other biologically active polypeptide. GlycoPEGylation™ is a Trademark of Neose Technologies and refers to technologies disclosed in commonly owned patents and patent applications, e.g., (WO2007/053731; WO2007/022512; WO2006/127896; WO2005/055946; WO2006/121569; and WO2005/070138).

IV. Compositions

Polypeptides

In a first aspect, the invention provides a sequon polypeptide. A sequon polypeptide has an amino acid sequence that includes at least one exogenous O-linked or S-linked glycosylation sequence of the invention. In one embodiment, the amino acid sequence of the sequon polypeptide includes an exogenous O-linked glycosylation sequence, which is a substrate for one or more wild-type, mutant or truncated glycosyltransferase. Preferred glycosyltransferases include GalNAc transferases, such as full-length or truncated GalNAc-T2 (e.g., human GalNAc-T2). Exemplary GalNAc-T2 enzymes are shown in Table 13 (SEQ ID NOs: 256-270).

In an exemplary embodiment, the sequon polypeptide of the invention is generated through recombinant technology by altering the amino acid sequence of a corresponding parent polypeptide (e.g., wild-type polypeptide). Methods for the preparation of recombinant polypeptides are known to those of skill in the art. Exemplary methods are described herein below. The amino acid sequence of the sequon polypeptide may contain a combination of naturally occurring and exogenous (i.e., non-naturally occurring) O-linked glycosylation sequences.

The parent polypeptide can be any polypeptide. Exemplary parent polypeptides include wild-type polypeptides and fragments thereof as well as polypeptides, which are modified from their naturally occurring counterpart (e.g., by previous mutation or truncation). A parent polypeptide may also be a fusion protein. In another embodiment, the parent polypeptide is a therapeutic polypeptide (i.e., authorized drug), such as those currently used as pharmaceutical agents. A non-limiting selection of parent polypeptides is shown in FIG. 28 of U.S. patent application Ser. No. 10/552,896 filed Jun. 8, 2006, which is incorporated herein by reference.

Exemplary parent polypeptides include growth factors, such as fibroblast growth factors (e.g., FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22 and FGF-23), blood coagulation factors (e.g., Factor V, Factor VII, Factor VIII, B-domain deleted Factor VIII, Factor IX, Factor X and Factor XIII), hormones, such as human growth hormone (hGH) and follicle stimulating hormone (FSH), as well as cytokines, such as interleukins (e.g., IL-1, IL-2, IL-12) and interferons (e.g., INF-alpha, INF-beta, INF-gamma).

Other exemplary parent polypeptides include enzymes, such as glucocerebrosidase, alpha-galactosidase (e.g., Fabrazyme™), acid-alpha-glucosidase (acid maltase), alpha-L-iduronidase (e.g., Aldurazyme™), thyroid peroxidase (TPO), beta-glucosidase (see e.g., enzymes described in U.S. patent application Ser. No. 10/411,044), and alpha-galactosidase A (see e.g., enzymes described in U.S. Pat. No. 7,125,843).

Other exemplary parent polypeptides include bone morphogenetic proteins (e.g., BMP-1, BMP-2, BMP-3, BMP-4, BMP-5, BMP-6, BMP-7, BMP-8, BMP-9, BMP-10, BMP-11, BMP-12, BMP-13, BMP-14, BMP-15), neurotrophins (e.g., NT-3, NT-4, NT-5), erythropoietins (EPO), growth differentiation factors (e.g., GDF-5), glial cell line-derived neurotrophic factor (GDNF), brain derived neurotrophic factor (BDNF), nerve growth factor (NGF), von Willebrand factor (vWF) protease, granulocyte colony stimulating factor (G-CSF), granulocyte-macrophage colony stimulating factor (GM-CSF), $\alpha_1$-antitrypsin (ATT, or $\alpha$-1 protease inhibitor), tissue-type plasminogen activator (TPA), hirudin, leptin, urokinase, human DNase, insulin, hepatitis B surface protein (HbsAg), human chorionic gonadotropin (hCG), chimeric diphtheria toxin-IL-2, glucagon-like peptides (e.g., GLP-1 and GLP-2), anti-thrombin III (AT-III), prokinetisin, CD4, $\alpha$-CD20, tumor necrosis factor receptor (TNF-R), P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein and extendin-4.

Also within the scope of the invention are parent polypeptides that are antibodies. The term antibody is meant to include antibody fragments (e.g., Fc domains), single chain antibodies, Lama antibodies, nano-bodies and the like. Also included in the term are antibody-fusion proteins, such as Ig chimeras. Preferred antibodies include humanized, monoclonal antibodies or fragments thereof. All known isotypes of such antibodies are within the scope of the invention. Exemplary antibodies include those to growth factors, such as endothelial growth factor (EGF), vascular endothelial growth factors (e.g., monoclonal antibody to VEGF-A, such as ranibizumab (Lucentis™)) and fibroblast growth factors, such as FGF-7, FGF-21 and FGF-23) and antibodies to their respective receptors. Other exemplary antibodies include anti-TNF-alpha monoclonal antibodies (see e.g., U.S. patent application Ser. No. 10/411,043), TNF receptor-IgG Fc region fusion protein (e.g., Enbrel™), anti-HER2 monoclonal antibodies (e.g., Herceptin™), monoclonal antibodies to protein F of respiratory syncytial virus (e.g., Synagis™), monoclonal antibodies to TNF-$\alpha$ (e.g., Remicade™), monoclonal antibodies to glycoproteins, such as IIb/IIIa (e.g., Reopro™), monoclonal antibodies to CD20 (e.g., Rituxan™), CD4 and alpha-CD3, monoclonal antibodies to PSGL-1 and CEA. Any modified (e.g., previously mutated) version of any of the above listed polypeptides is also within the scope of the invention.

In one exemplary embodiment, the parent polypeptide is not G-CSF. In another exemplary embodiment, the parent polypeptide is not hGH. In yet another exemplary embodiment, the parent polypeptide is not INF-alpha. In a further exemplary embodiment, the parent polypeptide is not FGF. In another exemplary embodiment, the parent polypeptide is not wild-type G-CSF. In another exemplary embodiment, the parent polypeptide is not wild-type hGH. In yet another exemplary embodiment, the parent polypeptide is not wild-type INF-alpha. In a further exemplary embodiment, the parent polypeptide is not a wild-type FGF polypeptide.

Glycosylation Sequence

Glycosylation sequences of the invention include O-linked glycosylation sequences and S-linked glycosylation sequences. The following discussion of O-linked glycosylation sequences is exemplary and is not meant to limit the scope of the invention.

In one embodiment, the O-linked glycosylation sequence of the invention is naturally present in a wild-type polypeptide. Polypeptide conjugates of such wild-type polypeptides are within the scope of the invention. In another embodiment, the O-linked glycosylation sequence is not present or not present at the same position, in a parent polpeptide (exogenous O-linked glycosylation sequence). Introduction of an exogenous O-linked glycosylation sequence into a parent polypeptide generates a sequon polypeptide of the invention. The O-linked glycosylation sequence may be introduced into the parent polypeptide by mutation. In another example, the O-linked glycosylation sequence is introduced into the amino acid sequence of a parent polypeptide by chemical synthesis of the sequon polypeptide.

The O-linked glycosylation sequence of the invention can be any short amino acid sequence. In one embodiment, the O-linked glycosylation sequence includes from about 2 to about 20, preferably about 2 to about 10, more preferably about 3 to about 9 and most preferably about 3 to about 6 amino acid residues. An O-linked glycosylation sequence of the invention includes at least one amino acid with a side chain having a hydroxyl group (e.g., serine or threonine). In one embodiment, this hydroxyl group becomes the site of glycosylation when the sequon polypeptide is subjected to an enzymatic glycosylation reaction. During this glycosylation reaction, the hydrogen atom of the hydroxyl group is replaced with a glycosyl moiety. Hence, the amino acid having the hydroxyl group that is modified with a glycosyl moiety during a glycosylation reaction is referred to as the "site of glycosylation" or "glycosylation site."

Positioning of O-Linked Glycosylation Sequences

In one embodiment, the O-linked or S-linked glycosylation sequence, when part of a polypeptide (e.g., a sequon polypeptide of the invention), is a substrate for a glycosyl transferase. In one example the glycosylation sequence is a substrate for a GalNAc transferase (e.g., human GalNAc-T2). In another example, the glycosylation sequence is a substrate for a modified enzyme, such as a lectin domain deleted GalNAc transferase (e.g., human GalNAc-T2) or lectin domain truncated GalNAc transferase (e.g., GalNAc-T2). The efficiency, with which each O-linked glycosylation sequence of the invention is glycosylated during an appropriate glycosylation reaction, may depend on the type and nature of the enzyme, and may also depend on the context of the glycosylation sequence, especially the three-dimensional structure of the polypeptide around the glycosylation site.

Generally, an O-linked glycosylation sequence can be introduced at any position within the amino acid sequence of the polypeptide. In one example, the glycosylation sequence is introduced at the N-terminus of the parent polypeptide (i.e., preceding the first amino acid or immediately following the first amino acid) (amino-terminal mutants). In another example, the glycosylation sequence is introduced near the amino-terminus (e.g., within 10 amino acid residues of the N-terminus) of the parent polypeptide. In another example, the glycosylation sequence is located at the C-terminus of the parent polypeptide immediately following the last amino acid of the parent polypeptide (carboxy-terminal mutants). In yet another example, the glycosylation sequence is introduced near the C-terminus (e.g., within 10 amino acid residues of the C-terminus) of the parent polypeptide. In yet another example, the O-linked glycosylation sequence is located anywhere between the N-terminus and the C-terminus of the parent polypeptide (internal mutants). It is generally preferred that the modified polypeptide be biologically active, even if that biological activity is altered from the biological activity of the corresponding parent polypeptide.

An important factor influencing glycosylation efficiencies of sequon polypeptides is the accessibility of the glycosylation site (e.g., a threonine side chain) for the glycosyltransferase (e.g., GalNAc transferase) and other reaction partners, including solvent molecules. If the glycosylation sequence is positioned within an internal domain of the polypeptide, glycosylation will likely be inefficient. Hence, in one embodiment, the glycosylation sequence is introduced at a region of the polypeptide, which corresponds to the polypeptide's solvent exposed surface. An exemplary polypeptide conformation is one, in which the hydroxyl group of the glycosylation sequence is not oriented inwardly, forming hydrogen bonds with other regions of the polypeptide. Another exemplary conformation is one, in which the hydroxyl group is unlikely to form hydrogen bonds with neighboring proteins.

In one example, the glycosylation sequence is created within a pre-selected, specific region of the parent protein. In nature, glycosylation of the polypeptide backbone usually occurs within loop regions of the polypeptide and typically not within helical or beta-sheet structures. Therefore, in one embodiment, the sequon polypeptide of the invention is generated by introducing an O-linked glycosylation sequence into an area of the parent polypeptide, which corresponds to a loop domain.

For example, the crystal structure of the protein BMP-7 contains two extended loop regions between Ala$^{72}$ and Ala$^{86}$ as well as Ile$^{96}$ and Pro$^{103}$. Generating BMP-7 mutants, in which the O-linked glycosylation sequence is placed within those regions of the polypeptide sequence, may result in polypeptides, wherein the mutation causes little or no disruption of the original tertiary structure of the polypeptide (see e.g., Example 1.9).

However, the inventors have discovered that introduction of an O-linked glycosylation sequence at an amino acid position that falls within a beta-sheet or alpha-helical conformation can also lead to sequon polypeptides, which are efficiently glycosylated at the newly introduced O-linked glycosylation sequence. Introduction of an O-linked glycosylation sequence into a beta-sheet or alpha-helical domain may cause structural changes to the polypeptide, which, in turn, enable efficient glycosylation.

The crystal structure of a protein can be used to identify those domains of a wild-type or parent polypeptide that are most suitable for introduction of an O-linked glycosylation sequence and may allow for the pre-selection of promising modification sites.

When a crystal structures is not available, the amino acid sequence of the polypeptide can be used to pre-select promising modification sites (e.g., prediction of loop domains versus alpha-helical domains). However, even if the three-dimensional structure of the polypeptide is known, structural dynamics and enzyme/receptor interactions are variable in solution. Hence, the identification of suitable mutation sites as well as the selection of suitable glycosylation sequences, may involve the creation of several sequon polypeptides (e.g., libraries of sequon polypeptides of the invention) and testing those variants for desirable characteristics using appropriate screening protocols, e.g., those described herein.

In one embodiment, the parent polypeptide is an antibody or antibody fragment. In one example, the constant region (e.g., $C_H2$ domain) of an antibody or antibody fragment is modified with an O-linked glycosylation sequence of the invention. In one example, the O-linked glycosylation sequence is introduced in such a way that a naturally occurring N-linked glycosylation sequence is replaced or functionally impaired. In another embodiment sequon scanning is performed through a selected area of the $C_H2$ domain creating a library of antibodies, each including an exogenous O-linked glycosylation sequence of the invention. In yet another embodiment, resulting polypeptide variants are subjected to an enzymatic glycosylation reaction adding a glycosyl moiety to the introduced glycosylation sequence. Those variants that are sufficiently glycosylated can be anlyzed for their ability to bind a suitable receptor (e.g., $F_c$ receptor, such as $F_c\gamma$RIIIa). In one embodiment, such glycosylated antibody or antibody fragment exhibits increased binding affinity to the $F_c$ receptor when compared with the parent antibody or a naturally glycosylated version thereof. This aspect of the invention is further described in U.S. Provisional Patent Application 60/881,130 filed Jan. 18, 2007, the disclosure of which is incorporated herein in its entirety. The described modification can change the effector function of the antibody. In one embodiment, the glycosylated antibody variant exhibits reduced effector function, e.g., reduced binding affinity to a receptor found on the surface of a natural killer cell or on the surface of a killer T-cell.

In another embodiment, the O-linked or S-linked glycosylation sequence is not introduced within the parent polypeptide sequence, but rather the sequence of the parent polypeptide is extended though addition of a peptide linker fragment to either the N- or C-terminus of the parent polypeptide, wherein the peptide linker fragment includes an O-linked or S-linked glycosylation sequence of the invention, such as "PTP". The peptide linker fragement can have any number of amino acids. In one embodiment the peptide linker fragment includes at least about 5, at least about 10, at least about 15, at least about 20, at least about 30, at least about 50 or more than 50 amino acid residues. The peptide linker fragment optionally includes an internal or terminal amino acid residue that has a reactive functional group, such as an amino group (e.g., lysine) or a sufhydryl group (e.g., cysteine). Such reactive functional group may be used to link the polypeptide to another moiety, such as another polypeptide, a cytotoxin, a small-molecule drug or another modifying group of the invention. This aspect of the invention is further described in U.S. Provisional Patent Application 60/881,130 filed Jan. 18, 2007, the disclosure of which is incorporated herein in its entirety.

In a representative embodiment, the invention provides a polypeptide that includes a C-terminal sequence having the following formula, wherein the integer s is 0 or 1:

(SEQ ID NO: 3)

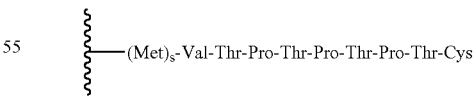
—(Met)$_s$-Val-Thr-Pro-Thr-Pro-Thr-Pro-Thr-Cys

Those of skill in the art will appreciate that dimers and oligomers of the structure above can be utilized to form higher oligomers of the polypeptide to which the peptide linker fragment is attached. In an exemplary embodiment, the peptide linker fragment includes a lysine residue that serves as a branching point for the linker, e.g., the amino group of the lysine serves as an attachment point for an "arm" of the linker. In an exemplary embodiment, the lysine replaces the methionine moiety.

In an exemplary embodiment, at least one threonine residue of the peptide linker fragment can be glycosylated. In another embodiment two, more preferably three and still more preferably four of the threonine moieties of the peptide linker fragment are glycosylated.

In another exemplary embodiment, the linker fragment is dimerized with another linker fragment of identical or different structure through formation of a disulfide bond. Thus, representative polypeptides of the invention include a linking group having the formula:

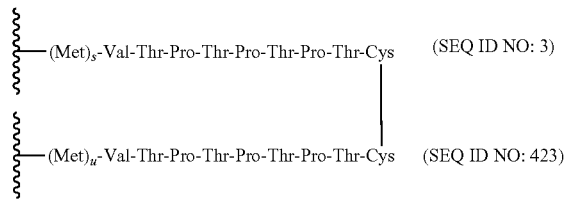

wherein the indices u and s are independently selected from 0 and 1.

In one embodiment, the parent polypeptide that is modified with a peptide linker fragment of the invention is an antibody or antibody fragment. In one example according to this embodiment, the parent polypeptide is scFv. Methods described herein can be used to prepare scFvs of the present invention in which the scFv or the linker is modified with a glycosyl moiety or a modifying group attached to the peptide through a glycosyl linking group. Exemplary methods of glycosylation and glycoconjugation are set forth in, e.g., PCT/US02/32263 and U.S. patent application Ser. No. 10/411,012, each of which is incorporated by reference herein in its entirety.

The Presence of Basic Amino Acid Residues Influence Glycosylation Efficiency

The inventors have discovered that glycosylation is most efficient when the O-linked glycosylation sequence includes a proline (P) residue near the site of glycosylation. In addition, for certain O-linked glycosylation sequences (e.g., PTEI) (SEQ ID NO: 139), and in some instances, a second proline residue immediately following the glycosylation sequence (e.g., PTEIP) (SEQ ID NO: 140) further promotes glycosylation efficiency when using GalNAc-T2 as the glycosyltransferase.

However, the inventors have also discovered that the exemplary sequences PTxP and PSxP, wherein x represents any amino acid, and wherein the two proline residues are separated by only two amino acids, is essentially not glycosylated by GalNAc-T2. Hence, in one embodiment, the O-linked glycosylation sequence of the invention does not include PSxP and PTxP.

The inventors have further discovered that the replacement of a basic amino acid residue (e.g. lysine), which is in proximity to an O-linked glycosylation site, with an uncharged amino acid, leads to significantly improved glycosylation rates when using certain enzymes.

For example, the enzyme human GalNAc-T2 preferably recognizes O-linked glycosylation sequences of the invention, wherein at least 3 amino acid residues are found between the site of glycosylation (e.g., a threonine or serine residue within the O-linked glycosylation sequence) and any lysine (K) or arginine (R) residue. For example, while the sequence PTxyzK (wherein x, y, and z represent any non-basic amino acid), may be glycosylated by GalNAc-T2, the sequence PTxyK is unlikely to be glycosyated by GalNAc-T2. Hence, in a preferred embodiment, in which GalNAc-T2 is used for glycosylation, the O-linked glycosylation sequence of the invention is introduced at a position within the amino acid sequence of the parent polypeptide that is not in proximity to a lysine (K) or arginine (R) residue. In another embodiment, the mutation is extended to replace one or more proximate basic amino acid with a non-basic amino acid, such as an uncharged amino acid (e.g., alanine) or an acidic amino acid, such as aspartic acid or glutamic acid. Exemplary sequences are given in Example 1.3. (SEQ ID NOs: 279-283)

The inventors have also discovered that if two O-linked glycosylation sequences are centered around a single proline residue (P in Scheme 1, below), GalNAc-T2 can add multiple GalNAc residues to such structure. Depending on the sequence, the enzyme adds a GalNAc moiety at either position 4 or position 1, given that a threonine or serine residue is present. Interestingly, if a first GalNAc moiety is added to position 4, a second GalNAc moiety can be added to positions 3 and/or 6, if a suitable amino acid residue is present. However, if position 4 is not glycosylated, then positions 3 and 6 are also not glycosylated. This may be explained by binding of the enzyme's lectin domain to the initially added GalNAc residue and subsequent directing of the catalyic activity to positions 3 and/or 6. Hence, in one embodiment, in order to reduce multiple glycosylation, a glycosyltransferase with a deleted or truncated lectin domain may be used in the glycosylation reaction. Amino acid sequences for exemplary truncated GalNAc-T2 enzymes are provided herein in Table 13 (e.g., SEQ ID NOs: 256-270).

Scheme 1: General Structure of an Exemplary O-linked Glycosylation Sequence

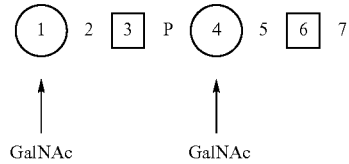

In Scheme 1, amino acid positions 1-7 represent glutamic acid (E), glutamine (Q), aspartic acid (D), asparagine (N), threonine (T), serine (S) or any other uncharged amino acid.

In one embodiment, certain amino acid residues are included into the O-linked glycosylation sequence to modulate expressability of the mutated polypeptide in a particular organism, such as E. coli (compare e.g., Example 1), proteolytic stability, structural characteristics and/or other properties of the polypeptide.

In one embodiment, the O-linked glycosylation sequence of the invention includes an amino acid sequence according to Formula (I). In another embodiment, the O-linked glycosylation sequence includes an amino sequence according to Formula (II). In yet another embodiment, the O-linked glycosylation sequence has an amino acid sequence according to Formula (I). In a further embodiment, the O-linked glycosylation sequence has an amino acid sequence according to Formula (II).

$$(X)_m \ P \ O^* \ U \ (B)_p (Z)_r (J)_s (O)_t (P)_n; \quad \text{(I)} \quad \text{(SEQ ID NO: 1)}$$

and $$(X)_m (B^1)_p \ T \ U \ B \ (Z)_r (P)_n (J)_s \quad \text{(II)} \quad \text{(SEQ ID NO: 2)}$$

In Formulae (I) and (II), the integers m, n, p, r, s and t are independently selected from 0 and 1. X, U, B, Z, J and O can be any amino acid. In a preferred embodiment, U is a member selected from proline (P), glutamic acid (E), glutamine (Q), aspartic acid (D), asparagine (N), threonine (T), serine (S) and uncharged amino acids. X, $B^1$ and B are preferably members independently selected from glutamic acid (E), glutamine (Q), aspartic acid (D), asparagine (N), threonine (T), serine (S) and uncharged amino acids. Z, J and O are preferably members independently selected from glutamic acid (E), glutamine (Q), aspartic acid (D), asparagine (N), threonine (T), serine (S), tyrosine (Y), methionine (M) and uncharged amino acids. P is proline, T is threonine, and S is serine.

In one embodiment, the O-linked glycosylation sequence is $(X)_m PO^*(P)_n$ (SEQ ID NO: 4). In another embodiment, the O-linked glycosylation sequence is $(X)_m PO^*EI(P)_n$ (SEQ ID NO: 5). In another embodiment, the O-linked glycosylation sequence is $(X)_m PO^*QA(P)_n$ (SEQ ID NO: 6). In another embodiment, the O-linked glycosylation sequence is $(X)_m PO^*QAS(P)_n$ (SEQ ID NO: 7). In another embodiment, the O-linked glycosylation sequence is $(X)_m PO^*QAY(P)_n$ (SEQ ID NO: 8). In another embodiment, the O-linked glycosylation sequence is $(X)_m PO^*QTY(P)_n$ (SEQ ID NO: 9). In another embodiment, the O-linked glycosylation sequence is $(X)_m PO^*INT(P)_n$ (SEQ ID NO: 10). In another embodiment, the O-linked glycosylation sequence is $(X)_m PO^*INA(P)_n$ (SEQ ID NO: 11). In another embodiment, the O-linked glycosylation sequence is $(X)_m PO^*VGS(P)_n$ (SEQ ID NO: 12). In another embodiment, the O-linked glycosylation sequence is $(X)_m PO^*TGS(P)_n$ (SEQ ID NO: 13). In another embodiment, the O-linked glycosylation sequence is $(X)_m PO^*TVS(P)_n$ (SEQ ID NO: 14). In another embodiment, the O-linked glycosylation sequence is $(X)_m PO^*TVA(P)_n$ (SEQ ID NO: 15). In another embodiment, the O-linked glycosylation sequence is $(X)_m PO^*TVL(P)_n$ (SEQ ID NO: 16). In another embodiment, the O-linked glycosylation sequence is $(X)_m PO^*VL(P)_n$ (SEQ ID NO: 17). In another embodiment, the O-linked glycosylation sequence is $(X)_m PO^*VGS(P)_n$ (SEQ ID NO: 18). In another embodiment, the O-linked glycosylation sequence is $(X)_m PO^*QGA(P)_n$ (SEQ ID NO: 19). In another embodiment, the O-linked glycosylation sequence is $(X)_m PO^*QGAM(P)_n$ (SEQ ID NO: 20). In another embodiment, the O-linked glycosylation sequence is $(X)_m TET(P)_n$ (SEQ ID NO: 21). In another embodiment, the O-linked glycosylation sequence is $(X)_m PO^*ETQI(P)_n$ (SEQ ID NO: 22). In another embodiment, the O-linked glycosylation sequence is $(X)_m PO^*VL(P)_n$. In another embodiment, the O-linked glycosylation sequence is $(X)_m PO^*TTQ(P)_n$ (SEQ ID NO: 23). In another embodiment, the O-linked glycosylation sequence is $(X)_m PO^*TLY(P)_n$ (SEQ ID NO: 24). In another embodiment, the O-linked glycosylation sequence is $(X)_m PO^*TLYV(P)_n$ (SEQ ID NO: 25). In another embodiment, the O-linked glycosylation sequence is $(X)_m PO^*LS(P)_n$ (SEQ ID NO: 26). In another embodiment, the O-linked glycosylation sequence is $(X)_m PO^*DA(P)_n$ (SEQ ID NO: 27). In another embodiment, the O-linked glycosylation sequence is $(X)_m PO^*EN(P)_n$ (SEQ ID NO: 28). In another embodiment, the O-linked glycosylation sequence is $(X)_m PO^*SG(P)_n$ (SEQ ID NO: 29). In another embodiment, the O-linked glycosylation sequence is $(X)_m PO^*QD(P)_n$ (SEQ ID NO: 30). In another embodiment, the O-linked glycosylation sequence is $(X)_m PO^*AS(P)_n$ (SEQ ID NO: 31). In another embodiment, the O-linked glycosylation sequence is $(X)_m PO^*LS(P)_n$ (SEQ ID NO: 32). In another embodiment, the O-linked glycosylation sequence is $(X)_m PO^*SS(P)_n$ (SEQ ID NO: 33). In another embodiment, the O-linked glycosylation sequence is $(X)_m PO^*SMV(P)_n$ (SEQ ID NO: 34). In another embodiment, the O-linked glycosylation sequence is $(X)_m PO^*ATQ(P)_n$ (SEQ ID NO: 35). In another embodiment, the O-linked glycosylation sequence is $(X)_m PO^*SAV(P)_n$ (SEQ ID NO: 36). In another embodiment, the O-linked glycosylation sequence is $(X)_m PO^*SVG(P)_n$ (SEQ ID NO: 37). In another embodiment, the O-linked glycosylation sequence is $(X)_m PEO^*Y(P)_n$ (SEQ ID NO: 38). In another embodiment, the O-linked glycosylation sequence is $(X)_m PO^*SG(P)_n$ (SEQ ID NO: 39). In another embodiment, the O-linked glycosylation sequence is $(X)_m PO^*DG(P)_n$ (SEQ ID NO: 40). In another embodiment, the O-linked glycosylation sequence is $(X)_m PO^*TGS(P)_n$ (SEQ ID NO: 41). In another embodiment, the O-linked glycosylation sequence is $(X)_m PO^*SAD(P)_n$ (SEQ ID NO: 42). In another embodiment, the O-linked glycosylation sequence is $(X)_m PO^*SGA(P)_n$ (SEQ ID NO: 43). In another embodiment, the O-linked glycosylation sequence is $(X)_m PO^*INA(P)_n$ (SEQ ID NO: 44). In another embodiment, the O-linked glycosylation sequence is $(X)_m TGS(P)_n$ (SEQ ID NO: 45). In another embodiment, the O-linked glycosylation sequence is $(X)_m TQS(P)_n$ (SEQ ID NO: 46). In another embodiment, the O-linked glycosylation sequence is $(X)_m PO^*NQE(P)_n$ (SEQ ID NO: 47). In another embodiment, the O-linked glycosylation sequence is $(X)_m PO^*GYA(P)_n$ (SEQ ID NO: 48). In another embodiment, the O-linked glycosylation sequence is $(X)_m MIAT(P)_n$ (SEQ ID NO: 49).

In one embodiment, in the above sequences, the integer m is 0. In another embodiment, m is 1. In one embodiment, the integer n is 0. In another embodiment, n is 1. In one embodiment, O* is serine (S). In another embodiment O* is threonine (T). P is proline. X can be any amino acid. In one embodiment, X is glutamic acid (E). In another embodiment, X is glutamine (Q). In another embodiment, X is aspartic acid (D). In another embodiment, X is asparagine (N). In another embodiment, X is threonine (T). In another embodiment, X is serine (S). In yet another embodiment, X is an uncharged amino acid, such as alanine (A), glycine (G) or valine (V). In the above sequences, each T (threonine) is optionally and independently replaced with S (serine) and each serine (S) is optionally and independently replaced with T (threonine).

Exemplary O-linked glycosylation sequences according to this embodiment, include: $(X)_m PTP$ (SEQ ID NO: 50), $(X)_m PTEI(P)_n$ (SEQ ID NO: 51), $(X)_m PTQA(P)_n$ (SEQ ID NO: 52), $(X)_m PTQAS(P)_n$ (SEQ ID NO: 53), $(X)_m PTQAY(P)_n$ (SEQ ID NO: 54), $(X)_m PTQTY(P)_n$ (SEQ ID NO: 55), $(X)_m PTINT(P)_n$ (SEQ ID NO: 56), $(X)_m PTINA(P)_n$ (SEQ ID NO: 57), $(X)_m PTVGS(P)_n$ (SEQ ID NO: 58), $(X)_m PTTGS(P)_n$ (SEQ ID NO: 59), $(X)_m PTTVS(P)_n$ (SEQ ID NO: 60), $(X)_m PTTVA(P)_n$ (SEQ ID NO: 61), $(X)_m PTTVL(P)_n$ (SEQ ID NO: 62), $(X)_m PTVL(P)_n$ (SEQ ID NO: 63), $(X)_m PTVGS(P)_n$ (SEQ ID NO: 64), $(X)_m PTQGA(P)_n$ (SEQ ID NO: 65), $(X)_m PTQGAM(P)_n$ (SEQ ID NO: 66), $(X)_m TET(P)_n$ (SEQ ID NO: 67), $(X)_m PTETQI(P)_n$ (SEQ ID NO: 68), $(X)_m PTVL(P)_n$ (SEQ ID NO: 69), $(X)_m PTTTQ(P)_n$ (SEQ ID NO: 70), $(X)_m PTTLY(P)_n$ (SEQ ID NO: 71), $(X)_m PTTLYV(P)_n$ (SEQ ID NO: 72), $(X)_m PTLS(P)_n$ (SEQ ID NO: 73), $(X)_m PTDA(P)_n$ (SEQ ID NO: 74), $(X)_m PTEN(P)_n$ (SEQ ID NO: 75), $(X)_m PSSG(P)_n$ (SEQ ID NO: 76), $(X)_m PTQD(P)_n$ (SEQ ID NO: 77), $(X)_m PTAS(P)_n$ (SEQ ID NO: 78), $(X)_m PTLS(P)_n$ (SEQ ID NO: 79), $(X)_m PTSS(P)_n$ (SEQ ID NO: 80), $(X)_m PTSMV(P)_n$ (SEQ ID NO: 81), $(X)_m PTATQ(P)_n$ (SEQ ID NO: 82), $(X)_m PTSAV(P)_n$ (SEQ ID NO: 83), $(X)_m PTSVG(P)_n$ (SEQ ID NO: 84), $(X)_m PETY(P)_n$ (SEQ ID NO: 85), $(X)_m PSDG(P)_n$ (SEQ ID NO: 86), $(X)_m PSTGS(P)_n$ (SEQ ID NO: 87), $(X)_m PTSAD(P)_n$ (SEQ ID NO: 88), $(X)_m PTSGA(P)_n$ (SEQ ID NO: 89), $(X)_m PTINA(P)_n$ (SEQ ID NO: 90), (X)$_m$TGS(P)$_n$ (SEQ ID NO: 91), (X)$_m$TQS(P)$_n$ (SEQ ID NO: 92), (X)$_m$PTNQE(P)$_n$ (SEQ ID NO: 93), (X)$_m$PTGYA(P)$_n$ (SEQ ID NO: 94) and (X)$_m$MIAT(P)$_n$ (SEQ ID NO: 49), wherein m, n and X are defined as above. In one embodiment, in these sequences, each T (threonine) is optionally and independently replaced with S (serine) and each serine (S) is optionally and independently replaced with T (threonine).

In another exemplary embodiment, the O-linked glycosylation sequence of the invention has an amino acid sequence selected from: XPO*P (SEQ ID NO: 95), XPO*QA(P)$_n$ (SEQ ID NO: 96), XPO*EI(P)$_n$ (SEQ ID NO: 97), XPO*INT (P)$_n$ (SEQ ID NO: 98), XPO*TVS (SEQ ID NO: 99), (X)$_m$PO*TVSP (SEQ ID NO: 100), XPO*QGA (SEQ ID NO: 101), (X)$_m$PO*QGAP (SEQ ID NO: 102), XPO*QGAM (P)$_n$ (SEQ ID NO: 103), (X)$_m$PO*VL (SEQ ID NO: 104), XPO*VL(P)$_n$ (SEQ ID NO: 105), XPO*TVL (SEQ ID NO: 106), (X)$_m$PO*TVLP (SEQ ID NO: 107), (X)$_m$PO*TLYVP (SEQ ID NO: 108), XPO*TLYV(P)$_n$ (SEQ ID NO: 109), (X)$_m$PO*DA(P)$_n$ (SEQ ID NO: 110), (X)$_m$PO*QD(P)$_n$ (SEQ ID NO: 111), (X)$_m$PO*AS(P)$_n$ (SEQ ID NO: 112), XPO*SAV (SEQ ID NO: 113), (X)$_m$PO*SAVP (SEQ ID NO: 114) and XTET(P)$_n$ (SEQ ID NO: 115). In these sequences, each T (threonine) can optionally and independently be replaced with S (serine) and each serine (S) can optionally and independently be replaced with T (threonine). The integers m and n as well as X are defined as above.

In yet another exemplary embodiment, the O-linked glycosylation sequence of the invention has an amino acid sequence selected from: XPTP (SEQ ID NO: 116), XPTQA (P)$_n$ (SEQ ID NO: 117), XPTEI(P)$_n$ (SEQ ID NO: 118), XPTINT(P)$_n$ (SEQ ID NO: 119), XPTTVS (SEQ ID NO: 120), (X)$_m$PTTVSP (SEQ ID NO: 121), XPTQGA (SEQ ID NO: 122), (X)$_m$PTQGAP (SEQ ID NO: 123), XPTQGAM (P)$_n$ (SEQ ID NO: 124), XTETP (SEQ ID NO: 125), (X)$_m$PTVL (SEQ ID NO: 126), XPTVL(P)$_n$ (SEQ ID NO: 127), XPTTVL (SEQ ID NO: 128), (X)$_m$PTTVLP (SEQ ID NO: 129), (X)$_m$PTTLYVP (SEQ ID NO: 130), XPTTLYV (P)$_n$ (SEQ ID NO: 131), (X)$_m$PTDA(P)$_n$ (SEQ ID NO: 132), (X)$_m$PTQD(P)$_n$ (SEQ ID NO: 133), (X)$_m$PTAS(P)$_n$ (SEQ ID NO: 134), XPTSAV (SEQ ID NO: 135), (X)$_m$PTSAVP (SEQ ID NO: 136) and XTET(P)$_n$ (SEQ ID NO: 137). In one embodiment, each T (threonine) is optionally and independently replaced with S (serine) and each serine (S) is optionally and independently replaced with T (threonine). The integers m and n as well as X are defined as above.

In one embodiment, the O-linked glycosylation sequence of the invention is PTP (SEQ ID NO: 138). In another embodiment, the O-linked glycosylation sequence is PTEI (SEQ ID NO: 139). In another embodiment, the O-linked glycosylation sequence is PTEIP (SEQ ID NO: 140). In another embodiment, the O-linked glycosylation sequence is PTQA (SEQ ID NO: 141). In another embodiment, the O-linked glycosylation sequence is PTQAP (SEQ ID NO: 142). In another embodiment, the O-linked glycosylation sequence is PTINT (SEQ ID NO: 143). In another embodiment, the O-linked glycosylation sequence is PTINTP (SEQ ID NO: 144). In another embodiment, the O-linked glycosylation sequence is PTTVS (SEQ ID NO: 145). In another embodiment, the O-linked glycosylation sequence is PTTVL (SEQ ID NO: 146). In another embodiment, the O-linked glycosylation sequence is PTQGAM (SEQ ID NO: 147). In another embodiment, the O-linked glycosylation sequence is PTQGAMP (SEQ ID NO: 148). In another embodiment, the O-linked glycosylation sequence is TETP (SEQ ID NO: 149). In another embodiment, the O-linked glycosylation sequence is PTVL (SEQ ID NO: 150). In another embodiment, the O-linked glycosylation sequence is PTVLP (SEQ ID NO: 151). In another embodiment, the O-linked glycosylation sequence is PTLSP (SEQ ID NO: 152). In another embodiment, the O-linked glycosylation sequence is PTDAP (SEQ ID NO: 153). In another embodiment, the O-linked glycosylation sequence is PTENP (SEQ ID NO: 154). In another embodiment, the O-linked glycosylation sequence is PTQDP (SEQ ID NO: 155). In another embodiment, the O-linked glycosylation sequence is PTASP (SEQ ID NO: 156). In another embodiment, the O-linked glycosylation sequence is PTTVSP (SEQ ID NO: 157). In another embodiment, the O-linked glycosylation sequence is PTQGA (SEQ ID NO: 158). In another embodiment, the O-linked glycosylation sequence is PTSAV (SEQ ID NO: 159). In another embodiment, the O-linked glycosylation sequence is PTTLYV (SEQ ID NO: 160). In another embodiment, the O-linked glycosylation sequence is PTTLYVP (SEQ ID NO: 161). In another embodiment, the O-linked glycosylation sequence is PSSGP (SEQ ID NO: 162). In another embodiment, the O-linked glycosylation sequence is PSDGP (SEQ ID NO: 163).

In an exemplary embodiment, in which the parent polypeptide is glucagon-like peptide-1 (GLP-1), the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418). In another exemplary embodiment, in which the parent polypeptide is wild-type GLP-1 the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418). In another exemplary embodiment, in which the parent polypeptide is wild-type GLP-1, the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418), unless the O-linked glycosylation sequence is not designed around a proline residue that is present in the wild-type G-CSF polypeptide.

In another exemplary embodiment, in which the parent polypeptide is G-CSF, the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138). In another exemplary embodiment, in which the parent polypeptide is wild-type G-CSF the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138). In another embodiment, in which the parent polypeptide is wild-type G-CSF the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138), unless the O-linked glycosylation sequence is not designed around a proline residue that is present in the wild-type G-CSF polypeptide.

In another exemplary embodiment, in which the parent polypeptide is human growth hormon (hGH), the O-linked glycosylation sequence is preferably not selected from PTQGA (SEQ ID NO: 158), PTQGAM (SEQ ID NO: 147), PTQGAMP (SEQ ID NO: 148), PTVLP (SEQ ID NO: 151), PTTVS (SEQ ID NO: 145), PTTLYV (SEQ ID NO: 160), PTINT (SEQ ID NO: 143), PTEIP (SEQ ID NO: 140), PTQA (SEQ ID NO: 141) and TETP (SEQ ID NO: 149). In another exemplary embodiment, in which the parent polypeptide is wild-type hGH, the O-linked glycosylation sequence is preferably not selected from PTQGAM (SEQ ID NO: 147), PTQGAMP (SEQ ID NO: 148), PTTVS (SEQ ID NO: 145), PTTLYV (SEQ ID NO: 160), PTINT (SEQ ID NO: 143), PTQA (SEQ ID NO: 141) and TETP (SEQ ID NO: 149). In yet another exemplary embodiment, in which the parent polypeptide is wild-type hGH, the O-linked glycosylation sequence is preferably not selected from PTQGAM (SEQ ID NO: 147), PTQGAMP (SEQ ID NO: 148), PTTVS (SEQ ID NO: 145), PTTLYV (SEQ ID NO: 160), PTINT (SEQ ID NO: 143), PTQA (SEQ ID NO: 141) and TETP (SEQ ID NO: 149), unless the O-linked glycosylation sequence is not designed around a proline residue that is present in the wild-type hGH polypeptide.

In another exemplary embodiment, in which the parent polypeptide is INF-alpha, the O-linked glycosylation sequence is preferably not TETP (SEQ ID NO: 149). In another exemplary embodiment, in which the parent polypeptide is wild-type INF-alpha, the O-linked glycosylation sequence is preferably not TETP (SEQ ID NO: 149). In yet another exemplary embodiment, in which the parent polypeptide is wild-type INF-alpha, the O-linked glycosylation sequence is preferably not TETP (SEQ ID NO: 149), unless the O-linked glycosylation sequence is not designed around a proline residue that is present in the wild-type INF-alpha polypeptide.

In another exemplary embodiment, in which the parent polypeptide is FGF (e.g., FGF-1, FGF-2, FGF-18, FGF-20, FGF-21), the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420).

In another exemplary embodiment, in which the parent polypeptide is a wild-type FGF, the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420). In yet another exemplary embodiment, in which the parent polypeptide is a wild-type FGF, the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420), unless the O-linked glycosylation sequence is not designed around a proline residue that is present in the wild-type FGF polypeptide.

In one embodiment, the O-linked glycosylation sequences is glycosylated with high efficiency when subjected to a suitable glycosylation reaction. For example, the reaction yield for a suitable glycosylation reaction is at least about 50%, at least about 60%, at least about 70%, at least about 80%, at least about 90% or at least about 95%. In another embodiment, the O-linked glycosylation sequence is glycosylated with a GalNAc residue at only one amino acid residue per glycosylation sequence when the enzyme is GalNAc-T2.

Sequon Polypeptides

The O-linked glycosylation sequences of the invention can be introduced into any parent polypeptide, creating a sequon polypeptide of the invention. The sequon polypeptides of the invention can be generated using methods known in the art and described herein below (e.g., through recombinant technology or chemical synthesis). In one embodiment, the parent sequence is modified in such a way that the O-linked-glycosylation sequence is inserted into the parent sequence adding the entire length and respective number of amino acids to the amino acid sequence of the parent polypeptide. In another embodiment, the O-linked glycosylation sequence replaces one or more amino acids of the parent polypeptide. In another embodiment, the variation is introduced into the parent polypeptide, using one or more of the pre-existing amino acids to be part of the glycosylation sequence. For instance, a proline residue in the parent pepide is maintained and those amino acids immediately following the proline are mutated to create an O-linked-glycosylation sequence of the invention. In yet another embodiment, the O-linked glycosylation sequence is created employing a combination of amino acid insertion and replacement of existing amino acids.

In certain embodiments, a particular parent polypeptide of the invention is used in conjunction with a particular O-linked glycosylation sequence of the invention. Exemplary parent polypeptide/O-linked glycosylation sequence combinations are summarized in Table 2 (FIG. 6). Each row in FIG. 6 represents an exemplary embodiment of the invention. The combinations shown may be used in all aspects of the invention including single sequon polypeptides, libraries of sequon polypeptides, sequon polypeptide conjugates and methods of the invention. One of skill in the art will appreciate that the embodiments set forth in FIG. 6 for the indicated parent polypeptides can equally apply to other parent polypeptides set forth herein.

Libraries of Sequon Polypeptides

One strategy for the identification of polypeptides, which are glycosylated or glycoPEGylated efficiently (e.g., with a satisfactory yield) when subjected to a glycosylation or glycoPEGylation reaction, is to insert an O-linked glycosylation sequence of the invention at a variety of different positions within the amino acid sequence of a parent polypeptide, including e.g., beta-sheet domains and alpha-helical domains, and then to test a number of the resulting sequon polypeptides for their ability to function as an efficient substrate for a glycosyltransferase, such as human GalNAc-T2.

Hence, in another aspect, the invention provides a library of sequon polypeptides including a plurality of different members, wherein each member of the library corresponds to a common parent polypeptide and includes at least one independently selected exogenous O-linked or S-linked glycosylation sequence of the invention. In one embodiment, each member of the library includes the same O-linked glycosylation sequence, each at a different amino acid position within the parent polypeptide. In another embodiment, each member of the library includes a different O-linked glycosylation sequence, however at the same amino acid position within the parent polypeptide. O-linked glycosylation sequences, which are useful in conjunction with the libaries of the invention are described herein. In one embodiment, the O-linked glycosylation sequence used in a library of the invention has an amino acid sequence according to Formula (I) (SEQ ID NO: 1). In another embodiment, the O-linked glycosylation sequence used in a library of the invention has an amino acid sequence according to Formula (II) (SEQ ID NO: 2). Formula (I) and Formula (II) are described herein, below.

In a preferred embodiment, the O-linked glycosylation sequence used in conjunction with the libraries of the invention has an amino acid sequence, which is from: $(X)_m PT(P)_n$ (SEQ ID NO: 409), $(X)_m PTEI(P)_n$ (SEQ ID NO: 51), $(X)_m PTQA(P)_n$ (SEQ ID NO: 52), $(X)_m PTQAS(P)_n$ (SEQ ID NO: 53), $(X)_m PTQAY(P)_n$ (SEQ ID NO: 54), $(X)_m PTQTY(P)_n$ (SEQ ID NO: 55), $(X)_m PTINT(P)_n$ (SEQ ID NO: 56), $(X)_m PTINA(P)_n$ (SEQ ID NO: 57), $(X)_m PTVGS(P)_n$ (SEQ ID NO: 58), $(X)_m PTTGS(P)_n$ (SEQ ID NO: 59), $(X)_m PTTVS(P)_n$ (SEQ ID NO: 60), $(X)_m PTTVA(P)_n$ (SEQ ID NO: 61), $(X)_m PTTVL(P)_n$ (SEQ ID NO: 62), $(X)_m PTVL(P)_n$ (SEQ ID NO: 63), $(X)_m PTVGS(P)_n$ (SEQ ID NO: 64), $(X)_m PTQGA(P)_n$ (SEQ ID NO: 65), $(X)_m PTQGAM(P)_n$ (SEQ ID NO: 66), $(X)_m TET(P)_n$ (SEQ ID NO: 67), $(X)_m PTETQI(P)_n$ (SEQ ID NO: 68), $(X)_m PTVL(P)_n$ (SEQ ID NO: 69), $(X)_m PTTTQ(P)_n$ (SEQ ID NO: 70), $(X)_m PTTLY(P)_n$ (SEQ ID NO: 71), $(X)_m PTTLYV(P)_n$ (SEQ ID NO: 72), $(X)_m PTLS(P)_n$ (SEQ ID NO: 73), $(X)_m PTDA(P)_n$ (SEQ ID NO: 74), $(X)_m PTEN(P)_n$ (SEQ ID NO: 75), $(X)_m PSSG(P)_n$ (SEQ ID NO: 76), $(X)_m PTQD(P)_n$ (SEQ ID NO: 77), $(X)_m PTAS(P)_n$ (SEQ ID NO: 78), $(X)_m PTLS(P)_n$ (SEQ ID NO: 79), $(X)_m PTSS(P)_n$ (SEQ ID NO: 80), $(X)_m PTSMV(P)_n$ (SEQ ID NO: 81), $(X)_m PTATQ(P)_n$ (SEQ ID NO: 82), $(X)_m PTSAV(P)_n$ (SEQ ID NO: 83), $(X)_m PTSVG(P)_n$ (SEQ ID NO: 84), $(X)_m PETY(P)_n$ (SEQ ID NO: 85), $(X)_m PSDG(P)_n$ (SEQ ID NO: 86), $(X)_m PSTGS(P)_n$ (SEQ ID NO: 87), $(X)_m PTSAD(P)_n$ (SEQ ID NO: 88), $(X)_m PTSGA(P)_n$ (SEQ ID NO: 89), $(X)_m PTINA(P)_n$ (SEQ ID NO: 90), $(X)_m TGS(P)_n$ (SEQ ID NO: 91), $(X)_m TQS(P)_n$ (SEQ ID NO: 92), $(X)_m PTNQE(P)_n$ (SEQ ID NO: 93), $(X)_m PTGYA(P)_n$ (SEQ ID NO: 94) and $(X)_m MIAT(P)_n$ (SEQ ID NO: 49), wherein m and n are integers independently selected from 0 and 1. X can be any amino acid and is preferably a member selected from glutamic acid (E), glutamine (Q), aspartic acid (D), asparagine (N), threonine (T), serine (S) and uncharged amino acids. Each T (threonine) is optionally and independently replaced with S (serine).

In one embodiment, in which each member of the library has a common O-linked glycosylation sequence, the parent polypeptide has an amino acid sequence that includes "m" amino acids. In one example, the library of sequon polypeptides includes (a) a first sequon polypeptide having the O-linked glycosylation sequence at a first amino acid position $(AA)_n$ within the parent polypeptide, wherein n is a member selected from 1 to m; and (b) at least one additional sequon polypeptide, wherein in each additional sequon polypeptide the O-linked glycosylation sequence is introduced at an additional amino acid position, each additional amino acid position selected from $(AA)_{n+x}$ and $(AA)_{n-x}$, wherein x is a member selected from 1 to (m−n). For example, a first sequon polypeptide is generated through introduction of a selected O-linked glycosylation sequence at the first amino acid position. Subsequent sequon polypeptides may then be generated by introducing the same O-linked glycosylation sequence at an amino acid position, which is located further towards the N- or C-terminus of the parent polypeptide.

In this context, when n−x is 0 $(AA_0)$ then the glycosylation sequence is introduced immediately preceding the N-terminal amino acid of the parent polypeptide. An exemplary sequon polypeptide may have the partial sequence: "PTPM$^1$...."

The first amino acid position $(AA)_n$ can be anywhere within the amino acid sequence of the parent polypeptide. In one embodiment, the first amino acid position is selected (e.g., at the beginning of a loop domain).

Each additional amino acid position can be anywhere within the parent polypeptide. In one example, the library of sequon polypeptides includes a second sequon polypeptide having the O-linked glycosylation sequence at an amino acid position selected from $(AA)_{n+p}$ and $(AA)_{n-p}$, wherein p is selected from 1 to about 10, preferably from 1 to about 8, more preferably from from 1 to about 6, even more preferably from 1 to about 4 and most preferably from 1 to about 2. In one embodiment, the library of sequon polypeptides includes a first sequon polypeptide having an O-linked glycosylation sequence at amino acid position $(AA)_n$ and a second sequon polypeptide having an O-linked glycosylation sequence at amino acid position $(AA)_{n+1}$ or $(AA)_{n-1}$.

In another example, each of the additional amino acid position is immediately adjacent to a previously selected amino acid position. In yet another example, each additional amino acid position is exactly 1, 2, 3, 4, 5, 6, 7, 8, 9 or 10 amino acid(s) removed from a previously selected amino acid position.

Introduction of an O-linked or S-linked glycosylation sequence "at a given amino acid position" of the parent polypeptide means that the mutation is introduced starting immediately next to the given amino acid position (towards the C-terminus). Introduction can occur through full insertion (not replacing any existing amino acids), or by replacing any number of existing amino acids.

In an exemplary embodiment, the library of sequon polypeptides is generated by introducing the O-linked glycosylation sequence at consecutive amino acid positions of the parent polypeptide, each located immediately adjacent to the previously selected amino acid position, thereby "scanning" the glycosylation sequence through the amino acid chain, until a desired, final amino acid position is reached. Immediately adjacent means exactly one amino acid position further towards the N- or C-terminus of the parent polypeptide. For instance, the first mutant is created by introduction of the glycosylation sequence at amino acid position $AA_n$. The second member of the library is generated through introduction of the glycosylation site at amino acid position $AA_{n+1}$ the third mutant at $AA_{n+2}$, and so forth. This procedure has been termed "sequon scanning". Examples for sequon scanning are provided herein, e.g., in Example 1.9. One of skill in the art will appreciate that sequon scanning can involve designing the library so that the first member has the glycosylation sequence at amino acid position $(AA)_n$, the second member at amino acid position $(AA)_{n+2}$, the third at $(AA)_{n+4}$ etc. Likewise, the members of the library may be characterized by other strategic placements of the glycosylation sequence. For example:

A) member 1: $(AA)_n$; member 2: $(AA)_{n+3}$; member 3: $(AA)_{n+6}$; member 4: $(AA)_{n+9}$ etc.
B) member 1: $(AA)_n$; member 2: $(AA)_{n+4}$; member 3: $(AA)_{n+8}$; member 4: $(AA)_{n-12}$ etc.
C) member 1: $(AA)_n$; member 2: $(AA)_{n+5}$; member 3: $(AA)_{n+10}$; member 4: $(AA)_{n+15}$ etc.

In one embodiment, a first library of sequon polypeptides is generated by scanning a selected O-linked or S-linked glycosylation sequence of the invention through a particular region of the parent polypeptide (e.g., from the beginning of a particular loop region to the end of that loop region). A second library is then generated by scanning the same glycosylation sequence through another region of the polypeptide, "skipping" those amino acid positions, which are located between the first region and the second region. The part of the polypeptide chain that is left out may, for instance, correspond to a binding domain important for biological activity or another region of the polypeptide sequence known to be unsuitable for glycosylation. Any number of additional libraries can be generated by performing "sequon scanning" for additional stretches of the polypeptide. In an exemplary embodiment, a library is generated by scanning the O-linked glycosylation sequence through the entire polypeptide introducing the mutation at each amino acid position within the parent polypeptide.

In one embodiment, the members of the library are part of a mixture of polypeptides. For example, a cell culture is infected with a plurality of expression vectors, wherein each vector includes the nucleic acid sequence for a different sequon polypeptide of the invention. Upon expression, the culture broth may contain a plurality of different sequon polypeptides, and thus includes a library of sequon polypeptides. This technique may be useful to determine, which sequon polypeptide of a library is expressed most efficiently in a given expression system.

In another embodiment, the members of the library exist isolated from each other. For example, at least two of the sequon polypeptides of the above mixture may be isolated. Together, the isolated polypeptides represent a library. Alternatively, each sequon polypeptide of the library is expressed separately and the sequon polypeptides are optionally isolated. In another example, each member of the library is synthesized by chemical means and optionally purified.

Exemplary Sequon Polypeptides

An exemplary parent polypeptide is recombinant human BMP-7. The selection of BMP-7 as an exemplary parent polypeptide is for illustrative purposes and is not meant to limit the scope of the invention. A person of skill in the art will appreciate that any parent polypeptide (e.g., those set forth herein) are equally suitable for the following exemplary modifications. Any polypeptide variant thus obtained falls within the scope of the invention. Biologically active BMP-7 variants of the present invention include any BMP-7 polypeptide, in part or in whole, that includes at least one modification that does not result in substantial or entire loss of its biological activity as measured by any suitable functional assay known to one skilled in the art. The following sequence (140 amino acids) represents a biologically active portion of the full-length BMP-7 sequence (sequence S.1):

(SEQ ID NO: 164)
M$^{1}$STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGCH

Exemplary BMP-7 variant polypeptides, which are based on the above parent polypeptide sequence, are listed in Tables 3-11, below. In a preferred embodiment, sequon polypeptides are generated taking the substrate requirements of the glycosyltransferase into consideration. For example, when using a full-length or truncated GalNAc-T2 (preferably human GalNAc-T2) as the glycosyltransferase, any basic amino acid residue, such as lysine (K) or arginine (R), which is found in proximity (e.g., within three amino acid residues) of the site of glycosylation (e.g., threonine) is optionally replaced with another amino acid. In Tables 1-10, below, such basic amino acids are marked by underlining. The replacement amino acid is preferably an uncharged amino acid, such as alanine.

In one exemplary embodiment, mutations are introduced into the the wild-type BMP-7 amino acid sequence S.1 (SEQ ID NO: 164) replacing the corresponding number of amino acids in the parent sequence, resulting in a sequon polypeptide that contains the same number of amino acid residues as the parent polypeptide. For instance, directly substituting three amino acids normally in BMP-7 with the O-linked glycosylation sequence "proline-threonine-proline" (PTP) and then sequentially moving the PTP sequence towards the C-terminus of the polypeptide provides 137 BMP-7 variants each including PTP. Exemplary sequences according to this embodiment are listed in Table 3, below.

TABLE 3

Exemplary library of BMP-7 variants including 140 amino acids wherein three existing amino acids are replaced with the O-linked glycosylation sequence "PTP"
Basic amino acids in proximity to the site of glycosylation, which can optionally be replaced with an uncharged amino acid, are marked by underlining.

Introduction at position 1, replacing 3 existing amino acids:

(SEQ ID NO: 165)
M$^{1}$PTPSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH

Introduction at position 2, replacing 3 existing amino acids:

(SEQ ID NO: 166)
M$^{1}$SPTPKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH

Introduction at position 3, replacing 3 existing amino acids:

(SEQ ID NO: 167)
M$^{1}$STPTPQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH

Additional BMP-7 variants can be generated by "scanning" the glycosylation sequence through the entire sequence in the above fashion. All variant BMP-7 sequences thus obtained are within the scope of the invention. The final sequon polypeptide so generated has the following sequence:

Introduction at Position 137, Replacing 3 Existing Amino Acids:

(SEQ ID NO: 168)
M$^{1}$STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACPTP

In another exemplary embodiment, the O-linked glycosylation sequence is introduced into the wild-type BMP-7 amino acid sequence S.1 (SEQ ID NO: 164) by adding one or more amino acids to the parent sequence. For instance, the O-linked glycosylation sequence PTP is added to the parent BMP-7 sequence replacing either 2, 1 or none of the amino acids in the parent sequence. In this example, the maximum number of added amino acid residues corresponds to the length of the inserted glycosylation sequence. In an exemplary embodiment, the parent sequence is extended by exactly one amino acid. For example, the O-linked glycosylation sequence PTP is added to the parent BMP-7 peptide replacing 2 amino acids normally present in BMP-7. Exemplary sequences according to this embodiment are listed in Table 4, below.

TABLE 4

Exemplary library of mutant BMP-7 polypeptides including 141 amino acids, wherein two existing amino acids are replaced with the O-linked glycosylation sequence "PTP"
Basic amino acids in proximity to the site of glycosylation, which can optionally be replaced with an uncharged amino acid, are marked by underlining.

Introduction at position 1, replacing 2 amino acids (ST)

(SEQ ID NO: 169)
M¹PTPGSKQRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH

Introduction at position 2, replacing 2 amino acids (TG)

(SEQ ID NO: 170)
M¹SPTP<u>K</u>QRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH

Introduction at position 3, replacing 2 amino acids (GS)

(SEQ ID NO: 171)
M¹STPTP<u>K</u>QRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH

Introduction at position 4, replacing 2 amino acids (SK)

(SEQ ID NO: 172)
M¹STGPTP<u>Q</u>RSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH

Introduction at position 5, replacing 2 amino acids (KQ)

(SEQ ID NO: 173)
M¹STGSPTP<u>R</u>SQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH

Additional BMP-7 variants can be generated by "scanning" the glycosylation sequence through the entire sequence in the above fashion until the following sequence is reached:

Introduction at position 138, replacing 2 existing amino acids (CH):

(SEQ ID NO: 174)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGPTP

All BMP-7 variants thus obtained are within the scope of the invention.

Another example involves the addition of an O-linked glycosylation sequence (e.g., PTP) to the parent polypeptide (e.g., BMP-7) replacing 1 amino acid normally present in the parent polypeptide (double amino acid insertion). Exemplary sequences according to this embodiment are listed in Table 5, below.

TABLE 5

Exemplary library of BMP-7 mutants including PTP; replacement of one existing amino acid (142 amino acids)
Basic amino acids in proximity to the site of glycosylation, which can optionally be replaced with an uncharged amino acid, are marked by underlining.

Introduction at position 1, replacing 1 amino acid (S)

(SEQ ID NO: 175)
M¹PTPTGSKQRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH

Introduction at position 2, replacing 1 amino acid (T)

(SEQ ID NO: 176)
M¹SPTPGSKQRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH

Introduction at position 3, replacing 1 amino acid (G)

(SEQ ID NO: 177)
M¹STPTPS<u>K</u>QRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH

Introduction at position 4, replacing 1 amino acid (S)

(SEQ ID NO: 178)
M¹STGPTP<u>K</u>QRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH

Introduction at position 5, replacing 1 amino acid (K)

(SEQ ID NO: 179)
M¹STGSPTP<u>Q</u>RSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH

Additional BMP-7 variants can be generated by "scanning" the glycosylation sequence through the entire sequence in the above fashion until the following sequence is reached:

Introduction at position 139, replacing 1 existing amino acid (H):

(SEQ ID NO: 180)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGCPTP

All BMP-7 variants thus obtained are within the scope of the invention.

Yet another example involves the creation of an O-linked glycosylation sequence within the parent polypeptide (e.g., BMP-7) replacing none of the amino acids normally present in the parent polypeptide and adding the entire length of the glycosylation sequence (e.g., triple amino acid insertion for PTP). Exemplary sequences according to this embodiment are listed in Table 6, below.

TABLE 6

Exemplary library of BMP-7 variants including PTP; addition of 3 amino acids (143 amino acids) Basic amino acids in proximity to the site of glycosylation, which can optionally be replaced with an uncharged amino acid, are marked by underlining.

Introduction at position 1, adding 3 amino acids (SEQ ID NO: 181)
M¹PTPSTGSKQRSQNRSKTPKNQEALRMANVAENSSSDQRQACKKHELYV
SFRDLGWQDWIIAPEGYAAYYCEGECAFPLNSYMNATNHAIVQTLVHFIN
PETVPKPCCAPTQLNAISVLYFDDSSNVILKKYRNMVVRACGCH Introduction at position 2, adding 3 amino acids (SEQ ID NO: 182)
M¹SPTPTGSKQRSQNRSKTPKNQEALRMANVAENSSSDQRQACKKHELYV
SFRDLGWQDWIIAPEGYAAYYCEGECAFPLNSYMNATNHAIVQTLVHFIN
PETVPKPCCAPTQLNAISVLYFDDSSNVILKKYRNMVVRACGCH Introduction at position 3, adding 3 amino acids (SEQ ID NO: 183)
M¹STPTPGSKQRSQNRSKTPKNQEALRMANVAENSSSDQRQACKKHELYV
SFRDLGWQDWIIAPEGYAAYYCEGECAFPLNSYMNATNHAIVQTLVHFIN
PETVPKPCCAPTQLNAISVLYFDDSSNVILKKYRNMVVRACGCH Intruduction at position 4, adding 3 amino acids (SEQ ID NO: 184)
M¹STGPTPS<u>K</u>QRSQNRSKTPKNQEALRMANVAENSSSDQRQACKKHELYV
SFRDLGWQDWIIAPEGYAAYYCEGECAFPLNSYMNATNHAIVQTLVHFIN
PETVPKPCCAPTQLNAISVLYFDDSSNVILKKYRNMVVRACGCH Additional BMP-7 mutants can be generated by "scanning" the glycosylation sequence through the entire sequence in the above fashion until a final sequence is reached:

Introduction at position 140, adding 3 amino acids:

(SEQ ID NO: 185)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGCHPTP

All BMP-7 variants thus obtained are within the scope of the invention.

BMP-7 variants analogous to those examples in Tables 1-5 can be generated using any of the O-linked glycosylation sequences of the invention. All resulting BMP-7 variants are within the scope of the invention. For instance, instead of PTP the sequences PTINT (SEQ ID NO: 143) or PTTVS (SEQ ID NO: 145) can be used. In an exemplary embodiment PTINT is introduced into the parent polypeptide replacing 5 amino acids normally present in BMP-7. Exemplary sequences according to this embodiment are listed in Table 7, below.

TABLE 7

Exemplary library of BMP-7 variants including PTINT; replacement of 5 amino acids (140 amino acids)

(SEQ ID NO: 186)
M¹PTINTQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH (SEQ ID NO: 187)
M¹SPTINTRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH (SEQ ID NO: 188)
M¹STPTINTSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH (SEQ ID NO: 189)
M¹STGPTINTQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCH

Additional BMP-7 mutants can be generated by "scanning" the glycosylation sequence through the entire sequence in the above fashion until a final sequence is reached:

(SEQ ID NO: 190)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRPTINT

All mutant BMP-7 sequences thus obtained are within the scope of the invention.

In another example the O-linked glycosylation sequence PTINT is added to the parent polypeptide (e.g., BMP-7) at or close to either the N- or C-terminal of the parent sequence, adding 1 to 5 amino acids to the parent polypeptide. Exemplary sequences according to this embodiment are listed in Table 8, below.

TABLE 8

Exemplary libraries of BMP-7 variants including PTINT (141-145 amino acids)

Amino-terminal mutants:
Introduction at position 1, adding 5 amino acids (SEQ ID NO: 191)
M¹PTINTSTGSKQRSQNRSKTPKNQEALRMANVAENSSSDQRQACKKHEL
YVSFRDLGWQDWIIAPEGYAAYYCEGECAFPLNSYMNATNHAIVQTLVHF
INPETVPKPCCAPTQLNAISVLYFDDSSNVILKKYRNMVVRACGCH Introduction at position 1, adding 4 amino acids, replacing 1 amino acid (S)

(SEQ ID NO: 192)
M¹PTINTTGSKQRSQNRSKTPKNQEALRMANVAENSSSDQRQACKKHELY
VSFRDLGWQDWIIAPEGYAAYYCEGECAFPLNSYMNATNHAIVQTLVHFI
NPETVPKPCCAPTQLNAISVLYFDDSSNVILKKYRNMVVRACGCH

Introduction at position 1, adding 3 amino acids, replacing 2 amino acids (ST)

(SEQ ID NO: 193)
M¹PTINTGSKQRSQNRSKTPKNQEALRMANVAENSSSDQRQACKKHELYV
SFRDLGWQDWIIAPEGYAAYYCEGECAFPLNSYMNATNHAIVQTLVHFIN
PETVPKPCCAPTQLNAISVLYFDDSSNVILKKYRNMVVRACGCH

TABLE 8-continued

Exemplary libraries of BMP-7 variants including PTINT (141-145 amino acids)

Introduction at position 1, adding 2 amino acids, replacing 3 amino acids (STG)

(SEQ ID NO: 194)
M$^{1}$PTINTSKQRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH

Introduction at position 1, adding 1 amino acids, replacing 4 amino acids (STGS)

(SEQ ID NO: 195)
M$^{1}$PTINTKQRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH

Carboxy-terminal mutants
Introduction at position 140, adding 5 amino acids (SEQ ID NO: 196)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCHPTINT

Introduction at position 139, adding 4 amino acids, replacing 1 amino acid (H)

(SEQ ID NO: 197)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGCPTINT

Introduction at position 138, adding 3 amino acids, replacing 2 amino acid (CH)

(SEQ ID NO: 198)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACGPTINT

Introduction at position 137, adding 2 amino acids, replacing 3 amino acid (GCH)

(SEQ ID NO: 199)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACPTINT

Introduction at position 136, adding 1 amino acids, replacing 4 amino acid (CGCH)

(SEQ ID NO: 200)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRAPTINT

Yet another example involves insertion of the O-linked glycosylation sequence PTTVS (SEQ ID NO: 145) into the parent polypeptide (e.g., BMP-7), adding 1 to 5 amino acids to the parent sequence. Exemplary sequences according to this embodiment are listed in Table 9, below.

TABLE 9

Exemplary library of BMP-7 variants including PTTVS
Basic amino acids in proximity to the site of glycosylation, which can optionally be replaced with an uncharged amino acid, are marked by underlining.

Insertion of one amino acid (SEQ ID NO: 201)
M$^{1}$PTTVSKQRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH (SEQ ID NO: 202)
M$^{1}$SPTTVSQRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH (SEQ ID NO: 203)
M$^{1}$STPTTVSRSQNRSKTPKNQEALRMANVAENSSSDQRQACKKHELYVSF
RDLGWQDWIIAPEGYAAYYCEGECAFPLNSYMNATNHAIVQTLVHFINPE
TVPKPCCAPTQLNAISVLYFDDSSNVILKKYRNMVVRACGCH Additional BMP-7 mutants can be generated by "scanning" the glycosylation sequence through the entire sequence in the above fashion until a final sequence is reached:

(SEQ ID NO: 204)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRAPTTVS

All BMP-7 variants thus obtained are within the scope of the invention.

Insertion of two amino acids (SEQ ID NO: 205)
M$^{1}$PTTVSSKQRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH (SEQ ID NO: 206)
M$^{1}$SPTTVSKQRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH (SEQ ID NO: 207)
M$^{1}$STPTTVSQRSQNRSKTPKNQEALRMANVAENSSSDQRQACKKHELYVS
FRDLGWQDWIIAPEGYAAYYCEGECAFPLNSYMNATNHAIVQTLVHFINP
ETVPKPCCAPTQLNAISVLYFDDSSNVILKKYRNMVVRACGCH Additional BMP-7 variants can be generated by "scanning" the glycosylation sequence through the entire sequence in the above fashion until a final sequence is reached:

(SEQ ID NO: 208)
M$^{1}$STGSKQRSQNRSKTPKNQEALRMANVAENSSSDQRQACKKHELYVSFR
DLGWQDWIIAPEGYAAYYCEGECAFPLNSYMNATNHAIVQTLVHFINPET
VPKPCCAPTQLNAISVLYFDDSSNVILKKYRNMVVRACPTTVS

All BMP-7 variants thus obtained are within the scope of the invention.

```
Insertion of three amino acids
                                       (SEQ ID NO: 209)
M¹PTTVSGSKQRSQNRSKTPKNQEALRMANVAENSSSDQRQACKKHELYV

SFRDLGWQDWIIAPEGYAAYYCEGECAFPLNSYMNATNHAIVQTLVHFIN

PETVPKPCCAPTQLNAISVLYFDDSSNVILKKYRNMVVRACGCH (SEQ ID NO: 210)
M¹SPTTVSSKQRSQNRSKTPKNQEALRMANVAENSSSDQRQACKKHELYV

SFRDLGWQDWIIAPEGYAAYYCEGECAFPLNSYMNATNHAIVQTLVHFIN

PETVPKPCCAPTQLNAISVLYFDDSSNVILKKYRNMVVRACGCH (SEQ ID NO: 211)
M¹STPTTVSKQRSQNRSKTPKNQEALRMANVAENSSSDQRQACKKHELYV

SFRDLGWQDWIIAPEGYAAYYCEGECAFPLNSYMNATNHAIVQTLVHFIN

PETVPKPCCAPTQLNAISVLYFDDSSNVILKKYRNMVVRACGCH
```

Additional BMP-7 variants can be generated by "scanning" the glycosylation sequence through the entire sequence in the above fashion until a final sequence is reached:

```
                                       (SEQ ID NO: 212)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGPTTVS
```

All BMP-7 variants thus obtained are within the scope of the invention.

```
Insertion of four amino acids
                                       (SEQ ID NO: 213)
M¹PTTVSTGSKQRSQNRSKTPKNQEALRMANVAENSSSDQRQACKKHELY

VSFRDLGWQDWIIAPEGYAAYYCEGECAFPLNSYMNATNHAIVQTLVHFI

NPETVPKPCCAPTQLNAISVLYFDDSSNVILKKYRNMVVRACGCH (SEQ ID NO: 214)
M¹SPTTVSGSKQRSQNRSKTPKNQEALRMANVAENSSSDQRQACKKHELY

VSFRDLGWQDWIIAPEGYAAYYCEGECAFPLNSYMNATNHAIVQTLVHFI

NPETVPKPCCAPTQLNAISVLYFDDSSNVILKKYRNMVVRACGCH (SEQ ID NO: 215)
M¹STPTTVSSKQRSQNRSKTPKNQEALRMANVAENSSSDQRQACKKHELY

VSFRDLGWQDWIIAPEGYAAYYCEGECAFPLNSYMNATNHAIVQTLVHFI

NPETVPKPCCAPTQLNAISVLYFDDSSNVILKKYRNMVVRACGCH
```

Additional BMP-7 variants can be generated by "scanning" the glycosylation sequence through the entire sequence in the above fashion until a final sequence is reached:

```
                                       (SEQ ID NO: 216)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGCPTTVS
```

All BMP-7 variants thus obtained are within the scope of the invention.

```
Insertion of five amino acids
                                       (SEQ ID NO: 217)
M¹PTTVSSTGSKQRSQNRSKTPKNQEALRMANVAENSSSDQRQACKKHEL

YVSFRDLGWQDWIIAPEGYAAYYCEGECAFPLNSYMNATNHAIVQTLVHF

INPETVPKPCCAPTQLNAISVLYFDDSSNVILKKYRNMVVRACGCH (SEQ ID NO: 218)
M¹SPTTVSTGSKQRSQNRSKTPKNQEALRMANVAENSSSDQRQACKKHEL

YVSFRDLGWQDWIIAPEGYAAYYCEGECAFPLNSYMNATNHAIVQTLVHF

INPETVPKPCCAPTQLNAISVLYFDDSSNVILKKYRNMVVRACGCH (SEQ ID NO: 219)
M¹STPTTVSGSKQRSQNRSKTPKNQEALRMANVAENSSSDQRQACKKHEL

YVSFRDLGWQDWIIAPEGYAAYYCEGECAFPLNSYMNATNHAIVQTLVHF

INPETVPKPCCAPTQLNAISVLYFDDSSNVILKKYRNMVVRACGCH
```

Additional BMP-7 variants can be generated by "scanning" the glycosylation sequence through the entire sequence in the above fashion until a final sequence is reached:

```
                                       (SEQ ID NO: 220)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGCHPTTVS
```

All BMP-7 variants thus obtained are within the scope of the invention.

Other examples for sequon polypeptides containing O-linked glycosylation sequences are disclosed in U.S. Provisional Patent Applications 60/710,401 filed Aug. 22, 2005; and 60/720,030, filed Sep. 23, 2005; WO2004/99231 and WO2004/10327, which are incorporated herein by reference for all purposes.

In one example, the O-linked glycosylation sequence (e.g., PTP) is placed at all possible amino acid positions within selected polypeptide regions either by substitution of existing amino acids and/or by insertion. Exemplary sequences according to this embodiment are listed in Table 10 and Table 11, below.

TABLE 10

Exemplary library of BMP-7 variants including PTP between $A^{73}$ and $A^{82}$

Substitution of existing amino acids

```
                                       (SEQ ID NO: 221)
                                              (parent)
---A⁷³FPLNSYMNA⁸²TNHAIVQTLVHFI⁹⁵NPETVPKP¹⁰³---

(SEQ ID NO: 222)
---P⁷³TPLNSYMNA⁸²TNHAIVQTLVHFI⁹⁵NPETVPKP¹⁰³---

(SEQ ID NO: 223)
---A⁷³PTPNSYMNA⁸²TNHAIVQTLVHFI⁹⁵NPETVPKP¹⁰³---

(SEQ ID NO: 224)
---A⁷³FPTPSYMNA⁸²TNHAIVQTLVHFI⁹⁵NPETVPKP¹⁰³---

(SEQ ID NO: 225)
---A⁷³FPPTPYMNA⁸²TNHAIVQTLVHFI⁹⁵NPETVPKP¹⁰³---

(SEQ ID NO: 226)
---A⁷³FPLPTPMNA⁸²TNHAIVQTLVHFI⁹⁵NPETVPKP¹⁰³---
```

TABLE 10-continued

Exemplary library of BMP-7 variants including PTP between A$^{73}$ and A$^{82}$

---A$^{73}$FPLNPTPNA$^{82}$TNHAIVQTLVHFI$^{95}$NPETVPKP$^{103}$--- (SEQ ID NO: 227)

---A$^{73}$FPLNSPTPA$^{82}$TNHAIVQTLVHFI$^{95}$NPETVPKP$^{103}$--- (SEQ ID NO: 228)

---A$^{73}$FPLNSYPTP$^{82}$TNHAIVQTLVHFI$^{95}$NPETVPKP$^{103}$--- (SEQ ID NO: 229)

TABLE 11

Exemplary library of BMP-7 variants including PTP between I$^{95}$ and P$^{103}$
Basic amino acids in proximity to the site of glycosylation, which can optionally be replaced with an uncharged amino acid, are marked by underlining.

Substitution of existing amino acids

---A$^{73}$FPLNSYMNA$^{82}$TNHAIVQTLVHFP$^{95}$TPETVPKP$^{103}$ (SEQ ID NO: 230)

---A$^{73}$FPLNSYMNA$^{82}$TNHAIVQTLVHFI$^{95}$PTPTVPKP$^{103}$ (SEQ ID NO: 231)

---A$^{73}$FPLNSYMNA$^{82}$TNHAIVQTLVHFI$^{95}$NPTPVPKP$^{103}$ (SEQ ID NO: 232)

---A$^{73}$FPLNSYMNA$^{82}$TNHAIVQTLVHFI$^{95}$NPPTP<u>K</u>P$^{103}$ (SEQ ID NO: 233)

---A$^{73}$FPLNSYMNA$^{82}$TNHAIVQTLVHFI$^{95}$NPEPTP<u>K</u>P$^{103}$ (SEQ ID NO: 234)

---A$^{73}$FPLNSYMNA$^{82}$TNHAIVQTLVHFI$^{95}$NPETPTPP$^{103}$ (SEQ ID NO: 235)

---A$^{73}$FPLNSYMNA$^{82}$TNHAIVQTLVHFI$^{95}$NPETVPTP$^{103}$ (SEQ ID NO: 236)

Insertion (with one amino acid added) between existing amino acids

---P$^{73}$TPPLNSYMNA$^{82}$TNHAIVQTLVHFI$^{95}$NPETVPKP$^{103}$ (SEQ ID NO: 237)

---A$^{73}$PTPLNSYMNA$^{82}$TNHAIVQTLVHFI$^{95}$NPETVPKP$^{103}$ (SEQ ID NO: 238)

---A$^{73}$FPTPNSYMNA$^{82}$TNHAIVQTLVHFI$^{95}$NPETVPKP$^{103}$ (SEQ ID NO: 239)

---A$^{73}$FPPTPSYMNA$^{82}$TNHAIVQTLVHFI$^{95}$NPETVPKP$^{103}$ (SEQ ID NO: 240)

---A$^{73}$FPLPTPYMNA$^{82}$TNHAIVQTLVHFI$^{95}$NPETVPKP$^{103}$ (SEQ ID NO: 241)

---A$^{73}$FPLNPTPMNA$^{82}$TNHAIVQTLVHFI$^{95}$NPETVPKP$^{103}$ (SEQ ID NO: 242)

---A$^{73}$FPLNSPTPNA$^{82}$TNHAIVQTLVHFI$^{95}$NPETVPKP$^{103}$ (SEQ ID NO: 243)

---A$^{73}$FPLNSYPTPA$^{82}$TNHAIVQTLVHFI$^{95}$NPETVPKP$^{103}$ (SEQ ID NO: 244)

---A$^{73}$FPLNSYMPTP$^{82}$TNHAIVQTLVHFI$^{95}$NPETVPKP$^{103}$ (SEQ ID NO: 245)

TABLE 11-continued

Exemplary library of BMP-7 variants including PTP between I$^{95}$ and P$^{103}$
Basic amino acids in proximity to the site of glycosylation, which can optionally be replaced with an uncharged amino acid, are marked by underlining.

Insertion (with one amino acid added) between existing amino acids

---A$^{73}$FPLNSYMNA$^{82}$TNHAIVQTLVHFP$^{95}$TPPETVPKP$^{103}$ (SEQ ID NO: 246)

---A$^{73}$FPLNSYMNA$^{82}$TNHAIVQTLVHFI$^{95}$PTPETVPKP$^{103}$ (SEQ ID NO: 247)

---A$^{73}$FPLNSYMNA$^{82}$TNHAIVQTLVHFI$^{95}$NPTPTVPKP$^{103}$ (SEQ ID NO: 248)

---A$^{73}$FPLNSYMNA$^{82}$TNHAIVQTLVHFI$^{95}$NPPTPVPKP$^{103}$ (SEQ ID NO: 249)

---A$^{73}$FPLNSYMNA$^{82}$TNHAIVQTLVHFI$^{95}$NPEPTPP<u>K</u>P$^{103}$ (SEQ ID NO: 250)

---A$^{73}$FPLNSYMNA$^{82}$TNHAIVQTLVHFI$^{95}$NPETPTP<u>K</u>P$^{103}$ (SEQ ID NO: 251)

---A$^{73}$FPLNSYMNA$^{82}$TNHAIVQTLVHFI$^{95}$NPETVPTPP$^{103}$ (SEQ ID NO: 252)

---A$^{73}$FPLNSYMNA$^{82}$TNHAIVQTLVHFI$^{95}$NPETVPPTP$^{103}$ (SEQ ID NO: 253)

The above substitutions and insertions can be made using any O-linked glycosylation sequences of the invention. All BMP-7 variants thus obtained are within the scope of the invention.

In another exemplary embodiment, one or more O-glycosylation sequences, such as those set forth above is inserted into a blood coagulation Factor, e.g., Factor VII, Factor VIII or Factor IX polypeptide. As set forth in the context of BMP-7, the O-glycosylation sequence can be inserted in any of the various motifs exemplified with BMP-7. For example, the O-glycosylation sequence can be inserted into the wild type sequence without replacing any amino acid(s) native to the wild type sequence. In an exemplary embodiment, the O-glycosylation sequence is inserted at or near the N- or C-terminus of the polypeptide. In another exemplary embodiment, one or more amino acid residue native to the wild type polypeptide sequence is removed prior to insertion of the O-glycosylation site. In yet another exemplary embodiment, one or more amino acid residue native to the wild type sequence is a component of the O-glycosylation sequence (e.g., a proline) and the O-glycosylation sequence encompasses the wild type amino acid(s). The wild type amino acid(s) can be at either terminus of the O-glycosylation sequence or internal to the O-glycosylation sequence.

Furthermore, any preexisting N-linked glycosylation sequence can be replaced with an O-linked glycosylation sequence of the invention. In addition, an O-linked glycosylation sequence can be inserted adjacent to one or more N-linked glycosylation sequences. In a preferred embodiment, the presence of the O-linked glycosylation sequence prevents the glycosylation of the N-linked glycosylation sequence.

In a representative example, the parent polypeptide is Factor VIII. In this embodiment, the O-linked glycosylation sequence can be inserted into the A-, B-, or C-domain according to any of the motifs set forth above. More than one O-linked glycosylation site can be inserted into a single domain or more than one domain; again, according to any of the motifs above. For example, an O-glycosylation site can be inserted into each of the A, B and C domains, the A and C domains, the A and B domains or the B and C domains. Alternatively, an O-linked glycosylation sequence can flank the A and B domain or the B and C domain. An exemplary amino acid sequence for Factor VIII is provided in FIG. 4 (SEQ ID NO: 254).

In another exemplary embodiment, the Factor VIII polypeptide is a B-domain deleted (BDD) Factor VIII polypeptide. In this embodiment, the O-linked glycosylation sequence can be inserted into the peptide linker joining the 80 Kd and 90 Kd subunits of the Factor VIII heterodimer. Alternatively, the O-linked glycosylation sequence can flank the A domain and the linker or the C domain and linker. As set forth above in the context of BMP-7, the O-linked glycosylation sequence can be inserted without replacement of existing amino acids, or may be inserted replacing one or more amino acids of the parent polypeptide. An exemplary sequence for B-domain deleted (BDD) Factor VIII is provided in FIG. 5 (SEQ ID NO: 255).

Other B-domain deleted Factor VII polypeptides are also suitable for use with the invention, including, for example, the B-domain deleted Factor VII polypeptide disclosed in Sandberg et al., *Seminars in Hematology* 38(2):4-12 (2000), the disclosure of which is incorporated herein by reference.

In a further exemplary embodiment, the parent polypeptide is hGH and the O-glycosylation site is added according to any of the above-recited motifs.

As will be apparent to one of skill in the art, that polypeptides including more than one mutant O-linked glycosylation sequence of the invention are also within the scope of the present invention. Additional mutations may be introduced to allow for the modulation of polypeptide properties, such e.g., biological activity, metabolic stability (e.g., reduced proteolysis), pharmacokinetics and the like.

Figure 1B:
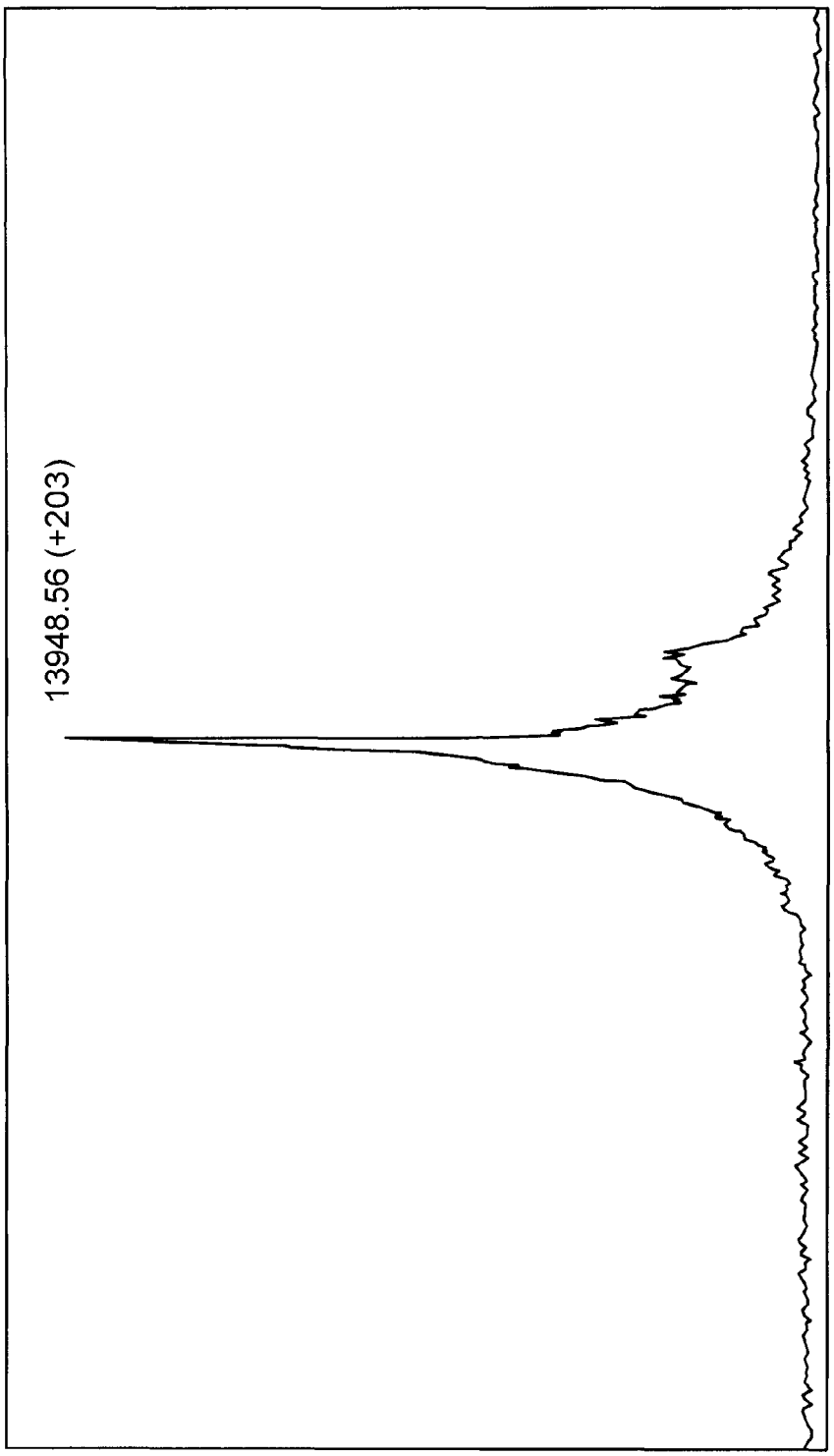
FIG. 1B shows a MALFI-TOF mass spectrum of glycosylated NT-3. The purified NT-3 mutant was incubated with the glycosyltransferase GalNAc-T2 and UDP-GalNAc as described in Example 2. The reaction product is characterized by an expected mass increase of about 203 Da (expected: +203.2), which corresponds to the addition of a single GalNAc residue when compared to unglycosylated polypeptide.
Figure 2A:
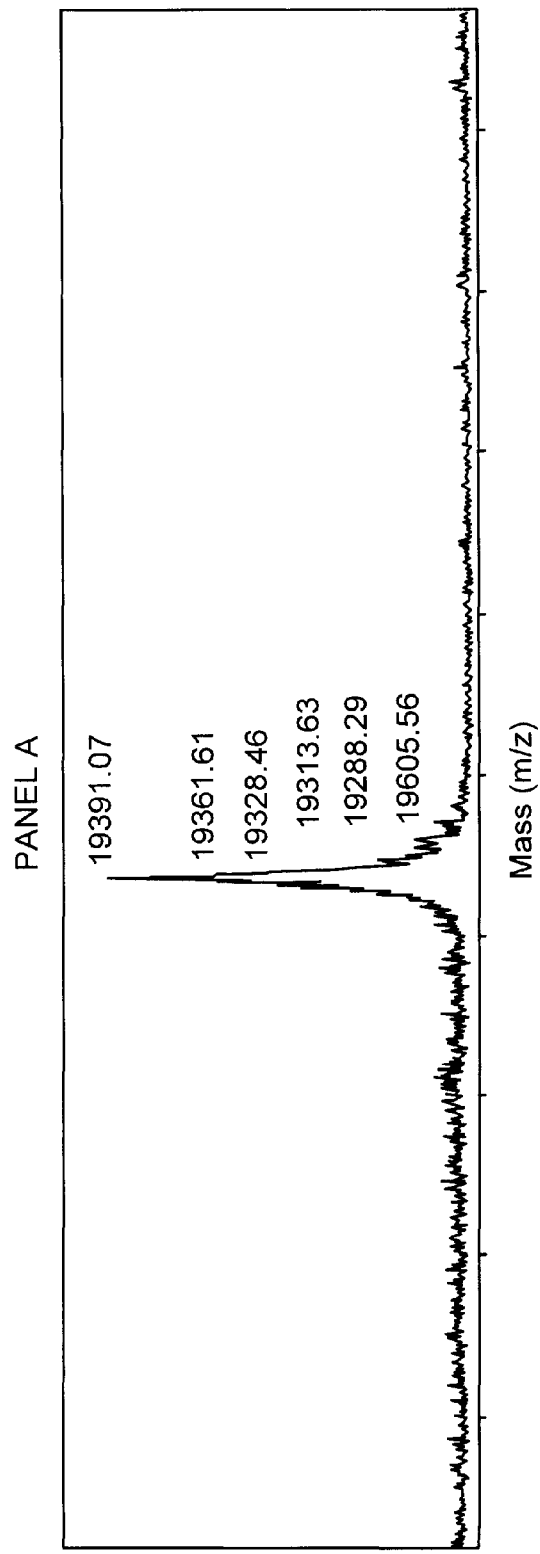
FIG. 2A shows a MALFI-TOF mass spectrum of non-glycosylated FGF-21. The polypeptide was expressed as a soluble protein in a trxB, gor, supp E. coli strain, refolded and purified.
Figure 2B:
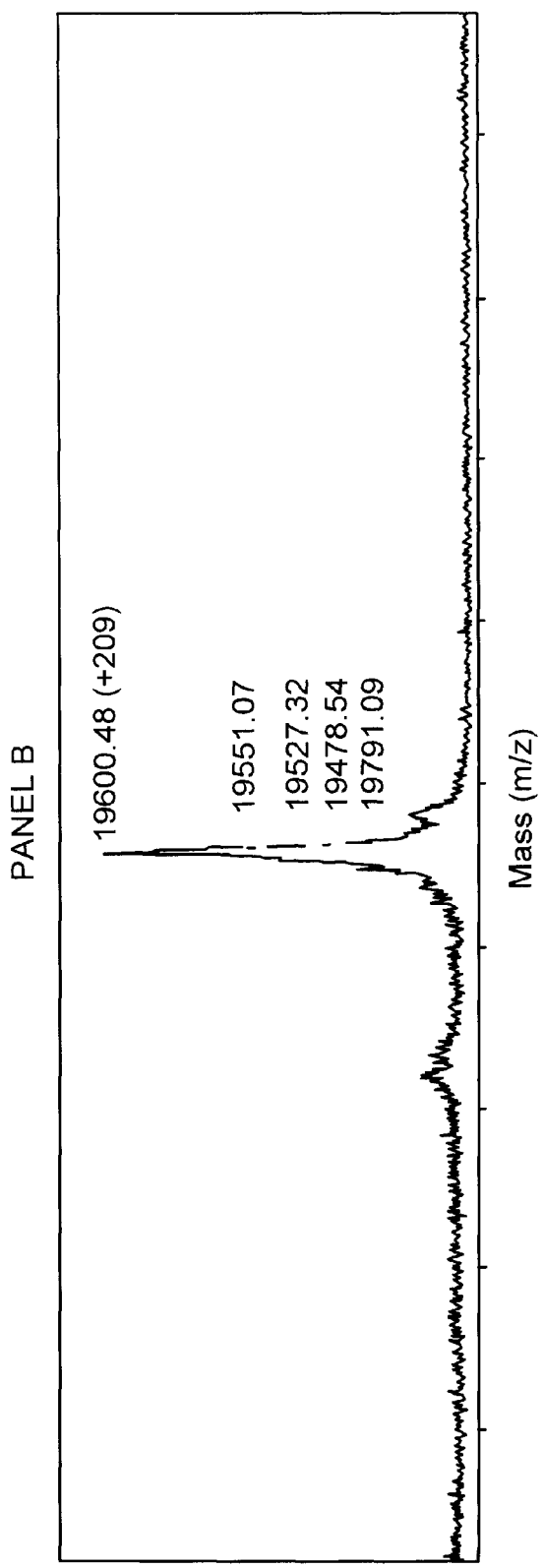
FIG. 2B shows a MALFI-TOF mass spectrum of glycosylated FGF-21. The purified FGF-21 mutant was incubated with the glycosyltransferase GalNAc-T2 and UDP-GalNAc as described in Example 4. The reaction product is characterized by an expected mass increase of about 203 Da (expected: +203.2, observed: 209), which corresponds to the addition of a single GalNAc residue when compared to unglycosylated polypeptide.
Figure 3:
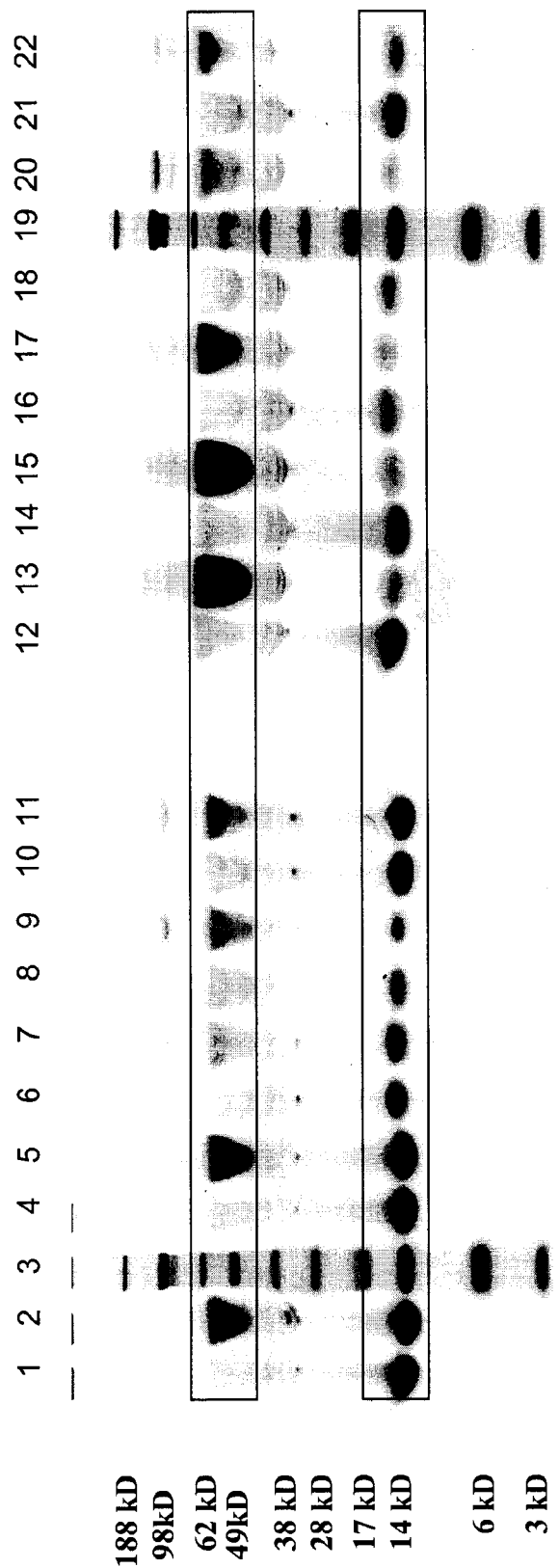
FIG. 3 shows the result of SDS PAGE gel electrophoresis for various non-PEGylated and glycoPEGylated human NT-3 mutant polypeptides. NT-3 variants were purified and glycoPEGylated as described in Example 2. The reactions were analyzed by SDS-PAGE and stained with SimplyBlue safestain. Gel A: NT-3 variant A.1 in Table 16 (SEQ ID NO: 342) treated with GalNAc-T2 (lane 1), NT-3 variant A.1 in Table 16 (SEQ ID NO: 342) treated with GalNAc-T2/ST6GalNAc1 (lane 2); molecular weight marker (lane 3); NT-3 variant A.2 in Table 16 (SEQ ID NO: 343) treated with GalNAc-T2 (lane 4), NT-3 variant A.2 in Table 16 (SEQ ID NO: 343) treated with GalNAc-T2/ST6GalNAc1 (lane 5), NT-3 variant A.4 in Table 16 (SEQ ID NO: 346) treated with GalNAc-T2 (lane 6), NT-3 variant A.4 in Table 16 (SEQ ID NO: 346) treated with GalNAc-T2/ST6GalNAc1 (lane 7); NT-3 variant A.5 in Table 16 (SEQ ID NO: 347) treated with GalNAc-T2 (lane 8), NT-3 variant A.5 in Table 16 (SEQ ID NO: 347) treated with GalNAc-T2/ST6GalNAc1 (lane 9); NT-3 variant A.7 in Table 16 (SEQ ID NO: 350) treated with GalNAc-T2 (lane 10); NT-3 variant A.7 in Table 16 (SEQ ID NO: 350) treated with GalNAc-T2/ST6GalNAc1 (lane 11); NT-3 variant A.1 in Table 16 (SEQ ID NO: 342) treated with GalNAc-T2/Core-1 (lane 12); NT-3 variant A.1 in Table 16 (SEQ ID NO: 342) treated with GalNAc-T2/Core-1/ST3Gal1 (lane 13); NT-3 variant A.2 in Table 16 (SEQ ID NO: 343) treated with GalNAc-T2/Core-1 (lane 14); NT-3 variant A.2 in Table 16 (SEQ ID NO: 343) treated with GalNAc-T2/Core-1/ST3Gal1 (lane 15); NT-3 variant A.4 in Table 16 (SEQ ID NO: 346) treated with GalNAc-T2/Core-1 (lane 16), NT-3 variant A.4 in Table 16 (SEQ ID NO: 346) treated with GalNAc-T2/Core-1/ST3Gal1 (lane 17), NT-3 variant A.5 in Table 16 (SEQ ID NO: 347) treated with GalNAc-T2/Core-1 (lane 18), molecular weight marker (lane 19); NT-3 variant A.5 in Table 16 (SEQ ID NO: 347) treated with GalNAc-T2/Core-1/ST3Gal1 (lane 20), NT-3 variant A.7 in Table 16 (SEQ ID NO: 350) treated with GalNAc-T2/Core-1 (lane 21), NT-3 variant A.7 in Table 16 (SEQ ID NO: 350) treated with GalNAc-T2/Core-1/ST3Gal1 (lane 22). Bands in the lower boxed area with a molecular weight of approximately 14 kD, correspond to the non-PEGylated NT-3 mutants. Bands in the upper boxed area with a molecular weight of approximately 49-62 kD correspond to the glycoPEGylated NT-3 variants.

Once a variety of variants are prepared, they can be evaluated for their ability to function as a substrate for O-linked glycosylation or glycoPEGylation, for instance using a GalNAc transferase, such as GalNAc-T2. Successful glycosylation and/or glycoPEGylation may be detected and quantified using methods known in the art, such as mass spectroscopy (e.g., MALDI-TOF or Q-TOF), gel electrophoresis (e.g., in combination with densitometry) or chromatographic analyses (e.g., HPLC). Biological assays, such as enzyme inhibition assays, receptor-binding assays and/or cell-based assays can be used to analyze biological activities of a given polypeptide or polypeptide conjugate. Evaluation strategies are described in more detail herein, below (see e.g., "Identification of Lead polypeptides", Example 2, Example 4 and FIGS. 1-3). It will be within the abilities of a person skilled in the art to select and/or develop an appropriate assay system useful for the chemical and biological evaluation of each polypeptide.

Polypeptide Conjugates

In another aspect, the present invention provides a covalent conjugate between a glycosylated or non-glycosylated polypeptide (e.g., a sequon polypeptide) and a selected modifying group (e.g., a polymeric modifying group), in which the modifying group is conjugated to the polypeptide via a glycosyl linking group (e.g., an intact glycosyl linking group). The glycosyl linking group is interposed between and covalently linked to both the polypeptide and the modifying group. The glycosyl linking group is either directly bound to an amino acid residue of the O-linked glycosylation sequence of the invention, or, alternatively, it is bound to an O-linked glycosylation sequence through one or more additional glycosyl residues. Methods of preparing the conjugates of the invention are set forth herein and in U.S. Pat. Nos. 5,876,980; 6,030,815; 5,728,554; and 5,922,577, as well as WO 98/31826; WO2003/031464; WO2005/070138; WO2004/99231; WO2004/10327; WO2006/074279; and U.S. Patent Application Publication 2003180835, all of which are incorporated herein by reference for all purposes.

The conjugates of the invention will typically correspond to the general structure:

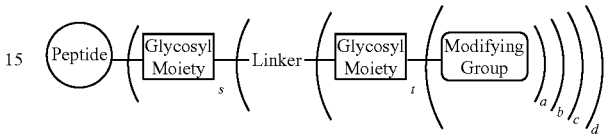

in which the symbols a, b, c, d and s represent a positive, non-zero integer; and t is either 0 or a positive integer. The "modifying group" includes a therapeutic agent, a bioactive agent, a detectable label, a polymer (e.g., water-soluble polymer) or the like. The linker can be any of a wide array of linking groups, infra. Alternatively, the linker may be a single bond. The identity of the polypeptide is without limitation.

Exemplary polypeptide conjugates include an O-linked GalNAc residue that is bound to the O-linked glycosylation sequence (e.g., through the action of a GalNAc transferase). In one embodiment, GalNAc itself is derivatized with a modifying group and represents the glycosyl linking group. In another embodiment, additional glycosyl residues are bound to the GalNAc moiety. For example, a Gal or Sia moiety, each of which can act as the glycosyl linking group, is added to the GalNAc group. In representative embodiments, the O-linked saccharyl residue is GalNAc-X*, GalNAc-Gal-X*, GalNAc-Sia-X*, GalNAc-Gal-Sia-X*, or GalNAc-Gal-Gal-Sia-X*, in which X* is a modifying group.

The polypeptide is preferably O-glycosylated at the O-linked glycosylation sequence with a GalNAc moiety. Additional sugar residues can be added to the O-linked GalNAc moiety using a glycosyltransferase that is known to add to GalNAc, such as Core-1-Gal transferases and ST6GalNAc transferases (e.g., ST6GalNAc-1). Alternatively, more than one sugar moiety can be added either to the polypeptide directly or to the already existing O-linked-GalNAc residue. Glycosyltransferases useful for this embodiment include ST3Gal transferases (e.g., ST3Gal1 and CST-I or CST-II) and ST8-sialyltransferases. Together these methods can result in glycosyl structures including two or more sugar residues.

In one embodiment, the present invention provides polypeptide conjugates that are highly homogenous in their substitution patterns. Using the methods of the invention, it is possible to form polypeptide conjugates in which essentially all of the modified sugar moieties across a population of conjugates of the invention are attached to a structurally identical amino acid or glycosyl residue. Thus, in an exemplary embodiment, the invention provides a sequon polypeptide conjugate including one or more water-soluble polymeric moiety covalently bound to an amino acid residue (e.g., serine or threonine) within an O-linked glycosylation sequence through a glycosyl linking group. In one example, each amino acid residue having a glycosyl linking group attached thereto has the same structure. In another exemplary embodiment, essentially each member of the population of water-soluble polymeric moieties is bound via a glycosyl linking group to a glycosyl residue of the polypeptide, and each glycosyl residue of the polypeptide to which the glycosyl linking group is attached has the same structure.

In one aspect, the invention provides a covalent conjugate comprising a sequon polypeptide having an O-linked glycosylation sequence (e.g., an exogenous O-linked glycosylation sequence), said polypeptide conjugate comprising a moiety according to Formula (V):

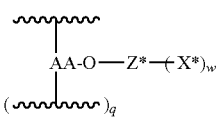

(V)

In Formula (V), w is an integer selected from 0 and 1. AA-O— is a moiety derived from an amino acid within the within the O-linked glycosylation sequence. Typically, the moiety AA-O— is derived from an amino acid having a hydroxyl (OH) group (e.g., serine or threonine). In one embodiment, the integer q is 0 and the amino acid is an N-terminal or C-terminal amino acid. In another embodiment, q is 1 and the amino acid is an internal amino acid. $Z^*$ is a glycosyl moiety, which is selected from mono- and oligasaccharides. $Z^*$ may be a glycosyl-mimetic moiety.

In one embodiment, w in Formula (V) is 1 and the polypeptide conjugate of the invention includes at least one modifying group. In one example, $X^*$ is a modifying group (e.g., a polymeric modifying group). In another example, $X^*$ is a glycosyl linking group covalently linked to a modifying group. In an exemplary embodiment, $X^*$ in Formula (V) includes a sialyl moiety (Sia). In another embodiment, $X^*$ includes a galactosyl moiety (Gal). In yet another embodiment, $X^*$ includes a combination of Sia and Gal moieties (e.g., a Gal-Sia moiety). In a further embodiment, $X^*$ includes a GalNAc moiety. In a preferred embodiment, $X^*$ is a Sia moiety.

In an exemplary embodiment, $Z^*$ in Formula (V) includes a Gal moiety. In another exemplary embodiment, $Z^*$ includes a GalNAc moiety. In yet another embodiment, $Z^*$ includes a GlcNAc moiety. In a further embodiment, $Z^*$ includes a Xyl, Glc or Sia moiety. $Z^*$ can also be a combination of Gal, GalNAc, GlcNAc, Sia, Xyl and Glc moieties. In one embodiment, $Z^*$ includes a GalNAc-mimetic moiety. In one embodiment, $Z^*$ is a GalNAc moiety. In another embodiment, $Z^*$ is a GalNAc-Gal moiety. In yet another embodiment, $Z^*$ is a GalNAc-Sia moiety. In a further embodiment $Z^*$ is a GalNAc-Gal-Sia moiety.

In an exemplary embodiment, the covalent conjugate includes a moiety having the following formula, in which $R^{40}$ is H or $C_1$-$C_3$ unsubstituted alkyl:

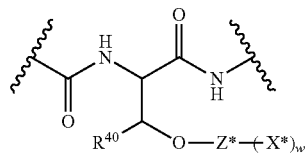

In a preferred embodiment, $R^{40}$ in the above formula is methyl.

Glycosyl Linking Group

The saccharide component of the modified sugar, when interposed between the polypeptide and a modifying group, becomes a "glycosyl linking group." In an exemplary embodiment, the glycosyl linking group is formed from a mono- or oligosaccharide that, after modification with a modifying group, is a substrate for an appropriate glycosyltransferase. In another exemplary embodiment, the glycosyl linking group is formed from a glycosyl-mimetic moiety. The polypeptide conjugates of the invention can include glycosyl linking groups that are mono- or multi-valent (e.g., antennary structures). Thus, conjugates of the invention include both species in which a selected moiety is attached to a polypeptide via a monovalent glycosyl linking group. Also included within the invention are conjugates in which more than one modifying group is attached to a polypeptide via a multivalent linking group.

In an exemplary embodiment, $X^*$ in Formula (V) includes a moiety according to Formula (VI):

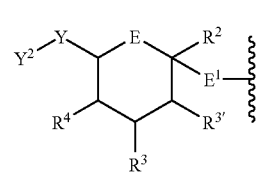

(VI)

In one embodiment, in Formula (VI), E is O. In another embodiment, E is S. In yet another embodiment, E is $NR^{27}$ or $CHR^{28}$, wherein $R^{27}$ and $R^{28}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In one embodiment, $E^1$ is O. In another embodiment $E^1$ is S.

In one embodiment, in Formula (VI), $R^2$ is H. In another embodiment, $R^2$ is $-R^1$. In yet another embodiment $R^2$ is $-CH_2R^1$. In a further embodiment, $R^2$ is $-C(X^1)R^1$. In these embodiments, $R^1$ is $OR^9$, $SR^9$, $NR^{10}R^{11}$, substituted or unsubstituted alkyl or substituted or unsubstituted heteroalkyl, wherein $R^9$ is a member selected from H, a metal ion, substituted or unsubstituted alkyl, substituted or unsubstituted heteroalkyl and acyl. $R^{10}$ and $R^{11}$ are members independently selected from H, substituted or unsubstituted alkyl, substituted or unsubstituted heteroalkyl and acyl. In one embodiment, $X^1$ is O. In another embodiment, $X^1$ is a member selected from substitued or unsubstituted alkenyl, S and $NR^8$, wherein $R^8$ is a member selected from H, OH, substituted or unsubstituted alkyl and substituted or unsubstituted heteroalkyl.

In one embodiment, in Formula (VI), Y is $CH_2$. In another embodiment, Y is $CH(OH)CH_2$. In yet another embodiment, Y is $CH(OH)CH(OH)CH_2$. In a further embodiment, Y is CH. In one embodiment Y is CH(OH)CH. In another embodiment Y is CH(OH)CH(OH)CH. In yet another embodiment, Y is CH(OH). In a further embodiment, Y is CH(OH)CH(OH). In one embodiment Y is CH(OH)CH(OH)CH(OH). $Y^2$ is a member selected from H, $OR^6$, $R^6$, substituted or unsubstituted alkyl, substituted or unsubstituted heteroalkyl,

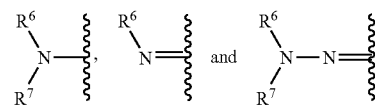

wherein $R^6$ and $R^7$ are members independently selected from H, $L^a$-$R^{6b}$, $C(O)R^{6b}$, $C(O)$-$L^a$-$R^{6b}$, $C(O)NH$-$L^a$-$R^{6b}$, $C(O)$-$L^a$-$R^{6b}$ substituted or unsubstituted alkyl and substituted or unsubstituted heteroalkyl. $R^{6b}$ is a member selected from H, substituted or unsubstituted alkyl, substituted or unsubstituted heteroalkyl and a modifying group.

In Formula (VI), $R^3$, $R^{3'}$ and $R^4$ are members independently selected from H, $OR^{3''}$, $SR^{3''}$, substituted or unsubstituted alkyl, substituted or unsubstituted heteroalkyl, -$L^a$-$R^{6c}$, —C(O)-$L^a$-$R^{6c}$, —NH-$L^a$-$R^{6c}$, =N-$L^a R^{6c}$ and —NHC(O)-$L^a$-$R^{6c}$, —NHC(O)NH-$L^a$-$R^{6c}$, —NHC(O)O-$L^a$-$R^{6c}$, wherein $R^{3''}$ is a member selected from H, substituted or unsubstituted alkyl and substituted or unsubstituted heteroalkyl. $R^{6c}$ is a member selected from H, substituted or unsubstituted alkyl, substituted or unsubstituted heteroalkyl, substituted or unsubstituted aryl, substituted or unsubstituted heteroaryl, substituted or unsubstituted heterocycloalkyl, $NR^{13}R^{14}$ and a modifying group, wherein $R^{13}$ and $R^{14}$ are members independently selected from H, substituted or unsubstituted alkyl and substituted or unsubstituted heteroalkyl.

In the above embodiments, each $L^a$ is a member independently selected from a bond and a linker group.

In another embodiment, X* in Formula (VI) includes a moiety according to Formula (VII):

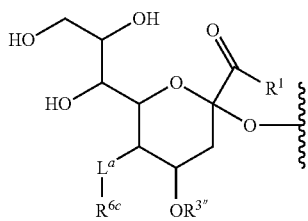

(VII)

wherein $R^1$, $L^a$, $R^{3''}$ and $R^{6c}$ are defined as above. In one embodiment, in Formula (VII) $R^1$ is $OR^9$. In one example according to this embodiment, $R^9$ is H, a negative charge or metal counterion.

In yet another embodiment, at least one of $R^{6b}$ (Formula VI) and $R^{6c}$ (Formula VI or Formula VII) is a member selected from:

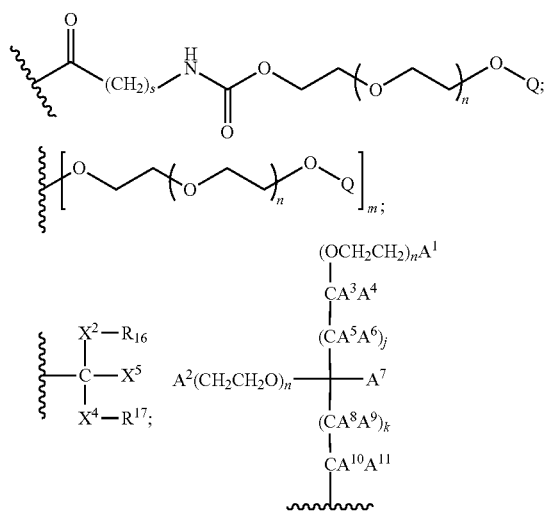

wherein s, j and k are integers independently selected from 0 to 20; each n is an integer independently selected from 0 to 2500; and m is an integer from 1-5. Q is a member selected from H and $C_1$-$C_6$ alkyl. $R^{16}$ and $R^{17}$ are independently selected polymeric moieties; $X^2$ and $X^4$ are independently selected linkage fragments joining polymeric moieties $R^{16}$ and $R^{17}$ to C. $X^5$ is a non-reactive group. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted heterocycloalkyl, substituted or unsubstituted aryl, substituted or unsubstituted heteroaryl, —$NA^{12}A^{13}$, —$OA^{12}$ and —$SiA^{12}A^{13}$ wherein $A^{12}$ and $A^{13}$ are members independently selected from substituted or unsubstituted alkyl, substituted or unsubstituted heteroalkyl, substituted or unsubstituted heterocycloalkyl, substituted or unsubstituted aryl, and substituted or unsubstituted heteroaryl.

In another embodiment, X* in Formula (VI) includes a moiety according to Formula (III):

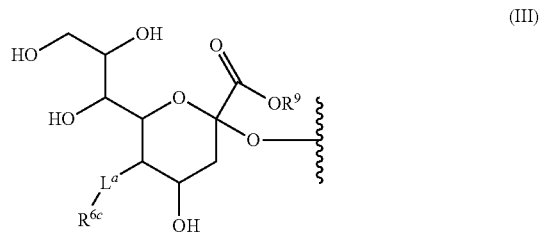

(III)

wherein $R^9$ is H, a single negative charge or a metal counterion. (-$L^a$-$R^{6c}$ is also referred to herein as $R^p$).

In one embodiment, in Formula (VIII), -$L^a$-$R^{6c}$ is:

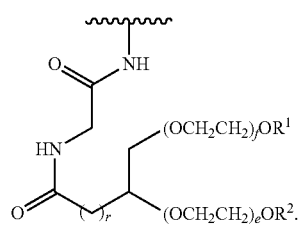

In another embodiment, in Formula (VIII), -$L^a$-$R^{6c}$ is:

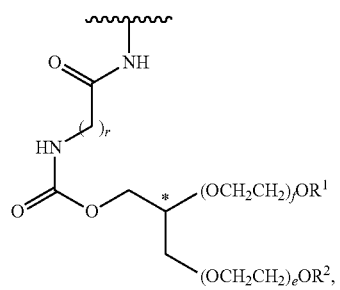

wherein the stereocenter indicated with "*" can be racemic or defined. In one embodiment, the stereocenter has (S) configuration. In another embodiment, the stereocenter has (R) configuration.

In yet another embodiment, in Formula (VIII), $-L^a-R^{6c}$ is:

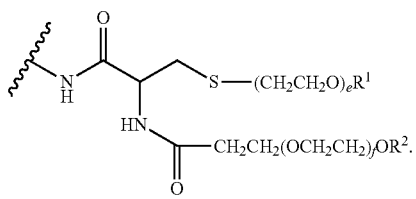

In yet another embodiment, in Formula (VIII), $-L^a-R^{6c}$ is:

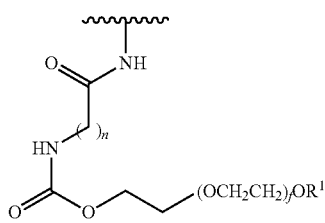

In each of the above embodiment of Formula (VIII), r is an integer selected from 1 to 20 and f and e are integers independently selected from 1-5000.

Modifying Group

The modifying group of the invention can be any chemical moiety. Exemplary modifying groups are discussed below. The modifying groups can be selected for their ability to alter the properties (e.g., biological or physicochemical properties) of a given polypeptide. Exemplary polypeptide properties that may be altered by the use of modifying groups include, but are not limited to, pharmacokinetics, pharmacodynamics, metabolic stability, biodistribution, water solubility, lipophilicity, tissue targeting capabilities and the therapeutic activity profile. Preferred modifying groups are those which improve pharmacodynamics and pharmacokinetics of a polypeptide conjugate of the invention that has been modified with such modifying group. Other modifying groups may be useful for the modification of polypeptides that can be used in diagnostic applications or in in vitro biological assay systems.

For example, the in vivo half-life of therapeutic glycopeptides can be enhanced with polyethylene glycol (PEG) moieties. Chemical modification of polypeptides with PEG (PEGylation) increases their molecular size and typically decreases surface- and functional group-accessibility, each of which are dependent on the number and size of the PEG moieties attached to the polypeptide. Frequently, this modification results in an improvement of plasma half-live and in proteolytic-stability, as well as a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). For example, PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)). Thus, in another embodiment, the in vivo half-life of a polypeptide derivatized with a PEG moiety by a method of the invention is increased relative to the in vivo half-life of the non-derivatized parent polypeptide.

The increase in polypeptide in vivo half-life is best expressed as a range of percent increase relative to the parent polypeptide. The lower end of the range of percent increase is about 40%, about 60%, about 80%, about 100%, about 150% or about 200%. The upper end of the range is about 60%, about 80%, about 100%, about 150%, or more than about 250%.

Water-Soluble Polymeric Modifying Groups

In one embodiment, the modifying group is a polymeric modifying group selected from linear and branched. In one example, the modifying group includes one or more polymeric moiety, wherein each polymeric moiety is independently selected.

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly(amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

The use of reactive derivatives of the modifying group (e.g., a reactive PEG analog) to attach the modifying group to one or more polypeptide moiety is within the scope of the present invention. The invention is not limited by the identity of the reactive analog.

In a preferred embodiment, the modifying group is PEG or a PEG analog. Many activated derivatives of poly(ethyleneglycol) are available commercially and are described in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al, *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al, *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood,* 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

Methods for activation of polymers can be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11:141-45 (1985)).

Activated PEG molecules useful in the present invention and methods of making those reagents are known in the art and are described, for example, in WO04/083259.

Activating, or leaving groups, appropriate for activating linear PEGs of use in preparing the compounds set forth herein include, but are not limited to the species:

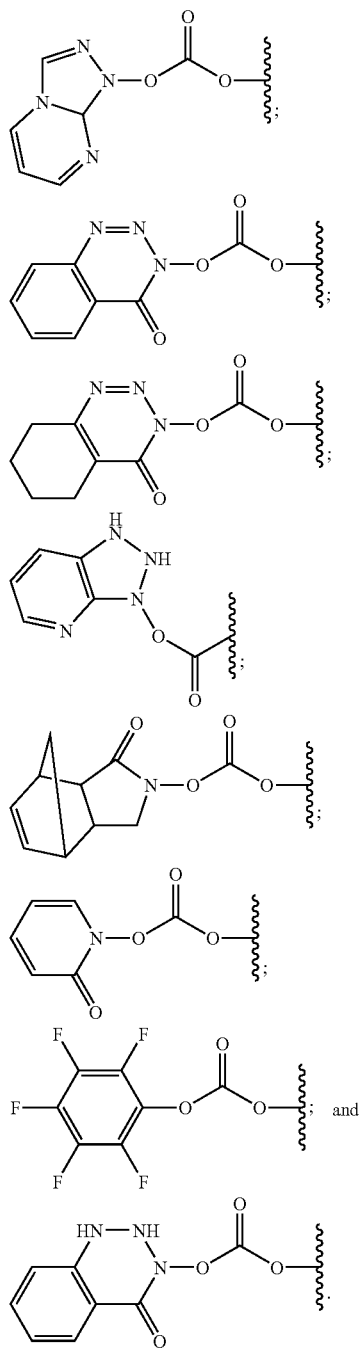

Exemplary water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a polypeptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a polypeptide, forming conjugates between the poly(ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

An exemplary water-soluble polymer is poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2000-60,000 is preferably used and more preferably of from about 5,000 to about 40,000.

Exemplary poly(ethylene glycol) molecules of use in the invention include, but are not limited to, those having the formula:

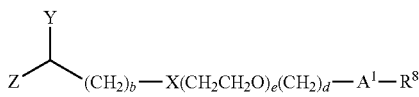

in which R[8] is H, OH, NH$_2$, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, H$_2$N—(CH$_2$)$_q$—, HS—(CH$_2$)$_q$, or —(CH$_2$)$_q$C(Y)Z[1]. The index "e" represents an integer from 1 to 2500. The indices b, d, and q independently represent integers from 0 to 20. The symbols Z and Z[1] independently represent OH, NH$_2$, leaving groups, e.g., imidazole, p-nitrophenyl, HOBT, tetrazole, halide, S—R[9], the alcohol portion of activated esters; —(CH$_2$)$_p$C(Y[1])V, or —(CH$_2$)$_p$U(CH$_2$)$_s$C(Y[1])$_v$. The symbol Y represents H(2), =O, =S, =N—R[10]. The symbols X, Y, Y[1], A[1], and U independently represent the moieties O, S, N—R[11]. The symbol V represents OH, NH$_2$, halogen, S—R[12], the alcohol component of activated esters, the amine component of activated amides, sugar-nucleotides, and proteins. The indices p, q, s and v are members independently selected from the integers from 0 to 20. The symbols R[9], R[10], R[11] and R[12] independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

The poly(ethylene glycol) useful in forming the conjugate of the invention is either linear or branched. Branched poly(ethylene glycol) molecules suitable for use in the invention include, but are not limited to, those described by the following formula:

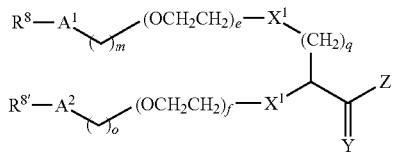

in which R[8] and R[8'] are members independently selected from the groups defined for R[8], above. A[1] and A[2] are members independently selected from the groups defined for A[1], above. The indices e, f, o, and q are as described above. Z and Y are as described above. X[1] and X[1'] are members independently selected from S, SC(O)NH, HNC(O)S, SC(O)O, O NH, NHC (O), (O)CNH and NHC(O)O, OC(O)NH.

In other exemplary embodiments, the branched PEG is based upon a cysteine, serine or di-lysine core. In another exemplary embodiments, the poly(ethylene glycol) molecule is selected from the following structures:

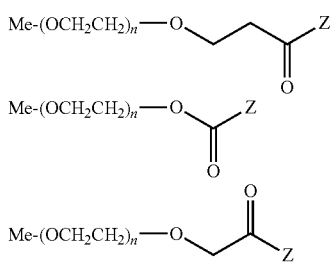

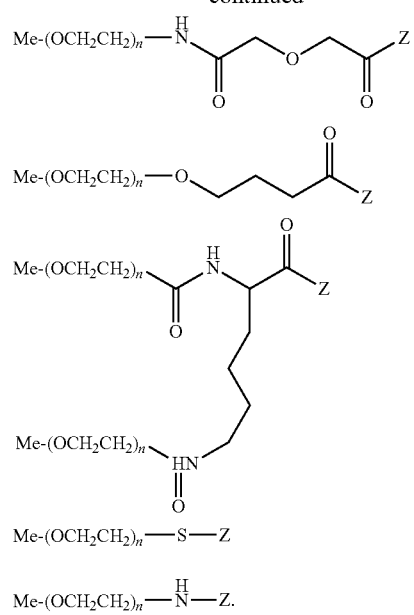

In a further embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is less than or equal to 40,000 daltons.

Representative polymeric modifying moieties include structures that are based on side chain-containing amino acids, e.g., serine, cysteine, lysine, and small peptides, e.g., lys-lys. Exemplary structures include:

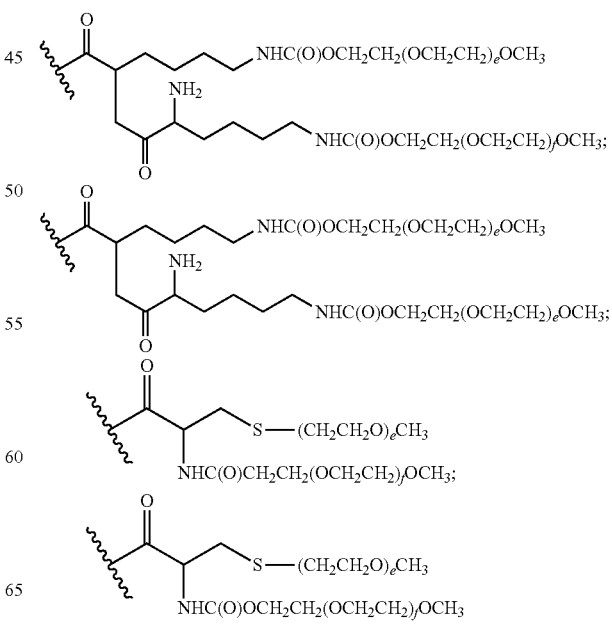

-continued

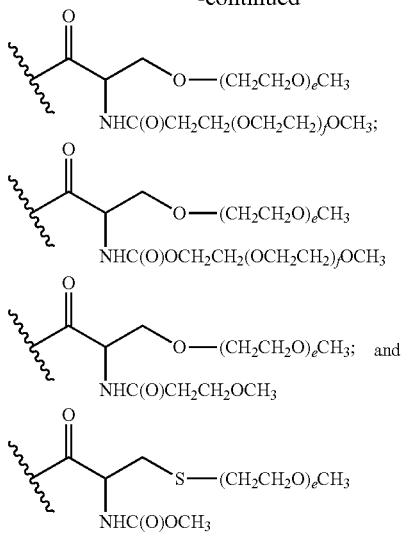

Those of skill will appreciate that the free amine in the di-lysine structures can also be pegylated through an amide or urethane bond with a PEG moiety.

In yet another embodiment, the polymeric modifying moiety is a branched PEG moiety that is based upon a tri-lysine peptide. The tri-lysine can be mono-, di-, tri-, or tetra-PEG-ylated. Exemplary species according to this embodiment have the formulae:

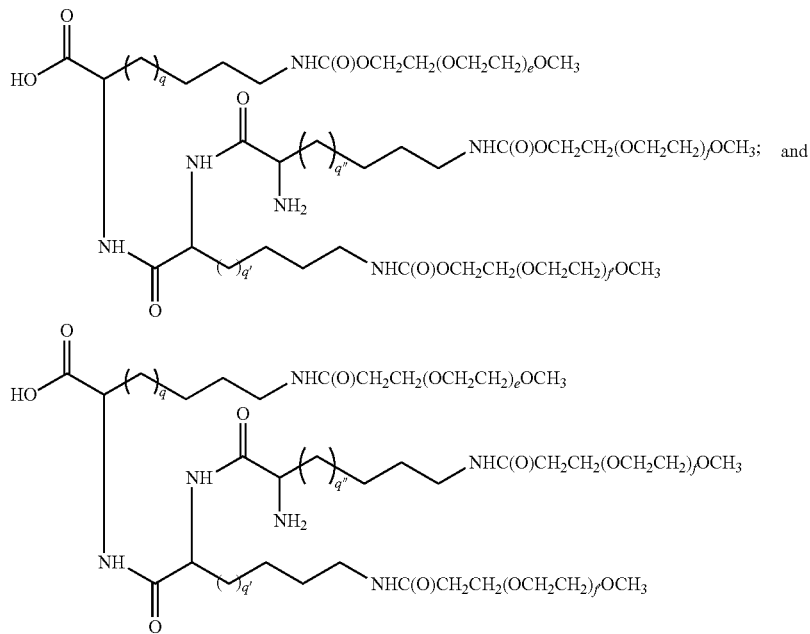

in which the indices e, f and f' are independently selected integers from 1 to 2500; and the indices q, q' and q" are independently selected integers from 1 to 20.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

An exemplary precursor useful to form a polypeptide conjugate with a branched modifying group that includes one or more polymeric moiety (e.g., PEG) has the formula:

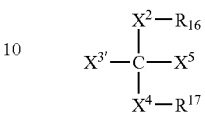

In one embodiment, the branched polymer species according to this formula are essentially pure water-soluble polymers. $X^{3'}$ is a moiety that includes an ionizable (e.g., OH, COOH, $H_2PO_4$, $HSO_3$, $NH_2$, and salts thereof, etc.) or other reactive functional group, e.g., infra. C is carbon. $X^5$ is a non-reactive group (e.g., H, $CH_3$, OH and the like). In one embodiment, $X^5$ is preferably not a polymeric moiety. $R^{16}$ and $R^{17}$ are independently selected from non-reactive groups (e.g., H, unsubstituted alkyl, unsubstituted heteroalkyl) and polymeric arms (e.g., PEG). $X^2$ and $X^4$ are linkage fragments that are preferably essentially non-reactive under physiological conditions. $X^2$ and $X^4$ are independently selected. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join the polymeric arms $R^{16}$ and $R^{17}$ to C. In one embodiment, when $X^{3'}$ is reacted with a reactive functional group of complementary reactivity on a linker, sugar or linker-sugar cassette, $X^{3'}$ is converted to a component of a linkage fragment.

Exemplary linkage fragments including $X^2$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, one of the above precursors or an activated derivative thereof, is reacted with, and thereby bound to a sugar, an activated sugar or a sugar nucleotide through a reaction between $X^{3'}$ and a group of complementary reactivity on the sugar moiety, e.g., an amine. Alternatively, $X^{3'}$ reacts with a reactive functional group on a precursor to linker $L^a$ according to Scheme 2, below.

Scheme 2:

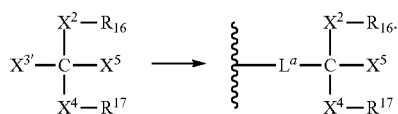

In an exemplary embodiment, the modifying group is derived from a natural or unnatural amino acid, amino acid analogue or amino acid mimetic, or a small peptide formed from one or more such species. For example, certain branched polymers found in the compounds of the invention have the formula:

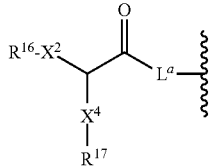

In this example, the linkage fragment C(O)$L^a$ is formed by the reaction of a reactive functional group, e.g., $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an amino-saccharide (e.g., Sia, GalNH$_2$, GlcNH$_2$, ManNH$_2$, etc.), forming an amide. Additional exemplary reactive functional groups and activated precursors are described hereinbelow. The symbols have the same identity as those discussed above.

In another exemplary embodiment, $L^a$ is a linking moiety having the structure:

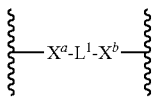

in which $X^a$ and $X^b$ are independently selected linkage fragments and $L^1$ is selected from a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (e.g., Lys-Lys-Lys) in which the alpha-amine moiety(ies) and/or side chain heteroatom(s) are modified with a polymeric modifying moiety.

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g. 1 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa and 80 kDa is of use in the present invention.

In other exemplary embodiments, the polypeptide conjugate includes a moiety selected from the group:

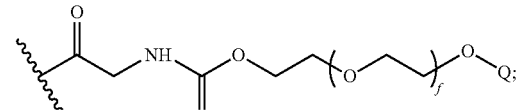

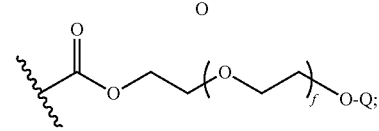

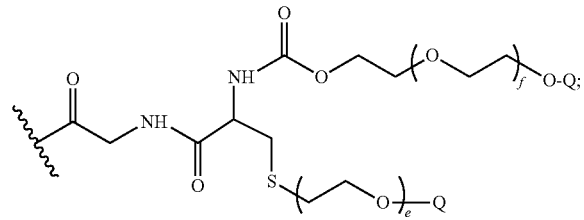

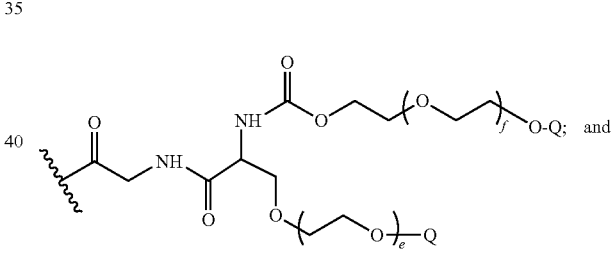

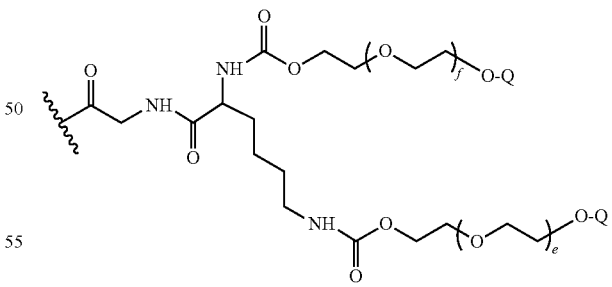

In each of the formulae above, the indices e and f are independently selected from the integers from 1 to 2500. In further exemplary embodiments, e and f are selected to provide a PEG moiety that is about 1 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa and 80 kDa. The symbol Q represents substituted or unsubstituted alkyl (e.g., $C_1$-$C_6$ alkyl e.g., methyl), substituted or unsubstituted heteroalkyl or H.

Other branched polymers have structures based on di-lysine (Lys-Lys) peptides, e.g.:
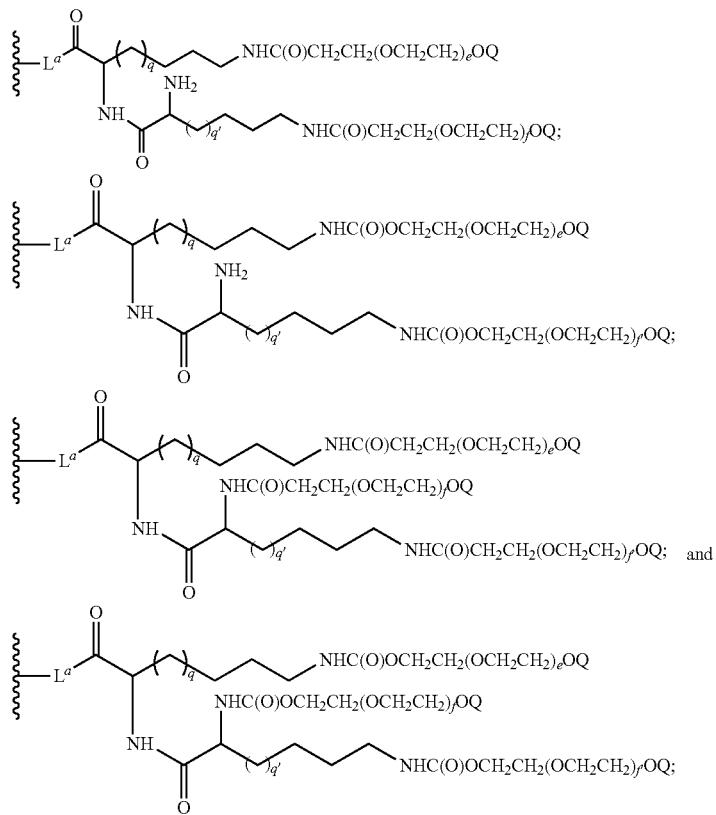
and tri-lysine peptides (Lys-Lys-Lys), e.g.:
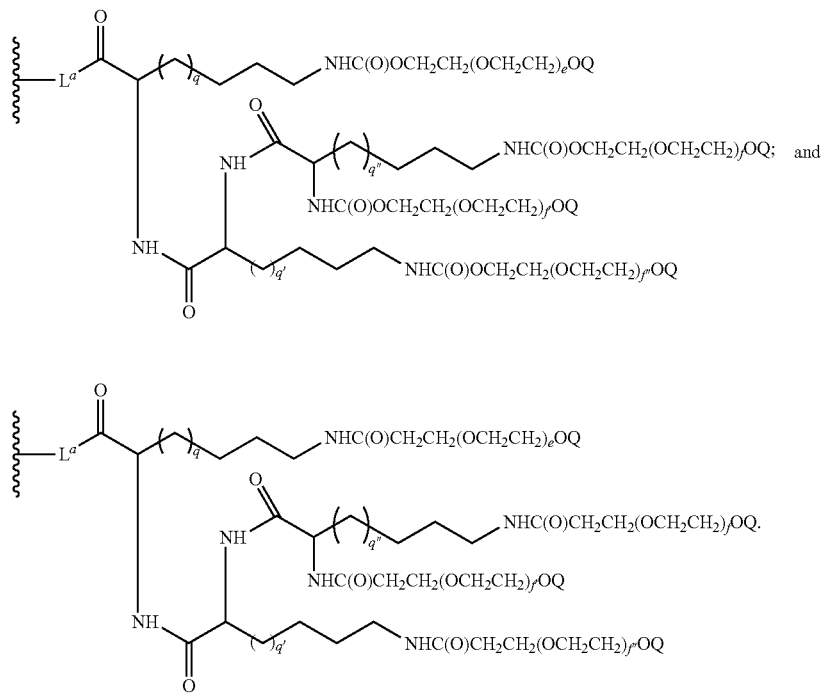

In each of the figures above, the indices e, f, f' and f" represent integers independently selected from 1 to 2500. The indices q, q' and q" represent integers independently selected from 1 to 20.

In another exemplary embodiment, the conjugates of the invention include a formula which is a member selected from:

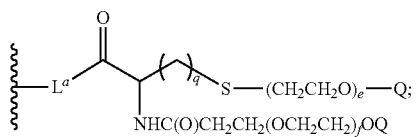

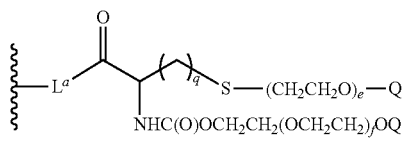

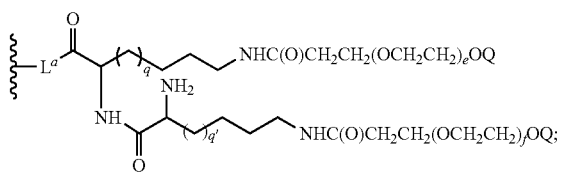

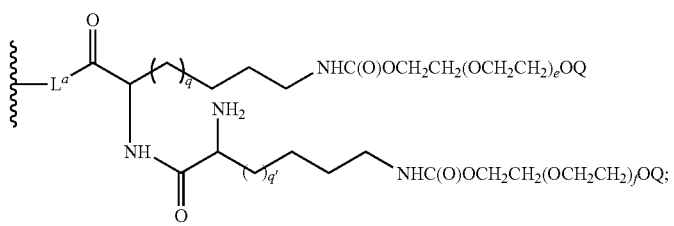

wherein Q is a member selected from H and substituted or unsubstituted $C_1$-$C_6$ alkyl. The indices e and f are integers independently selected from 1 to 2500, and the index q is an integer selected from 0 to 20.

In another exemplary embodiment, the conjugates of the invention include a formula which is a member selected from:

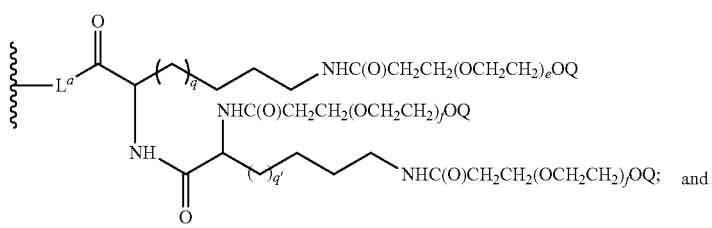

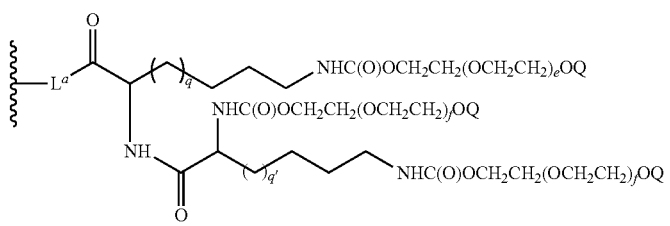

wherein Q is a member selected from H and substituted or unsubstituted $C_1$-$C_6$ alkyl, preferably Me. The indices e, f and f' are integers independently selected from 1 to 2500, and q and q' are integers independently selected from 1 to 20.

In another exemplary embodiment, the conjugate of the invention includes a structure according to the following formula:

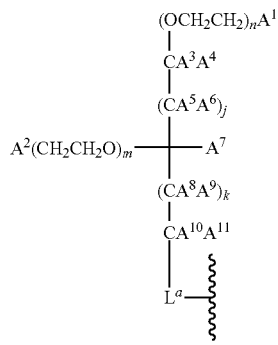

wherein the indices m and n are integers independently selected from 0 to 5000. The indices j and k are integers independently selected from 0 to 20. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted aryl, substituted or unsubstituted cycloalkyl, substituted or unsubstituted heterocycloalkyl, substituted or unsubstituted heteroaryl, —$NA^{12}A^{13}$, —$OA^{12}$ and —$SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In one embodiment according to the formula above, the branched polymer has a structure according to the following formula:

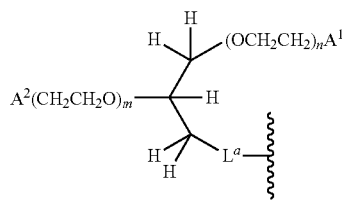

In an exemplary embodiment, $A^1$ and $A^2$ are members independently selected from —$OCH_3$ and OH.

In another exemplary embodiment, the linker $L^a$ is a member selected from aminoglycine derivatives. Exemplary polymeric modifying groups according to this embodiment have a structure according to the following formulae:

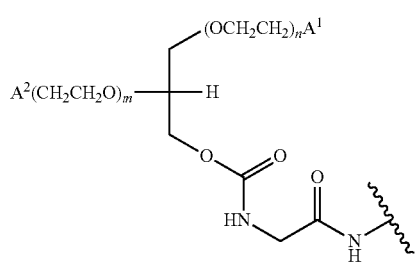

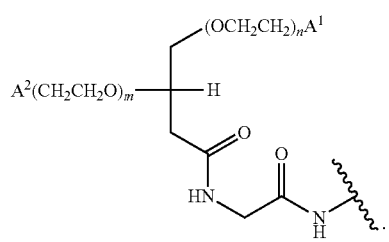

In one example, $A^1$ and $A^2$ are members independently selected from $OCH_3$ and OH. Exemplary polymeric modifying groups according to this example include:

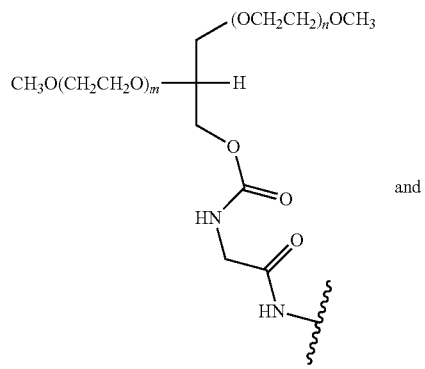

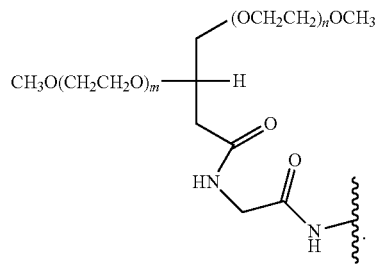

In each of the above embodiment, wherein the modifying group includes a stereocenter, for example those including an amino acid linker or a glycerol-based linker, the stereocenter can be either either racemic or defined. In one embodiment, in which such stereocenter is defined, it has (S) configuration. In another embodiment, the stereocenter has (R) configuration.

Those of skill in the art will appreciate that one or more of the m-PEG arms of the branched polymer can be replaced by a PEG moiety with a different terminus, e.g., OH, COOH, $NH_2$, $C_2$-$C_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

The branched PEG species set forth herein are readily prepared by methods such as that set forth in the Scheme 3, below:

Scheme 3: Preparation of a branched PEG species

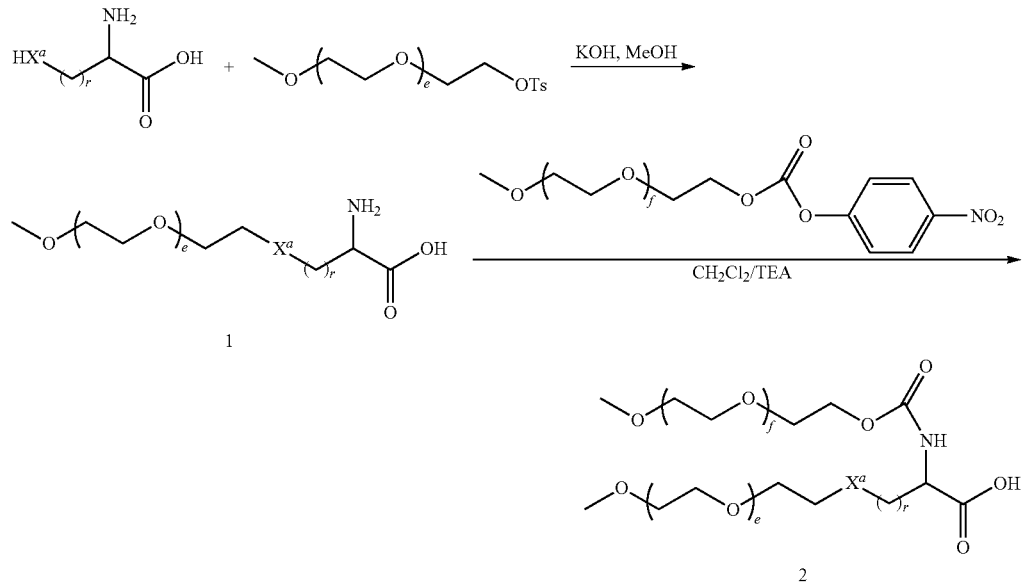

in which $X^a$ is O or S and r is an integer from 1 to 5. The indices e and f are independently selected integers from 1 to 2500.

Thus, according to Scheme 3, a natural or unnatural amino acid is contacted with an activated m-PEG derivative, in this case the tosylate, forming 1 by alkylating the side-chain heteroatom $X^a$. The mono-functionalized m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In an exemplary embodiment, the modifying group is a PEG moiety, however, any modifying group, e.g., water-soluble polymer, water-insoluble polymer, therapeutic moiety, etc., can be incorporated in a glycosyl moiety through an appropriate linkage. The modified sugar is formed by enzymatic means, chemical means or a combination thereof, thereby producing a modified sugar. In an exemplary embodiment, the sugars are substituted with an active amine at any position that allows for the attachment of the modifying moiety, yet still allows the sugar to function as a substrate for an enzyme capable of coupling the modified sugar to the G-CSF polypeptide. In an exemplary embodiment, when galactosamine is the modified sugar, the amine moiety is attached to the carbon atom at the 6-position.

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic polypeptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate)polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly($\alpha$-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the bioresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a difunctional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene)oxide. Such poly(alkylene) oxides can include, for example, poly(ethylene)oxide, poly (propylene)oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

Other Modifying Groups

The present invention also provides conjugates analogous to those described above in which the polypeptide is conjugated to a therapeutic moiety, diagnostic moiety, targeting moiety, toxin moiety or the like via a glycosyl linking group. Each of the above-recited moieties can be a small molecule, natural polymer (e.g., polypeptide) or a synthetic polymer.

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), IL-2 and IFN-α.

In an exemplary targeted conjugate, interferon alpha 2β (IFN-α2β) is conjugated to transferrin via a bifunctional linker that includes a glycosyl linking group at each terminus of the PEG moiety (Scheme 1). For example, one terminus of the PEG linker is functionalized with an intact sialic acid linker that is attached to transferrin and the other is functionalized with an intact C-linked Man linker that is attached to IFN-α 2β.

Biomolecules

In another embodiment, the modified sugar bears a biomolecule. In still further embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a polypeptide via a method of the invention.

Biomolecules useful in practicing the present invention can be derived from any source. The biomolecules can be isolated from natural sources or they can be produced by synthetic methods. Polypeptides can be natural polypeptides or mutated polypeptides. Mutations can be effected by chemical mutagenesis, site-directed mutagenesis or other means of inducing mutations known to those of skill in the art. polypeptides useful in practicing the instant invention include, for example, enzymes, antigens, antibodies and receptors. Antibodies can be either polyclonal or monoclonal; either intact or fragments. The polypeptides are optionally the products of a program of directed evolution Both naturally derived and synthetic polypeptides and nucleic acids are of use in conjunction with the present invention; these molecules can be attached to a sugar residue component or a crosslinking agent by any available reactive group. For example, polypeptides can be attached through a reactive amine, carboxyl, sulfhydryl, or hydroxyl group. The reactive group can reside at a polypeptide terminus or at a site internal to the polypeptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further embodiment, the biomolecule is selected to direct the polypeptide modified by the methods of the invention to a specific tissue, thereby enhancing the delivery of the polypeptide to that tissue relative to the amount of underivatized polypeptide that is delivered to the tissue. In a still further embodiment, the amount of derivatized polypeptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated polypeptide is elaborated by the attachment of an avidin or streptavidin moiety bearing one or more modifying groups.

Therapeutic Moieties

In another embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In another embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. Preferred therapeutic moieties are essentially non-fluorescent, or emit such a minimal amount of fluorescence that they are inappropriate for use as a fluorescent marker in an assay. Moreover, it is generally preferred to use therapeutic moieties that are not sugars. An exception to this preference is the use of a sugar that is modified by covalent attachment of another entity, such as a PEG, biomolecule, therapeutic moiety, diagnostic moiety and the like. In another exemplary embodiment, a therapeutic sugar moiety is conjugated to a linker arm and the sugar-linker arm cassette is subsequently conjugated to a polypeptide via a method of the invention.

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g, esterase, reductase, oxidase), light, heat and the like. Many cleavable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989).

Classes of useful therapeutic moieties include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, caramiphen and carbetapentane); antipruritic drugs (e.g., methdilazine and trimeprazine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyramide, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltiazem, amiodarone, isoxsuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chloroprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, the duocarmycins, Chlicheamycin and related structures and analogues thereof.

The therapeutic moiety can also be a hormone (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

Modified Sugars

Modified glycosyl donor species ("modified sugars") are preferably selected from modified sugar nucleotides, activated modified sugars and modified sugars that are simple saccharides that are neither nucleotides nor activated. Any desired carbohydrate or non-carbohydrate structure can be added to a polypeptide using the methods of the invention. Typically, the structure will be a monosaccharide, but the present invention is not limited to the use of modified monosaccharide sugars; oligosaccharides, polysaccharides and glycosyl-mimetic moieties are useful as well.

The modifying group is attached to a sugar moiety by enzymatic means, chemical means or a combination thereof, thereby producing a modified sugar. The sugars are substituted at any position that allows for the attachment of the modifying group, yet which still allows the sugar to function as a substrate for the enzyme used to ligate the modified sugar to the polypeptide. In an exemplary embodiment, when sialic acid is the sugar, the sialic acid is substituted with the modifying group at either the pyruvyl side chain or at the 5-position on the amine moiety that is normally acetylated in sialic acid.

Sugar Nucleotides

In certain embodiments of the present invention, a modified sugar nucleotide is utilized to add the modified sugar to the polypeptide. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, and a GDP-glycoside. Even more preferably, the modified sugar nucleotide is selected from an UDP-galactose, UDP-galactosamine, UDP-glucose, UDP-glucosamine, GDP-mannose, GDP-fucose, CMP-sialic acid, and CMP-NeuAc. N-acetylamine derivatives of the sugar nucleotides are also of use in the methods of the invention.

In one example, the nucleotide sugar species is modified with a water-soluble polymer. An exemplary modified sugar nucleotide bears a sugar group that is modified through an amine moiety on the sugar. Modified sugar nucleotides, e.g., saccharyl-amine derivatives of a sugar nucleotide, are also of use in the methods of the invention. For example, a saccharyl amine (without the modifying group) can be enzymatically conjugated to a polypeptide (or other species) and the free saccharyl amine moiety subsequently be conjugated to a desired modifying group. Alternatively, the modified sugar nucleotide can function as a substrate for an enzyme that transfers the modified sugar to a saccharyl acceptor on the polypeptide.

In an exemplary embodiment, the modified sugar is based upon a 6-amino-N-acetyl-glycosyl moiety. As shown in Scheme 4, below for N-acetylgalactosamine, the modified sugar nucleotide can be readily prepared using standard methods.

Scheme 4: Preparation of an Exemplary Modified Sugar Nucleotide

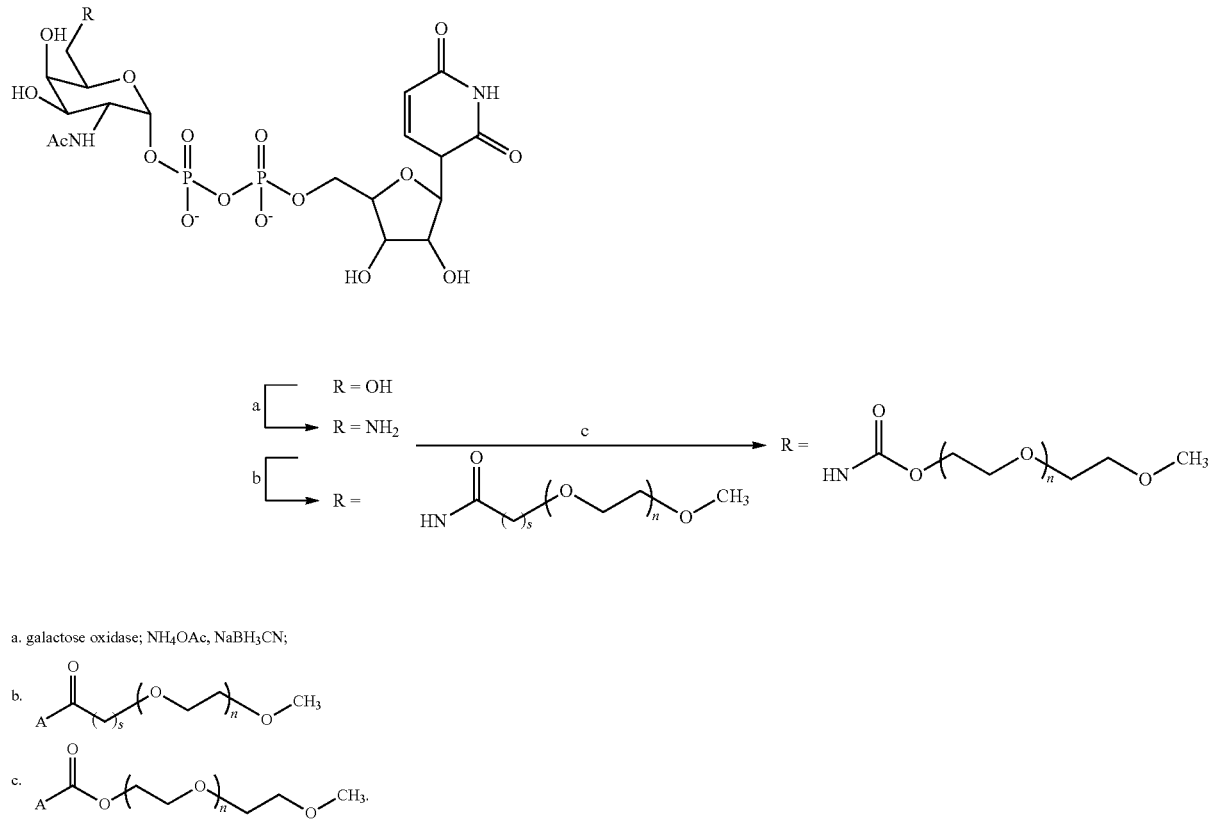

In Scheme 4, above, the index n represents an integer from 0 to 2500, preferably from 10 to 1500, and more preferably from 10 to 1200. The symbol "A" represents an activating group, e.g., a halo, a component of an activated ester (e.g., a N-hydroxysuccinimide ester), a component of a carbonate (e.g., p-nitrophenyl carbonate) and the like. Those of skill in the art will appreciate that other PEG-amide nucleotide sugars are readily prepared by this and analogous methods.

In other exemplary embodiments, the amide moiety is replaced by a group such as a urethane or a urea.

In still further embodiments, $R^1$ is a branched PEG, for example, one of those species set forth above. Illustrative compounds according to this embodiment include:

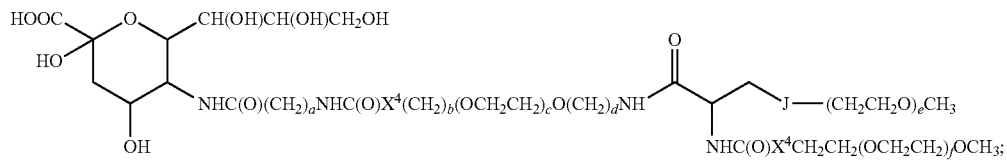

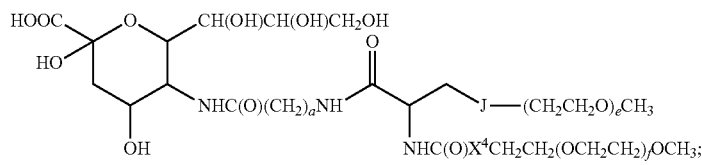

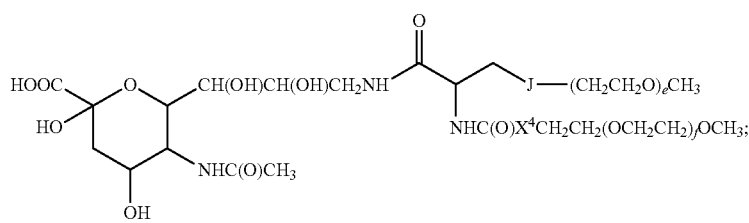

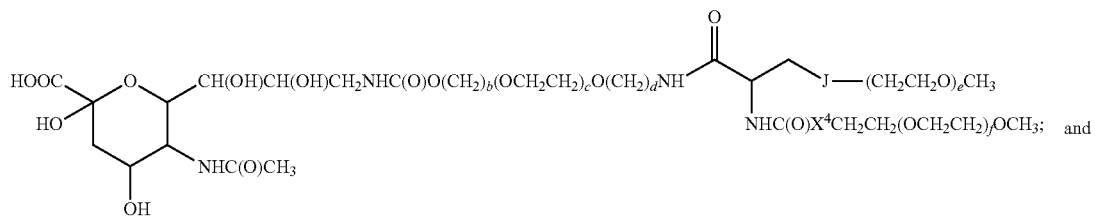

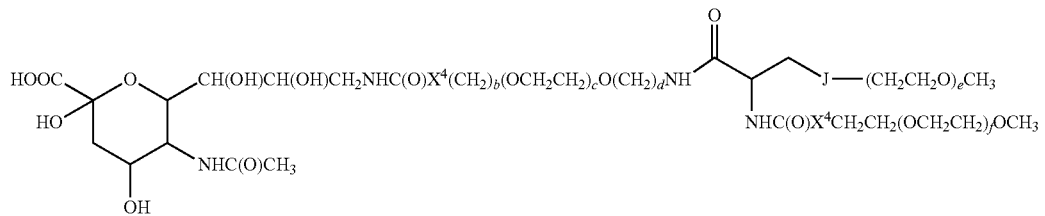

in which $X^4$ is a bond or O, and J is S or O.

Moreover, as discussed above, the present invention provides polypeptide conjugates that are formed using nucleotide sugars that are modified with a water-soluble polymer, which is either straight-chain or branched. For example, compounds having the formula shown below are within the scope of the present invention:

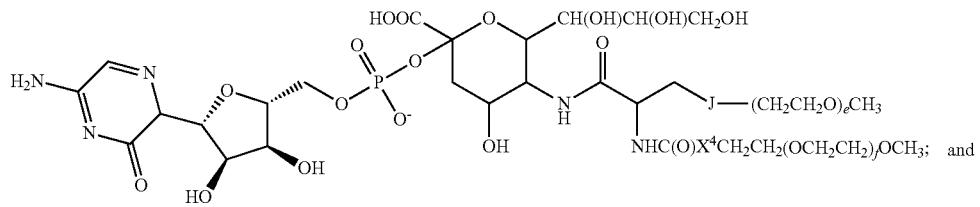

-continued

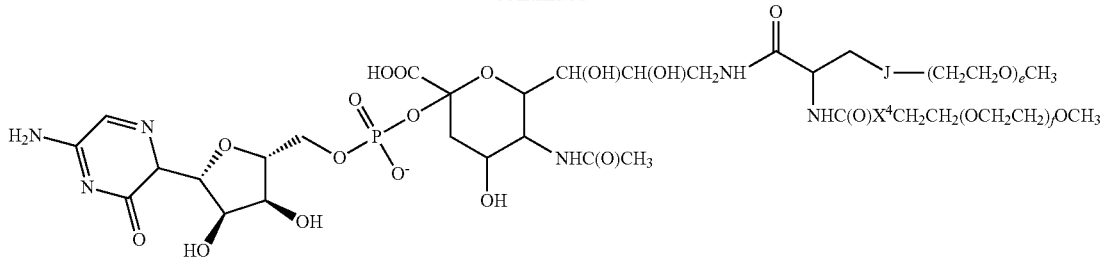

in which $X^4$ is O or a bond, and J is S or O.

Similarly, the invention provides polypeptide conjugates that are formed using nucleotide sugars of those modified sugar species in which the carbon at the 6-position is modified:

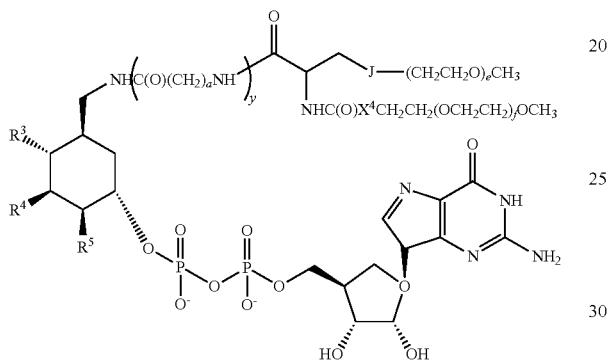

in which $X^4$ is a bond or O, J is S or O, and y is 0 or 1.

Also provided are polypeptide and glycopeptide conjugates having the following formulae:

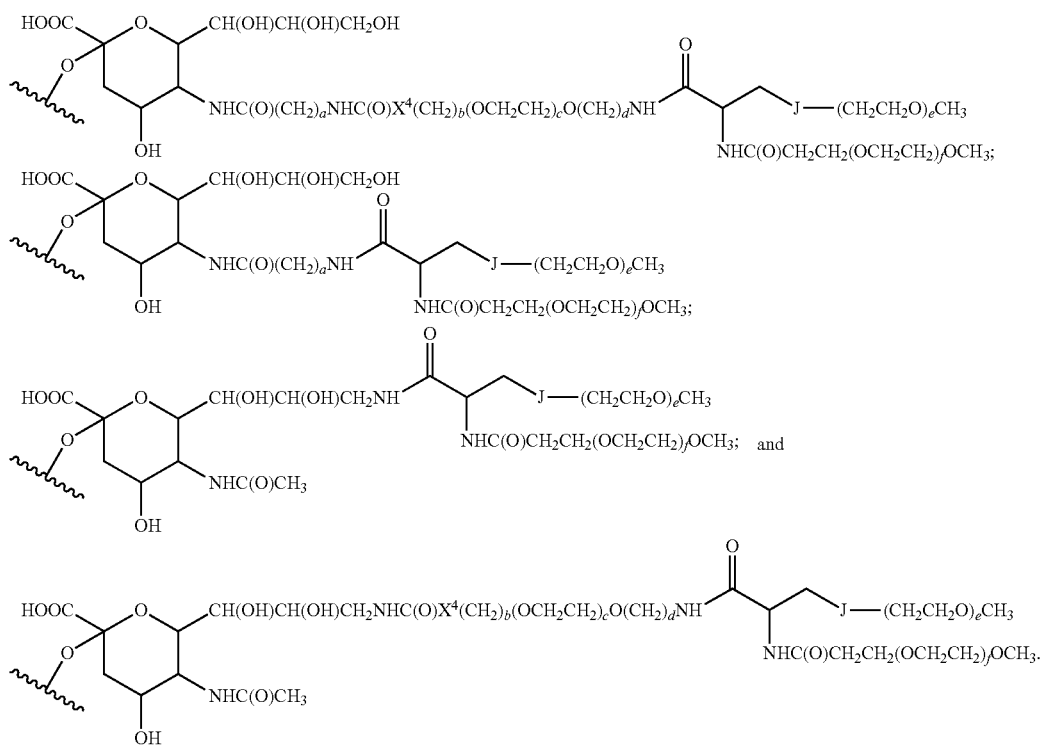

wherein J is S or O.

Activated Sugars

In other embodiments, the modified sugar is an activated sugar. Activated, modified sugars, which are useful in the present invention, are typically glycosides which have been synthetically altered to include a leaving group. In one example, the activated sugar is used in an enzymatic reaction to transfer the activated sugar onto an acceptor on the polypeptide or glycopeptide. In another example, the activated sugar is added to the polypeptide or glycopeptide by chemical means. "Leaving group" (or activating group) refers to those moieties, which are easily displaced in enzyme-regulated nucleophilic substitution reactions or alternatively, are replaced in a chemical reaction utilizing a nucleophilic reaction partner (e.g., a glycosyl moiety carrying a sufhydryl group). It is within the abilities of a skilled person to select a suitable leaving group for each type of reaction. Many activated sugars are known in the art. See, for example, Vocadlo et al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of leaving groups include halogen (e.g, fluoro, chloro, bromo), tosylate ester, mesylate ester, triflate ester and the like. Preferred leaving groups, for use in enzyme mediated reactions, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred. For non-enzymatic, nucleophilic substitutions, these and other leaving groups may be useful. For instance, the activated donor glycoside can be a dinitrophenyl (DNP), or bromo-glycoside.

By way of illustration, glycosyl fluorides can be prepared from the free sugar by first acetylating and then treating the sugar moiety with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a further exemplary embodiment, the modified sugar is an oligosaccharide having an antennary structure. In another embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the polypeptide attaches multiple copies of the modifying group to the polypeptide. The general structure of a typical conjugate of the invention as set forth in the drawing above encompasses multivalent species resulting from preparing a conjugate of the invention utilizing an antennary structure. Many antennary saccharide structures are known in the art, and the present method can be practiced with them without limitation.

Preparation of Modified Sugars

In general, a covalent bond between the sugar moiety and the modifying group is formed through the use of reactive functional groups, which are typically transformed by the linking process into a new organic functional group or unreactive species. In order to form the bond, the modifying group and the sugar moiety carry complimentary reactive functional groups. The reactive functional group(s), can be located at any position on the sugar moiety.

Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Reactive Functional Groups

Useful reactive functional groups pendent from a sugar nucleus or modifying group include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Cross-Linking Groups

Preparation of the modified sugar for use in the methods of the present invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., Biochemistry 28: 1856 (1989); Bhatia et al., Anal. Biochem. 178: 408 (1989); Janda et al, J. Am. Chem. Soc. 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

A variety of reagents are used to modify the components of the modified sugar with intramolecular chemical crosslinks (for reviews of crosslinking reagents and crosslinking procedures see: Wold, F., Meth. Enzymol. 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., Meth. Enzymol. 91: 580-609, 1983; Mattson et al, Mol. Biol. Rep. 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

In addition to the use of site-specific reactive moieties, the present invention contemplates the use of non-specific reactive groups to link the sugar to the modifying group.

Exemplary non-specific cross-linkers include photoactivatable groups, completely inert in the dark, which are converted to reactive species upon absorption of a photon of appropriate energy. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In yet a further embodiment, the linker group is provided with a group that can be cleaved to release the modifying group from the sugar residue. Many cleaveable groups are known in the art. See, for example, Jung et al., Biochem. Biophys. Acta 761: 152-162 (1983); Joshi et al., J. Biol. Chem. 265: 14518-14525 (1990); Zarling et al. J. Immunol. 124: 913-920 (1980); Bouizar et al., Eur. J. Biochem. 155: 141-147 (1986); Park et al., J. Biol. Chem. 261: 205-210 (1986); Browning et al., J. Immunol. 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., Biochem. Biophys. Res. Commun. 102: 1048 (1991)). Preferred cleaveable groups comprise a cleaveable moiety which is a member selected from the group consisting of disulfide, ester, imide, carbonate, nitrobenzyl, phenacyl and benzoin groups.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., Curr. Med. Chem. 6: 93 (1999) and and Schafer et al., J. Org. Chem. 65: 24 (2000).

In an exemplary embodiment, the polypeptide that is modified by a method of the invention is a glycopeptide that is produced in prokaryotic cells (e.g., E. coli), eukaryotic cells including yeast and mammalian cells (e.g., CHO cells), or in a transgenic animal and thus contains N- and/or O-linked oligosaccharide chains, which are incompletely sialylated. The oligosaccharide chains of the glycopeptide lacking a sialic acid and containing a terminal galactose residue can be glyco-PEG-ylated, glyco-PPG-ylated or otherwise modified with a modified sialic acid.

In Scheme 5, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG or PPG attachment by reacting compound 3 with an activated (m-) PEG or (m-) PPG derivative (e.g., PEG-C(O)NHS, PPG-C(O)NHS), producing 4 or 5, respectively.

Scheme 5

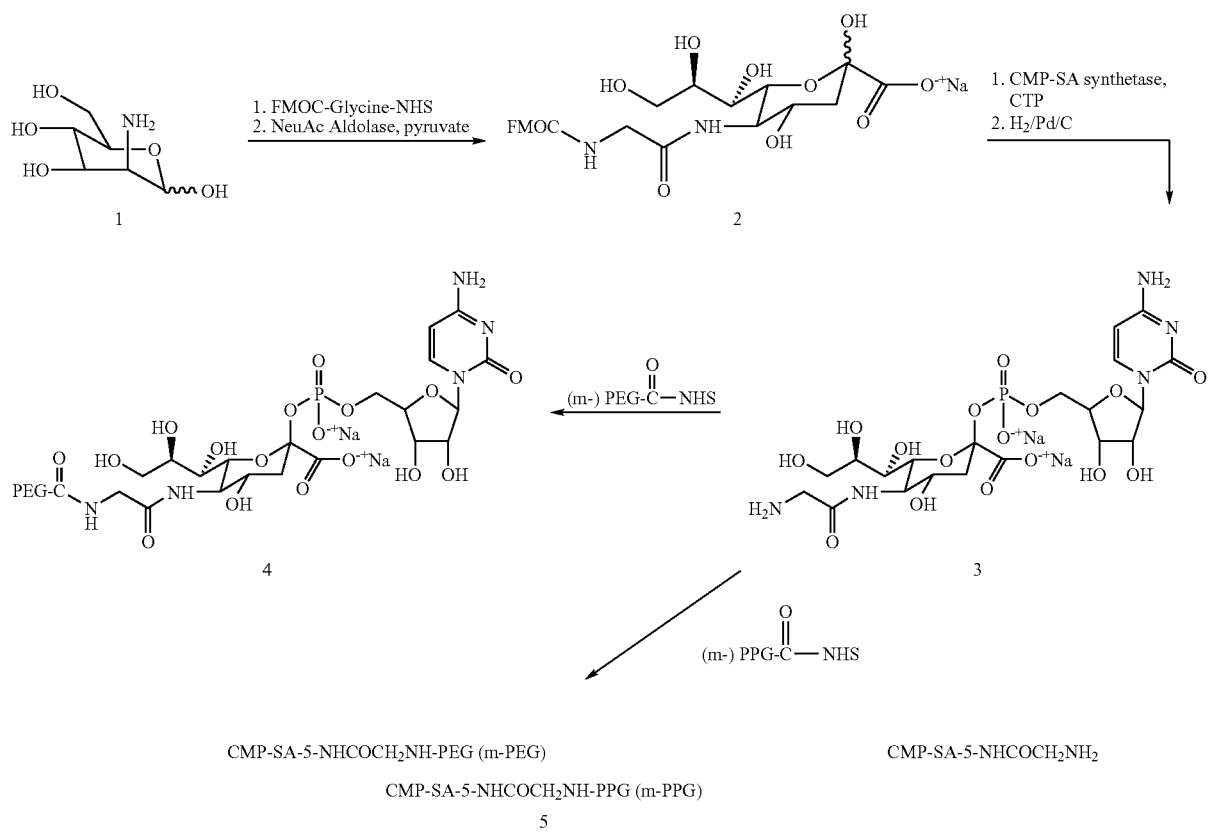

Table 11, below sets forth representative examples of sugar monophosphates that are derivatized with a PEG or PPG moiety. Certain of the compounds of Table 2 are prepared by the method of Scheme 4. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 11

Examples of sugar monophosphates derivatized with PEG or PPG

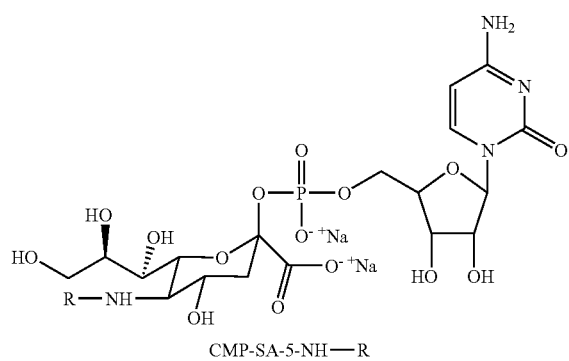

TABLE 11-continued

Examples of sugar monophosphates derivatized with PEG or PPG

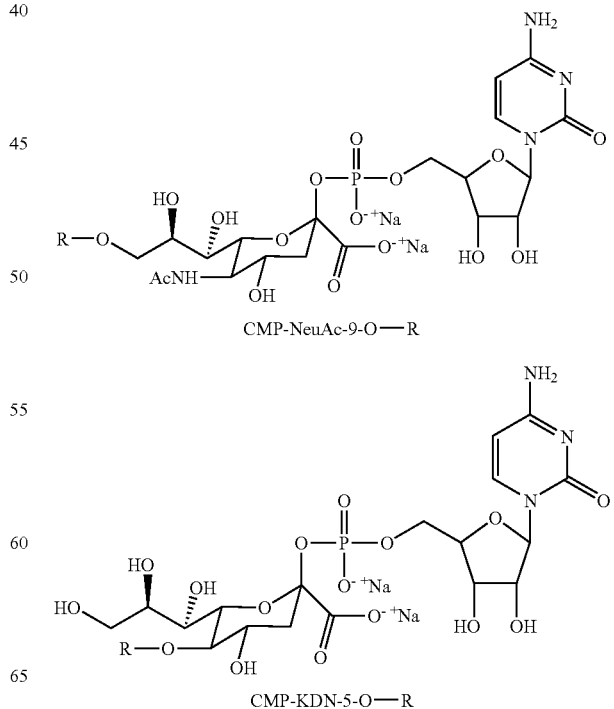

TABLE 11-continued
Examples of sugar monophosphates derivatized with PEG or PPG
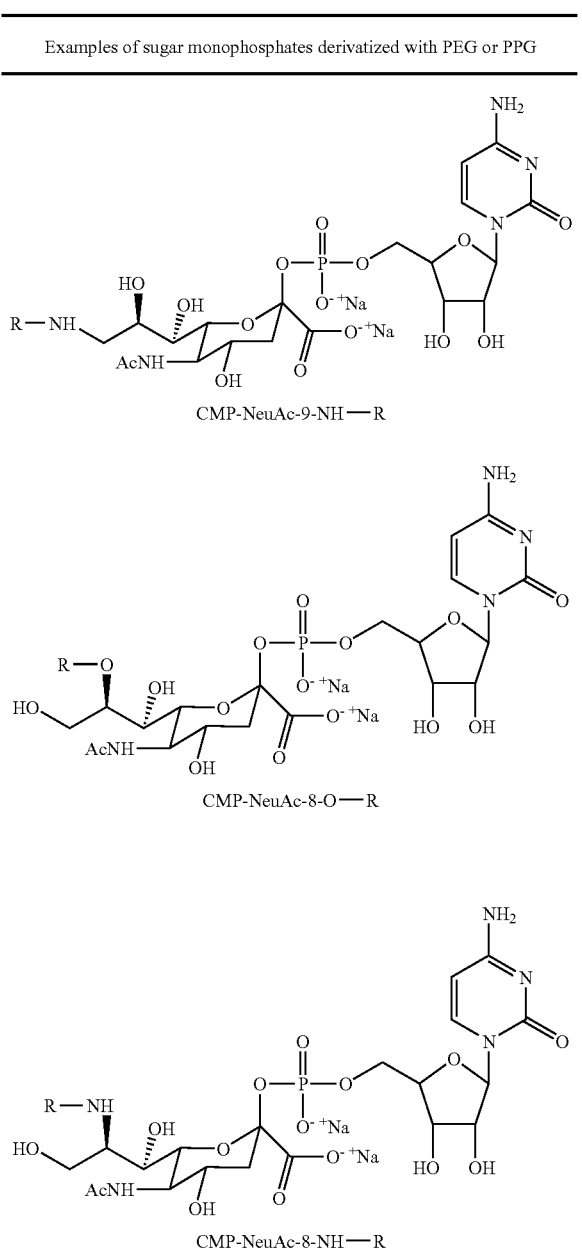
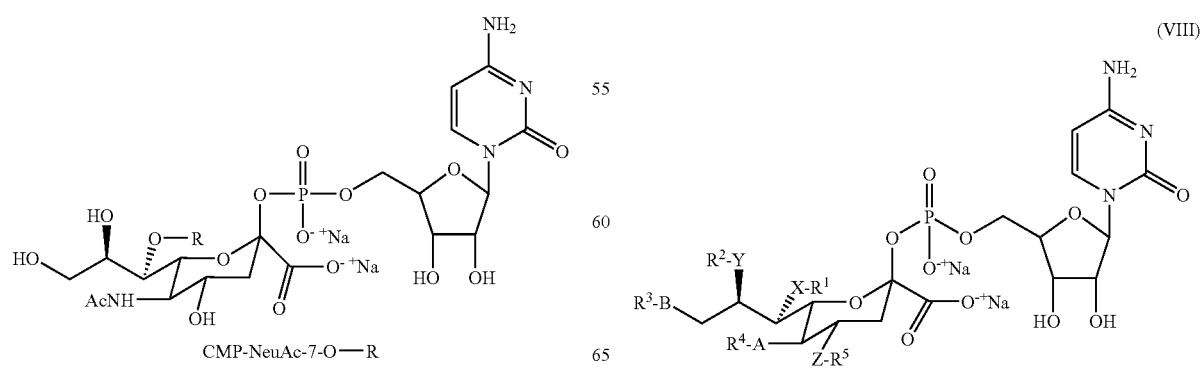
The modified sugar phosphates of use in practicing the present invention can be substituted in other positions as well as those set forth above. Presently preferred substitutions of sialic acid are set forth in Formula (VIII):

in which X is a linking group, which is preferably selected from —O—, —N(H)—, —S, CH$_2$—, and —N(R)$_2$, in which each R is a member independently selected from R$^1$-R$^5$. The symbols Y, Z, A and B each represent a group that is selected from the group set forth above for the identity of X. X, Y, Z, A and B are each independently selected and, therefore, they can be the same or different. The symbols R$^1$, R$^2$, R$^3$, R$^4$ and R$^5$ represent H, a water-soluble polymer, therapeutic moiety, biomolecule or other moiety. Alternatively, these symbols represent a linker that is bound to a water-soluble polymer, therapeutic moiety, biomolecule or other moiety.

Exemplary moieties attached to the conjugates disclosed herein include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, SLe$_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY(ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the polypeptide. For example, TPCH(S-(2-thiopyridyl)-L-cysteine hydrazide and TPMPH ((S-(2-thiopyridyl)mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal polypeptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al, *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

Preferred Specific Sites in Crosslinking Reagents
1. Amino-Reactive Groups

In one embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, $\alpha$- and $\epsilon$-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form $\alpha$-$\beta$ unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

2. Sulfhydryl-Reactive Groups

In another embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodiimde (Yamada et al., *Biochemistry* 20: 4836-4842, 1981).

Preferred Nonspecific Sites in Crosslinking Reagents

In addition to the use of site-specific reactive moieties, the present invention contemplates the use of non-specific reactive groups to link the sugar to the modifying group.

Exemplary non-specific cross-linkers include photoactivatable groups, completely inert in the dark, which are converted to reactive species upon absorption of a photon of appropriate energy. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

Homobifunctional Reagents

1. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl)suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOES), ethylene glycolbis(succinimidylsuccinate) (EGS), ethylene glycolbis(sulfosuccinimidylsuccinate) (sulfo-EGS), dithiobis(succinimidyl-propionate) (DSP), and dithiobis(sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3, 3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxy-diphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene)bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio)propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4-((iodoacetyl)-amino)methylcyclohexane-1-carboxylate (SIAC).

An example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Specific embodiments according to the invention include:

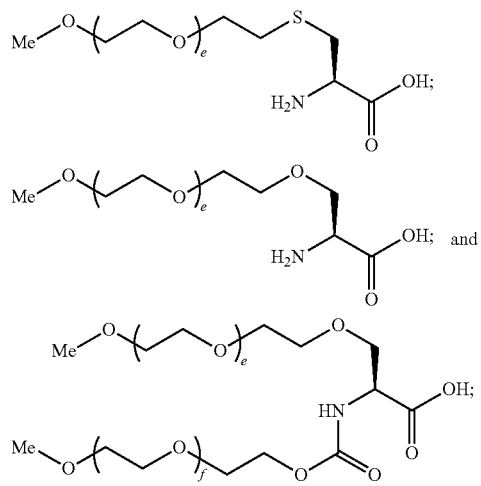

and carbonates and active esters of these species, such as:

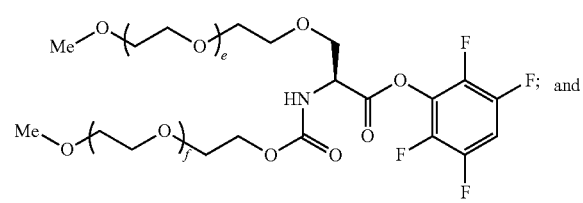

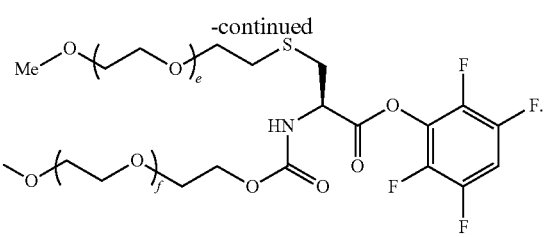

Exemplary Conjugates of the Invention

In an exemplary embodiment, the polypeptide is an interferon. The interferons are antiviral glycoproteins that, in humans, are secreted by human primary fibroblasts after induction with virus or double-stranded RNA. Interferons are of interest as therapeutics, e.g, antiviral agents (e.g., hepatitis B and C), antitumor agents (e.g., hepatocellular carcinoma) and in the treatment of multiple sclerosis. For references relevant to interferon-α, see, Asano, et al., *Eur. J. Cancer,* 27(Suppl 4):S21-S25 (1991); Nagy, et al., *Anticancer Research,* 8(3):467-470 (1988); Dron, et al., *J. Biol Regul. Homeost. Agents,* 3(1):13-19 (1989); Habib, et al., *Am Surg.,* 67(3):257-260 (March 2001); and Sugyiama, et al., *Eur. J. Biochem.,* 217:921-927 (1993). For references discussing infereon-β, see, e.g., Yu, et al, *J. Neuroimmunol.,* 64(1):91-100 (1996); Schmidt, J., *J. Neurosci. Res.,* 65(1):59-67 (2001); Wender, et al., *Folia Neuropathol.,* 39(2):91-93 (2001); Martin, et al., *Springer Semin. Immunopathol.,* 18(1): 1-24 (1996); Takane, et al., *J. Pharmacol. Exp. Ther.,* 294(2): 746-752 (2000); Sburlati, et al., *Biotechnol. Prog.,* 14:189-192 (1998); Dodd, et al., *Biochimica et Biophysica Acta,* 787:183-187 (1984); Edelbaum, et al., *J. Interferon Res.,* 12:449-453 (1992); Conradt, et al., *J. Biol. Chem.,* 262(30): 14600-14605 (1987); Civas, et al., *Eur. J. Biochem.,* 173:311-316 (1988); Demolder, et al., *J. Biotechnol.,* 32:179-189 (1994); Sedmak, et al., *J. Interferon Res.,* 9(Suppl 1):S61-S65 (1989); Kagawa, et al., *J. Biol. Chem.,* 263(33):17508-17515 (1988); Hershenson, et al., U.S. Pat. No. 4,894,330; Jayaram, et al., *J. Interferon Res.,* 3(2):177-180 (1983); Menge, et al, *Develop. Biol. Standard.,* 66:391-401 (1987); Vonk, et al., *J. Interferon Res.,* 3(2):169-175 (1983); and Adolf, et al., *J. Interferon Res.,* 10:255-267 (1990).

In an exemplary interferon conjugate, interferon alpha, e.g., interferon alpha 2b and 2a, is conjugated to a water soluble polymer through an intact glycosyl linker.

In a further exemplary embodiment, the invention provides a conjugate of human granulocyte colony stimulating factor (G-CSF). G-CSF is a glycoprotein that stimulates proliferation, differentiation and activation of neutropoietic progenitor cells into functionally mature neutrophils. Injected G-CSF is rapidly cleared from the body. See, for example, Nohynek, et al., *Cancer Chemother. Pharmacol.,* 39:259-266 (1997); Lord, et al., *Clinical Cancer Research,* 7(7):2085-2090 (July 2001); Rotondaro, et al., *Molecular Biotechnology,* 11(2): 117-128 (1999); and Bonig, et al., *Bone Marrow Transplantation,* 28: 259-264 (2001).

The present invention encompasses a method for the modification of GM-CSF. GM-CSF is well known in the art as a cytokine produced by activated T-cells, macrophages, endothelial cells, and stromal fibroblasts. GM-CSF primarily acts on the bone marrow to increase the production of inflammatory leukocytes, and further functions as an endocrine hormone to initiate the replenishment of neutrophils consumed during inflammatory functions. Further GM-CSF is a macrophage-activating factor and promotes the differentiation of Lagerhans cells into dendritic cells. Like G-CSF, GM-CSF also has clinical applications in bone marrow replacement following chemotherapy Nucleic Acids In another aspect, the invention provides an isolated nucleic acid encoding a sequon polypeptide of the invention. The sequon polypeptide includes within its amino acid sequence one or more exogenous O-linked glycosylation sequence of the invention. In one embodiment, the nucleic acid of the invention is part of an expression vector. In another related embodiment, the present invention provides a cell including the nucleic acid of the present invention. Exemplary cells include host cells such as various strains of E. coli, insect cells and mammalian cells, such as CHO cells.

Pharmaceutical Compositions

Polypeptides conjugates of the invention have a broad range of pharmaceutical applications. For example, glycoconjugated erythropoietin (EPO) may be used for treating general anemia, aplastic anemia, chemo-induced injury (such as injury to bone marrow), chronic renal failure, nephritis, and thalassemia. Modified EPO may be further used for treating neurological disorders such as brain/spine injury, multiple sclerosis, and Alzheimer's disease.

A second example is interferon-α (IFN-α), which may be used for treating AIDS and hepatitis B or C, viral infections caused by a variety of viruses such as human papilloma virus (HBV), coronavirus, human immunodeficiency virus (HIV), herpes simplex virus (HSV), and varicella-zoster virus (VZV), cancers such as hairy cell leukemia, AIDS-related Kaposi's sarcoma, malignant melanoma, follicular non-Hodgkins lymphoma, Philladephia chromosome (Ph)-positive, chronic phase myelogenous leukemia (CML), renal cancer, myeloma, chronic myelogenous leukemia, cancers of the head and neck, bone cancers, as well as cervical dysplasia and disorders of the central nervous system (CNS) such as multiple sclerosis. In addition, IFN-α modified according to the methods of the present invention is useful for treating an assortment of other diseases and conditions such as Sjogren's symdrome (an autoimmune disease), Behcet's disease (an autoimmune inflammatory disease), fibromyalgia (a musculoskeletal pain/fatigue disorder), aphthous ulcer (canker sores), chronic fatigue syndrome, and pulmonary fibrosis.

Another example is interferon-β, which is useful for treating CNS disorders such as multiple sclerosis (either relapsing/remitting or chronic progressive), AIDS and hepatitis B or C, viral infections caused by a variety of viruses such as human papilloma virus (HBV), human immunodeficiency virus (HIV), herpes simplex virus (HSV), and varicella-zoster virus (VZV), otological infections, musculoskeletal infections, as well as cancers including breast cancer, brain cancer, colorectal cancer, non-small cell lung cancer, head and neck cancer, basal cell cancer, cervical dysplasia, melanoma, skin cancer, and liver cancer. IFN-β modified according to the methods of the present invention is also used in treating other diseases and conditions such as transplant rejection (e.g., bone marrow transplant), Huntington's chorea, colitis, brain inflammation, pulmonary fibrosis, macular degeneration, hepatic cirrhosis, and keratoconjunctivitis.

Granulocyte colony stimulating factor (G-CSF) is a further example. G-CSF modified according to the methods of the present invention may be used as an adjunct in chemotherapy for treating cancers, and to prevent or alleviate conditions or complications associated with certain medical procedures, e.g., chemo-induced bone marrow injury; leucopenia (general); chemo-induced febrile neutropenia; neutropenia associated with bone marrow transplants; and severe, chronic neutropenia. Modified G-CSF may also be used for transplantation; peripheral blood cell mobilization; mobilization of peripheral blood progenitor cells for collection in patients who will receive myeloablative or myelosuppressive chemotherapy; and reduction in duration of neutropenia, fever, antibiotic use, hospitalization following induction/consolidation treatment for acute myeloid leukemia (AML). Other condictions or disorders may be treated with modified G-CSF include asthma and allergic rhinitis.

As one additional example, human growth hormone (hGH) modified according to the methods of the present invention may be used to treat growth-related conditions such as dwarfism, short-stature in children and adults, cachexia/muscle wasting, general muscular atrophy, and sex chromosome abnormality (e.g., Turner's Syndrome). Other conditions may be treated using modified hGH include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomia. Moreover, modified hGH may also be used to promote various processes, e.g., general tissue regeneration, bone regeneration, and wound healing, or as a vaccine adjunct.

Thus, in another aspect, the invention provides a pharmaceutical composition including at least one polypeptide or polypeptide conjugate of the invention and a pharmaceutically acceptable diluent, carrier, vehicle, additive or combinations thereof. In an exemplary embodiment, the pharmaceutical composition includes a covalent conjugate between a water-soluble polymer (e.g., a non-naturally-occurring water-soluble polymer), and a glycosylated or non-glycosylated polypeptide of the invention as well as a pharmaceutically acceptable diluent. Exemplary water-soluble polymers include poly(ethylene glycol) and methoxy-poly(ethylene glycol). Alternatively, the polypeptide is conjugated to a modifying group other than a poly(ethylene glycol) derivative, such as a therapeutic moiety or a biomolecule. The modifying group is conjugated to the polypeptide via an intact glycosyl linking group interposed between and covalently linked to both the polypeptide and the modifying group. In another exemplary embodiment, the Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable matrices, such as microspheres (e.g., polylactate polyglycolate), may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered subcutaneously or parenterally, e.g., intravenously. Thus, the invention provides compositions for parenteral administration, which include the compound dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and meta-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

Without intending to limit the scope of the invention, in each of the embodiments set forth above (e.g., those relating to compositions, such as sequon polypeptides, polypeptide conjugates, libraries of polypeptides, pharmaceutical compositions, nucleic acids encoding polypeptides and the like), the following exemplary embodiments are generally preferred:

In one exemplary embodiment, in which the parent polypeptide is glucagon-like peptide-1 (GLP-1), the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418). In another exemplary embodiment, in which the parent polypeptide is wild-type GLP-1 the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418). In another exemplary embodiment, in which the parent polypeptide is wild-type GLP-1, the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418), unless the O-linked glycosylation sequence is not designed around a proline residue that is present in the wild-type G-CSF polypeptide.

In another exemplary embodiment, in which the parent polypeptide is G-CSF, the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138). In another exemplary embodiment, in which the parent polypeptide is wild-type G-CSF the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138). In another exemplary embodiment, in which the parent polypeptide is wild-type G-CSF the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138), unless the O-linked glycosylation sequence is not designed around a proline residue that is present in the wild-type G-CSF polypeptide.

In another exemplary embodiment, in which the parent polypeptide is human growth hormon (hGH), the O-linked glycosylation sequence is preferably not selected from PTQGA (SEQ ID NO: 158), PTQGAM (SEQ ID NO: 147), PTQGAMP (SEQ ID NO: 148), PTVLP (SEQ ID NO: 151), PTTVS (SEQ ID NO: 145), PTTLYV (SEQ ID NO: 160), PTINT (SEQ ID NO: 143), PTEIP (SEQ ID NO: 140), PTQA (SEQ ID NO: 141) and TETP (SEQ ID NO: 149). In another exemplary embodiment, in which the parent polypeptide is wild-type hGH, the O-linked glycosylation sequence is preferably not selected from PTQGAM (SEQ ID NO: 147), PTQGAMP (SEQ ID NO: 148), PTTVS (SEQ ID NO: 145), PTTLYV (SEQ ID NO: 160), PTINT (SEQ ID NO: 143), PTQA (SEQ ID NO: 141) and TETP (SEQ ID NO: 149). In yet another exemplary embodiment, in which the parent polypeptide is wild-type hGH, the O-linked glycosylation sequence is preferably not selected from PTQGAM (SEQ ID NO: 147), PTQGAMP (SEQ ID NO: 148), PTTVS (SEQ ID NO: 145), PTTLYV (SEQ ID NO: 160), PTINT (SEQ ID NO: 143), PTQA (SEQ ID NO: 141) and TETP (SEQ ID NO: 149), unless the O-linked glycosylation sequence is not designed around a proline residue that is present in the wild-type hGH polypeptide.

In another exemplary embodiment, in which the parent polypeptide is INF-alpha, the O-linked glycosylation sequence is preferably not TETP (SEQ ID NO: 149). In another exemplary embodiment, in which the parent polypeptide is wild-type INF-alpha, the O-linked glycosylation sequence is preferably not TETP (SEQ ID NO: 149). In yet another exemplary embodiment, in which the parent polypeptide is wild-type INF-alpha, the O-linked glycosylation sequence is preferably not TETP (SEQ ID NO: 149), unless the O-linked glycosylation sequence is not designed around a proline residue that is present in the wild-type INF-alpha polypeptide.

In another exemplary embodiment, in which the parent polypeptide is FGF (e.g., FGF-1, FGF-2, FGF-18, FGF-20, FGF-21), the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420). In another exemplary embodiment, in which the parent polypeptide is a wild-type FGF, the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420). In yet another exemplary embodiment, in which the parent polypeptide is a wild-type FGF, the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420), unless the O-linked glycosylation sequence is not designed around a proline residue that is present in the wild-type FGF polypeptide.

V. Methods

Identification of Sequon Polypeptides as Substrates for Glycosyltransferases

One strategy for the identification of sequon polypeptides that can be glycosylated with a satisfactory yield when subjected to a glycosylation reaction, is to prepare a library of sequon polypeptides, wherein each sequon polypeptide includes at least one O-linked or S-linked glycosylation sequence of the invention, and to test each sequon polypeptide for its ability to function as an efficient substrate for a glycosyltransferase. A library of sequon polypeptides can be generated by including a selected O-linked or S-linked glycosylation sequence of the invention at different positions within the amino acid sequence of a parent polypeptide.

Library of Sequon Polypeptides

In one aspect, the invention provides methods of generating one or more library of sequon polypeptides, wherein the sequon polypeptides corresponds to a parent polypeptide (e.g., wild-type polypeptide). In one embodiment, the parent polypeptide has an amino acid sequence including m amino acids. Each amino acid position within the amino acid sequence is represented by $(AA)_n$, wherein n is a member selected from 1 to m. An exemplary method of generating a library of sequon polypeptides includes the steps of: (i) producing a first sequon polypeptide (e.g., recombinantly, chemically or by other means) by introducing an O-linked glycosylation sequence of the invention at a first amino acid position $(AA)_n$ within the parent polypeptide; (ii) producing at least one additional sequon polypeptide by introducing an O-linked glycosylation sequence at an additional amino acid position. In one embodiment, the additional amino acid position is $(AA)_{n+x}$. In another embodiment, the additional amino acid position is $(AA)_{n-x}$. In these embodiments, x is a member selected from 1 to (m−n). In one embodiment the additional sequon polypeptide includes the same O-linked glycosylation sequence as the first sequon polypeptide. In another embodiment, the additional sequon polypeptide includes a different O-linked glycosylation sequence than the first sequon polypeptide. In an exemplary embodiment, the library of sequon polypeptides is generated by "sequon scanning" described herein above. Exemplary parent polypeptides and O-linked glycosylation sequences useful in the libraries of the invention are also described herein.

Identification of Lead Polypeptides

It may be desirable to select among the members of the library those polypeptides that are effectively glycosylated and/or glycoPEGylated when subjected to an enzymatic glycosylation and/or glycoPEGylation reaction. Sequon polypeptides, which are found to be effectively glycosylated and/or glycoPEGylated are termed "lead polypeptides". In an exemplary embodiment, the yield of the enzymatic glycosylation or glycoPEGylation reaction is used to select one or more lead polypeptides. In another exemplary embodiment, the yield of the enzymatic glycosylation or glycoPEGylation for a lead polypeptide is between about 10% and about 100%, preferably between about 30% and about 100%, more preferably between about 50% and about 100% and most preferably between about 70% and about 100%. Lead polypeptides that can be efficiently glycosylated are optionally further evaluated by subjecting the glycosylated lead polypeptide to another enzymatic glycosylation or glycoPEGylation reaction.

Thus, the invention provides methods for identifying a lead polypeptide. An exemplary method includes the steps of: (i) generating a library of sequon polypeptides of the invention; (ii) subjecting at least one member of the library to an enzymatic glycosylation reaction (or optionally an enzymatic glycoPEGylation reaction). In one embodiment, during this reaction, a glycosyl moiety is transferred from a glycosyl donor molecule onto at least one O-linked glycosylation sequence, wherein the glycosyl moiety is optionally derivatized with a modifying group. The method may further include: (iii) measuring the yield for the enzymatic glycosylation or glycoPEGylation reaction for at least one member of the library. The measuring can be accomplished using any method known in the art and those described herein below. The method may further include prior to step (ii): (iv) purifying at least one member of the library.

The transferred glycosyl moiety of step (ii) can be any glycosyl moiety including mono- and oligosaccharides as well as glycosyl-mimetic groups. In an exemplary embodiment, the glycosyl moiety, which is added to the sequon polypeptide in an initial glycosylation reaction, is a Gal moiety. In another exemplary embodiment, the glycosyl moiety is a GalNAc moiety. Subsequent glycosylation reactions can be employed to add additional glycosyl residues (e.g, Gal) to the resulting GalNAc-polypeptide. The modifying group can be any modifying group of the invention, including water soluble polymers such as mPEG. In one embodiment, the enzymatic glycosylation reaction of step (ii) occurs in a host cell, in which the polypeptide is expressed. In another embodiment, step (ii) and step (ii) are performed in the same reaction vessel. The method may further include (v): subjecting the product of step (ii) to a PEGylation reaction. In one embodiment, the PEGylation reaction is an enzymatic glycoPEGylation reaction. In another embodiment, the PEGylation reaction is a chemical PEGylation reaction. The method may further include: (vi) measuring the yield for the PEGylation reaction. Methods useful for measuring the yield of the PEGylation reaction are described below. The method may further include: (vii) generating an expression vector including a nucleic acid sequence encoding the sequon polypeptide. The method may further include: (viii): transfecting a host cell with the expression vector.

Methods of generating sequon polypeptides (including any lead polypeptide) are known in the art. Exemplary methods are described herein. The method may include: (i) generating an expression vector including a nucleic acid sequence corresponding to the sequon polypeptide. The method may further include: (ii) transfecting a host cell with the expression vector. The method can further include: (iii) expressing the sequon polypeptide in a host cell. The method may further include: (iv) isolating the sequon polypeptide. The method may further include: (v) enzymatically glycosylating the sequon polypeptide at the O-linked glycosylation sequence, for example using a glycosyl transferase, such as GalNAc-T2. A sequon polypeptide of interest (e.g., a selected lead polypeptide) can be expressed on an industrial scale (e.g., leading to the isolation of more than 250 mg, preferably more than 500 mg of protein). The sequon polypeptide In an exemplary embodiment, each member of a library of sequon polypeptides is subjected to an enzymatic glycosylation reaction. For example, each sequon polypeptide is separately subjected to a glycosylation reaction and the yield of the glycosylation reaction is determined for one or more selected reaction condition.

In an exemplary embodiment, one or more sequon polypeptide of the library is purified prior to further processing, such as glycosylation and/or glycoPEGylation.

In another example, groups of sequon polypeptides can be combined and the resulting mixture of sequon polypeptides can be subjected to a glycosylation or glycoPEGylation reaction. In one exemplary embodiment, a mixture containing all members of the library is subjected to a glycosylation reaction. In one example, according to this embodiment, the glycosyl donor reagent can be added to the glycosylation reaction mixture in a less than stoichiometric amount (with respect to glycosylation sites present) creating an environment in which the sequon polypeptides compete as substrates for the enzyme. Those sequon polypeptides, which are substrates for the enzyme, can then be identified, for instance by virtue of mass spectral analysis with or without prior separation or purification of the glycosylated mixture. This same approach may be used for a group of sequon polypeptides which each contain a different O-linked glycosylation sequences of the invention.

The yield for the enzymatic glycosylation reaction, enzymatic glycoPEGylation reaction or chemical glycoPEGylation reaction can be determined using any suitable method known in the art. In an exemplary embodiment, the method used to distinguish between a glycosylated or glycoPEGylated polypeptide and an unreacted (e.g., non-glycosylated or glycoPEGylated) polypeptide is determined using a technique involving mass spectroscopy (e.g., LC-MS, MALDI-TOF). In another exemplary embodiment, the yield is determined using a technique involving gel electrophoresis. In yet another exemplary embodiment, the yield is determined using a technique involving nuclear magnetic resonace (NMR). In a further exemplary embodiment, the yield is determined using a technique involving chromatography, such as HPLC or GC. In one embodiment a multi-well plate (e.g., a 96-well plate) is used to carry out a number of glycosylation reactions in parallel. The plate may optionally be equipped with a separation or filtration medium (e.g., gel-filtration membrane) in the bottom of each well. Spinning may be used to pre-condition each sample prior to analysis by mass spectroscopy or other means.

Glycosylation Within a Host Cell

Initial glycosylation of a mutant O-linked glycosylation sequence, which is part of a sequon polypeptide of the invention, can also occur within a host cell, in which the polypeptide is expressed. This technology is, for instance, described in U.S. Provisional Patent Application No. 60/842,926 filed on Sep. 6, 2006, which is incorporated herein by reference in its entirety. The host cell may be a prokaryotic microorganism, such as *E. coli* or *Pseudomonas* strains). In an exemplary embodiment, the host cell is a trxB gor supp mutant *E. coli* cell.

In another exemplary embodiment, intracellular glycosylation is accomplished by co-expressing the polypeptide and an enzyme that can use the polypeptide as a substrate and can glycosylate the polypeptide intracellularly in the host cell and growing the host cell under conditions that allow intracellular transfer of a sugar moiety to the glycosylation sequence. An exemplary enzyme is "active nucleotide sugar:polypeptide glycosyltransferase protein" (e.g., a soluble active eukaryotic N-acetylgalactosaminyl transferase). In another exemplary embodiment, the microorganism in which the sequon polypeptide is expressed has an intracelluar oxidizing environment. The microorganism may be genetically modified to have the intracellular oxidizing environment. Intracellualr glycosylation is not limited to the transfer of a single glycosyl residue. Several glycosyl residues can be added sequentially by co-expression of required enzymes and the presence of respective glycosyl donors. This approach can also be used to produce sequon polypeptides on a commercial scale.

Methods are available to determine whether or not a sequon polypeptide is efficiently glycosylated within the mutant O-linked glycosylation sequence inside the host cell. For example the cell lysate (after one or more purification steps) is analyzed by mass spectroscopy to measure the ratio between glycosylated and non-glycosylated sequon polypeptide. In another example, the cell lysate is analyzed by gel electrophoresis separating glycosylated from non-glycosylated polypeptides.

Further Evaluation of Lead Polypeptides

In one embodiment, in which the initial screening procedure involves enzymatic glycosylation using an unmodified glycosyl moiety (e.g., transfer of a GalNAc moiety by GalNAc-T2), selected lead polypeptides may be further evaluated for their capability of being an efficient substrate for further modification, e.g., through another enzymatic reaction or a chemical modification. In an exemplary embodiment, subsequent "screening" involves subjecting a glycosylated lead polypeptide to another glycosylation—(e.g., addition of Gal) and/or PEGylation reaction.

A PEGylation reaction can, for instance, be a chemical PEGylation reaction or an enzymatic glycoPEGylation reaction. In order to identify a lead polypeptide, which is efficiently glycoPEGylated, at least one lead polypeptide (optionally previously glycosylated) is subjected to a PEGylation reaction and the yield for this reaction is determined. In one example, PEGylation yields for each lead polypeptide are determined. In an exemplary embodiment, the yield for the PEGylation reaction is between about 10% and about 100%, preferably between about 30% and about 100%, more preferably between about 50% and about 100% and most preferably between about 70% and about 100%. The PEGylation yield can be determined using any analyical method known in the art, which is suitable for polypeptide analysis, such as mass spectroscopy (e.g., MALDI-TOF, Q-TOF), gel electrophoresis (e.g., in combination with means for quantification, such as densitometry), NMR techniques as well as chromatographic methods, such as HPLC using appropriate column materials useful for the separation of PEGylated and non-PEGylated species of the analyzed polypeptide. As described above for glycosylation, a multiwell plate (e.g., a 96-well plate) can be used to carry out a number of PEGylation reactions in parallel. The plate may optionally be equipped with a separation or filtration medium (e.g., gel-filtration membrane) in the bottom of each well. Spinning and reconstitution may be used to pre-condition each sample prior to analysis by mass spectroscopy or other means.

In another exemplary embodiment, glycosylation and glycoPEGylation of a sequon polypeptide occur in a "one pot reaction" as described below. In one example, the sequon polypeptide is contacted with a first enzyme (e.g., GalNAc-T2) and an appropriate donor molecule (e.g., UDP-GalNAc). The mixture is incubated for a suitable amount of time before a second enzyme (e.g., Core-1-GalT1) and a second glycosyl donor (e.g., UDP-Gal) are added. Any number of additional glycosylation/glycoPEGylation reactions can be performed in this manner. Alternatively, more than one enzyme and more than one glycosyl donor can be contacted with the mutant polypeptide to add more than one glycosyl residue in one reaction step. For example, the mutant polypeptide is contacted with 3 different enzymes (e.g., GalNAc-T2, Core-1-GalT1 and ST3Gal1) and three different glycosyl donor moieties (e.g, UDP-GalNAc, UDP-Gal and CMP-SA-PEG) in a suitable buffer system to generate a glycoPEGylated mutant polypeptide, such as polypeptide-GalNAc-Gal-SA-PEG (see, Example 4.6). Overall yields can be determined using the methods described above.

Formation of Polypeptide Conjugates

In another aspect, the invention provides methods of forming a covalent conjugate between a modifying group and a polypeptide. The polypeptide conjugates of the invention are formed between glycosylated or non-glycosylated polypeptides and diverse species such as water-soluble polymers, therapeutic moieties, biomolecules, diagnostic moieties, targeting moieties and the like. The polymer, therapeutic moiety or biomolecule is conjugated to the polypeptide via a glycosyl linking group, which is interposed between, and covalently linked to both the polypeptide and the modifying group (e.g. water-soluble polymer). The sugar moiety of the modified sugar is preferably selected from nucleotide sugars, activated sugars and sugars, which are neither nucleotides nor activated.

In an exemplary embodiment, the polypeptide conjugate is formed through enzymatic attachment of a modified sugar to the polypeptide. The modified sugar is directly added to an O-linked glycosylation sequence, or to a glycosyl residue, which is either directly or indirectly (e.g., through one or more glycosyl residue) attached to an O-linked glycosylation sequence.

An exemplary method of making a polypeptide conjugate of the invention includes the steps of: (i) recombinantly producing a sequon polypeptide that includes an O-linked glycosylation sequence of the invention, and (ii) enzymatically glycosylating the sequon polypeptide at the O-linked glycosylation sequence. In an exemplary embodiment, the method includes contacting the mutant polypeptide with a mixture containing a glycosyl donor (e.g., a modified sugar) and an enzyme, such as a glycosyltransferase (e.g., human GalNAc-T2) for which the glycosyl donor is a substrate. The reaction is conducted under conditions appropriate for the enzyme to form a covalent bond between the glycosyl moiety and the polypeptide.

Using the exquisite selectivity of enzymes, such as glycosyltransferases, the present method provides polypeptides that bear modifying groups at one or more specific locations. Thus, according to the present invention, a modified sugar is attached directly to an O-linked glycosylation sequence within the polypeptide chain or, alternatively, the modified sugar is appended onto a carbohydrate moiety of a glycopeptide. Polypeptides in which modified sugars are bound to both a glycosylated site and directly to an amino acid residue of the polypeptide backbone are also within the scope of the present invention.

In contrast to known chemical and enzymatic peptide elaboration strategies, the methods of the invention, make it possible to assemble polypeptides and glycopeptides that have a substantially homogeneous derivatization pattern. The enzymes used in the invention are generally selective for a particular amino acid residue or combination of amino acid residues of the polypeptide. The methods of the invention also provide practical means for large-scale production of modified polypeptides and glycopeptides.

In an exemplary embodiment, the polypeptide is O-glycosylated and functionalized with a water-soluble polymer in the following manner: The polypeptide is produced with an available O-linked glycosylation sequence. GalNAc is added to a serine or threonine residue within the glycosylation sequence and the resulting GalNAc-peptide is sialylated with a sialic acid-modifying group cassette using ST6Gal-1. Alternatively, the GalNac-peptide is galactosylated using Core-1-GalT-1 and the product is sialylated with a sialic acid-modifying group cassette using ST3Gal-1. An exemplary conjugate according to this method has the following linkages: Thr-α-1-GalNAc-β-1,3-Gal-α2,3-Sia*, in which Sia* is the sialic acid-modifying group cassette.

Glycosylation steps may be performed separately, or combined in a "single pot" reaction using multiple enzymes and saccharyl donors. For example, in the three enzyme reaction set forth above the GalNAc tranferase, GalT and SiaT as well as respective glycosyl donor molecules may be combined in a single vessel. Alternatively, the GalNAc reaction can be performed first and both the GalT and SiaT and the appropriate saccharyl donors be added subsequently. Another example involves adding each enzyme and an appropriate glycosyl donor sequentially conducting the reaction in a "single pot" motif Combinations of the methods set forth above are also useful in preparing the compounds of the invention.

In the conjugates of the invention, the Sia-modifying group cassette can be linked to the Gal in an α-2,6, or α-2,3 linkage.

The present invention also provides means of adding (or removing) one or more selected glycosyl residues to a polypeptide, after which a modified sugar is conjugated to at least one of the selected glycosyl residues of the polypeptide. The present embodiment is useful, for example, when it is desired to conjugate the modified sugar to a selected glycosyl residue that is either not present on a polypeptide or is not present in a desired amount. Thus, prior to coupling a modified sugar to a polypeptide, the selected glycosyl residue is conjugated to the polypeptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide to trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., *Arch. Biochem. Biophys.* 259: 52 (1987) and by Edge et al., *Anal Biochem.* 118: 131 (1981). Enzymatic cleavage of carbohydrate moieties on polypeptide variants can be achieved by the use of a variety of endo- and exo-glycosidases as described by Thotakura et al, *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876, 980; 6,030,815; 5,728,554 and 5,922,577. Exemplary methods of use in the present invention are described in WO 87/05330 published Sep. 11, 1987, and in Aplin and Wriston, CRC Crit. Rev. Biochem., pp. 259-306 (1981).

Polypeptide Conjugates Including Two or More Polypeptides

Also provided are conjugates that include two or more polypeptides linked together through a linker arm, i.e., multifunctional conjugates; at least one polypeptide being O-glycosylated or including a mutant O-linked glycosylation sequence. The multi-functional conjugates of the invention can include two or more copies of the same polypeptide or a collection of diverse polypeptides with different structures, and/or properties. In exemplary conjugates according to this embodiment, the linker between the two polypeptides is attached to at least one of the polypeptides through an O-linked glycosyl residue, such as an O-linked glycosyl intact glycosyl linking group.

In one embodiment, the invention provides a method for linking two or more polypeptides through a linking group. The linking group is of any useful structure and may be selected from straight- and branched-chain structures. Preferably, each terminus of the linker, which is attached to a polypeptide, includes a modified sugar (i.e., a nascent intact glycosyl linking group).

In an exemplary method of the invention, two polypeptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second polypeptides to the first and second glycosylunits, respectively. In practice, the (glycosyl)$^1$-PEG-(glycosyl)$^2$ linker is contacted with the first polypeptide and a first transferase for which the first glycosyl unit is a substrate, thereby forming (peptide)$^1$-(glycosyl)$^1$-PEG-(glycosyl)$^2$. Transferase and/or unreacted polypeptide is then optionally removed from the reaction mixture. The second polypeptide and a second transferase for which the second glycosyl unit is a substrate are added to the (peptide)$^1$-(glycosyl)$^1$-PEG-(glycosyl)$^2$ conjugate, forming (peptide)$^1$-(glycosyl)$^1$-PEG-(glycosyl)$^2$-(peptide)$^2$; at least one of the glycosyl residues is either directly or indirectly O-linked. Those of skill in the art will appreciate that the method outlined above is also applicable to forming conjugates between more than two polypeptides by, for example, the use of a branched PEG, dendrimer, poly(amino acid), polsaccharide or the like In an exemplary embodiment, interferon alpha 2β (IFN-α 2β) is conjugated to transferrin via a bifunctional linker that includes an intact glycosyl linking group at each terminus of the PEG moiety (Scheme 6). The IFN conjugate has an in vivo half-life that is increased over that of IFN alone by virtue of the greater molecular sized of the conjugate. Moreover, the conjugation of IFN to transferrin serves to selectively target the conjugate to the brain. For example, one terminus of the PEG linker is functionalized with a CMP sialic acid and the other is functionalized with an UDP GalNAc. The linker is combined with IFN in the presence of a GalNAc transferase, resulting in the attachment of the GalNAc of the linker arm to a serine and/or threonine residue on the IFN.

Scheme 6:

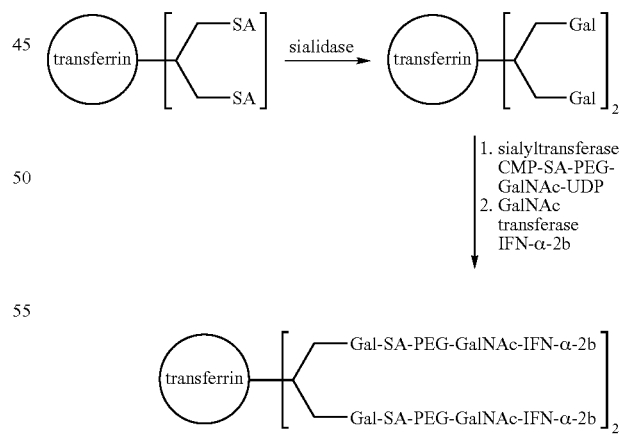

The processes described above can be carried through as many cycles as desired, and is not limited to forming a conjugate between two polypeptides with a single linker. Moreover, those of skill in the art will appreciate that the reactions functionalizing the intact glycosyl linking groups at the termini of the PEG (or other) linker with the polypeptide can occur simultaneously in the same reaction vessel, or they can be carried out in a step-wise fashion. When the reactions are carried out in a step-wise manner, the conjugate produced at each step is optionally purified from one or more reaction components (e.g., enzymes, peptides).

A still further exemplary embodiment is set forth in Scheme 7. Scheme 7 shows a method of preparing a conjugate that targets a selected protein, e.g., GM-CSF, to bone and increases the circulatory half-life of the selected protein.

Scheme 7:

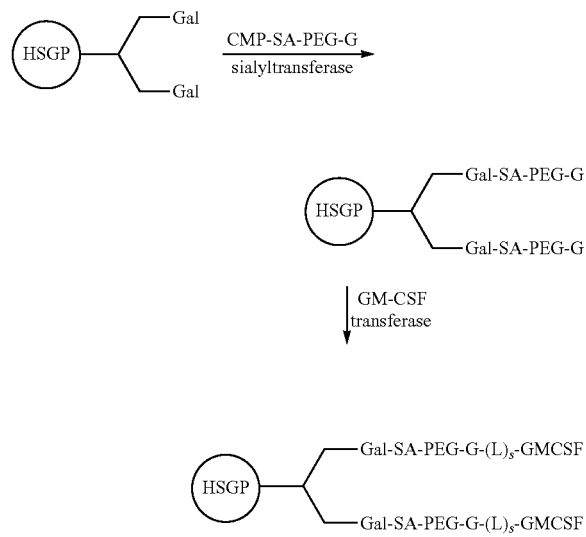

in which G is a glycosyl residue on an activated sugar moiety (e.g., sugar nucleotide), which is converted to an intact glycosyl linker group in the conjugate. When s is greater than 0, L is a saccharyl linking group such as GalNAc, or GalNAc-Gal.

In another exemplary embodiment in which a reactive PEG derivative is utilized, the invention provides a method for extending the blood-circulation half-life of a selected polypeptide, in essence targeting the polypeptide to the blood pool, by conjugating the polypeptide to a synthetic or natural polymer of a size sufficient to retard the filtration of the protein by the glomerulus (e.g., albumin). This embodiment of the invention is illustrated in Scheme 8, in which the exemplary polypeptide G-CSF is conjugated to albumin via a PEG linker using a combination of chemical and enzymatic modifications.

Scheme 8: Using an activated PEG analog to form a polypeptide conjugate

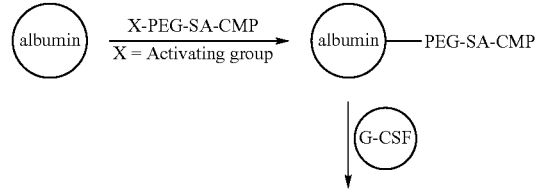

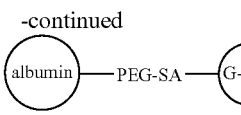

As shown in Scheme 8, a residue (e.g., amino acid side chain) of albumin is modified with a reactive PEG derivative, such as X-PEG-(CMP-sialic acid), in which X is an activating group (e.g, active ester, isothiocyanate, etc). The PEG derivative and G-CSF are combined and contacted with a transferase for which CMP-sialic acid is a substrate. In a further illustrative embodiment, an ε-amine of lysine is reacted with the N-hydroxysuccinimide ester of the PEG-linker to form the albumin conjugate. The CMP-sialic acid of the linker is enzymatically conjugated to an appropriate residue on GCSF, e.g, Gal, or GalNAc thereby forming the conjugate. Those of skill will appreciate that the above-described method is not limited to the reaction partners set forth. Moreover, the method can be practiced to form conjugates that include more than two protein moieties by, for example, utilizing a branched linker having more than two termini.

Enzymatic Conjugation of Modified Sugars to Polypeptides

The modified sugars are conjugated to a glycosylated or non-glycosylated polypeptide using an appropriate enzyme to mediate the conjugation. Preferably, the concentrations of the modified donor sugar(s), enzyme(s) and acceptor polypeptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, in WO 96/32491 and Ito et al., *Pure Appl. Chem.* 65: 753 (1993), as well as U.S. Pat. Nos. 5,352,670; 5,374,541 and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

The O-linked glycosyl moieties of the conjugates of the invention are generally originate with a GalNAc moiety that is attached to the polypeptide. Any member of the family of GalNAc transferases (e.g., those described herein in Table 13) can be used to bind a GalNAc moiety to the polypeptide (see e.g., Hassan H, Bennett E P, Mandel U, Hollingsworth M A, and Clausen H (2000); and Control of Mucin-Type O-Glycosylation: O-Glycan Occupancy is Directed by Substrate Specificities of Polypeptide GalNAc-Transferases; Eds. Ernst, Hart, and Sinay; Wiley-VCH chapter "Carbohydrates in Chemistry and Biology—a Comprehension Handbook", 273-292). The GalNAc moiety itself can be the glycosyl linking group and derivatized with a modifying group. Alternatively, the saccharyl residue is built out using one or more enzyme and one or more appropriate glycosyl donor substrate. The modified sugar may then be added to the extended glycosyl moiety.

The enzyme catalyzes the reaction, usually by a synthesis step that is analogous to the reverse reaction of the endoglycanase hydrolysis step. In these embodiments, the glycosyl donor molecule (e.g., a desired oligo- or mono-saccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In another embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 32° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified polypeptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated polypeptide. The exemplary modified sialic acid is labeled with (m-) PEG. The focus of the following discussion on the use of PEG-modified sialic acid and glycosylated polypeptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of a modifying group (e.g., mPEG or mPPG) onto a polypeptide or glycopeptide. In one embodiment, the method utilizes modified sugars, which include the modifying group in combination with an appropriate glycosyltransferase or glycosynthase. By selecting the glycosyltransferase that will make the desired carbohydrate linkage and utilizing the modified sugar as the donor substrate, the modifying group can be introduced directly onto the polypeptide backbone, onto existing sugar residues of a glycopeptide or onto sugar residues that have been added to a polypeptide. In another embodiment, the method utilizes modified sugars, which carry a masked reactive functional group, which can be used for attachment of the modifying group after transfer of the modified sugar onto the polypeptide or glycopeptide.

In one example, the glycosyltransferase is a sialyltransferase, used to append a modified sialyl residue to a glycopeptide. The glycosidic acceptor for the sialyl residue can be added to an O-linked glycosylation sequence, e.g., during expression of the polypeptide or can be added chemically or enzymatically after expression of the polypeptide, using the appropriate glycosidase(s), glycosyltransferase(s) or combinations thereof. Suitable acceptor moieties, include, for example, galactosyl acceptors such as GalNAc, Galβ1, 4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In an exemplary embodiment, a GalNAc residue is added to an O-linked glycosylation sequence by the action of a GalNAc transferase. Hassan H, Bennett E P, Mandel U, Hollingsworth M A, and Clausen H (2000), Control of Mucin-Type O-Glycosylation: O-Glycan Occupancy is Directed by Substrate Specificities of Polypeptide GalNAc-Transferases (Eds. Ernst, Hart, and Sinay), Wiley-VCH chapter "Carbohydrates in Chemistry and Biology—a Comprehension Handbook", pages 273-292. The method includes incubating the polypeptide to be modified with a reaction mixture that contains a suitable amount of a galactosyltransferase and a suitable galactosyl donor. The reaction is allowed to proceed substantially to completion or, alternatively, the reaction is terminated when a preselected amount of the galactose residue is added. Other methods of assembling a selected saccharide acceptor will be apparent to those of skill in the art.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, a biomolecule or the like.

In another exemplary embodiment, a water-soluble polymer is added to a GalNAc residue via a modified galactosyl (Gal) residue. Alternatively, an unmodified Gal can be added to the terminal GalNAc residue.

In yet a further example, a water-soluble polymer (e.g., PEG) is added onto a terminal Gal residue using a modified sialic acid moiety and an appropriate sialyltransferase. This embodiment is illustrated in Scheme 9, below.

Scheme 9: Addition of a Modified Sialy Moiety to a Glycoprotein

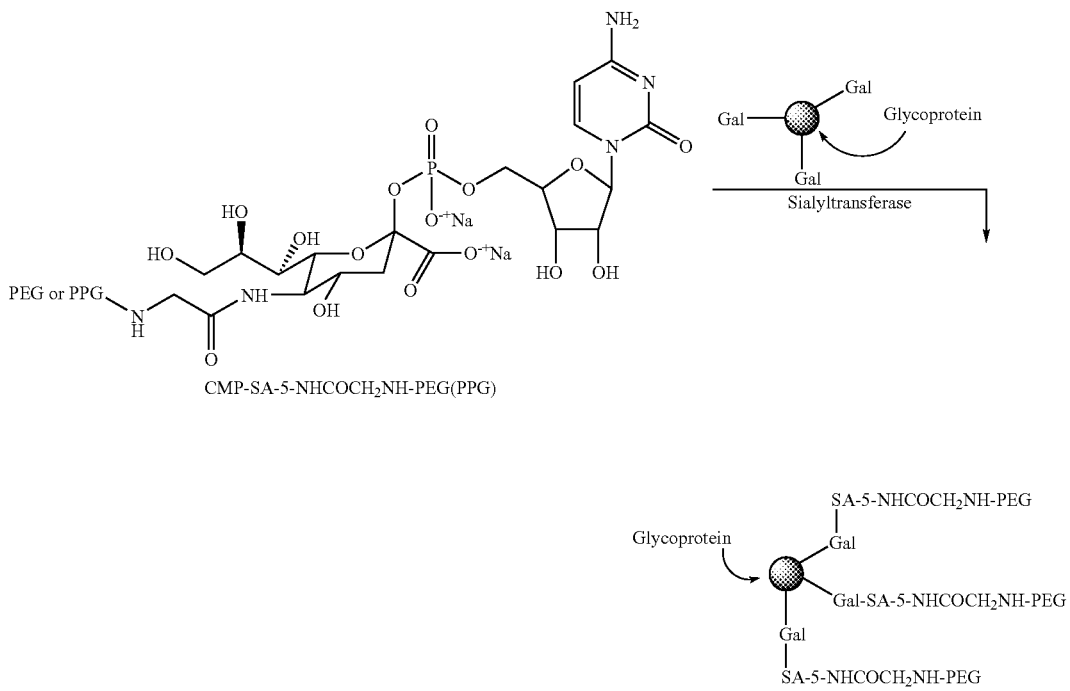

In yet a further approach, a masked reactive functionality is present on the sialic acid. The masked reactive group is preferably unaffected by the conditions used to attach the modified sialic acid to the polypeptide. After the covalent attachment of the modified sialic acid to the polypeptide, the mask is removed and the polypeptide is conjugated to the modifying group, such as a water soluble polymer (e.g., PEG or PPG) by reaction of the unmasked reactive group on the modified sugar residue with a reactive modifying group. This strategy is illustrated in Scheme 10, below.

Scheme 10: Modification of a Glycopeptide using a Sialyl Moiety Carrying a Reactive Functional Group

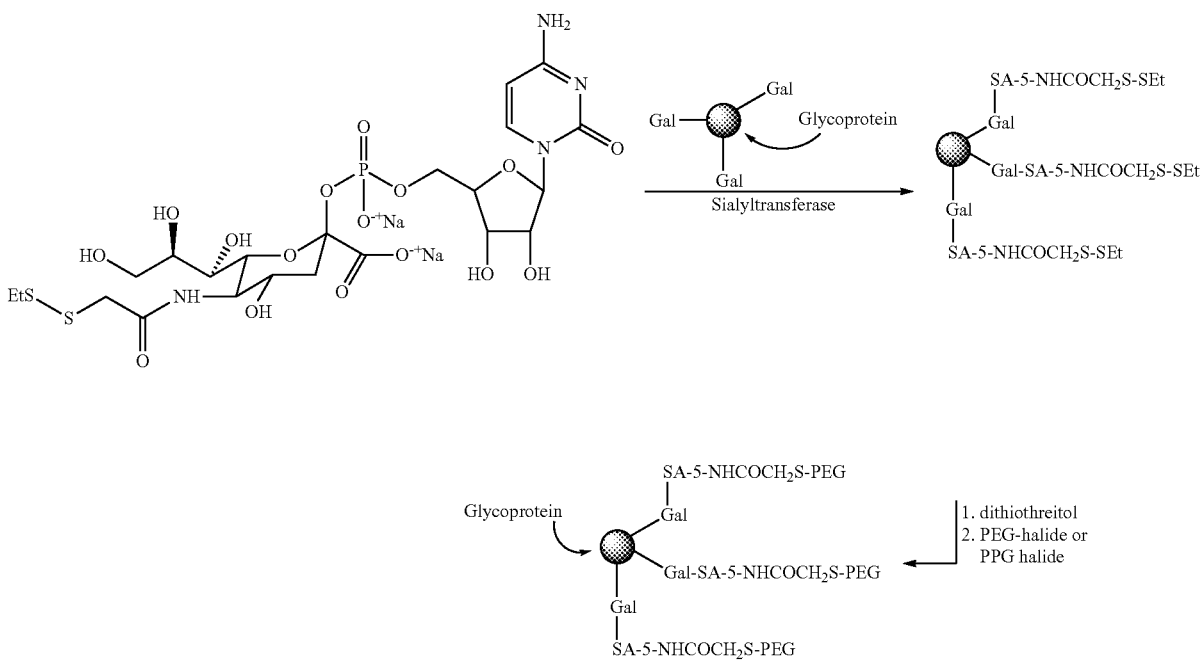

Any modified sugar can be used in combination with an appropriate glycosyltransferase, depending on the terminal sugars of the oligosaccharide side chains of the glycopeptide (Table 12).

TABLE 12

Exemplary Modified Sugars

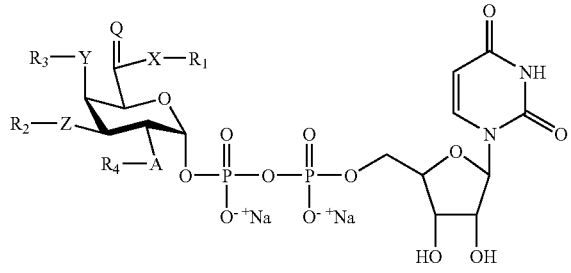

UDP-galactose-derivatives

UDP-galactosamine-derivatives
(when A = NH, R₄ may be acetyl)

UDP-Glucose-derivatives

TABLE 12-continued

Exemplary Modified Sugars

UDP-Glucosamine-derivatives
(when A = NH, R₄ may be acetyl)

GDP-Mannose-derivatives

GDP-fucose-derivatives

X = O, NH, S, CH₂, N—(R₁₋₅)₂.
Y = X; Z = X; A = X; B = X.
Q = H₂, O, S, NH, N—R.
R, R₁₋₄ = H, Linker-M, M.
M = Ligand of interest
Ligand of interest = acyl-PEG, acyl-PPG, alkyl-PEG, acyl-alkyl-PEG, acyl-alkyl-PFG, carbamoyl-PEG, carbamoyl-PPG, PEG, PPG, acyl-aryl-PEG, acyl-aiyl-PPG, aryl-PEG, aryl-PPG, Mannose-6-phosphate, heparin, heparan, SLex, Mannose, FGF, VFGF, protein, chondroitin, keratan, dermatan, albumin, integrins, peptides, etc.

In an alternative embodiment, the modified sugar is added directly to the peptide backbone using a glycosyltransferase known to transfer sugar residues to the O-linked glycosylation sequence on the polypeptide backbone. This exemplary embodiment is set forth in Scheme 11, below. Exemplary glycosyltransferases useful in practicing the present invention include, but are not limited to, GalNAc transferases (GalNAc T1 to GalNAc T20), GlcNAc transferases, fucosyltransferases, glucosyltransferases, xylosyltransferases, mannosyltransferases and the like. Use of this approach allows for the direct addition of modified sugars onto polypeptides that lack any carbohydrates or, alternatively, onto existing glycopeptides.

Scheme 11: Transfer of an Exemplary Modified Sugar onto a Polypeptide without Prior Glycosylation

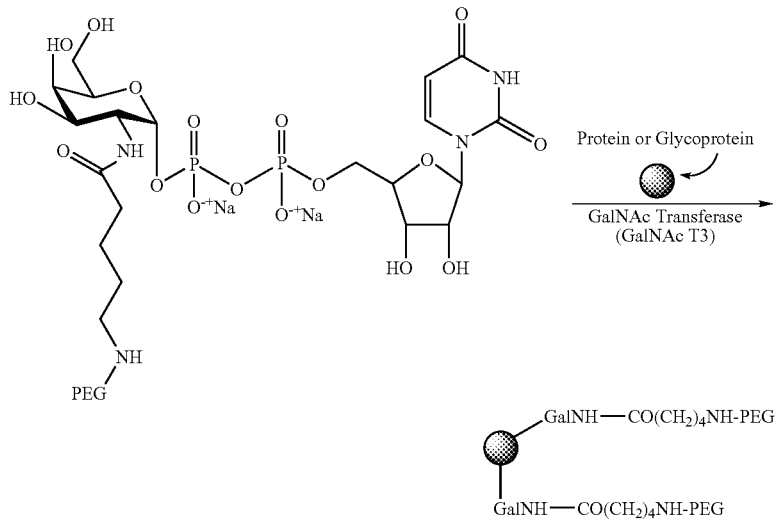

In each of the exemplary embodiments set forth above, one or more additional chemical or enzymatic modification steps can be utilized following the conjugation of the modified sugar to the polypeptide. In an exemplary embodiment, an enzyme (e.g., fucosyltransferase) is used to append a glycosyl unit (e.g., fucose) onto the terminal modified sugar attached to the polypeptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the polypeptide component to which the modified sugar is attached. In another example, a component of the modified sugar is deprotected following its conjugation to the polypeptide. One of skill will appreciate that there is an array of enzymatic and chemical procedures that are useful in the methods of the invention at a stage after the modified sugar is conjugated to the polypeptide. Further elaboration of the modified sugar-peptide conjugate is within the scope of the invention.

In another exemplary embodiment, the glycopeptide is conjugated to a targeting agent, e.g., transferrin (to deliver the polypeptide across the blood-brain barrier, and to endosomes), carnitine (to deliver the polypeptide to muscle cells; see, for example, LeBorgne et al., *Biochem. Pharmacol.* 59: 1357-63 (2000), and phosphonates, e.g., bisphosphonate (to target the polypeptide to bone and other calciferous tissues; see, for example, Modern Drug Discovery, August 2002, page 10). Other agents useful for targeting are apparent to those of skill in the art. For example, glucose, glutamine and IGF are also useful to target muscle.

The targeting moiety and therapeutic polypeptide are conjugated by any method discussed herein or otherwise known in the art. Those of skill will appreciate that polypeptides in addition to those set forth above can also be derivatized as set forth herein. Exemplary polypeptides are set forth in the Appendix attached to copending, commonly owned U.S. Provisional Patent Application No. 60/328,523 filed Oct. 10, 2001.

In an exemplary embodiment, the targeting agent and the therapeutic polypeptide are coupled via a linker moiety. In this embodiment, at least one of the therapeutic polypeptide or the targeting agent is coupled to the linker moiety via an intact glycosyl linking group according to a method of the invention. In an exemplary embodiment, the linker moiety includes a poly(ether) such as poly(ethylene glycol). In another exemplary embodiment, the linker moiety includes at least one bond that is degraded in vivo, releasing the therapeutic polypeptide from the targeting agent, following delivery of the conjugate to the targeted tissue or region of the body.

In yet another exemplary embodiment, the in vivo distribution of the therapeutic moiety is altered via altering a glycoform on the therapeutic moiety without conjugating the therapeutic polypeptide to a targeting moiety. For example, the therapeutic polypeptide can be shunted away from uptake by the reticuloendothelial system by capping a terminal galactose moiety of a glycosyl group with sialic acid (or a derivative thereof).

Enzymes

Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. Glycosyltransferase amino acid sequences and nucleotide sequences encoding glycosyltransferases from which the amino acid sequences can be deduced are found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence (See, for example, U.S. Pat. No. 4,683,195 to Mullis et al. and U.S. Pat. No. 4,683,202 to Mullis).

The glycosyltransferase may be synthesized in host cells transformed with vectors containing DNA encoding the glycosyltransferases enzyme. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the invention utilizes a prokaryotic enzyme. Such glycosyltransferases include enzymes involved in synthesis of lipooligosaccharides (LOS), which are produced by many gram negative bacteria (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK) (EMBL Accession No. U00039 (*E. coli*). Other glycosyltransferases for which amino acid sequences are known include those that are encoded by operons such as rfaB, which have been characterized in organisms such as *Klebsiella pneumoniae*, *E. coli*, *Salmonella typhimurium*, *Salmonella enterica*, *Yersinia enterocolitica*, *Mycobacterium leprosum*, and the rh1 operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

(a) GalNAc Transferases

The first step in O-linked glycosylation can be catalyzed by one or more members of a large family of UDP-GalNAc: polypeptide N-acetylgalactosaminyltransferases (GalNAc-transferases), which normally transfer GalNAc to serine and threonine acceptor sites (Hassan et al., *J. Biol. Chem.* 275: 38197-38205 (2000)). To date twelve members of the mammalian GalNAc-transferase family have been identified and characterized (Schwientek et al., *J. Biol. Chem.* 277: 22623-22638 (2002)), and several additional putative members of this gene family have been predicted from analysis of genome databases. The GalNAc-transferase isoforms have different kinetic properties and show differential expression patterns temporally and spatially, suggesting that they have distinct biological functions (Hassan et al., *J. Biol. Chem.* 275: 38197-38205 (2000)). Sequence analysis of GalNAc-transferases have led to the hypothesis that these enzymes contain two distinct subunits: a central catalytic unit, and a C-terminal unit with sequence similarity to the plant lectin ricin, designated the "lectin domain" (Hagen et al., *J. Biol. Chem.* 274: 6797-6803 (1999); Hazes, *Protein Eng.* 10: 1353-1356 (1997); Breton et al., *Curr. Opin. Struct. Biol.* 9: 563-571

(1999)). Previous experiments involving site-specific mutagenesis of selected conserved residues confirmed that mutations in the catalytic domain eliminated catalytic activity. In contrast, mutations in the "lectin domain" had no significant effects on catalytic activity of the GalNAc-transferase isoform, GalNAc-T1 (Tenno et al, *J. Biol. Chem.* 277 (49): 47088-96 (2002)). Thus, the C-terminal "lectin domain" was believed not to be functional and not to play roles for the enzymatic functions of GalNAc-transferases (Hagen et al., *J. Biol. Chem.* 274: 6797-6803 (1999)).

Polypeptide GalNAc-transferases, which have not displayed apparent GalNAc-glycopeptide specificities, also appear to be modulated by their putative lectin domains (PCT WO 01/85215 A2). Recently, it was found that mutations in the GalNAc-T1 putative lectin domain, similarly to those previously analysed in GalNAc-T4 (Hassan et al., *J. Biol. Chem.* 275: 38197-38205 (2000)), modified the activity of the enzyme in a similar fashion as GalNAc-T4. Thus, while wild type GalNAc-T1 added multiple consecutive GalNAc residues to a polypeptide substrate with multiple acceptor sites, mutated GalNAc-T1 failed to add more than one GalNAc residue to the same substrate (Tenno et al., *J. Biol. Chem.* 277(49): 47088-96 (2002)). More recently, the x-ray crystal structures of murine GalNAc-T1 (Fritz et al., *PNAS* 2004, 101(43): 15307-15312) as well as human GalNAc-T2 (Fritz et al., *J. Biol. Chem.* 2006, 281(13):8613-8619) have been determined. The human GalNAc-T2 structure revealed an unexpected flexibility between the catalytic and lectin domains and suggested a new mechanism used by GalNAc-T2 to capture glycosylated substrates. Kinetic analysis of GalNAc-T2 lacking the lectin domain confirmed the importance of this domain in acting on glycopeptide substrates. However, the enzymes activity with respect to non-glycosylated substrates was not significantly affected by the removal of the lectin domain. Thus, truncated human GalNAc-T2 enzymes lacking the lectin domain or those enzymes having a truncated lectin domain can be useful for the glycosylation of polypeptide substrates where further glycosylation of the resulting mono-glycosylated polypeptide is not desired.

Recent evidence demonstrates that some GalNAc-transferases exhibit unique activities with partially GalNAc-glycosylated glycopeptides. The catalytic actions of at least three GalNAc-transferase isoforms, GalNAc-T4, -T7, and -T10, selectively act on glycopeptides corresponding to mucin tandem repeat domains where only some of the clustered potential glycosylation sequences have been GalNAc glycosylated by other GalNAc-transferases (Bennett et al., *FEBS Letters* 460: 226-230 (1999); Ten Hagen et al., *J. Biol. Chem.* 276: 17395-17404 (2001); Bennett et al., *J. Biol. Chem.* 273: 30472-30481 (1998); Ten Hagen et al., *J. Biol. Chem.* 274: 27867-27874 (1999)). GalNAc-T4 and -T7 recognize different GalNAc-glycosylated polypeptides and catalyse transfer of GalNAc to acceptor substrate sites in addition to those that were previously utilized. One of the functions of such GalNAc-transferase activities is predicted to represent a control step of the density of O-glycan occupancy in glycoproteins with high density of O-linked glycosylation.

One example of this is the glycosylation of the cancer-associated mucin MUC1. MUC1 contains a tandem repeat O-linked glycosylated region of 20 residues (HGVTSAPDTRPAPGSTAPPA) (SEQ ID NO: 421) with five potential O-linked glycosylation sequences. GalNAc-T1, -T2, and -T3 can initiate glycosylation of the MUC1 tandem repeat and incorporate at only three sites (HGVTSAPDTRPAPG STAPPA (SEQ ID NO: 421), GalNAc attachment sites underlined). GalNAc-T4 is unique in that it is the only GalNAc-transferase isoform identified so far that can complete the O-linked glycan attachment to all five acceptor sites in the 20 amino acid tandem repeat sequence of the breast cancer associated mucin, MUC1. GalNAc-T4 transfers GalNAc to at least two sites not used by other GalNAc-transferase isoforms on the GalNAc$_4$TAP24 glycopeptide (TAPPAHGV TSAPDTRPAPGSTAPP (SEQ ID NO: 422), unique GalNAc-T4 attachment sites are in bold) (Bennett et al., *J. Biol. Chem.* 273: 30472-30481 (1998). An activity such as that exhibited by GalNAc-T4 appears to be required for production of the glycoform of MUC1 expressed by cancer cells where all potential sites are glycosylated (Muller et al., *J. Biol. Chem.* 274: 18165-18172 (1999)). Normal MUC1 from lactating mammary glands has approximately 2.6 O-linked glycans per repeat (Muller et al., *J. Biol. Chem.* 272: 24780-24793 (1997) and MUC1 derived from the cancer cell line T47D has 4.8 O-linked glycans per repeat (Muller et al., *J. Biol. Chem.* 274: 18165-18172 (1999)). The cancer-associated form of MUC1 is therefore associated with higher density of O-linked glycan occupancy and this is accomplished by a GalNAc-transferase activity identical to or similar to that of GalNAc-T4. Another enzyme, GalNAc-T11 is described, for example, in T. Schwientek et al., *J. Biol. Chem.* 2002, 277 (25):22623-22638.

Production of proteins such as the enzyme GalNAc T$_{I-XX}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sequences in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

Since it has been demonstrated that mutations of GalNAc transferases can be utilized to produce glycosylation patterns that are distinct from those produced by the wild-type enzymes, it is within the scope of the present invention to utilize one or more mutant or truncated GalNAc transferase in preparing the O-linked glycosylated polypeptides of the invention. Catalytic domains and truncation mutants of Gal-NAc-T2 proteins are described, for example, in U.S. Provisional Patent Application 60/576,530 filed Jun. 3, 2004; and U.S. Provisional Patent Application 60/598584, filed Aug. 3, 2004; both of which are herein incorporated by reference for all purposes. Catalytic domains can also be identified by alignment with known glycosyltransferases. Truncated GalNAc-T2 enzymes, such as human GalNAc-T2 (Δ51), human GalNAc-T2 (Δ51 Δ445) and methods of obtaining those enzymes are also described in WO 06/102652 (PCT/US06/011065, filed Mar. 24, 2006) and PCT/US05/00302, filed Jan. 6, 2005, which are herein incorporated by reference for all purposes. Exemplary GalNAc-T1, GalNAc-T2, GalNAc-T3 and GalNAc-T11 sequences are summarized in Table 13, below.

TABLE 13

Exemplary GalNAc-T1, GalNAc-T2, GalNAc-T3 and GalNAc-T11 Sequences

1. Human UDP-N-acetylgalactosaminyltransferase 2 (GalNAc-T2)

SEQ ID NO: 256
MRRRSRMLLCFAFLWVLGIAYYMYSGGGSALAGGAGGGAGRKEDWNEIDP
IKKKDLHHSNGEEKAQSMETLPPGKVRWPDFNQEAYVGGTMVRSGQDPYA
RNKFNQVESDKLRMDRAIPDTRHDQCQRKQWRVDLPATSVVITFHNEARS
ALLRTVVSVLKKSPPHLIKEIILVDDYSNDPEDGALLGKIEKVRVLRNDR
REGLMRSRVRGADAAQAKVLTFLDSHCECNEHWLEPLLERVAEDRTRVVS
PIIDVINMDNFQYVGASADLKGGFDWNLVFKWDYMTPEQRRSRQGNPVAP
IKTPMIAGGLFVMDKFYFEELGKYDMMMDVWGGENLEISFRVWQCGGSLE
IIPCSRVGHVFRKQHPYTFPGGSGTVFARNTRRAAEVWMDEYKNFYYAAV
PSARNVPYGNIQSRLELRKKLSCKPFKWYLENVYPELRVPDHQDIAFGAL
QQGTNCLDTLGHFADGVVGVYECHNAGGNQEWALTKEKSVKHMDLCLTVV
DRAPGSLIKLQGCRENDSRQKWEQIEGNSKLRHVGSNLCLDSRTAKSGGL
SVEVCGPALSQQWKFTLNLQQ

2. Truncated human UDP-N-acetylgalactosaminyl-transferase 2 (GalNAc-T2 Δ51)

SEQ ID NO: 257
KKKDLHHSNGEEKAQSMETLPPGKVRWPDFNQEAYVGGTMVRSGQDPYAR
NKFNQVESDKLRMDRAIPDTRHDQCQRKQWRVDLPATSVVITFHNEARSA
LLRTVVSVLKKSPPHLIKEIILVDDYSNDPEDGALLGKIEKVRVLRNDRR
EGLMRSRVRGADAAQAKVLTFLDSHCECNEHWLEPLLERVAEDRTRVVSP
IIDVINMDNFQYVGASADLKGGFDWNLVFKWDYMTPEQRRSRQGNPVAPI
KTPMIAGGLFVMDKFYFEELGKYDMMMDVWGGENLEISFRVWQCGGSLEI
IPCSRVGHVFRKQHPYTFPGGSGTVFARNTRRAAEVWMDEYKNFYYAAVP
SARNVPYGNIQSRLELRKKLSCKPFKWYLENVYPELRVPDHQDIAFGALQ
QGTNCLDTLGHFADGVVGVYECHNAGGNQEWALTKEKSVKHMDLCLTVVD
RAPGSLIKLQGCRENDSRQKWEQIEGNSKLRHVGSNLCLDSRTAKSGGLS
VEVCGPALSQQWKFTLNLQQ

3. Truncated human UDP-N-acetylgalactosaminyl-transferase 2 (GalNAc-T2 Δ1-51 Δ445-571)

SEQ ID NO: 258
KKKDLHHSNGEEKAQSMETLPPGKVRWPDFNQEAYVGGTMVRSGQDPYAR
NKFNQVESDKLRMDRAIPDTRHDQCQRKQWRVDLPATSVVITFHNEARSA
LLRTVVSVLKKSPPHLIKEIILVDDYSNDPEDGALLGKIEKVRVLRNDRR
EGLMRSRVRGADAAQAKVLTFLDSHCECNEHWLEPLLERVAEDRTRVVSP
IIDVINMDNFQYVGASADLKGGFDWNLVFKWDYMTPEQRRSRQGNPVAPI
KTPMIAGGLFVMDKFYFEELGKYDMMMDVWGGENLEISFRVWQCGGSLEI
IPCSRVGHVFRKQHPYTFPGGSGTVFARNTRRAAEVWMDEYKNFYYAAVP
SARNVPYGNIQSRLELRKKLSCKPFKWYLENVYPELRVPDHQD

4. Truncated human UDP-N-acetylgalactosaminyl-transferase 2 (GalNAc-T2 Δ51) (alternate form)

SEQ ID NO: 259
MSKKKDLHHSNGEEKAQSMETLPPGKVRWPDFNQEAYVGGTMVRSGQDPY
ARNKFNQVESDKLRMDRAIPDTRHDQCQRKQWRVDLPATSVVITFHNEAR
SALLRTVVSVLKKSPPHLIKEIILVDDYSNDPEDGALLGKIEKVRVLRND
RREGLMRSRVRGADAAQAKVLTFLDSHCECNEHWLEPLLERVAEDRTRVV
SPIIDVINMDNFQYVGASADLKGGFDWNLVFKWDYMTPEQRRSRQGNPVA
PIKTPMIAGGLFVMDKFYFEELGKYDMMMDVWGGENLEISFRVWQCGGSL
EIIPCSRVGHVFRKQHPYTFPGGSGTVFARNTRRAAEVWMDEYKNFYYAA
VPSARNVPYGNIQSRLELRKKLSCKPFKWYLENVYPELRVPDHQDIAFGA
LQQGTNCLDTLGHFADGVVGVYECHNAGGNQEWALTKEKSVKHMDLCLTV
VDRAPGSLIKLQGCRENDSRQKWEQIEGNSKLRHVGSNLCLDSRTAKSGG
LSVEVCGPALSQQWKFTLNLQQ

5. Truncated human UDP-N-acetylgalactosaminyltransferase 2 (GalNAc-T2 Δ1-51 Δ445-571) alternate form SEQ ID NO: 260
MSKKKDLHHSNGEEKAQSMETLPPGKVRWPDFNQEAYVGGTMVRSGQDPY
ARNKFNQVESDKLRMDRAIPDTRHDQCQRKQWRVDLPATSVVITFHNEAR
SALLRTVVSVLKKSPPHLIKEIILVDDYSNDPEDGALLGKIEKVRVLRND
RREGLMRSRVRGADAAQAKVLTFLDSHCECNEHWLEPLLERVAEDRTRVV
SPIIDVINMDNFQYVGASADLKGGFDWNLVFKWDYMTPEQRRSRQGNPVA
PIKTPMIAGGLFVMDKFYFEELGKYDMMMDVWGGENLEISFRVWQCGGSL
EIIPCSRVGHVFRKQHPYTFPGGSGTVFARNTRRAAEVWMDEYKNFYYAA
VPSARNVPYGNIQSRLELRKKLSCKPFKWYLENVYPELRVPDHQD 6. Truncated human UDP-N-acetylgalactosaminyl-transferase 2 (GalNAc-T2 Δ53)

SEQ ID NO: 261
KDLHHSNGEEKAQSMETLPPGKVRWPDFNQEAYVGGTMVRSGQDPYARNK
FNQVESDKLRMDRAIPDTRHDQCQRKQWRVDLPATSVVITFHNEARSALL
RTVVSVLKKSPPHLIKEIILVDDYSNDPEDGALLGKIEKVRVLRNDRREG
LMRSRVRGADAAQAKVLTFLDSHCECNEHWLEPLLERVAEDRTRVVSPII
DVINMDNFQYVGASADLKGGFDWNLVFKWDYMTPEQRRSRQGNPVAPIKT
PMIAGGLFVMDKFYFEELGKYDMMMDVWGGENLEISFRVWQCGGSLEIIP
CSRVGHVFRKQHPYTFPGGSGTVFARNTRRAAEVWMDEYKNFYYAAVPSA
RNVPYGNIQSRLELRKKLSCKPFKWYLENVYPELRVPDHQDIAFGALQQG
TNCLDTLGHFADGVVGVYECHNAGGNQEWALTKEKSVKHMDLCLTVVDRA
PGSLIKLQGCRENDSRQKWEQIEGNSKLRHVGSNLCLDSRTAKSGGLSVE
VCGPALSQQWKFTLNLQQ

7. Truncated human UDP-N-acetylgalactosaminyl-transferase 2 (GalNAc-T2 Δ1-53 Δ445-571)

SEQ ID NO: 262
KDLHHSNGEEKAQSMETLPPGKVRWPDFNQEAYVGGTMVRSGQDPYARNK
FNQVESDKLRMDRAIPDTRHDQCQRKQWRVDLPATSVVITFHNEARSALL
RTVVSVLKKSPPHLIKEIILVDDYSNDPEDGALLGKIEKVRVLRNDRREG
LMRSRVRGADAAQAKVLTFLDSHCECNEHWLEPLLERVAEDRTRVVSPII
DVINMDNFQYVGASADLKGGFDWNLVFKWDYMTPEQRRSRQGNPVAPIKT
PMIAGGLFVMDKFYFEELGKYDMMMDVWGGENLEISFRVWQCGGSLEIIP
CSRVGHVFRKQHPYTFPGGSGTVFARNTRRAAEVWMDEYKNFYYAAVPSA
RNVPYGNIQSRLELRKKLSCKPFKWYLENVYPELRVPDHQD

8. Truncated human UDP-N-acetylgalactosaminyl-transferase 2 (GalNAc-T2 Δ53) alternate form SEQ ID NO: 263
MSKDLHHSNGEEKAQSMETLPPGKVRWPDFNQEAYVGGTMVRSGQDPYAR
NKFNQVESDKLRMDRAIPDTRHDQCQRKQWRVDLPATSVVITFHNEARSA
LLRTVVSVLKKSPPHLIKEIILVDDYSNDPEDGALLGKIEKVRVLRNDRR
EGLMRSRVRGADAAQAKVLTFLDSHCECNEHWLEPLLERVAEDRTRVVSP
IIDVINMDNFQYVGASADLKGGFDWNLVFKWDYMTPEQRRSRQGNPVAPI
KTPMIAGGLFVMDKFYFEELGKYDMMMDVWGGENLEISFRVWQCGGSLEI
IPCSRVGHVFRKQHPYTFPGGSGTVFARNTRRAAEVWMDEYKNFYYAAVP
SARNVPYGNIQSRLELRKKLSCKPFKWYLENVYPELRVPDHQDIAFGALQ
QGTNCLDTLGHFADGVVGVYECHNAGGNQEWALTKEKSVKHMDLCLTVVD
RAPGSLIKLQGCRENDSRQKWEQIEGNSKLRHVGSNLCLDSRTAKSGGLS
VEVCGPALSQQWKFTLNLQQ 9. Truncated human UDP-N-acetylgalactosaminyl-transferase 2 (GalNAc-T2 Δ1-53 Δ445-571) alternate form SEQ ID NO: 264
MSKDLHHSNGEEKAQSMETLPPGKVRWPDFNQEAYVGGTMVRSGQDPYAR
NKFNQVESDKLRMDRAIPDTRHDQCQRKQWRVDLPATSVVITFHNEARSA
LLRTVVSVLKKSPPHLIKEIILVDDYSNDPEDGALLGKIEKVRVLRNDRR
EGLMRSRVRGADAAQAKVLTFLDSHCECNEHWLEPLLERVAEDRTRVVSP
IIDVINMDNFQYVGASADLKGGFDWNLVFKWDYMTPEQRRSRQGNPVAPI
KTPMIAGGLFVMDKFYFEELGKYDMMMDVWGGENLEISFRVWQCGGSLEI
IPCSRVGHVFRKQHPYTFPGGSGTVFARNTRRAAEVWMDEYKNFYYAAVP
SARNVPYGNIQSRLELRKKLSCKPFKWYLENVYPELRVPDHQD 10. Truncated human UDP-N-acetylgalactosaminyl-transferase 1 (GalNAc-T1 Δ40)

SEQ ID NO: 265
GLPAGDVLEPVQKPHEGPGEMGKPVVIPKEDQEKMKEMFKINQFNLMASE
MIALNRSLPDVRLEGCKTKVYPDNLPTTSVVIVFHNEAWSTLLRTVHSVI
NRSPRHMIEEIVLVDDASERDFLKRPLESYVKKLKVPVHVIRMEQRSGLI
RARLKGAAVSKGQVITFLDAHCECTVGWLEPLLARIKHDRRTVVCPIIDV
ISDDTFEYMAGSDMTYGGFNWKLNFRWYPVPQREMDRRKGDRTLPVRTPT
MAGGLFSIDRDYFQEIGTYDAGMDIWGGENLEISFRIWQCGGTLEIVTCS
HVGHVFRKATPYTFPGGTGQIINKNNRRLAEVWMDEFKNFFYIISPGVTK
VDYGDISSRVGLRHKLQCKPFSWYLENIYPDSQIPRHYFSLGEIRNVETN
QCLDNMARKENEKVGIFNCHGMGGNQVFSYTANKEIRTDDLCLDVSKLNG
PVTMLKCHHLKGNQLWEYDPVKLTLQHVNSNQCLDKATEEDSQVPSIRDC
NGSRSQQWLLRNVTLPEIF

TABLE 13-continued

Exemplary GalNAc-T1, GalNAc-T2, GalNAc-T3 and GalNAc-T11 Sequences

11. Truncated human UDP-N-acetylgalactosaminyl-transferase 1 (GalNAc-T1 Δ40) alternate form SEQ ID NO: 266
MGLPAGDVLEPVQKPHEGPGEMGKPVVIPKEDQEKMKEMFKINQFNLMAS
EMIALNRSLPDVRLEGCKTKVYPDNLPTTSVVIVFHNEAWSTLLRTVHSV
INRSPRHMIEEIVLVDDASERDFLKRPLESYVKKLKVPVHVIRMEQRSGL
IRARLKGAAVSKGQVITFLDAHCECTVGWLEPLLARIKHDRRTVVCPIID
VISDDTFEYMAGSDMTYGGFNWKLNFRWYPVPQREMDRRKGDRTLPVRTP
TMAGGLFSIDRDYFQEIGTYDAGMDIWGGENLEISFRIWQCGGTLEIVTC
SHVGHVFRKATPYTFPGGTGQIINKNNRRLAEVWMDEFKNFFYIISPGVT
KVDYGDISSRVGLRHKLQCKPFSWYLENIYPDSQIPRHYFSLGEIRNVET
NQCLDNMARKENEKVGIFNCHGMGGNQVFSYTANKEIRTDDLCLDVSKLN
GPVTMLKCHHLKGNQLWEYDPVKLTLQHVNSNQCLDKATEEDSQVPSIRD
CNGSRSQQWLLRNVTLPEIF 12. Human UDP-N-acetylgalactosaminyltransferase 3 (GalNAc-T3)

SEQ ID NO: 267
MAHLKRLVKLHIKRHYHKKFWKLGAVIFFFIIVLVLMQREVSVQYSKEES
RMERNMKNKNKMLDLMLEAVNNIKDAMPKMQIGAPVRQNIDAGERPCLQG
YYTAAELKPVLDRPPQDSNAPGASGKAFKTTNLSVEEQKEKERGEAKHCF
NAFASDRISLHRDLGPDTRPPECIEQKFKRCPPLPTTSVIIVFHNEAWST
LLRTVHSVLYSSPAILLKEIILVDDASVDEYLHDKLDEYVKQFSIVKIVR
QRERKGLITARLLGATVATAETLTFLDAHCECFYGWLEPLLARIAENYTA
VVSPDIASIDLNTFEFNKPSPYGSNHNRGNFDWSLSFGWESLPDHEKQRR
KDETYPIKTPTFAGGLFSISKEYFEYIGSYDEEMEIWGGENIEMSFRVWQ
CGGQLEIMPCSVVGHVFRSKSPHSFPKGTQVIARNQVRLAEVWMDEYKEI
FYRRNTDAAKIVKQKAPGDLSKRFEIKHRLRCKNFTWYLNNIYPEVYVPD
LNPVISGYIKSVGQPLCLDVGENNQGGKPLIMYTCHGLGGNQYFEYSAQH
EIRHNIQKELCLHAAQGLVQLKACTYKGHKTVVTGEQIWEIQKDQLLYNP
FLKMCLSANGEHPSLVSCNPSDPLQKWILSQND

13. Drosophila UDP-N-acetylgalactosaminyltransferase 3 (GalNAc-T3)

SEQ ID NO: 268
MGLRFQQLKKLWLLYLFLLFFAFFMFAISINLYVASIQGGDAEMRHPKPP
PKRRSLWPHKNIVAHYIGKGDIFGNMTADDYNINLFQPINGEGADGRPVV
VPPRDRFRMQRFFRLNSFNLLASDRIPLNRTLKDYRTPECRDKKYASGLP
STSVIIVFHNEAWSVLLRTITSVINRSPRHLLKEIILVDDASDRSYLKRQ
LESYVKVLAVPTRIFRMKKRSGLVPARLLGAENARGDVLTFLDAHCECSR
GWLEPLLSRIKESRKVVICPVIDIISDDNFSYTKTFENHWGAFNWQLSFR
WFSSDRKRQTAGNSSKDSTDPIATPGMAGGLFAIDRKYFYEMGSYDSNMR
VWGGENVEMSFRIWQCGGRVEISPCSHVGHVFRSSTPYTFPGGMSEVLTD
NLARAATVWMDDWQYFIMLYTSGLTLGAKDKVNVTERVALRERLQCKPFS
WYLENIWPEHFFPAPDRFFGKIIWLDGETECAQAYSKHMKNLPGRALSRE
WKRAFEEIDSKAEELMALIDLERDKCLRPLKEDVPRSSLSAVTVGDCTSH
AQSMDMFVITPKGQIMTNDNVCLTYRQQKLGVIKMLKNRNATTSNVMLAQ
CASDSSQLWTYDMDTQQISHRDTKLCLTLKAATNSRLQKVEKVVLSMECD
FKDITQKWGFIPLPWRM

14. Mouse UDP-N-acetylgalactosaminyltransferase 3 (GalNAc-T3)

SEQ ID NO: 269
MAHLKRLVKLHIKRHYHRKFWKLGAVIFFFLVVLILMQREVSVQYSKEES
KMERNLKNKNKMLDFMLEAVNNIKDAMPKMQIGAPIKENIDVRERPCLQG
YYTAAELKPVFDRPPQDSNAPGASGKPFKITHLSPEEQKEKERGETKHCF
NAFASDRISLHRDLGPDTRPPECIEQKFKRCPPLPTTSVIIVFHNEAWST
LLRTVHSVLYSSPAILLKEIILVDDASVDDYLHEKLEEYIKQFSIVKIVR
QQERKGLITARLLGAAVATAETLTFLDAHCECFYGWLEPLLARIAENYTA
VVSPDIASIDLNTFEFNKPSPYGNNHNRGNFDWSLSFGWESLPDHEKQRR
KDETYPIKTPTFAGGLFSISKKYFEHIGSYDEEMEIWGGENIEMSFRVWQ
CGGQLEIMPCSVVGHVFRSKSPHTFPKGTQVIARNQVRLAEVWMDEYKEI
FYRRNTDAAKIVKQKSFGDLSKRFEIKKRLQCKNFTWYLNTIYPEAYVPD
LNPVISGYIKSVGQPLCLDVGENNQGGKPLILYTCHGLGGNQYFEYSAQR
EIRHNIQKELCLHATQGVVQLKACVYKGHRTIAPGEQIWEIRKDQLLYNP
LFKMCLSSNGEHPNLVPCDATDLLQKWIFSQND

15. Human UDP-N-acetylgalactosaminyltransferase 11 (GalNAc-T11)

SEQ ID NO: 270
MGSVTVRYFCYGCLFTSATWTVLLFVYFNFSEVTQPLKNVPVKGSGPHGP
SPKKFYPRFTRGPSRVLEPQFKANKIDDVIDSRVEDPEEGHLKFSSELGM
IFNERDQELRDLGYQKHAFNMLISDRLGYHRDVPDTRNAACKEKFYPPDL
PAASVVICFYNEAFSALLRTVHSVIDRTPAHLLHEIILVDDDSDFDDLKG
ELDEYVQKYLPGKIKVIRNTKREGLIRGRMIGAAHATGEVLVFLDSHCEV
NVMWLQPLLAAIREDRHTVVCPVIDIISADTLAYSSSPVVRGGFNWGLHF
KWDLVPLSELGRAEGATAPIKSPTMAGGLFAMNRQYFHELGQYDSGMDIW
GGENLEISFRIWMCGGKLFIIPCSRVGHIFRKRRPYGSPEGQDTMTHNSL
RLAHVWLDEYKEQYFSLRPDLKTKSYGNISERVELRKKLGCKSFKWYLDN
VYPEMQISGSHAKPQQPIFVNRGPKRPKVLQRGRLYHLQTNKCLVAQGRP
SQKGGLVVLKACDYSDPNQIWIYNEEHELVLNSLLCLDMSETRSSDPPRL
MKCHGSGGSQQWTFGKNNRLYQVSVGQCLRAVDPLGQKGSVAMAICDGSS
SQQWHLEG (b) Fucosyltransferases In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4) GlcNAcβ-group in an oligosaccharide glycoside. Suitable fucosyltransferases for this reaction include the Galβ(1→3,4) GlcNAcβ1-α(1→3,4) fucosyltransferase (FTIII E.C. No. 2.4.1.65), which was first characterized from human milk (see, Palcic, et al., *Carbohydrate Res.* 190: 1-11 (1989); Prieels, et al., *J. Biol. Chem.* 256: 10456-10463 (1981); and Nunez, et al., *Can. J. Chem.* 59: 2086-2095 (1981)) and the Galβ(1→4) GlcNAcβ-αfucosyltransferases (FTIV, FTV, FTVI) which are found in human serum. FTVII (E.C. No. 2.4.1.65), a sialyl α(2→3) Galβ ((1→3) GlcNAcβ fucosyltransferase, has also been characterized. A recombinant form of the Galβ(1→3,4) GlcNAcβ-α(1→3,4) fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

(c) Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)). Also suitable in the practice of the invention are soluble forms of α1,3-galactosyltransferase such as that reported by Cho, S. K. and Cummings, R. D. (1997) *J. Biol. Chem.*, 272, 13622-13628.

In another embodiment, the galactosyltransferase is a β(1,3)-galactosyltransferases, such as Core-1-GalT1. Human Core-1-β1,3-galactosyltransferase has been described (see, e.g., Ju et al., *J. Biol. Chem.* 2002, 277(1): 178-186). *Drosophila melanogaster* enzymes are described in Correia et al., *PNAS* 2003, 100(11): 6404-6409 and Muller et al., *FEBS J.* 2005, 272(17): 4295-4305. Additional Core-1-β3 galactosyltransferases, including truncated versions thereof, are disclosed in WO/0144478 and U.S. Provisional Patent Application No. 60/842,926 filed Sep. 6, 2006. In an exemplary embodiment, the β(1,3)-galactosyltransferase is a member selected from enzymes described by PubMed Accession Number AAF52724 (transcript of CG9520-PC) and modified versions thereof, such as those variations, which are codon optimized for expression in bacteria. The sequence of an exemplary, soluble Core-1-GalT1 (Core-1-GalT1 Δ31) enzyme is shown below:

```
Sequence of Core-1-GalT1 Δ31
                                    (SEQ ID NO: 271)
GFCLAELFVYSTPERSEFMPYDGHRHGDVNDAHHSHDMMEMSGPEQDVGG

HEHVHENSTIAERLYSEVRVLCWIMTNPSNHQKKARHVKRTWGKRCNKLI

FMSSAKDDELDAVALPVGEGRNNLWGKTKEAYKYIYEHHINDADWFLKAD

DDTYTIVENMRYMLYPYSPETPVYFGCKFKPYVKQGYMSGGAGYVLSREA

VRRFVVEALPNPKLCKSDNSGAEDVEIGKCLQNVNVLAGDSRDSNGRGRF

FPFVPEHHLIPSHTDKKFWYWQYIFYKTDEGLDCCSDNAISFHYVSPNQM

YVLDYLIYHLRPYGIINTPDALPNKLAVGELMPEIKEQATESTSDGVSKR

SAETKTQ
```

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., *J. Biochem.* 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al, *Mol. Biol. Cell* 5: 519-528 (1994)).

(d) Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3) sialyltransferase referred to as α(2,3) sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 14, below).

TABLE 14

Sialyltransferases which use the Galβ1,4GlcNAc sequence as an acceptor substrate

| Sialyltransferase | Source | Sequence(s) formed | Ref. |
|---|---|---|---|
| ST6Gal I | Mammalian | NeuAcα2,6Galβ1,4GlcNAc- | 1 |
| ST3Gal III | Mammalian | NeuAcα2,3Galβ1,4GlcNAc- NeuAcα2,3Galβ1,3GlcNAc- | 1 |
| ST3Gal IV | Mammalian | NeuAcα2,3Galβ1,4GlcNAc- NeuAcα2,3Galβ1,3GlcNAc- | 1 |
| ST6Gal II | Mammalian | NeuAcα2,6Galβ1,4GlcNAc | |
| ST6Gal II | photobacterium | NeuAcα2,6Galβ1,4GlcNAc- | 2 |
| ST3Gal V | *N. meningitides N. gonorrhoeae* | NeuAcα2,3Galβ1,4GlcNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3) sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269:1394-1401) and genomic (Kitagawa et al. (1996) *J. Biol. Chem.* 271: 931-938) DNA sequences are known, facilitating production of this enzyme by recombinant expression. In another embodiment, the claimed sialylation methods use a rat ST3Gal III.

Other exemplary sialyltransferases of use in the present invention include those isolated from *Campylobacter jejuni*, including the α(2,3). See, e.g, WO99/49051.

Sialyltransferases other those listed in Table 5, are also useful in an economic and efficient large-scale process for sialylation of commercially important glycopeptides. As a simple test to find out the utility of these other enzymes, various amounts of each enzyme (1-100 mU/mg protein) are reacted with asialo-α$_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the polypeptide backbone can be used in place of asialo-α$_1$ AGP for this evaluation. Sialyltransferases with the ability to sialylate N-linked oligosaccharides of glycopeptides more efficiently than ST6Gal I are useful in a practical large-scale process for polypeptide sialylation (as illustrated for ST3Gal III in this disclosure). Other exemplary sialyltransferases are shown in FIG. 10.

Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Purification of Polypeptide Conjugates

The polypeptide conjugates produced by the processes described herein above can be used without purification. However, it is usually preferred to recover such products. Standard, well-known techniques for the purification of glycosylated saccharides, such as thin or thick layer chromatography, column chromatography, ion exchange chromatography, or membrane filtration. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have a molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the modified glycoprotein is produced intracellularly, as a first step, the particulate debris, including cells and cell debris, is removed, for example, by centrifugation or ultrafiltration. Optionally, the protein may be concentrated with a commercially available protein concentration filter, followed by separating the polypeptide variant from other impurities by one or more chromatographic steps, such as immunoaffinity chromatography, ion-exchange chromatography (e.g., on diethylaminoethyl (DEAE) or matrices containing carboxymethyl or sulfopropyl groups), hydroxy apatite chromatography and hydrophobic interaction chromatography (HIC). Exemplary stationary phases include Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, SP-Sepharose, or protein A Sepharose.

Other chromatographic techniques include SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps, e.g., SP Sepharose. Additionally, the modified glycoprotein may be purified by affinity chromatography. HPLC may also be employed for one or more purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the polypeptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

The modified glycopeptide of the invention resulting from a large-scale fermentation may be purified by methods analogous to those disclosed by Urdal et al., *J. Chromatog.* 296:171 (1984). This reference describes two sequential, RP-HPLC steps for purification of recombinant human IL-2 on a preparative HPLC column. Alternatively, techniques such as affinity chromatography may be utilized to purify the modified glycoprotein.

Acquisition of Polypeptide Coding Sequences

General Recombinant Technology

The creation of mutant polypeptides, which incorporate an O-linked glycosylation sequence of the invention can be accomplished by altering the amino acid sequence of a correponding parent polypeptide, by either mutation or by full chemical synthesis of the polypeptide. The polypeptide amino acid sequence is preferably altered through changes at the DNA level, particularly by mutating the DNA sequence encoding the polypeptide at preselected bases to generate codons that will translate into the desired amino acids. The DNA mutation(s) are preferably made using methods known in the art.

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

Nucleic acid sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Entire genes can also be chemically synthesized. Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type polypeptide genes, polynucleotide encoding mutant polypeptides, and synthetic oligonucleotides can be verified after cloning using, e.g., the chain termination method for sequencing double-stranded templates of Wallace et al., *Gene* 16: 21-26 (1981).

In an exemplary embodiment, the glycosylation sequence is added by shuffling polynucleotides. Polynucleotides encoding a candidate polypeptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

Cloning and Subcloning of a Wild-Type Peptide Coding Sequence

Numerous polynucleotide sequences encoding wild-type polypeptides have been determined and are available from a commercial supplier, e.g., human growth hormone, e.g., GenBank Accession Nos. NM 000515, NM 002059, NM 022556, NM 022557, NM 022558, NM 022559, NM 022560, NM 022561, and NM 022562.

The rapid progress in the studies of human genome has made possible a cloning approach where a human DNA sequence database can be searched for any gene segment that has a certain percentage of sequence homology to a known nucleotide sequence, such as one encoding a previously identified polypeptide. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a polypeptide can be isolated from a human cDNA or genomic DNA library using standard cloning techniques such as polymerase chain reaction (PCR), where homology-based primers can often be derived from a known nucleic acid sequence encoding a polypeptide. Most commonly used techniques for this purpose are described in standard texts, e.g., Sambrook and Russell, supra.

cDNA libraries suitable for obtaining a coding sequence for a wild-type polypeptide may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate the full-length polynucleotide sequence encoding the wild-type polypeptide from the cDNA library. A general description of appropriate procedures can be found in Sambrook and Russell, supra.

A similar procedure can be followed to obtain a full length sequence encoding a wild-type polypeptide, e.g., any one of the GenBank Accession Nos mentioned above, from a human genomic library. Human genomic libraries are commercially available or can be constructed according to various art-recognized methods. In general, to construct a genomic library, the DNA is first extracted from an tissue where a polypeptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, the full-length nucleic acid encoding a wild-type polypeptide is obtained.

Upon acquiring a nucleic acid sequence encoding a wild-type polypeptide, the coding sequence can be subcloned into a vector, for instance, an expression vector, so that a recombinant wild-type polypeptide can be produced from the resulting construct. Further modifications to the wild-type polypeptide coding sequence, e.g., nucleotide substitutions, may be subsequently made to alter the characteristics of the molecule.

Introducing Mutations into a Polypeptide Sequence

From an encoding polynucleotide sequence, the amino acid sequence of a wild-type polypeptide can be determined.

Subsequently, this amino acid sequence may be modified to alter the protein's glycosylation pattern, by introducing additional glycosylation sequence(s) at various locations in the amino acid sequence.

Several types of protein glycosylation sequences are well known in the art. For instance, in eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J* 7:540-550 (1993); and Orlean, *Saccharomyces* Vol. 3 (1996)). O-linked glycosylation takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995). Based on this knowledge, suitable mutations can thus be introduced into a wild-type polypeptide sequence to form new glycosylation sequences.

Although direct modification of an amino acid residue within a polypeptide sequence may be suitable to introduce a new N-linked or O-linked glycosylation sequence, more frequently, introduction of a new glycosylation sequence is accomplished by mutating the polynucleotide sequence encoding a polypeptide. This can be achieved by using any of known mutagenesis methods, some of which are discussed below.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

Modification of Nucleic Acids for Preferred Codon Usage in a Host Organism

The polynucleotide sequence encoding a polypeptide variant can be further altered to coincide with the preferred codon usage of a particular host. For example, the preferred codon usage of one strain of bacterial cells can be used to derive a polynucleotide that encodes a polypeptide variant of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the polpeptide variant coding sequences are verified by sequencing and are then subcloned into an appropriate expression vector for recombinant production in the same manner as the wild-type polypeptides.

Expression of Mutant Polypeptides

Following sequence verification, the polypeptide variant of the present invention can be produced using routine techniques in the field of recombinant genetics, relying on the polynucleotide sequences encoding the polypeptide disclosed herein.

Expression Systems

To obtain high-level expression of a nucleic acid encoding a mutant polypeptide of the present invention, one typically subclones a polynucleotide encoding the mutant polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant polypeptide in host cells. A typical expression cassette thus contains a promoter operably linked to the nucleic acid sequence encoding the mutant polypeptide and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322-based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

In some exemplary embodiments the expression vector is chosen from pCWin1, pCWin2, pCWin2/MBP, pCWin2-MBP-SBD (pMS$_{39}$), and pCWin2-MBP-MCS-SBD (pMXS$_{39}$) as disclosed in co-owned U.S. patent application filed Apr. 9, 2004 which is incorporated herein by reference.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

When periplasmic expression of a recombinant protein (e.g., a hgh mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant polypeptide or its coding sequence while still retaining the biological activity of the polypeptide. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast or insect cell lines that express large quantities of the mutant polypeptide, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant polypeptide.

Detection of Expression of Mutant Polypeptides in Host Cells

After the expression vector is introduced into appropriate host cells, the transfected cells are cultured under conditions favoring expression of the mutant polypeptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant polypeptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant polypeptide of the present invention (e.g., Harlow and Lane, *Antibodies, A Laboratory Manual*, Chapter 14, Cold Spring Harbor, 1988; Kohler and Milstein, *Nature*, 256: 495-497 (1975)). Such techniques require antibody preparation by selecting antibodies with high specificity against the mutant polypeptide or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.*, 6: 511-519 (1976). More detailed descriptions of preparing antibody against the mutant polypeptide of the present invention and conducting immunological assays detecting the mutant polypeptide are provided in a later section.

Purification of Recombinantly Produced Mutant Polypeptides

Once the expression of a recombinant mutant polypeptide in transfected host cells is confirmed, the host cells are then cultured in an appropriate scale for the purpose of purifying the recombinant polypeptide.

1. Purification from Bacteria

When the mutant polypeptides of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a mutant polypeptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide, e.g., the mutant polypeptide of the present invention, is expressed in host cells in a soluble form, its purification can follow standard protein purification procedures, for instance those described herein, below or purification can be accomplished using methods disclosed elsewhere, e.g., in PCT Publication No. WO2006/105426, which is incorporated by reference herein.

Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant polypeptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Ultrafiltration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The proteins of interest (such as the mutant polypeptide of the present invention) can also be separated from other proteins on the basis of their size, net surface charge, hydrophobicity, or affinity for ligands. In addition, antibodies raised against polypeptide can be conjugated to column matrices and the polypeptide be immunopurified. All of these methods are well known in the art.

It will be apparent to one of skill that chromatographic techniques can be performed at any scale and using equipment from many different manufacturers (e.g., Pharmacia Biotech).

Immunoassays for Detection of Mutant Polypeptide Expression

To confirm the production of a recombinant mutant polypeptide, immunological assays may be useful to detect in a sample the expression of the polypeptide. Immunological assays are also useful for quantifying the expression level of the recombinant hormone. Antibodies against a mutant polypeptide are necessary for carrying out these immunological assays.

Production of Antibodies Against Mutant Polypeptides

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant polypeptide of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant polypeptide of the present invention can be tested for their cross-reactivity against the wild-type polypeptide and thus distinguished from the antibodies against the wild-type protein. For instance, antisera obtained from an animal immunized with a mutant polypeptide can be run through a column on which a wild-type polypeptide is immobilized. The portion of the antisera that passes through the column recognizes only the mutant polypeptide and not the wild-type polypeptide. Similarly, monoclonal antibodies against a mutant polypeptide can also be screened for their exclusivity in recognizing only the mutant but not the wild-type polypeptide.

Polyclonal or monoclonal antibodies that specifically recognize only the mutant polypeptide of the present invention but not the wild-type polypeptide are useful for isolating the mutant protein from the wild-type protein, for example, by incubating a sample with a mutant peptide-specific polyclonal or monoclonal antibody immobilized on a solid support.

Immunoassays for Detecting Recombinant Poypeptide Expression

Once antibodies specific for a mutant polypeptide of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species to which the second antibody corresponds. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

Immunoassay Formats

Immunoassays for detecting a target protein of interest (e.g., a mutant human growth hormone) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of a mutant polypeptide in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against a mutant polypeptide.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

Methods of Treatment

In addition to the conjugates discussed above, the present invention provides methods of preventing, curing or ameliorating a disease state by administering a polypeptide conjugate of the invention to a subject at risk of developing the disease or a subject that has the disease. Additionally, the invention provides methods for targeting conjugates of the invention to a particular tissue or region of the body.

The following examples are provided to illustrate the compositions and methods of the present invention, but not to limit the claimed invention.

Preferred Embodiments of the Invention

In one embodiment, the invention provides a covalent conjugate between a glycosylated or non-glycosylated sequon polypeptide and a polymeric modifying group, said sequon polypeptide corresponding to a parent polypeptide and comprising an exogenous O-linked glycosylation sequence, said polymeric modifying group being conjugated to said sequon polypeptide at said O-linked glycosylation sequence via a glycosyl linking group, wherein said glycosyl linking group is interposed between and covalently linked to both said sequon polypeptide and said polymeric modifying group, with the proviso that said parent polypeptide is not a member selected from human growth hormone (hGH), granulocyte colony stimulating factor (G-CSF), interferon-alpha (INF-alpha), glucagon-like peptide-1 (GLP-1) and fibroblast growth factor (FGF).

The covalent conjugate of the above embodiment, wherein said polymeric modifying group is a member selected from linear and branched and comprises one or more polymeric moiety, wherein each polymeric moiety is independently selected.

The covalent conjugate of any of the embodiments set forth herein above, wherein said polymeric moiety is a member selected from poly(ethylene glycol) and methoxy-poly(ethylene glycol) (m-PEG).

The covalent conjugate of any of the embodiments set forth herein above, wherein said glycosyl linking group is an intact glycosyl linking group.

The covalent conjugate any of the embodiments set forth herein above, comprising a moiety according to Formula (III):

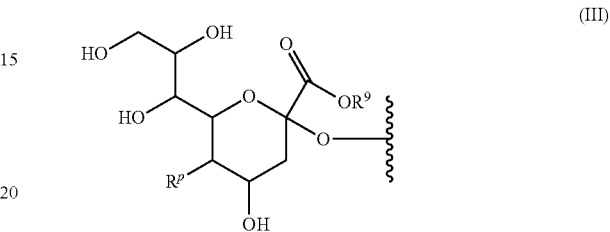

wherein $R^9$ is H, a negative charge or a salt counterion; and $R^p$ is a member selected from:

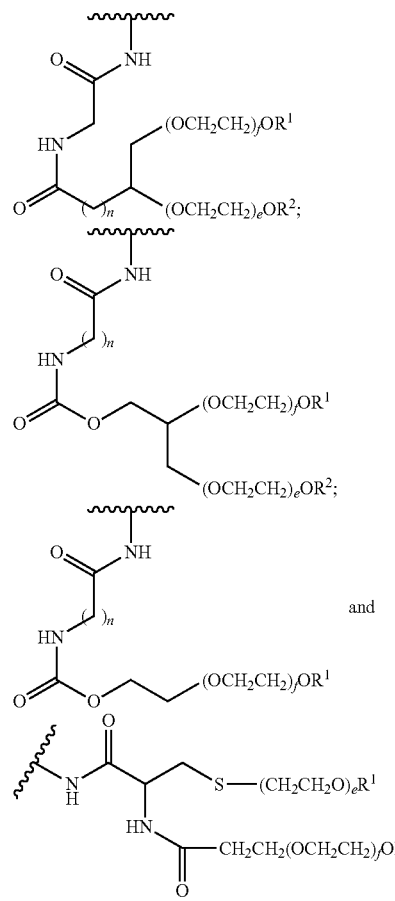

wherein n is an integer selected from 1 to 20 and f and e are integers independently selected from 1-2500.

The covalent conjugate any of the embodiments set forth herein above, wherein said parent-polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, erythropoietin (EPO), α₁-antitrypsin (α-1 protease inhibitor), glucocerebrosidase, tissue-type plasminogen activator (TPA), leptin, hirudin, urokinase, human DNase, insulin, hepatitis B surface protein (HbsAg), chimeric diphtheria toxin-IL-2, human chorionic gonadotropin (hCG), thyroid peroxidase (TPO), alpha-galactosidase, alpha-L-iduronidase, beta-glucosidase, alpha-galactosidase A, acid α-glucosidase (acid maltase), anti-thrombin III (AT III), follicle stimulating hormone (FSH), glucagon-like peptide-2 (GLP-2), Factor VII, Factor VIII, B-domain deleted Factor VIII, Factor IX, Factor X, Factor XIII, prokinetisin, extendin-4, CD4, tumor necrosis factor receptor (TNF-R), α-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-α, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

The covalent conjugate of any of the embodiments set forth herein above, wherein said exogenous O-linked glycosylation sequence is a member selected from: $(X)_m PTP$ (SEQ ID NO: 50), $(X)_m PTEI(P)_n$ (SEQ ID NO: 51), $(X)_m PTQA(P)_n$ (SEQ ID NO: 52), $(X)_m PTINT(P)_n$ (SEQ ID NO: 56), $(X)_m PTTVS(P)_n$ (SEQ ID NO: 60), $(X)_m PTTVL(P)_n$ (SEQ ID NO: 62), $(X)_m PTQGAM(P)_n$ (SEQ ID NO: 66), $(X)_m TET(P)_n$ (SEQ ID NO: 67), $(X)_m PTVL(P)_n$ (SEQ ID NO: 63), $(X)_m PTLS(P)_n$ (SEQ ID NO: 79), $(X)_m PTDA(P)_n$ (SEQ ID NO: 74), $(X)_m PTEN(P)_n$ (SEQ ID NO: 75), $(X)_m PTQD(P)_n$ (SEQ ID NO: 77), $(X)_m PTAS(P)_n$ (SEQ ID NO: 78), $(X)_m PTQGA(P)_n$ (SEQ ID NO: 65), $(X)_m PTSAV(P)_n$ (SEQ ID NO: 83), $(X)_m PTTLYV(P)_n$ (SEQ ID NO: 72), $(X)_m PSSG(P)_n$ (SEQ ID NO: 76) and $(X)_m PSDG(P)_n$ (SEQ ID NO: 86), wherein m and n are integers independently selected from 0 and 1; P is proline; and X is a member independently selected from glutamic acid (E), glutamine (Q), aspartic acid (D), asparagine (N), threonine (T), serine (S) and uncharged amino acids.

The covalent conjugate any of the embodiments set forth herein above, wherein said exogenous O-linked glycosylation sequence is a member selected from: PTP (SEQ ID NO: 138), PTEI (SEQ ID NO: 139), PTEIP (SEQ ID NO: 140), PTQA (SEQ ID NO: 141), PTQAP (SEQ ID NO: 142), PTINT (SEQ ID NO: 143), PTINTP (SEQ ID NO: 144), PTTVS (SEQ ID NO: 145), PTTVL (SEQ ID NO: 146), PTQGAM (SEQ ID NO: 147), PTQGAMP (SEQ ID NO: 148) and TETP (SEQ ID NO: 149).

A pharmaceutical composition comprising a covalent conjugate according any of the embodiments set forth herein above and a pharmaceutically acceptable carrier.

A polypeptide conjugate comprising a sequon polypeptide, said sequon polypeptide corresponding to a parent polypeptide and having an exogenous O-linked glycosylation sequence, said polypeptide conjugate comprising a moiety according to Formula (V):

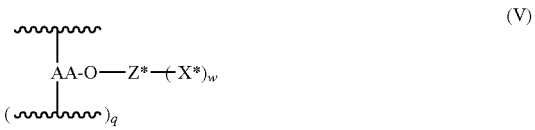

wherein w is an integer selected from 0 and 1; q is an integer selected from 0 and 1; AA-O— is a moiety derived from an amino acid having a side chain substituted with a hydroxyl group, said amino acid positioned within said O-linked glycosylation sequence; Z* is a member selected from a glycosyl moiety and a glycosyl linking group; and X* is a member selected from a polymeric modifying group and a glycosyl linking group covalently linked to a polymeric modifying group, with the proviso that said parent polypeptide is not a member selected from human growth hormone (hGH), granulocyte colony stimulating factor (G-CSF), interferon-alpha (INF-alpha), glucagon-like peptide-1 (GLP-1) and fibroblast growth factor (FGF).

The polypeptide conjugate according to any of the embodiments set forth herein above, wherein said amino acid is serine (S) or threonine (T).

The polypeptide conjugate any of the embodiments set forth herein above, wherein said exogenous O-linked glycosylation sequence is a member selected from: $(X)_m PTP$ (SEQ ID NO: 50), $(X)_m PTEI(P)_n$ (SEQ ID NO: 51), $(X)_m PTQA(P)_n$ (SEQ ID NO: 52), $(X)_m PTINT(P)_n$ (SEQ ID NO: 56), $(X)_m PTTVS(P)_n$ (SEQ ID NO: 60), $(X)_m PTTVL(P)_n$ (SEQ ID NO: 62), $(X)_m PTQGAM(P)_n$ (SEQ ID NO: 66), $(X)_m TET(P)_n$ (SEQ ID NO: 67), $(X)_m PTVL(P)_n$ (SEQ ID NO: 63), $(X)_m PTLS(P)_n$ (SEQ ID NO: 79), $(X)_m PTDA(P)_n$ (SEQ ID NO: 74), $(X)_m PTEN(P)_n$ (SEQ ID NO: 75), $(X)_m PTQD(P)_n$ (SEQ ID NO: 77), $(X)_m PTAS(P)_n$ (SEQ ID NO: 78), $(X)_m PTQGA(P)_n$ (SEQ ID NO: 65), $(X)_m PTSAV(P)_n$ (SEQ ID NO: 83), $(X)_m PTTLYV(P)_n$ (SEQ ID NO: 72), $(X)_m PSSG(P)_n$ (SEQ ID NO: 76) and $(X)_m PSDG(P)_n$ (SEQ ID NO: 86), wherein m and n are integers independently selected from 0 and 1; P is proline; and X is a member independently selected from glutamic acid (E), glutamine (Q), aspartic acid (D), asparagine (N), threonine (T), serine (S) and uncharged amino acids.

The polypeptide conjugate any of the embodiments set forth herein above, wherein said exogenous O-linked glycosylation sequence is a member selected from: PTP (SEQ ID NO: 138), PTEI (SEQ ID NO: 139), PTEIP (SEQ ID NO: 140), PTQA (SEQ ID NO: 141), PTQAP (SEQ ID NO: 142), PTINT (SEQ ID NO: 143), PTINTP (SEQ ID NO: 144), PTTVS (SEQ ID NO: 145), PTTVL (SEQ ID NO: 146), PTQGAM (SEQ ID NO: 147), PTQGAMP (SEQ ID NO: 148) and TETP (SEQ ID NO: 149).

The polypeptide conjugate according to any of the embodiments set forth herein above, wherein Z* is a member selected from GalNAc, GalNAc-Gal, GalNAc-Gal-Sia and GalNAc-Sia.

The polypeptide conjugate according to any of the embodiments set forth herein above, wherein said polymeric modifying group is a member selected from linear and branched and comprises one or more polymeric moiety, wherein each of said polymeric moiety is independently selected.

The polypeptide conjugate according to any of the embodiments set forth herein above, wherein said polymeric moiety is a member selected from poly(ethylene glycol) and derivatives thereof.

The polypeptide conjugate according to any of the embodiments set forth herein above, wherein w is 1.

The polypeptide conjugate according any of the embodiments set forth herein above, wherein X* comprises a moiety, which is a member selected from a sialyl (Sia) moiety, a galactosyl (Gal) moiety, a GalNAc moiety and a Gal-Sia moiety.

The polypeptide conjugate according to any of the embodiments set forth herein above, wherein said parent-polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, erythropoietin (EPO), $\alpha_1$-antitrypsin ($\alpha$-1 protease inhibitor), glucocerebrosidase, tissue-type plasminogen activator (TPA), leptin, hirudin, urokinase, human DNase, insulin, hepatitis B surface protein (HbsAg), chimeric diphtheria toxin-IL-2, human chorionic gonadotropin (hCG), thyroid peroxidase (TPO), alpha-galactosidase, alpha-L-iduronidase, beta-glucosidase, alpha-galactosidase A, acid $\alpha$-glucosidase (acid maltase), anti-thrombin III (AT III), follicle stimulating hormone, glucagon-like peptide-2 (GLP-2), Factor VII, Factor VIII, B-domain deleted Factor VIII, Factor IX, Factor X, Factor XIII, prokinetisin, extendin-4, CD4, tumor necrosis factor receptor (TNF-R), $\alpha$-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-$\alpha$, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

The polypeptide conjugate according to any of the embodiments set forth herein above, wherein X* comprises a moiety according to Formula (VI):

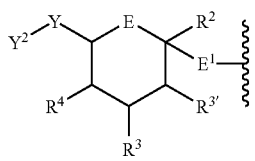

(VI)

wherein E is a member selected from O, S, $NR^{27}$ and $CHR^{28}$, wherein $R^{27}$ and $R^{28}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; $E^1$ is a member selected from O and S; $R^2$ is a member selected from H, $-R^1$, $-CH_2R^1$, and $-C(X^1)R^1$, wherein $R^1$ is a member selected from $OR^9$, $SR^9$, $NR^{10}R^{11}$, substituted or unsubstituted alkyl and substituted or unsubstituted heteroalkyl, wherein $R^9$ is a member selected from H, a negative charge, a metal ion, substituted or unsubstituted alkyl, substituted or unsubstituted heteroalkyl and acyl; $R^{10}$ and $R^{11}$ are members independently selected from H, substituted or unsubstituted alkyl, substituted or unsubstituted heteroalkyl and acyl; $X^1$ is a member selected from substitued or unsubstituted alkenyl, O, S and $NR^8$, wherein $R^8$ is a member selected from H, OH, substituted or unsubstituted alkyl and substituted or unsubstituted heteroalkyl; Y is a member selected from $CH_2$, $CH(OH)CH_2$, $CH(OH)CH(OH)CH_2$, CH, CH(OH)CH; CH(OH)CH(OH) CH, CH(OH), CH(OH)CH(OH), and CH(OH)CH(OH)CH (OH); $Y^2$ is a member selected from H, $OR^6$, $R^6$, substituted or unsubstituted alkyl, substituted or unsubstituted heteroalkyl,

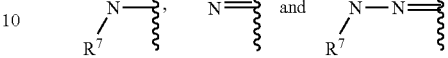

wherein $R^6$ and $R^7$ are members independently selected from H, $L^a$-$R^{6b}$, $C(O)R^{6b}$, $C(O)$-$L^a$-$R^{6b}$, substituted or unsubstituted alkyl and substituted or unsubstituted heteroalkyl, wherein $R^{6b}$ is a member selected from H, substituted or unsubstituted alkyl, substituted or unsubstituted heteroalkyl and a modifying group; $R^3$, $R^{3'}$ and $R^4$ are members independently selected from H, $OR^{3''}$, $SR^{3''}$, substituted or unsubstituted alkyl, substituted or unsubstituted heteroalkyl, -$L^a$-$R^{6c}$, $-C(O)$-$L^aR^{6c}$, $-NH$-$L^a$-$R^{6c}$, $=N$-$L^a$-$R^{6c}$ and $-NHC(O)$-$L^a$-$R^{6c}$, wherein $R^{3''}$ is a member selected from H, substituted or unsubstituted alkyl and substituted or unsubstituted heteroalkyl; and $R^{6c}$ is a member selected from H, substituted or unsubstituted alkyl, substituted or unsubstituted heteroalkyl, substituted or unsubstituted aryl, substituted or unsubstituted heteroaryl, substituted or unsubstituted heterocycloalkyl, $NR^{13}R^{14}$ and a modifying group, wherein $R^{13}$ and $R^{14}$ are members independently selected from H, substituted or unsubstituted alkyl and substituted or unsubstituted heteroalkyl; and each $L^a$ is a member independently selected from a bond and a linker group.

The polypeptide conjugate according to any of the embodiments set forth herein above, wherein X* comprises a moiety according to Formula (VII):

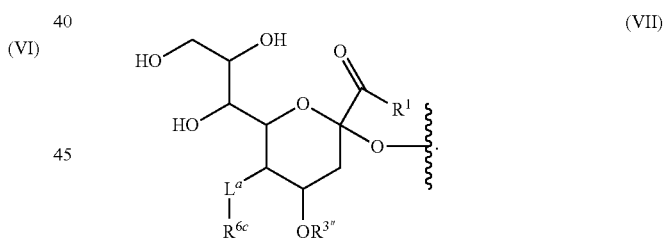

(VII)

The polypeptide conjugate according to any of the embodiments set forth herein above, wherein at least one of $R^{6b}$ and $R^{6c}$ is a member selected from:

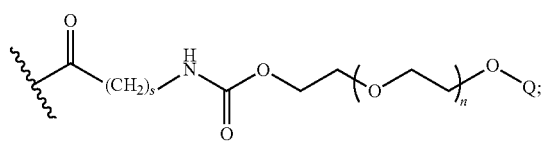

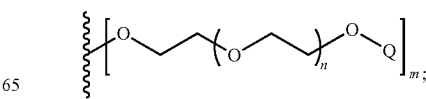

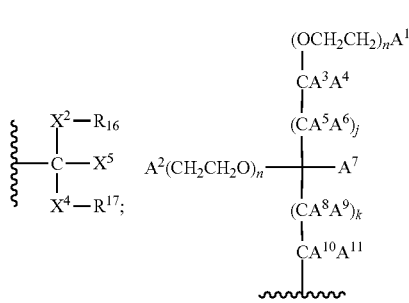

wherein s, j and k are integers independently selected from 0 to 20; each n is an integer independently selected from 0 to 2500; m is an integer from 1-5; Q is a member selected from H and $C_1$-$C_6$ alkyl; $R^{16}$ and $R^{17}$ are independently selected polymeric moieties; $X^2$ and $X^4$ are independently selected linkage fragments joining polymeric moieties $R^{16}$ and $R^{17}$ to C; $X^5$ is a non-reactive group other than a polymeric moiety; and $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted heterocycloalkyl, substituted or unsubstituted aryl, substituted or unsubstituted heteroaryl, —$NA^{12}A^{13}$, —$OA^{12}$ and —$SiA^{12}A^{13}$, wherein $A^{12}$ and $A^{13}$ are members independently selected from substituted or unsubstituted alkyl, substituted or unsubstituted heteroalkyl, substituted or unsubstituted heterocycloalkyl, substituted or unsubstituted aryl, and substituted or unsubstituted heteroaryl.

A pharmaceutical composition comprising a polypeptide conjugate according to any of the embodiments set forth herein above, and a pharmaceutically acceptable carrier.

A sequon polypeptide corresponding to a parent polypeptide, wherein said sequon polypeptide comprises an exogenous O-linked glycosylation sequence selected from SEQ ID NO: 1 and SEQ ID NO: 2:

$(X)_m P\ O^*\ U\ (B)_p (Z)_r (J)_s (O)_t (P)_n;$ (SEQ ID NO: 1)

and $(X)_m (B^1)_p T\ U\ B\ (Z)_r (J)_s (P)_n$ (SEQ ID NO: 2)

wherein m, n, p, r, s and t are integers independently selected from 0 and 1; P is proline; O* is a member selected from serine (S) and threonine (T); U is a member selected from proline (P), glutamic acid (E), glutamine (Q), aspartic acid (D), asparagine (N), threonine (T), serine (S) and uncharged amino acids; X, B and $B^1$ are members independently selected from glutamic acid (E), glutamine (Q), aspartic acid (D), asparagine (N), threonine (T), serine (S) and uncharged amino acids; and Z, J and O are members independently selected from glutamic acid (E), glutamine (Q), aspartic acid (D), asparagine (N), threonine (T), serine (S), tyrosine (Y), methionine (M) and uncharged amino acids, with the proviso that said parent polypeptide is not a member selected from human growth hormone (hGH), granulocyte colony stimulating factor (G-CSF), interferon-alpha (INF-alpha), glucagon-like peptide-1 (GLP-1) and fibroblast growth factor (FGF).

The sequon polypeptide according to any of the embodiments set forth herein above, wherein said exogenous O-linked glycosylation sequence is a member selected from: $(X)_m$PTP (SEQ ID NO: 50), $(X)_m$PTEI(P)$_n$ (SEQ ID NO: 51), $(X)_m$PTQA(P)$_n$ (SEQ ID NO: al, $(X)_m$PTINT(P)$_n$ (SEQ ID NO: 56), $(X)_m$PTTVS(P)$_n$ (SEQ ID NO: 60), $(X)_m$PTTVL (P)$_n$ (SEQ ID NO: 62), $(X)_m$PTQGAM(P)$_n$ (SEQ ID NO: 66), $(X)_m$TET(P)$_n$ (SEQ ID NO: 67), $(X)_m$PTVL(P)$_n$ (SEQ ID NO: 63), $(X)_m$PTLS(P)$_n$ (SEQ ID NO: 79), $(X)_m$PTDA(P)$_n$ (SEQ ID NO: 74), $(X)_m$PTEN(P)$_n$ (SEQ ID NO: 75), $(X)_m$PTQD(P)$_n$ (SEQ ID NO: 77), $(X)_m$PTAS(P)$_n$ (SEQ ID NO: 78), $(X)_m$PTQGA(P)$_n$ (SEQ ID NO: 65), $(X)_m$PTSAV (P)$_n$ (SEQ ID NO: 83), $(X)_m$PTTLYV(P)$_n$ (SEQ ID NO: 72), $(X)_m$PSSG(P)$_n$ (SEQ ID NO: 76) and $(X)_m$PSDG(P)$_n$ (SEQ ID NO: 86), wherein m and n are integers independently selected from 0 and 1; P is proline; and X is a member independently selected from glutamic acid (E), glutamine (Q), aspartic acid (D), asparagine (N), threonine (T), serine (S) and uncharged amino acids.

The sequon polypeptide according to any of the embodiments set forth herein above, wherein said exogenous O-linked glycosylation sequence is a member selected from: PTP (SEQ ID NO: 138), PTEI (SEQ ID NO: 139), PTEIP (SEQ ID NO: 140), PTQA (SEQ ID NO: 141), PTQAP (SEQ ID NO: 142), PTINT (SEQ ID NO: 143), PTINTP (SEQ ID NO: 144), PTTVS (SEQ ID NO: 145), PTTVL (SEQ ID NO: 146), PTQGAM (SEQ ID NO: 147), PTQGAMP (SEQ ID NO: 148) and TETP (SEQ ID NO: 149).

The sequon polypeptide according to any of the embodiments set forth herein above, wherein said exogenous O-linked glycosylation sequence is a substrate for a GalNAc-transferase.

The sequon polypeptide of any of the embodiments set forth herein above, wherein at least 3 amino acids are found between said O* and a lysine (K) or arginine (R) residue.

The sequon polypeptide according to any of the embodiments set forth herein above, wherein said parent polypeptide is a therapeutic polypeptide.

The sequon polypeptide according to any of the embodiments set forth herein above, wherein said parent-polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, erythropoietin (EPO), $\alpha_1$-antitrypsin ($\alpha$-1 protease inhibitor), glucocerebrosidase, tissue-type plasminogen activator (TPA), leptin, hirudin, urokinase, human DNase, insulin, hepatitis B surface protein (HbsAg), chimeric diphtheria toxin-IL-2, human chorionic gonadotropin (hCG), thyroid peroxidase (TPO), alpha-galactosidase, alpha-L-iduronidase, beta-glucosidase, alpha-galactosidase A, acid $\alpha$-glucosidase (acid maltase), anti-thrombin III (AT III), follicle stimulating hormone, glucagon-like peptide-2 (GLP-2), Factor VII, Factor VIII, B-domain deleted Factor VIII, Factor IX, Factor X, Factor XIII, prokinetisin, extendin-4, CD4, tumor necrosis factor receptor (TNF-R), $\alpha$-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-$\alpha$, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

An isolated nucleic acid encoding said sequon polypeptide according to any of the embodiments set forth herein above.

An expression vector comprising said nucleic acid according to any of the embodiments set forth herein above.

A cell comprising said nucleic acid according to any of the embodiments set forth herein above.

A sequon polypeptide corresponding to a parent polypeptide, wherein said sequon polypeptide comprises an exogenous O-linked glycosylation sequence selected from: XPO*P (SEQ ID NO: 95), XPO*EI(P)$_n$ (SEQ ID NO: 97), (X)$_m$PO*EI (SEQ ID NO: 407), XPO*QA(P)$_n$ (SEQ ID NO: 96), XPO*TVS (SEQ ID NO: 99), (X)$_m$PO*TVSP (SEQ ID NO: 100), XPO*QGA (SEQ ID NO: 101), (X)$_m$PO*QGAP (SEQ ID NO: 102), XPO*QGAM(P)$_n$ (SEQ ID NO: 103), XTEO*P (SEQ ID NO: 408), (X)$_m$PO*VL (SEQ ID NO: 104), XPO*VL(P)$_n$ (SEQ ID NO: 105), XPO*TVL (SEQ ID NO: 106), (X)$_m$PO*TVLP (SEQ ID NO: 107), (X)$_m$PO*TLYVP (SEQ ID NO: 108), XPO*TLYV(P)$_n$ (SEQ ID NO: 109), (X)$_m$PO*LS(P)$_n$ (SEQ ID NO: 26), (X)$_m$PO*DA(P)$_n$ (SEQ ID NO: 110), (X)$_m$PO*EN(P)$_n$ (SEQ ID NO: 28), (X)$_m$PO*QD(P)$_n$ (SEQ ID NO: 30), (X)$_m$PO*AS (P)$_n$ (SEQ ID NO: 31), XPO*SAV (SEQ ID NO: 113), (X)$_m$PO*SAVP (SEQ ID NO: 114), (X)$_m$PO*SG(P)$_n$ (SEQ ID NO: 29), XTEO*P (SEQ ID NO: 408) and (X)$_m$PO*DG (P)$_n$ (SEQ ID NO: 40), wherein m and n are integers independently selected from 0 and 1; O* is a member selected from serine (S) and threonine (T); X is a member selected from glutamic acid (E), glutamine (Q), aspartic acid (D), asparagine (N), threonine (T), serine (S) and uncharged amino acids; each S (serine) is optionally and independently replaced with T (threonine); and each T (threonine) is optionally and independently replaced with S (serine).

The sequon polypeptide according to any of the embodiments set forth herein above, wherein said O-linked glycosylation sequence is a substrate for GalNAc-transferase.

The sequon polypeptide acceding to any of the embodiments set forth herein above, wherein at least 3 amino acids are found between said O* and a lysine (K) or arginine (R) residue.

The sequon polypeptide according to any of the embodiments set forth herein above, wherein said parent polypeptide is a therapeutic polypeptide.

The sequon polypeptide according to any of the embodiments set forth herein above, wherein said parent-polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, erythropoietin (EPO), granulocyte colony stimulating factor (G-CSF), granulocyte-macrophage colony stimulating factor (GM-CSF), interferon alpha, interferon beta, interferon gamma, $\alpha_1$-antitrypsin ($\alpha$-1 protease inhibitor), glucocerebrosidase, tissue-type plasminogen activator (TPA), interleukin-2 (IL-2), leptin, hirudin, urokinase, human DNase, insulin, hepatitis B surface protein (HbsAg), chimeric diphtheria toxin-IL-2, human growth hormone (hGH), human chorionic gonadotropin (hCG), thyroid peroxidase (TPO), alpha-galactosidase, alpha-L-iduronidase, beta-glucosidase, alpha-galactosidase A, acid $\alpha$-glucosidase (acid maltase), anti-thrombin III (AT III), follicle stimulating hormone (FSH), glucagon-like peptide-1 (GLP-1), glucagon-like peptide-2 (GLP-2), fibroblast growth factor 7 (FGF-7), fibroblast growth factor 21 (FGF-21), fibroblast growth factor 23 (FGF-23), Factor VII, Factor VIII, B-domain deleted Factor VIII, Factor IX, Factor X, Factor XIII, prokinetisin, extendin-4, CD4, tumor necrosis factor receptor (TNF-R), $\alpha$-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-$\alpha$, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

An isolated nucleic acid encoding said sequon polypeptide according to any of the embodiments set forth herein above.

An expression vector comprising said nucleic acid according to any of the embodiments set forth herein above.

A cell comprising said nucleic acid according to any of the embodiments set forth herein above.

A library of sequon polypeptides comprising a plurality of different members, wherein each member of said library corresponds to a common parent polypeptide and wherein each member of said library comprises an exogenous O-linked glycosylation sequence, wherein each of said O-linked glycosylation sequence is a member independently selected from SEQ ID NO: 1 and SEQ ID NO: 2:

$(X)_m P\ O^*\ U\ (B)_p (Z)_r (J)_s (O)_t (P)_n;$     (SEQ ID NO: 1)

and $(X)_m (B^1)_p T\ U\ B\ (Z)_r (J)_s (P)_n$     (SEQ ID NO: 2)

wherein m, n, p, r, s and t are integers independently selected from 0 and 1; P is proline; O* is a member selected from serine (S) and threonine (T); U is a member selected from proline (P), glutamic acid (E), glutamine (Q), aspartic acid (D), asparagine (N), threonine (T), serine (S) and uncharged amino acids; X, B and $B^1$ are members independently selected from glutamic acid (E), glutamine (Q), aspartic acid (D), asparagine (N), threonine (T), serine (S) and uncharged amino acids; and Z, J and O are members independently selected from glutamic acid (E), glutamine (Q), aspartic acid (D), asparagine (N), threonine (T), serine (S), tyrosine (Y), methionine (M) and uncharged amino acids.

The library according to any of the embodiments set forth herein above, wherein said exogenous O-linked glycosylation sequence is a member selected from: (X)$_m$PTP (SEQ ID NO: 50), (X)$_m$PTEI(P)$_n$ (SEQ ID NO: 51), (X)$_m$PTQA(P)$_n$ (SEQ ID NO: 52), (X)$_m$PTINT(P)$_n$ (SEQ ID NO: 56), (X)$_m$PTTVS(P)$_n$ (SEQ ID NO: 60), (X)$_m$PTTVL(P)$_n$ (SEQ ID NO: 62), (X)$_m$PTQGAM(P)$_n$ (SEQ ID NO: 66), (X)$_m$TET (P)$_n$ (SEQ ID NO: 67), (X)$_m$PTVL(P)$_n$ (SEQ ID NO: 63), (X)$_m$PTLS(P)$_n$ (SEQ ID NO: 79), (X)$_m$PTDA(P)$_n$ (SEQ ID NO: 74), (X)$_m$PTEN(P)$_n$ (SEQ ID NO: 75), (X)$_m$PTQD(P)$_n$ (SEQ ID NO: 77), (X)$_m$PTAS(P)$_n$ (SEQ ID NO: 78), (X)$_m$PTQGA(P)$_n$ (SEQ ID NO: 65), (X)$_m$PTSAV(P)$_n$ (SEQ ID NO: 83), (X)$_m$PTTLYV(P)$_n$ (SEQ ID NO: 72), (X)$_m$PSSG (P)$_n$ (SEQ ID NO: 76) and (X)$_m$PSDG(P)$_n$ (SEQ ID NO: 86), wherein m and n are integers independently selected from 0 and 1; P is proline; and X is a member independently selected from glutamic acid (E), glutamine (Q), aspartic acid (D), asparagine (N), threonine (T), serine (S) and uncharged amino acids.

The library according to any of the embodiments set forth herein above, wherein said exogenous O-linked glycosylation sequence is a member selected from: PTP (SEQ ID NO: 138), PTEI (SEQ ID NO: 139), PTEIP (SEQ ID NO: 140), PTQA (SEQ ID NO: 141), PTQAP (SEQ ID NO: 142), PTINT (SEQ ID NO: 143), PTINTP (SEQ ID NO: 144), PTTVS (SEQ ID NO: 145), PTTVL (SEQ ID NO: 146), PTQGAM (SEQ ID NO: 147), PTQGAMP (SEQ ID NO: 148) and TETP (SEQ ID NO: 149).

The library according to any of the embodiments set forth herein above, wherein each member of said library comprises the same O-linked glycosylation sequence at a different amino acid position within said parent polypeptide.

The library according to any of the embodiments set forth herein above, wherein each member of said library comprises a different O-linked glycosylation sequence at the same amino acid position within said parent polypeptide.

The library according to any of the embodiments set forth herein above, wherein said parent polypeptide has m amino acids, each amino acid corresponding to an amino acid position, said library comprising: (a) a first sequon polypeptide having said O-linked glycosylation sequence at a first amino acid position $(AA)_n$, wherein n is a member selected from 1 to m; and (b) at least one additional sequon polypeptide, each additional sequon polypeptide having said O-linked glycosylation sequence at an additional amino acid position, which is a member selected from $(AA)_{n-x}$ and $(AA)_{n-x}$, wherein x is a member selected from 1 to (m−n).

The library according to any of the embodiments set forth herein above, comprising a second sequon polypeptide having said O-linked glycosylation sequence at a second amino acid position selected from $(AA)_{n+p}$ and $(AA)_{n-p}$, wherein p is selected from 1 to 10.

The library according to any of the embodiments set forth herein above, wherein each of said additional amino acid position is adjacent to a previously selected amino acid position.

The library according any of the embodiments set forth herein above, wherein said O-linked glycosylation sequence is a substrate for a GalNAc-transferase.

The library according to any of the embodiments set forth herein above, wherein said GalNAc-transferase is a member selected from lectin-domain deleted GalNAc-T2 and lectin domain truncated GalNAc-T2.

The library according to any of the embodiments set forth herein above, wherein said parent polypeptide is a therapeutic polypeptide.

The library according to any of the embodiments set forth herein above, wherein said parent-polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, erythropoietin (EPO), granulocyte colony stimulating factor (G-CSF), granulocyte-macrophage colony stimulating factor (GM-CSF), interferon alpha, interferon beta, interferon gamma, $\alpha_1$-antitrypsin ($\alpha$-1 protease inhibitor), glucocerebrosidase, tissue-type plasminogen activator (TPA), interleukin-2 (IL-2), leptin, hirudin, urokinase, human DNase, insulin, hepatitis B surface protein (HbsAg), chimeric diphtheria toxin-IL-2, human growth hormone (hGH), human chorionic gonadotropin (hCG), thyroid peroxidase (TPO), alpha-galactosidase, alpha-L-iduronidase, beta-glucosidase, alpha-galactosidase A, acid $\alpha$-glucosidase (acid maltase), anti-thrombin III (AT III), follicle stimulating hormone (FSH), glucagon-like peptide-1 (GLP-1), glucagon-like peptide-2 (GLP-2), fibroblast growth factor 7 (FGF-7), fibroblast growth factor 21 (FGF-21), fibroblast growth factor 23 (FGF-23), Factor VII, Factor VIII, B-domain deleted Factor VIII, Factor IX, Factor X, Factor XIII, prokinetisin, extendin-4, CD4, tumor necrosis factor receptor (TNF-R), $\alpha$-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-$\alpha$, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

A method comprising: expressing a sequon polypeptide in a host cell, said sequon polypeptide corresponding to a parent polypeptide and comprising an exogenous O-linked glycosylation sequence selected from SEQ ID NO: 1 and SEQ ID NO: 2:

$(X)_m P\ O^*\ U\ (B)_p (Z)_r (J)_s (O)_t (P)_n;$     (SEQ ID NO: 1)

and $(X)_m (B^1)_p T\ U\ B\ (Z)_r (J)_s (P)_n$     (SEQ ID NO: 2)

wherein m, n, p, r, s and t are integers independently selected from 0 and 1; P is proline; O* is a member selected from serine (S) and threonine (T); U is a member selected from proline (P), glutamic acid (E), glutamine (Q), aspartic acid (D), asparagine (N), threonine (T), serine (S) and uncharged amino acids; X, B and $B^1$ are members independently selected from glutamic acid (E), glutamine (Q), aspartic acid (D), asparagine (N), threonine (T), serine (S) and uncharged amino acids; and Z, J and O are members independently selected from glutamic acid (E), glutamine (Q), aspartic acid (D), asparagine (N), threonine (T), serine (S), tyrosine (Y), methionine (M) and uncharged amino acids, with the proviso that said parent polypeptide is not a member selected from human growth hormone (hGH), granulocyte colony stimulating factor (G-CSF), interferon-alpha (INF-alpha), glucagon-like peptide-1 (GLP-1) and fibroblast growth factor (FGF).

The method according to any of the embodiments set forth herein above, further comprising isolating said sequon polypeptide.

The method according to any of the embodiments set forth herein above, further comprising enzymatically glycosylating said sequon polypeptide at said O-linked glycosylation sequence.

The method according to any of the embodiments set forth herein above, wherein said enzymatically glycosylating is accomplished using a glycosyltransferase.

The method according to any of the embodiments set forth herein above, wherein said glycosyltransferase is GalNAc-T2.

The method according to any of the embodiments set forth herein above, wherein said GalNAc-T2 is a member selected from lectin-domain deleted GalNAc-T2 and lectin domain truncated GalNAc-T2.

The method according to any of the embodiments set forth herein above, further comprising generating an expression vector comprising a nucleic acid sequence encoding said sequon polypeptide.

The method according to any of the embodiments set forth herein above, further comprising transfecting said host cell with said expression vector.

The method according to any of the embodiments set forth herein above, wherein said parent polypeptide is a therapeutic polypeptide.

The method according to any of the embodiments set forth herein above, wherein said parent-polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, erythropoietin (EPO), $\alpha_1$-antitrypsin ($\alpha$-1 protease inhibitor), glucocerebrosidase, tissue-type plasminogen activator (TPA), leptin, hirudin, urokinase, human DNase, insulin, hepatitis B surface protein (HbsAg), chimeric diphtheria toxin-IL-2, human chorionic gonadotropin (hCG), thyroid peroxidase (TPO), alpha-galactosidase, alpha-L-iduronidase, beta-glucosidase, alpha-galactosidase A, acid α-glucosidase (acid maltase), anti-thrombin III (AT III), follicle stimulating hormone (FSH), glucagon-like peptide-2 (GLP-2), Factor VII, Factor VIII, B-domain deleted Factor VIII, Factor IX, Factor X, Factor XIII, prokinetisin, extendin-4, CD4, tumor necrosis factor receptor (TNF-R), α-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-α, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

A method for making a polypeptide conjugate according to any of the embodiments set forth herein above, comprising the steps of: (i) recombinantly producing said sequon polypeptide; and (ii) enzymatically glycosylating said sequon polypeptide at said O-linked glycosylation sequence.

The method according to any of the embodiments set forth herein above, wherein said enzymatically glycosylating of step (ii) is accomplished using a GalNAc transferase.

The method according to any of the embodiments set forth herein above, wherein said GalNAc transferase is human GalNAc-T2.

The method according to any of the embodiments set forth herein above, wherein said GalNAc-T2 is a member selected from lectin-domain deleted GalNAc-T2 and lectin domain truncated GalNAc-T2.

A method for making a library of sequon polypeptides according to any of the embodiments set forth herein above, said method comprising: (i) recombinantly producing a first sequon polypeptide by introducing said O-linked glycosylation sequence at a first amino acid position $(AA)_n$; and (ii) recombinantly producing at least one additional sequon polypeptide by introducing said O-linked glycosylation sequence at an additional amino acid position selected from $(AA)_{n+x}$ and $(AA)_{-x}$, wherein x is a member selected from 1 to (m−n). A method for identifying a lead polypeptide, said method comprising: (i) generating a library of sequon polypeptides according to any of the embodiments set forth herein above; and (ii) subjecting at least one member of said library to an enzymatic glycosylation reaction, transferring a glycosyl moiety from a glycosyl donor molecule onto at least one of said O-linked glycosylation sequence, wherein said glycosyl moiety is optionally derivatized with a modifying group, thereby identifying said lead polypeptide.

The method according to any of the embodiments set forth herein above, further comprising measuring yield for said enzymatic glycosylation reaction for at least one member of said library.

The method according to any of the embodiments set forth herein above, wherein said measuring is accomplished by a member selected from mass spectroscopy, gel electrophoresis, nuclear magnetic resonance (NMR) and HPLC.

The method according to any of the embodiments set forth herein above, wherein said yield for said lead polypeptide is between about 50% and about 100%.

The method according to any of the embodiments set forth herein above, further comprising, prior to step (ii), purifying at least one member of said library.

The method according to any of the embodiments set forth herein above, wherein said glycosyl moiety of step (ii) comprises a member selected from a galactose moiety and a GalNAc moiety.

The method according to any of the embodiments set forth herein above, wherein said enzymatic glycosylation reaction of step (ii) occurs within a host cell, in which said at least one member of said library is expressed.

The method according to any of the embodiments set forth herein above, further comprising: (iii) subjecting the product of step (ii) to a PEGylation reaction, wherein said PEGylation reaction is a member selected from a chemical PEGylation reaction and an enzymatic glycoPEGylation reaction.

The method according to any of the embodiments set forth herein above, wherein step (ii) and step (iii) are performed in a single reaction vessel.

The method according to any of the embodiments set forth herein above, further comprising measuring yield of said PEGylation reaction.

The method according to any of the embodiments set forth herein above, wherein said measuring is accomplished by a member selected from mass spectroscopy, gel electrophoresis, nuclear magnetic resonance (NMR) and HPLC.

The method according to any of the embodiments set forth herein above, wherein said yield of said PEGylation reaction for said lead polypeptide is between about 50% and about 100%.

The method according to any of the embodiments set forth herein above, wherein said lead polypeptide upon said PEGylation reaction has a therapeutic activity essentially the same as the therapeutic activity of said parent polypeptide.

The method according to any of the embodiments set forth herein above, wherein said lead polypeptide upon said PEGylation reaction has a therapeutic activity distinct from the therapeutic activity of said parent polypeptide.

The method according to any of the embodiments set forth herein above, further comprising generating an expression vector comprising a nucleic acid sequence encoding said sequon polypeptide.

The method according to of the embodiments set forth herein above, further comprising transfecting said host cell with said expression vector.

Without intending to limit the scope of the invention, in each of the embodiments set forth above (e.g., those relating to methods of making sequon polypeptides, methods of making libraries and methods of identifying sequon polypeptides), the following exemplary embodiments are generally preferred: In one exemplary embodiment, in which the parent polypeptide is glucagon-like peptide-1 (GLP-1), the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418). In another exemplary embodiment, in which the parent polypeptide is wild-type GLP-1 the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418). In another exemplary embodiment, in which the parent polypeptide is wild-type GLP-1, the O-linked glycosylation sequence is preferably not selected from PTQ, PTT, PTQA (SEQ ID NO: 141), PTQG (SEQ ID NO: 410), PTQGA (SEQ ID NO: 158), PTQGAMP (SEQ ID NO: 148), PTQGAM (SEQ ID NO: 147), PTINT (SEQ ID NO: 143), PTQAY (SEQ ID NO: 411), PTTLY (SEQ ID NO: 412), PTGSLP (SEQ ID NO: 413), PTTSEP (SEQ ID NO: 414), PTAVIP (SEQ ID NO: 415), PTSGEP (SEQ ID NO: 416), PTTLYP (SEQ ID NO: 417), PTVLP (SEQ ID NO: 151), TETP (SEQ ID NO: 149), PSDGP (SEQ ID NO: 163) and PTEVP (SEQ ID NO: 418), unless the O-linked glycosylation sequence is not designed around a proline residue that is present in the wild-type G-CSF polypeptide.

In another exemplary embodiment, in which the parent polypeptide is G-CSF, the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138). In another exemplary embodiment, in which the parent polypeptide is wild-type G-CSF the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138). In another exemplary embodiment, in which the parent polypeptide is wild-type G-CSF the O-linked glycosylation sequence is preferably not selected from PTQGA (SEQ ID NO: 158), PTQGAM (SEQ ID NO: 147), PTQGAMP (SEQ ID NO: 148), APTP (SEQ ID NO: 419) and PTP (SEQ ID NO: 138), unless the O-linked glycosylation sequence is not designed around a proline residue that is present in the wild-type G-CSF polypeptide.

In another exemplary embodiment, in which the parent polypeptide is human growth hormon (hGH), the O-linked glycosylation sequence is preferably not selected from PTQGA (SEQ ID NO: 158), PTQGAM (SEQ ID NO: 147), PTQGAMP (SEQ ID NO: 148), PTVLP (SEQ ID NO: 151), PTTVS (SEQ ID NO: 145), PTTLYV (SEQ ID NO: 160), PTINT (SEQ ID NO: 143), PTEIP (SEQ ID NO: 140), PTQA (SEQ ID NO: 141) and TETP (SEQ ID NO: 149). In another exemplary embodiment, in which the parent polypeptide is wild-type hGH, the O-linked glycosylation sequence is preferably not selected from PTQGAM (SEQ ID NO: 147), PTQGAMP (SEQ ID NO: 148), PTTVS (SEQ ID NO: 145), PTTLYV (SEQ ID NO: 160), PTINT (SEQ ID NO: 143), PTQA (SEQ ID NO: 141) and TETP (SEQ ID NO: 149). In yet another exemplary embodiment, in which the parent polypeptide is wild-type hGH, the O-linked glycosylation sequence is preferably not selected from PTQGAM (SEQ ID NO: 147), PTQGAMP (SEQ ID NO: 148), PTTVS (SEQ ID NO: 145), PTTLYV (SEQ ID NO: 160), PTINT (SEQ ID NO: 143), PTQA (SEQ ID NO: 141) and TETP (SEQ ID NO: 149), unless the O-linked glycosylation sequence is not designed around a proline residue that is present in the wild-type hGH polypeptide.

In another exemplary embodiment, in which the parent polypeptide is INF-alpha, the O-linked glycosylation sequence is preferably not TETP (SEQ ID NO: 149). In another exemplary embodiment, in which the parent polypeptide is wild-type INF-alpha, the O-linked glycosylation sequence is preferably not TETP (SEQ ID NO: 149). In yet another exemplary embodiment, in which the parent polypeptide is wild-type INF-alpha, the O-linked glycosylation sequence is preferably not TETP (SEQ ID NO: 149), unless the O-linked glycosylation sequence is not designed around a proline residue that is present in the wild-type INF-alpha polypeptide.

In another exemplary embodiment, in which the parent polypeptide is FGF (e.g., FGF-1, FGF-2, FGF-18, FGF-20, FGF-21), the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420). In another exemplary embodiment, in which the parent polypeptide is a wild-type FGF, the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420). In yet another exemplary embodiment, in which the parent polypeptide is a wild-type FGF, the O-linked glycosylation sequence is preferably not selected from PTP (SEQ ID NO: 138), PTQGA (SEQ ID NO: 158), PTQGAM (SEQ ID NO: 147), PTQGAMP (SEQ ID NO: 148), PTEIP (SEQ ID NO: 140), PTTVS (SEQ ID NO: 145), PTINT (SEQ ID NO: 143), PTINTP (SEQ ID NO: 144), PTQA (SEQ ID NO: 141), PTQAP (SEQ ID NO: 142), PTSAV (SEQ ID NO: 159) and PTSAVAA (SEQ ID NO: 420), unless the O-linked glycosylation sequence is not designed around a proline residue that is present in the wild-type FGF polypeptide.

EXAMPLES

The following examples are provided by way of illustration only and are not meant to limit the scope of the invention. Those of skill in the art will readily recognize a variety of non-critical parameters that could be changed or modified to yield essentially similar results. Though the method is exemplified by reference to human BMP-7 and human NT-3, those of skill will appreciate that glycosylation sites can be incorporated into the peptide sequences of other proteins including other bone morphogenetic proteins and neurotrophins, e.g. BMP-2, in the manner set forth below.

Example 1

Incorporation of Glycosylation Sites into Bone Morphogenetic Protein-7 (BMP-7)

1.1. BMP-7 Sequence Information
An exemplary BMP-7 sequence is shown below (S.1).

```
Human Bone morphogenetic protein-7
                                    (SEQ ID NO: 164)
M¹STGSKQRSQNRSKTPKNQEALRMANVAENSSSDQRQACKKHELYVSFR

DLGWQDWIIAPEGYAAYYCEGECAFPLNSYMNATNHAIVQTLVHFINPET

VPKPCCAPTQLNAISVLYFDDSSNVILKKYRNMVVRACGCH
```

The N-terminal methionine may be present or absent in any BMP-7 mutant. In this example, the numbering of the amino acid residues is based on the initial unmodified sequence in which the left most residue, methionine (M), is numbered as position 1. To highlight how the mutant sequence differs in respect to the unmodified sequence, the numbering of unmodified amino acids as they appear in the mutant sequences below remains unchanged following the modification. More than one of the described sequence modifications may be present in a BMP-7 mutant of the present invention.

Preferred regions for introduction of mutations to create a glycosylation site(s) not present in the wild-type polypeptide are the nucleotide sequences that encode amino acids 1-6, 10-21, 27-36, 55-65, 73-80, 75-85 and 117-125. Sequon scanning using any of the mutant O-linked glycosylation sequences of the invention, e.g. PTP (SEQ ID NO: 138) or PTINT (SEQ ID NO: 143), can be used to insert a new glycosylation site(s) into the BMP-7 parent polypeptide.

This example describes amino acid sequence mutations introducing O-linked glycosylation sequence, e.g., serine or threonine residues, into the wild-type Bone Morphogenetic Protein-7 sequence. A number of mutant BMP-7 polypeptides were generated by introducing O-linked glycosylation sequences into 7 different regions of the peptide sequence, including the amino terminus. Sequon scanning was performed through the two loop regions between amino acids 72-86 and 96-103 using the O-linked glycosylation sequences PTP (SEQ ID NO: 138) and PTINT (SEQ ID NO: 143), respectively. Inclusion bodies for all BMP-7 mutants were prepared.

1.2. Mutations of M$^1$STGSK

In these amino-terminal mutants of BMP-7 the wild-type sequence M$^1$STGSK (SEQ ID NO: 272) was replaced with both amino acid insertions and amino acid replacements. Preferred mutations include:

| | | |
|---|---|---|
| M$^1$FPSTGSK, | (SEQ ID NO: 273) | C.1 |
| M$^1$FPTTGSK, | (SEQ ID NO: 274) | C.2 |
| M$^1$FPSTGSA, | (SEQ ID NO: 275) | C.3 |
| M$^1$FPTINTK, | (SEQ ID NO: 276) | C.4 |
| M$^1$FPTINTA, | (SEQ ID NO: 277) | C.5 |

In this example, phenylalanine (F) was included into the O-linked glycosylation sequence in order to improve *E. coli* expression yields for the N-terminal mutants.

1.3. Mutations of Q$^9$NRSKTP$^6$KNQEA

In these BMP-7 mutants, the wild-type Q$^9$NRSKTP$^{16}$KNQEA (SEQ ID NO: 278) was replaced with amino acid residues or insertions which create glycosylation site(s) in the vicinity of proline 16. Preferred examples include:

| | | |
|---|---|---|
| Q$^9$NGTETP$^{16}$KNQEA, | (SEQ ID NO: 279) | C.6 |
| Q$^9$NRSKTP$^{16}$TNQEA, | (SEQ ID NO: 280) | C.7 |
| Q$^9$NRSKTP$^{16}$TINTA, | (SEQ ID NO: 281) | C.8 |
| Q$^9$NRSATP$^{16}$TINTA, | (SEQ ID NO: 282) | C.9 |
| Q$^9$NRSATP$^{16}$TTVSA, | (SEQ ID NO: 283) | C.10 |

1.4. Mutations of VAEN$^{30}$SSDQR

In these mutants, the wild-type VAEN$^{30}$SSDQR sequence (SEQ ID NO: 284) was replaced with amino acid residues which create glycosylation site(s). Preferred examples include:

| | | |
|---|---|---|
| VAEP$^{30}$SSDQR, | (SEQ ID NO: 285) | C.11 |
| VAEP$^{30}$TSADQR, | (SEQ ID NO: 286) | C.12 |
| VATP$^{30}$TSADQR, | (SEQ ID NO: 287) | C.13 |

1.5. Mutations of DWIIAP$^{60}$EGYAA

In these BMP-7 mutants, the wild-type DWIIAP$^{60}$EGYAA (SEQ ID NO: 288) sequence was replaced with amino acid residues which create glycosylation site(s). Preferred examples include:

| | | |
|---|---|---|
| DWIIAP$^{60}$TGYAA, | (SEQ ID NO: 289) | C.14 |
| DWIIAP$^{60}$TINTA, | (SEQ ID NO: 290) | C.15 |
| DWIIAP$^{60}$TTVSA, | (SEQ ID NO: 291) | C.16 |

1.6. Mutations of AFP$^{75}$LNSYM

In these mutants, the wild-type AFP$^{75}$LNSYM (SEQ ID NO: 292) sequence was replaced with amino acid residues which create glycosylation site(s). Preferred examples include:

| | | |
|---|---|---|
| AFP$^{75}$TNSYM, | (SEQ ID NO: 293) | C.17 |
| AFP$^{75}$TINTM, | (SEQ ID NO: 294) | C.18 |
| AFP$^{75}$TTVSM, | (SEQ ID NO: 295) | C.19 |
| ASP$^{75}$TINTM, | (SEQ ID NO: 296) | C.20 |

1.7. Mutations of P$^{75}$LNSYMNATNH

In these BMP-7 mutants, the wild-type P$^{75}$LNSYMNATNH (SEQ ID NO: 297) sequence was replaced with amino acid residues which create glycosylation site(s). Preferred examples include:

| | | |
|---|---|---|
| P$^{75}$TQAPMNATNH, | (SEQ ID NO: 298) | C.21 |
| P$^{75}$TINTPNATNH, | (SEQ ID NO: 299) | C.22 |
| P$^{75}$TTVSPNATNH, | (SEQ ID NO: 300) | C.23 |
| P$^{75}$TEIPMNATNH, | (SEQ ID NO: 301) | C.24 |
| P$^{75}$LNSYPTATNH, | (SEQ ID NO: 302) | C.25 |
| P$^{75}$LNSSPTINTH, | (SEQ ID NO: 303) | C.26 |
| P$^{75}$LNSPTINTNH, | (SEQ ID NO: 304) | C.27 |
| P$^{75}$LNSPTTVSNH, | (SEQ ID NO: 305) | C.28 |

1.8. Mutations of YFDD$^{120}$SSNVI

In these BMP-7 mutants, the wild-type YFDD$^{120}$SSNVI (SEQ ID NO: 306) sequence was replaced with amino acid residues which create glycosylation site(s). Preferred examples include:

| | | |
|---|---|---|
| YFDP$^{120}$SSNVI, | (SEQ ID NO: 307) | C.29 |
| YFDP$^{120}$TTVSI, | (SEQ ID NO: 308) | C.30 |
| YFSP$^{120}$TTVSI, | (SEQ ID NO: 309) | C.31 |

1.9. Sequon Scanning within BMP-7

In these mutants, two different regions of the BMP-7 sequence were mutated using O-glycosylation sequences of the invention. Mutations in each region are considered separately below. Exemplary mutations include:

Sequon Scanning Within C$^{72}$AFPLNSYMNATHA using PTP and PTINT:

In these BMP-7 mutants, amino acids of the wild-type sequence C$^{72}$AFPLNSYMNATHA (SEQ ID NO: 310) were replaced with PTP or PTINT, and the mutation was scanned across the entire region creating glycosylation sequence(s) within each mutant. Examples include:

Exemplary Sequon Scanning Using PTP:

| | | |
|---|---|---|
| C$^{72}$APTPNSYMNATHA, | (SEQ ID NO: 311) | C.32 |
| C$^{72}$AFPTPSYMNATHA, | (SEQ ID NO: 312) | C.33 |
| C$^{72}$AFPPTPYMNATHA, | (SEQ ID NO: 313) | C.34 |
| C$^{72}$AFPLPTPMNATHA, | (SEQ ID NO: 314) | C.35 |
| C$^{72}$AFPLNPTPNATHA, | (SEQ ID NO: 315) | C.36 |
| C$^{72}$AFPLNSPTPATHA, | (SEQ ID NO: 316) | C.37 |
| C$^{72}$AFPLNSYPTPTHA, | (SEQ ID NO: 317) | C.38 |
| C$^{72}$AFPLNSYMPTPHA, | (SEQ ID NO: 318) | C.39 |
| C$^{72}$AFPLNSYMNPTPA, | (SEQ ID NO: 319) | C.40 |
| C$^{72}$AFPLNSYMNAPTP, | (SEQ ID NO: 320) | C.41 |

Exemplary Sequon Scanning Using PTINT:

| | | |
|---|---|---|
| C$^{72}$APTINTYMNATHA, | (SEQ ID NO: 321) | C.42 |
| C$^{72}$AFPTINTMNATHA, | (SEQ ID NO: 322) | C.43 |
| C$^{72}$AFPPTINTNATHA, | (SEQ ID NO: 323) | C.44 |
| C$^{72}$AFPLPTINTATHA, | (SEQ ID NO: 324) | C.45 |
| C$^{72}$AFPLNPTINTTHA, | (SEQ ID NO: 325) | C.46 |
| C$^{72}$AFPLNSPTINTHA, | (SEQ ID NO: 326) | C.47 |
| C$^{72}$AFPLNSYPTINTA, | (SEQ ID NO: 327) | C.48 |
| C$^{72}$AFPLNSYMPTINT, | (SEQ ID NO: 328) | C.49 |

Sequon Scanning Within N$^{96}$PETVPKPCC Using PTP and PTINT:

In these mutants, the wild-type sequence N$^{96}$PETVPKPCC (SEQ ID NO: 329) were replaced with PTP or PTINT, and the mutation was scanned across the entire region creating glycosylation site(s) within each mutant. Preferred examples include:

Exemplary Sequon Scanning Using PTP:

| | | |
|---|---|---|
| P$^{96}$TPTVPKPCC, | (SEQ ID NO: 330) | C.50 |
| N$^{96}$PTPVPKPCC, | (SEQ ID NO: 331) | C.51 |
| N$^{96}$PPTPPKPCC, | (SEQ ID NO: 332) | C.52 |
| N$^{96}$PEPTPKPCC, | (SEQ ID NO: 333) | C.53 |
| N$^{96}$PETPTPPCC, | (SEQ ID NO: 334) | C.54 |
| N$^{96}$PETVPTPCC, | (SEQ ID NO: 335) | C.55 |

Exemplary Sequon Scanning Using PTINT:

| | | |
|---|---|---|
| P$^{96}$TINTPKPCC, | (SEQ ID NO: 336) | C.56 |
| N$^{96}$PTINTKPCC, | (SEQ ID NO: 337) | C.57 |
| N$^{96}$PPTINTPCC, | (SEQ ID NO: 338) | C.58 |
| N$^{96}$PEPTINTCC, | (SEQ ID NO: 339) | C.59 |

1.10. Purification of BMP-7 Mutants

All BMP-7 mutant C.1 to C.59 were treated according to the following steps: (a) Fermentation, (b) cell lysis, (c) inclusion body (IB) isolation (e.g., by centrifugation), (d) IB solubilization, (e) IB purification (e.g., S-sepharose), and (f) IB refold.

Example 2

Incorporation of Glycosylation Sequences into Neutrotrophin-3 (NT-3)

2.1. NT-3 Sequence Information

An exemplary wild-type amino acid sequence (S.2) of human NT-3 is shown below.

```
Human Neurotrophin-3 (SEQ ID NO: 340):
MYAEHKSHRGEYSVCDSESLWVTDKSSAIDIRGHQVTVLGEIKTGNSPVK

QYFYETRCKEARPVKNGCRGIDDKHWNSQCKTSQTYVRALTSENNKLVGW

RWIRIDTSCVCALSRKIGRT
```

This example describes amino acid sequence mutations introducing O-linked glycosylation sequences into the wild-type NT-3 sequence S.2 (SEQ ID NO: 340) or any modified (e.g., previously mutated) version thereof. A number of mutants were created introducing O-linked glycosylation sites into 3 loop regions as well as the amino terminus.

The N-terminal methionine (M) may be present or absent in any NT-3 mutant. In this example, the numbering of the amino acid residues is based on the initial unmodified sequence in which the N-terminal residue, methionine (M), is numbered as position 1. To highlight how the mutant sequence differs with respect to the unmodified sequence, the numbering of unmodified amino acids as they appear in the mutant sequences below remains unchanged following the modification. More than one of the described sequence modifications may be present in an NT-3 mutant of the present invention.

Preferred regions for the introduction of mutations to create a glycosylation sequence of the invention within the NT-3 polypeptide are the nucleotide sequences that encode amino acids 1-9, 22-30, 45-54 and 91-99 of the wild-type NT-3 amino acid sequence (S.2).

2.2. Mutation of M$^1$YAEHKSHR

In these amino-terminal mutants the wild-type sequence M$^1$YAEHKSHR (SEQ ID NO: 341) is replaced with both amino acid insertions and amino acid replacements. Exemplary mutations include:

| | | |
|---|---|---|
| M$^1$FPTEIPLSR, | (SEQ ID NO: 342) | A.1 |
| M$^1$FPTEIPSHR, | (SEQ ID NO: 343) | A.2 |

2.3. Mutation of VTDK$^{25}$SSAID

In these mutants, the wild-type VTDK$^{25}$SSAID sequence (SEQ ID NO: 344) is replaced with amino acid residues which create glycosylation sequence(s). Preferred examples include:

| | | |
|---|---|---|
| VTDP[25]TINTD, | (SEQ ID NO: 345) | A.3 |
| VTDP[25]TTVSD, | (SEQ ID NO: 346) | A.4 |
| VTP[24]TTVSID, | (SEQ ID NO: 347) | A.5 |

2.4. Mutation of GNSP[48]VKQYFY

In these mutants, the wild-type sequence GNSP[48]VKQYFY (SEQ ID NO: 348) is replaced with amino acid residues which create glycosylation sequence(s). Preferred examples include:

| | | |
|---|---|---|
| GNSP[48]TTVSFY, | (SEQ ID NO: 349) | A.6 |
| GNSP[48]TINTFY, | (SEQ ID NO: 350) | A.7 |
| GNAP[48]TINTFY, | (SEQ ID NO: 351) | A.8 |

2.5. Mutation of TSE[93]NNKLVG

In these mutants, the wild-type sequence TSE[93]NNKLVG (SEQ ID NO: 352) is replaced with amino acid residues which create glycosylation sequence(s). Preferred examples include:

| | | |
|---|---|---|
| TSP[93]TINTVG, | (SEQ ID NO: 353) | A.9 |
| TAP[93]TINTVG, | (SEQ ID NO: 354) | A.10 |
| TSP[93]TTVSVG, | (SEQ ID NO: 355) | A.11 |
| TAP[93]TTVSVG, | (SEQ ID NO: 356) | A.12 |
| TSP[93]TQGAVG, | (SEQ ID NO: 357) | A.13 |
| TAP[93]TQGAVG, | (SEQ ID NO: 358) | A.14 |
| TSE[93]PTINTG, | (SEQ ID NO: 359) | A.15 |
| TSE[93]PTTVSG, | (SEQ ID NO: 360) | A.16 |

2.6. Expression and Purification of Human NT-3 Mutants

Expression

A variety of NT-3 mutants were tested for their expressibility in W3110 *E. coli*. at 37° C. Result: All tested mutants A.1 to A.16 (SEQ ID NOs: 342, 343, 345-347, 349-351, 353-360) were expresssed. After cell lysis, inclusion bodies were isolated by centrifugation.

Solubilization and Sulfitolization of hNT-3 Inclusion Bodies

The washed IB pellet was solubilized 100 mg/ml in a buffer containing 100 mM Tris-HCl, pH8.5, 100 mM NaCl, 5 mM EDTA, 100 mM sodium sulfite, 10 mM sodium tetrathionate, and 7.5 M urea. The solubilization was performed by stirring at room temperature for ~20 min. The suspension was further stirred at 4 C for additional 2 hrs. PEI (polyetheleneimine) was added to final concentration of 0.15% and stirred at 4 C for ~1 hr followed by incubation for another hour. The mixture was centrifuged for 30 min at 5000 rpm/4° C. using Sorvall RC-3B centrifuge. The supernatant was filtered through a 0.45 μm syringe filter, diluted at least 10 fold with SP-Sepharose Fast Flow (SPFF) equilibration buffer (50 mM sodium acetate, 5 M urea, pH5) and then loaded onto an SPFF column. The column was washed with the equilibration buffer. The protein was eluted with 50 mM MOPS, 5 M urea, 10 mM Glycine, pH 7.0.

Refolding and Purification of hNT-3 Mutants

The refolding buffer was composed of 0.1 M Tris, 2 M urea, 0.1 M NaCl, 15% PEG300, 10 mM glycine, 25 mM ethanolamine, pH 9.1. The major peak fractions from SPFF were pooled and diluted into the refolding buffer at a concentration of 0.1 mg/ml. The refolding was initiated by adding L-Cysteine to approximately 5 mM and incubated for 5 days at 4° C. with gentle stirring.

The pH of the refolded pool was adjusted to pH 7, filtered through 0.45 μm filter and loaded onto a Macroprep High S cation-exchange chromatography column equilibrated with 50 mM sodium phosphate, pH 7.0. The protein was eluted in the same buffer with a linear gradient of increasing concentrations of NaCl (0-1.5 M) and tetramethylammonium chloride (TMAC, 0-0.25M). The protein in the major peak was collected and used for glycosylation and GlycoPEGylation studies.

2.7. GlycoPEGylation of hNT-3 Mutants

Screening of hNT-3 Mutants for Glycosylation and GlycoPEGylation

All hNT-3 mutant proteins were purified using High S chromatography and were then exchanged into a reaction buffer containing 50 mM Tris HCl (pH 7.5), 20 mM NaCl, 0.001% polysorbate 80 and 0.02% $NaN_3$. The addition of GalNAc to the proteins was performed at 32° C. overnight in 50 μl reaction composed of ~1 mg/ml hNT-3, 50 mU GalNAc-T2/mg hNT-3, 0.7 mM UDP-GalNAc, and 0.7 mM $MnCl_2$. The incorporation of GalNAc was monitored by MALDI. A variety of mutants within A.1-A.16 (SEQ ID NOs: 342, 343, 345-347, 349-351, 353-360) were efficiently glycosylated by the addition of GalNAc. For these mutants the glycosylation rate was found to be greater than 50%.

When completed, the reaction mixture was split into two equal aliquots. One aliquot was used for direct PEGylation catalyzed by ST6GalNAcI. SA-CMP-PEG stock solution of varied PEG sizes (20K, 30K and branched 40K (NOF)) was added to a final molar ratio of approximately 3:1 relative to hNT-3. ST6GalNAcI was added to a final concentration of at least 20 mU/mg hNT-3. The reaction was performed at 32° C. and the PEGylation was assayed by SDS-PAGE.

The second aliquot was mixed with the enzyme mixture composed of UDP-Gal stock solution (42 mM), Core-1-GalT1 (1.4 U/ml), and reaction buffer described above. The galactosylation was performed at 32° C. overnight and the incorporation of galactosyl group was monitored by MALDI. When the galactosylation was complete, SA-CMP-PEG stock solution of varied PEG sizes (20K, 30K and branched 40K (NOF)) was added to final molar ratio of approximately 3:1 relative to hNT-3. ST3GalI was added to a final concentration of at least 20 mU/mg hNT-3. The reaction was performed at 32° C. and the PEGylation was assayed by SDS-PAGE.

2.8. Preparative GlycoPEGylation and Purification of Modified hNT-3 Mutants

The preparative GlycoPEGylation of selected hNT-3 mutants was accomplished in 3 steps: (a) Addition of GalNAc catalyzed by GalNAc-T2; (b) Incorporation of a galactosyl group catalyzed by Core-1-GalT1; (c) Addition of SA-PEG-20 kDa catalyzed by ST3GalI.

To the hNT-3 protein solution containing approximately 236 μg protein, UDP-GalNAc (50 mM), $MnCl_2$ (100 mM), and GalNAc-T2 (2.1 U/ml) were added. The reaction was performed at 32° C. for 20 hrs and continued 3 more hours after supplementing with UDP-GalNAc (50 mM) and GalNAc-T2 (2.1 U/ml) to drive the reaction to completion. UDP-Gal (42 mM) and Core-1-GalT1 (1.4 U/ml) were then added to the reaction mixture. The reaction was performed at 32° C. overnight. MALDI analysis demonstrated about 100% galactosylation. ST3GalI (0.65 U/ml) and SA-CMP-PEG-20K (0.1 mg/μl) were then added. The incubation was allowed to continue overnight.

The reaction mixture was diluted with water to ~10 ml and loaded onto a Source 15S column (~2 ml CV), which was pre-equilibrated with 50 mM sodium phosphate, pH 7.0. The protein was eluted at 0.5 ml/min over 80 min using a linear gradient of 50 mM sodium phosphate, pH 7.0, 1.5 M NaCl, 0.25 M TMAC. The fractions containing PEGylated hNT-3 were pooled, concentrated and further purified by size exclusion chromatography using a SUPERDEX200 column.

2.9. Summary of Results

Results for expression, in vitro glycosylation and in vitro glycoPEGylation of selected human NT-3 mutants are summarized in Table 16, below.

TABLE 16

In vitro glycosylation and glycoPEGylation of refolded human NT-3 mutants

| Mutant No. | Sequence | Glycosylation | GlycoPEGylation | |
|---|---|---|---|---|
| A.1 | M$^1$FPTEIPLSR | GalNAc | GalNAc-Gal-SA-PEG (20K, 30K, branched 40K*) | SEQ ID NO: 342 |
| A.2 | M$^1$FPTEIPSHR | GalNAc | GalNAc-Gal-SA-PEG (20K 30K, branched 40K*) | SEQ ID NO: 343 |
| A.3 | VTDP$^{25}$TINTD | GalNAc | GalNAc-Gal-SA-PEG (20K) | SEQ ID NO: 345 |
| A.4 | VTDP$^{25}$TTVSD | GalNAc | GalNAc-Gal-SA-PEG (20K) | SEQ ID NO: 346 |
| A.5 | VTP$^{24}$TTVSID | GalNAc | GalNAc-Gal-SA-PEG (20K) | SEQ ID NO: 347 |
| A.6 | GNSP$^{48}$TTVSFY | GalNAc | GalNAc-Gal-SA-PEG (20K) | SEQ ID NO: 349 |
| A.7 | GNSP$^{48}$TINTFY | GalNAc | GalNAc-Gal-SA-PEG (20K) | SEQ ID NO: 350 |
| A.8 | GNAP$^{48}$TINTFY | GalNAc | GalNAc-Gal-SA-PEG (20K) | SEQ ID NO: 351 |
| A.9 | TSP$^{93}$TINTVG | GalNAc | GalNAc-Gal-SA-PEG (20K) | SEQ ID NO: 353 |
| A.10 | TAP$^{93}$TINTVG | GalNAc | GalNAc-Gal-SA-PEG (20K) | SEQ ID NO: 354 |
| A.11 | TSP$^{93}$TTVSVG | GalNAc | GalNAc-Gal-SA-PEG (20K) | SEQ ID NO: 355 |

*40K-NOF-PEG

Example 3

Expression of Human BMP-7 and Human NT-3 Using Various Vectors and E. coli Host Cells The BMP-7 native sequence S.1 (SEQ ID NO: 164) and the above described BMP-7 mutants C.1 to C.31 (SEQ ID NOs: 273-277, 279-283, 285-287, 289-291, 293-296, 298-305, 307-309) (Example 1) as well as the NT-3 native sequence S.2 (SEQ ID NO: 340) and the above described NT-3 mutants A.1-A.16 (SEQ ID NOs: 342, 343, 345-347, 349-351, 353-360) (Example 2) can be expressed using a variety of vectors in different E. coli host cells. Experimental results for the native sequences are summarized in Table 17, below. In addition, all BMP-7 mutants C.1 to C.31 were expressed in W3110 E. coli at 37° C. as inclusion bodies.

TABLE 17

Expression of native human BMP-7 (S.1) (SEQ ID NO: 164) and native NT-3 (S.2) (SEQ ID NO: 340) in E. coli

| Protein | Vector | E. coli Host Cell | Induction Temperature |
|---|---|---|---|
| BMP-7 | pET24a | $trxb,gor,supp$-2 DE3 | 20° C. |
| BMP-7 | pET24a | NovaBlue (DE3) | 37° C. |
| BMP-7 | pET24a | NovaBlue (DE3) | 20° C. |
| BMP-7 | pcWin2 | W3110 | 37° C. |
| NT-3 | pET24a | $trxb,gor,supp$-2 DE3 | 20° C. |
| NT-3 | pcWin2 | $trxb,gor,supp$-2 | 20° C. |
| NT-3 | pcWin2 | W3110 | 37° C. |

BMP-7 and NT-3 or mutated BMP-7 and NT-3 can be glycosylated or glycoconjugated (see WO 03/31464, incorporated herein by reference). Preferably, a mutated BMP-7 or NT-3 is glycoPEGylated, wherein a polyethylene glycol (PEG) moiety is conjugated to the mutated BMP-7 or NT-3 polypeptide via a glycosyl linkage (see WO 03/31464, incorporated herein by reference). GlycoPEGylation of the protein is expected to result in improved biophysical properties that may include but are not limited to improved half-life, improved area under the curve (AUC) values, reduced clearance, and reduced immunogenicity.

Example 4

Introduction of O-Linked Glycosylation Sequences into FGF-21

4.1. Sequence Information

An exemplary amino acid sequence (S.3) for FGF-21 is shown below.

Fibroblast Growth Factor 21 (FGF-21)
(SEQ ID NO: 361)
MHP$^3$IP$^5$DSSP$^9$LLQFGGQVRQRYLYTDDAQQTEAHLEIREDGTVGGAAD

QSP$^{50}$ESLLQLKALKP$^{61}$GVIQILGVKTSRFLCQRP$^{79}$DGALYGSLHFD

P$^{91}$EACSFRELLLEDGYNVYQSEAHGLP$^{116}$LHLP$^{120}$GNKSP$^{125}$HRD

P$^{129}$AP131RGP$^{134}$ARFLP$^{139}$LP$^{141}$GLP$^{144}$P$^{145}$ALP$^{148}$EP$^{150}$

P$^{151}$GILAP$^{156}$QP$^{158}$P$^{159}$DVGSSDP$^{166}$LSMVGP$^{172}$SQGRSP$^{178}$S

YAS

A total of 48 O-glycosylation mutants were prepared and examined. The mutant O-linked glycosylation sequences were introduced into the parent polypeptide by building mutations around existing proline residues. Mutations at 9 different proline residues could be glycosylated (GalNAc-Gal) and glycoPEGylated with branched 40K-cys-PEG.

4.2. Mutagenesis and Cloning

A cDNA encoding the full-length mature form of the human FGF21 protein was synthesized based on the published sequence (NCBI Accession #NM 019113). The gene was PCR amplified using 2 sets of oligonucleotides that would incorporate the desired mutations and restriction sites for constructing the expression vectors. The synthetic genes were subcloned using flanking 5' NdeI and 3' XhoI into the expression vector backbones. Vectors used were either pCWin2 with a modified leader sequence or pCWM3. PCR, cloning, and bacterial transformations were performed using standard techniques (e.g. Current Protocols in Molecular Biology, Ausubel, F M, et al., John Wiley & Sons, Inc. 1998).

4.3. Expression of FGF-21

In a first step, wild-type FGF-21 was expressed in trxB gor supp mutant *E. coli* cells and tested for biological activity. The purified polypeptide was found to be biologically active in a glucose uptake assay using human primary adipocytes. All mutant polypeptides were then expressed using the same procedure. Overnight small-scale cultures of transformed trxB gor supp mutant *E. coli* cells were used to inoculate 50-150 mL of prewarmed animal-free LB containing 50 μg/ml kanamycin. The culture was incubated at 37° C. with shaking, and monitored at $OD_{600}$. When the $OD_{600}$ reached 0.6, the cultures were transferred to 18° C. shaking incubator for 30 minutes. Transformed cells were then induced with IPTG at 18° C. IPTG was added to 0.1 mM final concentration, and shaking incubation was continued for 16-20 hours at 18° C. Cells were harvested by centrifugation at 4° C., 7000×g for 15 minutes. Expression levels were found to be between 15 and 20% lysate protein as determined by densitometry of scanned electrophoresis gels.

4.4. Purification of FGF-21

Frozen Cell pellets from a representative 200 mls of a trxB gor supp mutant strain expressing FGF-21 were lysed in 40 ml of 50 mM BisTris pH7.0 by passing twice through a microfluidizer. Insoluble material was pelleted by centrifugation for 15 minutes at 13,000 rpm using a Sorvall SS34 rotor. All FGF-21 mutants were purified using two chromatographic steps. The final soluble material was passed through a 0.22 micron filter and was adsorbed onto a 1 ml QFF Column at 1 ml/min. The column was attached to an AKTA and eluted using a 20 CV gradient to 500 mM NaCl in the 50 mM BisTris pH 7.0. Fractions across the early part of the gradient were separated by SDS-PAGE and stained with coomassie to determine which fractions to pool. Pooled fractions were then further separated on an SEC column (Superdex 75 16/60) run at 0.5 mls/min using TBS buffer.

4.5. Glycosylation of FGF-21

Purified FGF-21 mutant polypeptides were tested for their capability to function as a substrate for the enzyme GalNAc-T2. MALDI was used to monitor the reactions. Exemplary reaction conditions were as follows: 10 mcg of each mutant FGF-21 protein in 20 mM BisTris pH 6.7, 50 mM NaCl, 10 mM $MnCl_2$ was incubated with 40 mU hGalNAc-T2/mg of protein and 10 molar equivalents of UDP-GalNAc for 6 h at 30° C. The results are summarized in Table 18, below.

Acetone was added at 3 times the volume of the reaction mixture and spun at maximum speed in a microfuge to precipitate the protein. The Acetone was removed and the pellet was allowed to air dry before it was resuspended with water. 0.5 ul were mixed with 0.5 ul of 10 mg/ml Sinapinic acid. The mixtures were then analyzed by MALDI.

Mutants B.1-B.4, B.18, B.20, B.22, B.28, B.29, B.31-B.36, B.41 and B.42 could be fully glycosylated with GalNAc using GalNAc-T2. Mutants B.19, B.23, B.37-B.40 and B.43-B.44 were partially glycosylated. Several mutants, such as B.18, B.20, B.29 and B.31-B.36 were glycosylated but additional GalNAc residues were added to a certain percentage of those mutants. The extent of glycosylation was estimated by obtaining a ratio of the product peak (AUC) to the reactant peak using a MALDI spectra.

4.6. GlycoPEGylation of FGF-21

Generally, when the polypeptide was glycosylated with GalNAc, subsequent addition of Gal and SA-PEG was efficient. In particular, FGF-21 mutants B.1-B.4, B.22, B.28, B.41 and B.42 were evaluated for the addition of Gal and 40 kDa PEG to the glycosylated (GalNAc) polypeptide. Exemplary reaction conditions are summarized below:

Reaction1: Addition of GalNAc 10 mcg of FGF-21 polypeptide (1 mg/ml) were incubated in 20 mM BisTris pH 6.7, 50 mM NaCl, 10 mM $MnCl_2$ containing 10 molar equivalents (0.4 mM) of UDP-GalNAc and MBP-hGalNAcT2 (40 mU/mg) for 6 hours at 30° C.

Reaction2: Addition of GalNAc, Gal and 40 kDa-PEG 10 mcg of FGF-21 polypeptide (1 mg/ml) were incubated in 20 mM BisTris pH 6.7, 50 mM NaCl, 10 mM $MnCl_2$ containing 10 molar equivalents (0.4 mM) of UDP-GalNAc, 10 molar equivalents of UDP-Gal (0.4 mM), 2 molar equivalents of CMP-SA-40 kPEG (0.08 mM) (40 KDa-cys-PEG), MBP-hGalNAcT2 (40 mU/mg), MBP-dCore-1-GalT1 (40 mU/mg) and ST3Gal1 (50 mU/mg) for 16 hours at 30° C. The reactions were analyzed using SDS-PAGE (see FIG. 3)

4.7. Summary of Results

Results for the expression of FGF-21 mutants in trxB gor supp mutant *E. coli* cells, glycosylation and glycoPEGylation reactions are summarized in Table 18, below. Selected mutants will be evaluated in a cell-based glucose uptake assay using human primary adipocytes.

TABLE 18

Evaluation of FGF-21 Mutants

| Mutant No. | Sequon Sequence | Addition of GalNAc | Glyco-PEGylation* | |
|---|---|---|---|---|
| B.1 | $P^5$TSSP | 100% | GalNAc-Gal-SA-PEG (40K) | SEQ ID NO: 362 |
| B.2 | $P^5$TQAP | 100% | GalNAc-Gal-SA-PEG (40K) | SEQ ID NO: 363 |
| B.3 | $P^3$TPDSS | 100% | GalNAc-Gal-SA-PEG (40K) | SEQ ID NO: 364 |
| B.4 | $M^1$FPTP | 100% | GalNAc-Gal-SA-PEG (40K) | SEQ ID NO: 365 |
| B.5 | $P^{50}$TSLL | 0% | NT | SEQ ID NO: 366 |
| B.6 | $P^{50}$TINT | NT | NT | SEQ ID NO: 367 |
| B.7 | $P^{50}$TVGS | NT | NT | SEQ ID NO: 368 |
| B.8 | $P^{50}$TQAG | NT | NT | SEQ ID NO: 369 |
| B.9 | $AP^{61}$TV | NT | NT | SEQ ID NO: 370 |
| B.10 | $AP^{61}$TSVG | NT | NT | SEQ ID NO: 371 |
| B.11 | $AP^{61}$TINT | NT | NT | SEQ ID NO: 372 |
| B.12 | $SP^{61}$TINT | NT | NT | SEQ ID NO: 373 |
| B.13 | $SP^{79}$T | 0% | NT | SEQ ID NO: 374 |

TABLE 18-continued

Evaluation of FGF-21 Mutants

| Mutant No. | Sequon Sequence | Addition of GalNAc | Glyco-PEGylation* | |
|---|---|---|---|---|
| B.14 | AP$^{79}$TQ | NT | NT | SEQ ID NO: 375 |
| B.15 | AP$^{79}$TINT | NT | NT | SEQ ID NO: 376 |
| B.16 | P$^{116}$TQAP | NT | NT | SEQ ID NO: 377 |
| B.17 | TP$^{116}$TEI | NT | NT | SEQ ID NO: 378 |
| B.18 | P$^{120}$TINT | 100% | NT | SEQ ID NO: 379 |
| B.19 | P$^{120}$TSVG | 10% | NT | SEQ ID NO: 380 |
| B.20 | P$^{120}$TET | 100% | NT | SEQ ID NO: 381 |
| B.21 | P$^{125}$TQA | 40% | NT | SEQ ID NO: 382 |
| B.22 | P$^{125}$TEI | 100% | GalNAc-Gal-SA-PEG (40K) | SEQ ID NO: 383 |
| B.23 | P$^{129}$T | 10% | NT | SEQ ID NO: 384 |
| B.24 | ADP$^{129}$TP$^{131}$A | NT | NT | SEQ ID NO: 385 |
| B.25 | PRGP$^{134}$TINT | NT | NT | SEQ ID NO: 386 |
| B.26 | PRGP$^{134}$TSVG | NT | NT | SEQ ID NO: 387 |
| B.27 | PAGP$^{134}$TINT | NT | NT | SEQ ID NO: 388 |
| B.28 | P$^{139}$TPG | 100% | GalNAc-Gal-SA-PEG (40K) | SEQ ID NO: 389 |
| B.29 | P$^{148}$TPPG | 100% | NT | SEQ ID NO: 390 |
| B.30 | P$^{151}$TINAP | NT | NT | SEQ ID NO: 391 |
| B.31 | P$^{151}$TINTP | 100% | NT | SEQ ID NO: 392 |
| B.32 | P$^{151}$TTV | 100% | NT | SEQ ID NO: 393 |
| B.33 | P$^{151}$TTVS | 100% | NT | SEQ ID NO: 394 |
| B.34 | P$^{156}$TPPD | 100% | NT | SEQ ID NO: 395 |
| B.35 | P$^{159}$TVGSS | 100% | NT | SEQ ID NO: 396 |
| B.36 | P$^{159}$TINT | 100% | NT | SEQ ID NO: 397 |
| B.37 | TETP$^{166}$ | 70% | NT | SEQ ID NO: 398 |
| B.38 | P$^{166}$TSMV | 10% | NT | SEQ ID NO: 399 |
| B.39 | P$^{166}$TSVG | 50% | NT | SEQ ID NO: 400 |
| B.40 | P$^{166}$TQGAM | 90% | NT | SEQ ID NO: 401 |
| B.41 | P$^{172}$TQGAS | 100% | GalNAc-Gal-SA-PEG (40K) | SEQ ID NO: 402 |
| B.42 | P$^{172}$TQGAM | 100% | GalNAc-Gal-SA-PEG (40K) | SEQ ID NO: 403 |
| B.43 | p$^{178}$TQ | 10% | NT | SEQ ID NO: 404 |
| B.44 | P$^{178}$TINT | 10% | NT | SEQ ID NO: 405 |

NT = not tested; PEG (40K) = 40KDa-cys-PEG

Example 5

Glycosylation of C-Terminal Linker

The peptide H$_2$N-Met-Val-Thr-Pro-Thr-Pro-Thr-Pro-Thr-CO$_2$ (SEQ ID NO: 406) (40 µg) was incubated with Sf9 derived GalNAc T2 (200 mUnit), UDP-GalNAc (1 mM final), MnCl$_2$ (10 mm final) and Tris pH 7.0 (50 mM final) in 200 µL. After 18 h incubation at 37° C., the reaction was stored at 4° C. The sample was then analyzed by LC/MS/MS to determine the number of GalNAc residues incorporated into the peptide.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety.

What is claimed is:

1. A method comprising expressing a sequon polypeptide in a host cell, wherein said sequon polypeptide corresponds to a parent polypeptide and comprises an exogenous O-linked glycosylation sequence comprising the amino acid sequence of SEQ ID NO: 1:

$(X)_m PO^* U(B)_p (Z)_r (J)_s (O)_t (P)_n$     (SEQ ID NO: 1)

wherein
m, n, and p are integers independently selected from the group consisting of 0 and 1;
r, s, and t are 0;
P is proline;
O* is serine (S) or threonine (T);
U is a member selected from the group consisting of proline (P), glutamic acid (E), glutamine (Q), asparagine (N), threonine (T), glycine (G), and alanine (A);
X and B are members independently selected from the group consisting of glutamic acid (E), glutamine (Q), aspartic acid (D), asparagine (N), threonine (T), and serine (S); and
Z, J and O are members independently selected from the group consisting of glutamic acid (E), glutamine (Q), aspartic acid (D), asparagine (N), threonine (T), serine (S), tyrosine (Y), and methionine (M),
wherein the O-linked glycosylation is at O*, and
wherein the parent polypeptide is selected from the group consisting of bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, α1-antitrypsin (α-1 protease inhibitor), tissue-type plasminogen activator (TPA), human chorionic gonadotropin (hCG), anti-thrombin III (AT III), follicle stimulating hormone (FSH), glucagon-like peptide-2 (GLP-2), Factor VII, Factor VIII, B-domain deleted Factor VIII, Factor IX, Factor X, and Factor XIII.

2. The method according to claim 1, further comprising isolating said sequon polypeptide.

3. The method according to claim 1, further comprising enzymatically glycosylating said sequon polypeptide at said O-linked glycosylation sequence.

4. The method according to claim 3, wherein said enzymatically glycosylating is accomplished using a glycosyltransferase.

5. The method according to claim 4, wherein said glycosyltransferase is N-acetylgalactosamine transferase 2 (GalNAc-T2).

6. The method of claim 5, wherein said GalNAc-T2 is a member selected from the group consisting of lectin-domain deleted GalNAc-T2 and lectin domain truncated GalNAc-T2.

7. The method according to claim 1, further comprising generating an expression vector comprising a nucleic acid sequence encoding said sequon polypeptide.

8. The method according to claim 7, further comprising transfecting said host cell with said expression vector.

9. A method for making a library of sequon polypeptides,
wherein said library of sequon polypeptides comprises a plurality of different members,
wherein each member of said library corresponds to a common parent polypeptide,
wherein each member of said library comprises an exogenous O-linked glycosylation sequence,
wherein each of said O-linked glycosylation sequence comprises the amino acid sequence of SEQ ID NO: 1:

$(X)_m PO^* U(B)_p (Z)_r (J)_s (O)_t (P)_n$     (SEQ ID NO: 1)

wherein
m, n, and p are integers independently selected from the group consisting of 0 and 1;
r, s, and t are 0;
P is proline;
O* is serine (S) or threonine (T);
U is a member selected from the group consisting of proline (P), glutamic acid (E), glutamine (Q), asparagine (N), threonine (T), glycine (G), and alanine (A);

X and B are members independently selected from the group consisting of glutamic acid (E), glutamine (Q), aspartic acid (D), asparagine (N), threonine (T), and serine (S); and Z, J and O are members independently selected from the group consisting of glutamic acid (E), glutamine (Q), aspartic acid (D), asparagine (N), threonine (T), serine (S), tyrosine (Y), and methionine (M), wherein the O-linked glycosylation is at O*, wherein the parent polypeptide is selected from the group consisting of bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, α1-antitrypsin (α-1 protease inhibitor), tissue-type plasminogen activator (TPA), human chorionic gonadotropin (hCG), anti-thrombin III (AT III), follicle stimulating hormone (FSH), glucagon-like peptide-2 (GLP-2), Factor VII, Factor VIII, B-domain deleted Factor VIII, Factor IX, Factor X, and Factor XIII, and wherein said parent polypeptide has y amino acids, each amino acid corresponding to an amino acid position, said library comprising:

(a) a first sequon polypeptide having said O-linked glycosylation sequence at a first amino acid position $(AA)_z$, wherein z is a member selected from 1 to y; and (b) at least one additional sequon polypeptide, each additional sequon polypeptide having said O-linked glycosylation sequence at an additional amino acid position, which is a member selected from $(AA)_{z+x}$ and $(AA)_{z-x}$, wherein x is a member selected from 1 to (y−z), said method comprising:

(i) recombinantly producing a first sequon polypeptide by introducing said O-linked glycosylation sequence at a first amino acid position $(AA)_z$; and (ii) recombinantly producing at least one additional sequon polypeptide by introducing said O-linked glycosylation sequence at an additional amino acid position selected from $(AA)_{z+x}$ and $(AA)_{z-x}$, wherein x is a member selected from 1 to (y−z).

10. A method for identifying a lead polypeptide, said method comprising:

(i) generating a library of sequon polypeptides, wherein said library of sequon polypeptides comprises a plurality of different members, wherein each member of said library corresponds to a common parent polypeptide, wherein each member of said library comprises an exogenous O-linked glycosylation sequence, and wherein each of said O-linked glycosylation sequence comprises the amino acid sequence of SEQ ID NO: 1:

$(X)_m PO^*U(B)_p(Z)_r(J)_s(O)_t(P)_n$        (SEQ ID NO: 1)

wherein m, n, and p are integers independently selected from the group consisting of 0 and 1;

r, s, and t are 0;

P is proline;

O* is serine (S) or threonine (T);

U is a member selected from the group consisting of proline (P), glutamic acid (E), glutamine (Q), asparagine (N), threonine (T), glycine (G), and alanine (A);

X and B are members independently selected from the group consisting of glutamic acid (E), glutamine (Q), aspartic acid (D), asparagine (N), threonine (T), and serine (S); and Z, J and O are members independently selected from the group consisting of glutamic acid (E), glutamine (Q), aspartic acid (D), asparagine (N), threonine (T), serine (S), tyrosine (Y), and methionine (M), wherein the O-linked glycosylation is at O*, wherein the parent polypeptide is selected from the group consisting of bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, α1-antitrypsin (α-1 protease inhibitor), tissue-type plasminogen activator (TPA), human chorionic gonadotropin (hCG), anti-thrombin III (AT III), follicle stimulating hormone (FSH), glucagon-like peptide-2 (GLP-2), Factor VII, Factor VIII, B-domain deleted Factor VIII, Factor IX, Factor X, and Factor XIII; and (ii) subjecting at least one member of said library to an enzymatic glycosylation reaction, transferring a glycosyl moiety from a glycosyl donor molecule onto at least one of said O-linked glycosylation sequences, wherein said glycosyl moiety is optionally derivatized with a modifying group, thereby identifying said lead polypeptide.

11. The method according to claim 10, further comprising measuring yield for said enzymatic glycosylation reaction for at least one member of said library.

12. The method according to claim 11, wherein said measuring is accomplished by a member selected from the group consisting of mass spectroscopy, gel electrophoresis, nuclear magnetic resonance (NMR) and HPLC.

13. The method according to claim 11, wherein said yield for said lead polypeptide is between about 50% and about 100%.

14. The method according to claim 10, further comprising, prior to step (ii), purifying at least one member of said library.

15. The method according to claim 10, wherein said glycosyl moiety of step (ii) comprises a member selected from the group consisting of a galactose moiety and a GalNAc moiety.

16. The method according to claim 10, wherein said enzymatic glycosylation reaction of step (ii) occurs within a host cell, in which said at least one member of said library is expressed.

17. The method according to claim 10, further comprising:

(iii) subjecting the product of step (ii) to a PEGylation reaction, wherein said PEGylation reaction is a member selected from the group consisting of a chemical PEGylation reaction and an enzymatic glycoPEGylation reaction.

18. The method according to claim 17, wherein step (ii) and step (iii) are performed in a single reaction vessel.

19. The method according to claim 17, further comprising measuring yield of said PEGylation reaction.

20. The method according to claim 19, wherein said measuring is accomplished by a member selected from the group consisting of mass spectroscopy, gel electrophoresis, nuclear magnetic resonance (NMR) and HPLC.

21. The method according to claim 19, wherein said yield of said PEGylation reaction for said lead polypeptide is between about 50% and about 100%.

22. The method according to claim 17, wherein said lead polypeptide upon said PEGylation reaction has a therapeutic activity essentially the same as the therapeutic activity of said parent polypeptide.

23. The method according to claim 17, wherein said lead polypeptide upon said PEGylation reaction has a therapeutic activity distinct from the therapeutic activity of said parent polypeptide.

24. The method according to claim 10, further comprising generating an expression vector comprising a nucleic acid sequence encoding said sequon polypeptide.

25. The method according to claim 24, further comprising transfecting said host cell with said expression vector.

* * * * *